(12) United States Patent
Sammut et al.

(10) Patent No.: US 10,494,344 B2
(45) Date of Patent: Dec. 3, 2019

(54) CARBON MONOXIDE RELEASING NORBORNENONE COMPOUNDS

(71) Applicant: OTAGO INNOVATION LIMITED, Dunedin (NZ)

(72) Inventors: Ivan Andrew Sammut, Port Chalmers (NZ); Joanne Clare Harrison, Port Chalmers (NZ); Russell James Hewitt, Singapore (SG); Morgayn Iona Read, Dunedin (NZ); Nathan John Stanley, Adelaide (AU); Laura Molly Woods, South Bend, IN (US); Jui Thiang Brian Kueh, Auckland (NZ); Morgan Jay-Smith, Auckland (NZ); Robin Andrew James Smith, Dunedin (NZ); Gregory Giles, Dunedin (NZ); Lesley Larsen, Dunedin (NZ); David Rennison, Auckland (NZ); Margaret Anne Brimble, Auckland (NZ); David Samuel Larsen, Dunedin (NZ)

(73) Assignee: Otago Innovation Limited (NZ)

( * ) Notice: Subject to any disclaimer, the term of this patent is extended or adjusted under 35 U.S.C. 154(b) by 0 days.

(21) Appl. No.: 15/779,929

(22) PCT Filed: Nov. 30, 2016

(86) PCT No.: PCT/NZ2016/050188
§ 371 (c)(1),
(2) Date: May 30, 2018

(87) PCT Pub. No.: WO2017/095237
PCT Pub. Date: Jun. 8, 2017

(65) Prior Publication Data
US 2018/0346420 A1    Dec. 6, 2018

Related U.S. Application Data

(60) Provisional application No. 62/261,072, filed on Nov. 30, 2015.

(51) Int. Cl.
| | |
|---|---|
| C07D 209/76 | (2006.01) |
| C07D 403/12 | (2006.01) |
| C07D 405/04 | (2006.01) |
| C07D 413/06 | (2006.01) |
| C07C 49/697 | (2006.01) |
| C07C 62/38 | (2006.01) |
| C07D 307/93 | (2006.01) |
| C07D 405/12 | (2006.01) |
| C07D 405/14 | (2006.01) |
| C07D 493/14 | (2006.01) |
| C07H 15/26 | (2006.01) |

(52) U.S. Cl.
CPC .......... *C07D 209/76* (2013.01); *C07C 49/697* (2013.01); *C07C 62/38* (2013.01); *C07D 307/93* (2013.01); *C07D 403/12* (2013.01); *C07D 405/04* (2013.01); *C07D 405/12* (2013.01); *C07D 405/14* (2013.01); *C07D 413/06* (2013.01); *C07D 493/14* (2013.01); *C07H 15/26* (2013.01); *C07C 2602/42* (2017.05); *C07C 2603/66* (2017.05)

(58) Field of Classification Search
CPC ........................... C07D 209/76; C07C 49/697
See application file for complete search history.

(56) References Cited

U.S. PATENT DOCUMENTS

2011/0196141 A1    8/2011   Vaijayanti et al.

FOREIGN PATENT DOCUMENTS

| WO | WO 2012/145520 A2 | 10/2012 |
|---|---|---|
| WO | WO 2013/013179 A1 | 1/2013 |

OTHER PUBLICATIONS

Strange et al (1975): STN International (Columbus, Ohio) HCAPLUS database, Accession No. 1975: 458230.*
Allen, C.F.H. et al, "Addition of ethylenic compounds to tetracyclones", Journal of Organic Chemistry, 1962, vol. 27, pp. 778-779.
Allen, C.F.H. et al, "The infrared absorption of carbonyl groups in bridged compounds", Journal of Organic Chemistry 1955, vol. 20, pp. 306-309.
Ardecky, R.J. et al., "Dienophilic reactions of 3-[{trimethylsilyloxy}]-3-buten-2-one", Journal of Organic Chemistry, 1981, vol. 46, pp. 1483-1485.
Eguchi, S. et al., "Synthesis and cycloaddition reactions of homoadamantano[4,5-e]cyclopentadienones. A facile route to [4,5]-fused homoadamantanobenzene derivatives", Journal of Organic Chemistry, 1987, vol. 52, pp. 496-500.
Faber, K. et al., "On the Prediction of the Enantioselectivity of *Candida rugosa* Lipase by Comparative Molecular Field Analysis", Biocatalysis, 1994, vol. 9, pp. 227-239.
Hoch, P.E., "A study of the acid and base hydrolysis of bridged ketones derived from Diels-Alder adducts of 1,2,3,4-tetrachloro-5,5-dimethoxycyclopentadine", Journal of Organic Chemistry 1961, vol. 26, pp. 2066-2072.
Mehta, G. et al., "Synthetic studies towards the novel diterpenoid rameswaralide: RCM mediated acquisition of the tricyclic core", Tetrahedron Letters, 2006, vol. 47, pp. 327-330.
Michael, J.P. et al., "Nitrobicyclo[2.2.1]heptanes. Part 8. Neighbouring-group participation by nitro groups during the reaction of endo-nitrobicyciclo[2.2.1]heptenes with electrophiles", Journal of the Chemical Society, Perkin Transaction 1, 1991, pp. 1855-1862.

(Continued)

*Primary Examiner* — Golam M Shameem
(74) *Attorney, Agent, or Firm* — Brinks Gilson & Lione; Ryan L. Marshall

(57) ABSTRACT

The present invention provides organic compounds which are capable of releasing carbon monoxide under physiological conditions or pH trigger, and to the use of such compounds for conditioning a cell, tissue or organ, for example, to protect against ischaemic injury during a transplant event.

16 Claims, 9 Drawing Sheets

(56) References Cited

OTHER PUBLICATIONS

Oku, A. et al., "regioselective Diels-Alder reaction of 2-substituted aerylonitriles with cyclic dienones and hydrolytic ring cleavage of the adducts", Journal of Organic Chemistry, 1981, vol. 46, pp. 4152-4157.
Ranganathan, D. et al., "Nitroethylene: a stable, clean, and reactive agent for organic synthesis", Journal of Organic Chemistry, 1980, vol. 45, pp. 1185-1189.
Srikrishna, A. et al., "Cyclopropane Formation vs. the Homoallyl-Homoallyl Radical Rearrangement in 7-Oxygen-Substituted Norborn-5-en-2-yl Radicals", Journal of Organic Chemistry, 1997, vol. 62, pp. 5232-5234.
International Search Report, WO 2017/095237A1.
Yasuda, M. et al., "Frontier-controlled cycloaddition reactions of phencyclone with electron-rich dienophiles via charge-transfer complexes: kinctic study and its mechanistic aspects", Journal of Organic Chemistry, 1981, vol. 46, pp. 3836-3841.
Zefirov, N.S. et al., "Transformation of Cycloolefins into α-Ethoxysulfo-Substituted Ketones via $SO_3$-Mediated Nitrosation", Journal of Organic Chemistry, 1995, vol. 60, pp. 6771-6775.
CAS RN 56457-54-6: STN entry date: Nov. 16, 1984.
CAS RN 928822-38-2: STN entry date: Apr. 1, 2007.
CAS RN 1005267-40-2: STN entry date: Feb. 24, 2008.
Janczewski, M. et al., "The infrared absorption of carbonyl groups in bridged compounds." Journal of Organic Chemistry 1955, vol. 20, pp. 306-309.
Sasaki, T. et al., "Molecular design by cycloaddition reactions. XXV. High peri- and regiospecificity of phencyclone." Journal of Organic Chemistry, 1796, vol. 41., pp. 1105-1112.

\* cited by examiner

ApopTag® Staining

US 10,494,344 B2

CARBON MONOXIDE RELEASING NORBORNENONE COMPOUNDS

CROSS REFERENCE TO RELATED APPLICATIONS

This application is a 371 national phase of PCT/NZ2016/050188, filed Nov. 30, 2016, which claims the benefit of the filing date of U.S. Provisional Application No. 62/261,072, filed Nov. 30, 2015, the disclosures of which are incorporated, in their entirety, by this reference.

FIELD OF THE INVENTION

This disclosure relates to norbornenone compounds, which are capable of releasing carbon monoxide. This disclosure also relates to compositions and formulations comprising the norbornenone compounds. This disclosure further relates to prophylactic and therapeutic methods in which it is desirable to deliver carbon monoxide to a subject, or for conditioning a cell, tissue or organ for transplantation obtained from a subject with carbon monoxide, using the norbornenone compounds, compositions and/or formulations.

BACKGROUND TO THE INVENTION

The endogenous existence of carbon monoxide (CO)-activated protective signalling pathways, including vasodilatory, antiapoptotic, antithrombotic, anti-inflammatory and immunomodulatory, has previously been established. Delivery of CO gas at low concentrations protects organs from ischaemic injury by decreasing cell death and most significantly inducing a preconditioning response. Carbon monoxide has been found to bind to hemoproteins, such as, myoglobin, soluble guanylate cyclase (sGC), inducible nitric oxide synthase, cytochrome p-450, cytochrome-c oxidase, NADPH oxidase and the parent enzyme heme oxygenase. This CO interaction can modulate the activity or level of expression of these key protein targets to produce a plethora of downstream signalling events. The anti-inflammatory effects of CO are mediated by p38 MAPK signalling and inhibition of the potent pro-inflammatory damage recognition molecule HMBG1 results in a reduction of pro-inflammatory cytokines, such as TNF-α, and increase in the expression of the anti-inflammatory interleukin-10.

The protective and physiological effects of low levels of CO have been studied in a number of both animal and clinical models with the literature extensively reviewed[1]. The results of previous studies have been so compelling that the FDA has granted approval for the application of low dose CO gas in a range of clinical trials such as CO gas delivery by inhalation in heart valve replacement surgery[2] and in renal transplant procedure recipients[3]. Inhalation of CO (100-125 ppm) in chronic obstructive pulmonary disease patients, reduced sputum neutrophils and improved bronchial responsiveness. In renal transplant patients low dose CO gas (2 or 3 mg/kg) during surgery has been demonstrated to improve post-transplant kidney function (reduced serum creatinine and increased glomular filtration rate; GFR). However, the difficulty of controlling gas delivery in a clinical setting, combined with the hazardous consequences of any gas leak, have been acknowledged as significant impediments in the use of CO in gaseous form. Metal-based CO-releasing molecules have been developed as an alternative CO delivery system with the advantage of greater ease of administration and control, potentially enabling a safer, tightly controlled method of low dose CO delivery. These molecules have been extensively studied and their beneficial effects demonstrated in transplantation and disease models (e.g. Caumartin, 2011)[4]. However, currently available molecules contain metal cores, which have potential to induce toxic effects.

In relation to organ removal and transplantation, there has been little improvement in clinical outcomes in non-heart beating transplantation since the early 1980's yet cadaveric organ donation provides an under-utilised source of additional organs with which to boost the donor pool. All transplant organs are subject to rapid deterioration during storage. This attrition adds further pressure to the considerable imbalance between the numbers of available donors compared to patients requiring transplant and procedures able to be undertaken. While dialysis is now considered as a "bridge to transplant", the average life expectancy of a kidney dialysis patient is reduced fourfold compared to healthy age-matched individuals, with only 35% of dialysis patients expected to survive beyond 5 years. Cadaveric organs traditionally have worse outcomes than grafts obtained from live or brain stem dead donors on life support. However, CO has been shown to improve organ function and survival, even in cross specie animal transplant studies. Studies have affirmed the feasibility and desirability of developing CO releasing molecules to harness the therapeutic effects of CO. However, several studies have highlighted the toxic effects of current metal based CO releasing molecules.

Consequently, there is a clear need to develop novel, alternative compounds and agents capable of releasing carbon monoxide for the treatment or conditioning of subjects or cells, tissues or organs obtained from subjects. It would also be desirable to develop carbon monoxide releasing agents which have properties for protecting transplanted cells, tissues or organs, provide low toxicity and are suitable for use in perfusion formulations.

SUMMARY OF THE INVENTION

The present inventors have identified norbornenone compounds capable of releasing carbon monoxide in, for example, biological environments while providing appropriate stability for use in various formulations and methods, such as perfusion formulations for protecting a cell, tissue or organ undergoing a transplant event. The norbornenone compounds also provide for alternative carbon monoxide releasing compounds that are free of metals and associated toxicity issues, and according to at least some examples are advantageously water soluble.

In a first aspect of the present invention there is provided a norbornenone compound of Formula 1, or a biologically or pharmaceutically acceptable salt thereof:

Formula 1

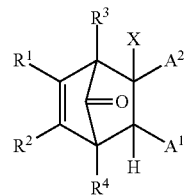

wherein

R$^1$, R$^2$, R$^3$ and R$^4$, are each independently selected from hydrogen, halo, CN, NO$_2$, OC(O)R$^5$, C(O)R$^5$, C(O)OR$^5$, OR$^5$, OS(O)$_2$R$^5$, NR$^5$R$^6$, SR$^5$, C$_{1-20}$alkyl, C$_{2-20}$alkenyl, C$_{2-20}$alkynyl, monocyclic and polycyclic carbocyclyl or heterocyclyl, polyethylene glycol, amino acid, and saccharide; wherein the C$_{1-20}$alkyl, C$_{2-20}$alkenyl, C$_{2-20}$alkynyl, are each optionally interrupted with one or more heteroatoms selected from O, N and S; and wherein the C$_{1-20}$alkyl, C$_{2-20}$alkenyl, C$_{2-20}$alkynyl, carbocycle, and heterocycle, are each optionally substituted with 1-3 substituents independently selected from halo, CN, NO$_2$, OC(O)R$^5$, C(O)R$^5$, C(O)OR$^5$, OR$^5$, OS(O)$_2$R$^5$, NR$^5$R$^6$, SR$^5$, polyethylene glycol, amino acid, and saccharide; and R$^5$ and R$^6$ are each independently selected from hydrogen, C$_{1-10}$alkyl, and C$_{1-10}$haloalkyl; and wherein two or more of R$^1$, R$^2$, R$^3$ and R$^4$, may together form an optionally substituted monocyclic or polycyclic carbocyclyl or heterocyclyl;

X is selected from halo, NO$_2$, ONO$_2$, OP(O)(OR$^7$), OC(O)R$^7$, OS(O)$_2$R$^7$, OS(O)$_2$OR$^7$, SR$^7$, S(O)R$^7$, S(O)$_2$R$^7$, OR$^7$, and NR$^7$R$^8$; and R$^7$ and R$^8$ are each independently selected from hydrogen, C$_{1-10}$alkyl, C$_{1-10}$haloalkyl, aryl, arylalkyl and arylhaloalkyl;

A$^1$ and A$^2$ are each independently selected from hydrogen, halo, CN, NO$_2$, S(O)R$^9$, S(O)$_2$R$^9$, S(O)$_2$OR$^9$, SR$^9$, NR$^9$R$^{10}$, C(=O)R$^9$, C(=S)R$^9$, C(=CR$^{10}$R$^{11}$)R$^9$, or A$^1$ and A$^2$ together form an optionally substituted monocyclic or polycyclic carbocyclyl or heterocyclyl; R$^9$ is selected from hydrogen, hydroxyl, C$_{1-20}$alkyl, C$_{1-20}$haloalkyl, aryl, arylalkyl and arylhaloalkyl; and R$^{10}$ and R$^{11}$ are each independently selected from hydrogen, C$_{1-10}$alkyl, and C$_{1-10}$haloalkyl.

The compound of Formula 1 does not include any of the following compounds:

3,3a,5,6-tetrachloro-3a,4,7,7a-tetrahydro-4,7-methano-1H-indene-1,8-dione;

(1α,4α,4aβ,4bα,5β,8β,8aαβ,12bβ)8a,12b-dibromo-1,2,3,4,5,6,7,8-octachloro-1,4,4a,4b,5,8,8a,12b-octahydro-1,4:5,8-dimethanotriphenylene-13,14-dione;

4,7,7a-tribromo-3a,4,7,7a-tetrahydro-2,3,5,6-tetraphenyl-4,7-methano-1H-indene-1,8-dione;

7,7a-dibromo-2,3,4,5-tetrachloro-3a,4,7,7a-tetrahydro-4,7-methano-1H-indene-1,8-dione;

4,7a-dibromo-2,3,6,7-tetrachloro-3a,4,7,7a-tetrahydro-4,7-methano-1H-indene-1,8-dione;

methyl (2-exo,3-endo)-3-nitro-7-oxo-1,4,5,6-tetraphenyl-bicyclo[2.2.1]hept-5-ene-2-carboxylate;

1,2,3,4-tetraphenyl-5-(phenylthio)-bicyclo[2.2.1]hept-2-en-7-one;

2-[(4-bromophenyl)thio]-1,2,3,4-tetrahydro-1,4-diphenyl-1,4-methanotriphenylen-13-one;

(1α,4α,5β)-1,4-dimethyl-2,3-diphenyl-5-(phenylsulfinyl)-bicyclo[2.2.1]hept-2-en-7-one.

In an example, a compound of Formula 1 is selected from a compound of Formula 1a or Formula 1b, or a biologically or pharmaceutically acceptable salt thereof:

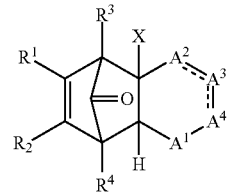

Formula 1a

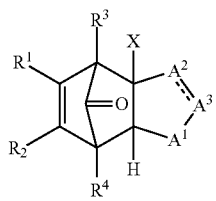

Formula 1b wherein

R$^1$, R$^2$, R$^3$, R$^4$, and X, are each selected from one or more embodiments as described above or herein;

each A$^1$ is independently selected from C=O, C=S, C=CR$^{12}$R$^{13}$, S=O, S(=O)$_2$, S, NR$^{14}$;

each A$^2$, A$^3$ and A$^4$, are independently selected from CR$^{14}$R$^{15}$, CR$^{14}$, C=O, C=S, C=CR$^{12}$R$^{13}$, S=O, S(=O)$_2$, O, S, N, NR$^{14}$; and the dotted lines denote optional double bonds;

R$^{12}$ and R$^{13}$ are each independently selected from hydrogen, C$_{1-10}$alkyl, and C$_{1-10}$haloalkyl;

R$^{14}$ and R$^{15}$ are each independently selected from hydrogen, halo, CN, NO$_2$, OC(O)R$^5$, C(O)R$^5$, C(O)OR$^5$, OR$^5$, OS(O)$_2$R$^5$, NR$^5$R$^6$, SR$^5$, C$_{1-20}$alkyl, C$_{2-20}$alkenyl, C$_{2-20}$alkynyl, monocyclic and polycyclic carbocyclyl or heterocyclyl, polyethylene glycol, amino acid, and mono- or poly-saccharide; wherein the C$_{1-20}$alkyl, C$_{2-20}$alkenyl, C$_{2-20}$alkynyl, are each optionally interrupted with one or more heteroatoms selected from O, N and S; and wherein the C$_{1-20}$alkyl, C$_{2-20}$alkenyl, C$_{2-20}$alkynyl, carbocycle, and heterocycle, are each optionally substituted with one or more substituents independently selected from halo, CN, NO$_2$, OC(O)R$^5$, C=O, C(O)R$^5$, C(O)OR$^5$, OR$^5$, OS(O)$_2$R$^5$, NR$^5$R$^6$, SR$^5$, monocyclic and polycyclic heterocyclyl, polyethylene glycol, amino acid, and mono- or poly-saccharide; and R$^5$ and R$^6$ are each independently selected from hydrogen, C$_{1-10}$alkyl, and C$_{1-10}$haloalkyl.

In a related example, a norbornenone compound of Formula 1 or Formula 1a is selected from a compound of Formula 1a(i), or a biologically or pharmaceutically acceptable salt thereof:

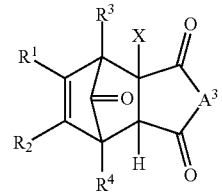

Formula 1a(i)

wherein

R$^1$, R$^2$, R$^3$, R$^4$, and X, are each selected from one or more embodiments as described above or herein;

A$^3$ is selected from O, S, CR$^{14}$R$^{15}$ and NR$^{14}$;

R$^{14}$ and R$^{15}$ are each independently selected from hydrogen, halo, CN, NO$_2$, OC(O)R$^5$, C(O)R$^5$, C(O)OR$^5$, OR$^5$, OS(O)$_2$R$^5$, NR$^5$R$^6$, SR$^5$, C$_{1-20}$alkyl, C$_{2-20}$alkenyl, C$_{2-20}$alkynyl, monocyclic and polycyclic carbocyclyl or heterocyclyl, polyethylene glycol, amino acid, and mono- or poly-saccharide; wherein the C$_{1-20}$alkyl, C$_{2-20}$alkenyl, C$_{2-20}$alkynyl, are each optionally interrupted with one or more heteroatoms selected from O, N and S; and wherein the C$_{1-20}$alkyl, C$_{2-20}$alkenyl, C$_{2-20}$alkynyl, carbocycle, and heterocycle, are each optionally substituted with one or more substituents independently selected from halo, CN, $NO_2$, $OC(O)R^5$, $C=O$, $C(O)R^5$, $C(O)OR^5$, $OR^5$, $OS(O)_2R^5$, $NR^5R^6$, $SR^5$, monocyclic and polycyclic heterocyclyl, polyethylene glycol, amino acid, and mono- or poly-saccharide; and $R^5$ and $R^6$ are each independently selected from hydrogen, $C_{1-10}$alkyl, and $C_{1-10}$haloalkyl.

In yet a further related example, a norbornenone compound of Formula 1, Formula 1a or Formula 1a(i) is selected from a compound of Formula 1a(ii) or a biologically or pharmaceutically acceptable salt thereof:

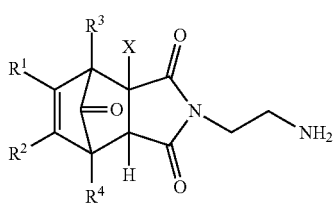

Forumula 1a(ii)

wherein
$R^1$, $R^2$, $R^3$, $R^4$, and X, are each selected from one or more examples as described above or herein.

In yet another related example, a norbornenone compound of Formula 1, Formula 1a, Formula 1a(i) or Formula 1a(ii) is a compound of Formula 1a(iii) or a biologically or pharmaceutically acceptable salt thereof:

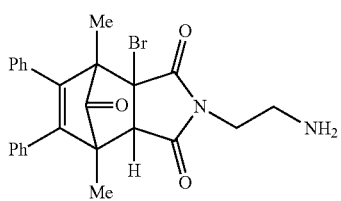

Formula 1a(iii)

In a second aspect of the present invention there is provided a composition comprising a compound of Formula 1 as described herein. In an example, the composition comprises a compound of Formula 1 selected from the group consisting of Formula 1a, Formula 1a(i), Formula 1a(ii), Formula 1a(iii) and Formula 1b.

In a third aspect of the present invention there is provided a biological or pharmaceutical composition comprising a compound of Formula 1 as described herein. In an example, the biological or pharmaceutical composition comprises a compound of Formula 1 selected from the group consisting of Formula 1a, Formula 1a(i), Formula 1a(ii), Formula 1a(iii) and Formula 1b. The biological or pharmaceutical composition may optionally comprise an acceptable excipient or carrier.

In a fourth aspect of the present invention there is provided a formulation comprising a compound of Formula 1 as described herein and an acceptable excipient or carrier. In an example, the formulation is a perfusion formulation. The perfusion formulation may comprise Ringer's lactate (RL), Marshall's hypertonic citrate (HOC), Bretschneider's histidine-tryptophan-ketoglutarate (HTK), EuroCollins solution, Belzer UW, Viaspan, KPS-1, STEEN Solution, Perfadex, IGL-1, Celsior, Polysol, SCOT15, Aedesta, Lifor, Custodial HTK, Renograf, Hypothermosol, HBS Solution, and siRNA Transplant Solution, Ross-Marshall Citrate Solutions, Celsior Solution, Phosphate-Buffered Sucrose Solution, ET-Kyoto, TranSend, HetaFreeze, MaPersol and CryoStor.

In a fifth aspect of the present invention there is provided a method for delivering carbon monoxide to a target comprising providing a norbornenone compound of Formula 1 as described herein to the target, or proximal to the target, optionally in combination with a pH trigger sufficient to deliver carbon monoxide to the target.

In an example, the target is a biological or non-biological target. In a related example, the non-biological target is a metal catalysed carbonylation reaction[5] or for calibrating carbon monoxide sensitive instruments. In a further related example, the biological target is a physiological target. The physiological target may be selected from the group consisting of a subject, cell, tissue or organ.

The compositions and formulations according to the present invention comprise the norborneone compound for Formula 1, or a biologically or pharmaceutically acceptable salt thereof.

In a sixth aspect of the present invention there is provided a method of delivering a physiologically effective amount of carbon monoxide to a physiological target comprising administering a norbornenone compound of Formula 1 as described herein, or a composition or formulation as described herein, to the physiological target.

The method according to the sixth aspect of the present invention optionally comprises providing a pH trigger sufficient to trigger release of carbon monoxide thereby delivering carbon monoxide to the physiological target. In another example, the pH environment of the physiological target will be sufficient to trigger release of carbon monoxide when the norborneone compound is delivered to the target.

In a further example, the physiological target is a subject, or cell, tissue or organ obtained from a subject.

Administration may be via one or more of oral, parenteral, topical, intravenous, subcutaneous, nasal, inhalatory, intramuscular, intraperitoneal and suppository routes. In one example, the administration is oral administration.

In yet a further example, the norbornenone compound of Formula 1 is present in amount sufficient to release a desired amount of carbon monoxide to the physiological target.

In another example, the method according to the sixth aspect of the present invention is for the prevention or treatment of at least one of transplant organ injury, cell and tissue transplantation, ischaemic and ischaemia-reperfusion organ injury, hyperoxia-induced injury, transplant rejection, apoptosis, arteriosclerosis, myocardial infarction, angina, stroke, oxidative stress, hypertension, endotoxic shock, inflammation, inflammation-related disease, haemorrhagic shock, sepsis, adult respiratory disease syndrome, chronic obstructive pulmonary disease, pre-eclampsia, cancer, radiation damage, neuropathic pain, hepatosteatosis, platelet activation, attenuation of venom-mediated catalysis of fibrinogen, cerebral malaria, acute liver failure and acute kidney injury.

In yet another example, the method according to the sixth aspect of the present invention is for protecting a cell, tissue or organ from ischaemic injury either before, during or after transplantation surgery. The method may be an ex-vivo method for protecting the cell, tissue or organ against ischaemic injury during a transplant event, for example, during transportation or storage of the cell, tissue or organ.

In a seventh aspect of the present invention there is provided a method for enhancing the viability of a cell, tissue or organ during a transplant event, the method comprising conditioning the cell, tissue or organ with a norbornenone compound of Formula 1 as described herein, or a composition or formulation described herein, in an amount sufficient to enhance the viability of the cell, tissue or organ.

In an example, conditioning comprises pre-conditioning, peri-conditioning and/or post-conditioning of the cell, tissue or organ obtained from a subject. In a related example, conditioning of the cell, tissue or organ obtained from the subject may occur during syngenic, allogenic or xenotransplant procedures.

In a related example, the cell is selected from the group consisting of stem cells, progenitor cells, pancreatic cells, lymphocyte cells and macrophage cells. In a further related example, the organ or tissue is selected from the group consisting of heart, lung, intestine, kidney, liver, pancreas, vasculature, dermal/skin, bone, adipose, cartilage, hair follicle and corneal tissues.

In other examples, the tissue comprises a tissue for xenotransplantation, for example, for the purpose of determining personalised medicine applications. In a related example, the tissue is a tumour tissue, and xenotransplantation is performed for the purpose of determining a personalised cancer treatment regime. In yet a further related example, the tumour tissue is derived from a patient having breast cancer, bone cancer, bladder cancer, ovarian cancer, cervical cancer, endometrial cancer, lung cancer, gastric cancer, stomach cancer, colorectal cancer, prostate cancer, cervical cancer, bladder cancer, pancreatic cancer, bone cancer, embryonic cancer, melanoma, skin cancer, sarcoma, brain cancer, glioma, cancers of the blood, adrenocortical carcinoma, lymphomas, central nervous system cancers, cardiovascular tumours, esophageal cancer, head and neck cancer, eye cancer, fallopian tube cancer, gallbladder cancer, liver cancer, renal cancer, malignant mesothelioma, neuroblastoma, penile cancer, pituitary tumour, thyroid cancer, prostate cancer, uterine cancer, vulvar cancer and Wilms' tumour.

In an eighth aspect of the present invention there is provided a method for preventing ischaemic injury pre-, peri- and post-surgery, the method comprising administering a norbornenone compound of Formula 1 as described herein, or a composition or formulation as described herein, in an amount sufficient to prevent ischaemic injury during surgery.

In an example, the norbornenone compound of Formula 1 is administered to the subject prior to surgery.

In a related example, the surgery may be selected from the group consisting of cardiovascular (e.g. cardiopulmonary bypass, surgeries to correct atherosclerosis, angioplasty restenosis, vein graft stenosis, thrombosis, myocardial infarction and hypertension) cerebrovascular, surgery associated with cancer re-section, free and pedical tissue grafting and reconstructive surgery.

In a ninth aspect of the present invention, there is provided norbornenone compound of Formula 1 as described herein, or a composition or formulation as described herein, for use in prophylactic and therapeutic methods in which it is desirable to deliver carbon monoxide to a subject, or for conditioning a cell, tissue or organ for transplantation obtained from a subject.

In a tenth aspect of the present invention there is provided a carbon monoxide releasing agent comprising a norbornenone compound of Formula 1 as described herein, or a composition or formulation as described herein, for the prevention or treatment of at least one of transplant organ injury, cell and tissue transplantation, ischaemic and ischaemia-reperfusion organ injury, hyperoxia-induced injury, transplant rejection, apoptosis, arteriosclerosis, myocardial infarction, angina, stroke, oxidative stress, hypertension, endotoxic shock, inflammation, inflammation-related disease, haemorrhagic shock, sepsis, adult respiratory disease syndrome, chronic obstructive pulmonary disease, pre-eclampsia, cancer, radiation damage, neuropathic pain, hepatosteatosis, platelet activation, attenuation of venom-mediated catalysis of fibrinogen, cerebral malaria, acute liver failure and acute kidney injury in a subject or cell, tissue or organ obtained from a subject.

In an eleventh aspect of the present invention, there is provided a use of a norbornenone compound of Formula 1 as described herein, or a composition or formulation as described herein, for the prevention or treatment of at least one of transplant organ injury, cell and tissue transplantation, ischaemic and ischaemia-reperfusion organ injury, hyperoxia-induced injury, transplant rejection, apoptosis, arteriosclerosis, myocardial infarction, angina, stroke, oxidative stress, hypertension, endotoxic shock, inflammation, inflammation-related disease, haemorrhagic shock, sepsis, adult respiratory disease syndrome, chronic obstructive pulmonary disease, pre-eclampsia, cancer, radiation damage, neuropathic pain, hepatosteatosis, platelet activation, attenuation of venom-mediated catalysis of fibrinogen, cerebral malaria and acute liver failure in a subject or cell, tissue or organ obtained from a subject.

In a twelfth aspect of the present invention, there is provided a use of a norbornenone compound of Formula 1 as described herein, or a composition or formulation as described herein, in the manufacture of a medicament for the prevention or treatment of at least one of transplant organ injury, cell and tissue transplantation, ischaemic and ischaemia-reperfusion organ injury, hyperoxia-induced injury, transplant rejection, apoptosis, arteriosclerosis, myocardial infarction, angina, stroke, oxidative stress, hypertension, endotoxic shock, inflammation, inflammation-related disease, haemorrhagic shock, sepsis, adult respiratory disease syndrome, chronic obstructive pulmonary disease, pre-eclampsia, cancer, radiation damage, neuropathic pain, hepatosteatosis, platelet activation, attenuation of venom-mediated catalysis of fibrinogen, cerebral malaria, acute liver failure and acute kidney injury in a subject or cell, tissue or organ obtained from a subject.

It will be appreciated that any one or more of the examples for one aspect may also provide one or more examples for any other aspect of the present invention, as described above or herein.

BRIEF DESCRIPTION OF THE FIGURES

Examples of the present disclosure will now be further described and illustrated with reference to the accompanying figures in which.

DETAILED DESCRIPTION

Figure 1:
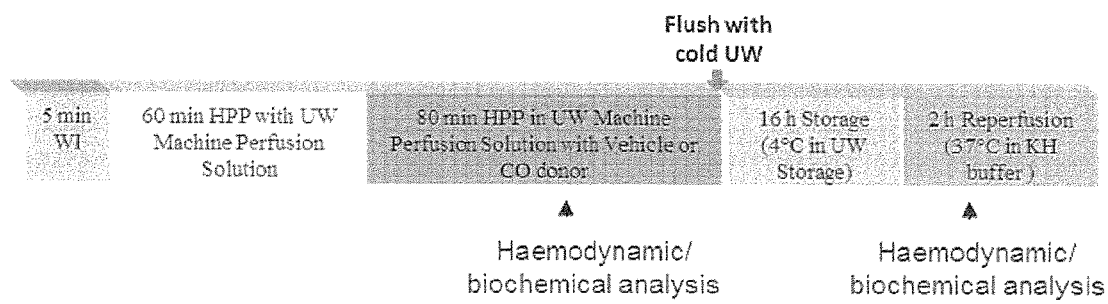
FIG. 1 shows a timescale representation of the norbornenone compound administration within the organ retrieval, hypothermic perfusion, organ storage and reperfusion protocol employed for renal grafts.

The present invention provides novel norbornenone compounds in which release of carbon monoxide may be controlled by using a pH trigger. Advantageously, this means the norbornenone compounds of the present invention may find use in both biological and non-biological applications where release of carbon monoxide may be desired. However, and importantly, pH induced/triggered release of carbon monoxide by the norbornenone compounds of the present invention is in a range that is aligned to physiological pH, meaning that the norbornenone compounds are particularly well suited to biological applications. For example, in the prevention of ischaemic injury in a subject, or in perfusion formulations for use during storage or transport of cells, tissues or organs undergoing transplantation.

The norbornenone compounds disclosed herein have been developed to contain a group that can undergo an elimination reaction in various biological or physiological environments, for example at about pH>7, to form unstable norbornadienone intermediates that are capable of spontaneously releasing carbon monoxide, as shown in Scheme 1 below. The elimination of HX, for example, would be facilitated when the substituent of group $A^1$ is electron withdrawing, facilitating an $E1_{CB}$ process. Advantageously, the norbornenone compounds are stable in solid form at room temperature and also to light for over a year. The norbornenone compounds, at least according to some embodiments as disclosed herein, are also stable as solutions where the pH<7. According to at least some embodiments described herein, the norbornenone compounds may also provide low toxicity and suitable water solubilities.

Scheme 1: General strategy to develop bridged carbonyl compounds as CO donor molecules.

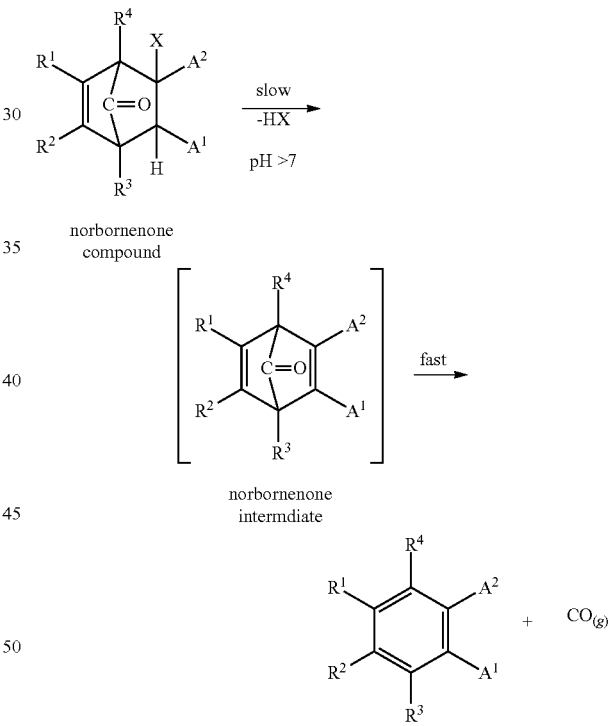

Specific Terms

The terms "carbocyclic" and "carbocyclyl" represent a monocyclic or polycyclic ring system wherein the ring atoms are all carbon atoms, e.g., of about 3 to about 20 carbon atoms, and which may be aromatic, non-aromatic, saturated, or unsaturated, and may be substituted and/or carry fused rings. Examples of such groups include benzene, cyclopentyl, cyclohexyl, or fully or partially hydrogenated phenyl, naphthyl and fluorenyl. It will be appreciated that the polycyclic ring system includes bicyclic and tricyclic ring systems.

"Heterocyclic" or "heterocyclyl" whether used alone, or in compound words such as heterocyclyloxy, represents a monocyclic or polycyclic ring system wherein the ring atoms are provided by at least two different elements, typically a combination of carbon and one or more of nitrogen, sulphur and oxygen, although may include other elements for ring atoms such as selenium, boron, phosphorus, bismuth and silicon, and wherein the ring system is about 3 to about 20 atoms, and which may be aromatic such as a "hetaryl" group, non-aromatic, saturated, or unsaturated, and may be substituted and/or carry fused rings. For example, the heterocyclyl may be (i) an optionally substituted cycloalkyl or cycloalkenyl group, e.g., of about 3 to about 20 ring members, which may contain one or more heteroatoms such as nitrogen, oxygen, or sulfur (examples include pyrrolidinyl, morpholino, thiomorpholino, or fully or partially hydrogenated thienyl, furyl, pyrrolyl, thiazolyl, oxazolyl, oxazinyl, thiazinyl, pyridyl and azepinyl); (ii) an optionally substituted partially saturated monocyclic or polycyclic ring system in which an aryl (or heteroaryl) ring and a heterocyclic group are fused together to form a cyclic structure (examples include chromanyl, dihydrobenzofuryl and indolinyl); or (iii) an optionally substituted fully or partially saturated polycyclic fused ring system that has one or more bridges (examples include quinuclidinyl and dihydro-1,4-epoxynaphthyl). It will be appreciated that the polycyclic ring system includes bicyclic and tricyclic ring systems.

As will be understood, an "aromatic" group means a cyclic group having 4m+2π electrons, where m is an integer equal to or greater than 1. As used herein, "aromatic" is used interchangeably with "aryl" to refer to an aromatic group, regardless of the valency of aromatic group.

"Aryl" whether used alone, or in compound words such as arylalkyl, aryloxy or arylthio, represents: (i) an optionally substituted mono- or polycyclic aromatic carbocyclic moiety, e.g., of about 6 to about 20 carbon atoms, such as phenyl, naphthyl or fluorenyl; or, (ii) an optionally substituted partially saturated polycyclic carbocyclic aromatic ring system in which an aryl and a cycloalkyl or cycloalkenyl group are fused together to form a cyclic structure such as a tetrahydronaphthyl, indenyl, indanyl or fluorene ring. It will be appreciated that the polycyclic ring system includes bicyclic and tricyclic ring systems.

A "hetaryl", "heteroaryl" or heteroaromatic group, is an aromatic group or ring containing one or more heteroatoms, such as N, O, S, Se, Si or P. As used herein, "heteroaromatic" is used interchangeably with "hetaryl" or "heteroaryl", and a heteroaryl group refers to monovalent aromatic groups, bivalent aromatic groups and higher multivalency aromatic groups containing one or more heteroatoms. For example, "heteroaryl" whether used alone, or in compound words such as heteroaryloxy represents: (i) an optionally substituted mono- or polycyclic aromatic organic moiety, e.g., of about 5 to about 20 ring members in which one or more of the ring members is/are element(s) other than carbon, for example nitrogen, oxygen, sulfur or silicon; the heteroatom(s) interrupting a carbocyclic ring structure and having a sufficient number of delocalized π electrons to provide aromatic character, provided that the rings do not contain adjacent oxygen and/or sulfur atoms. Typical 6-membered heteroaryl groups are pyrazinyl, pyridazinyl, pyrazolyl, pyridyl and pyrimidinyl. All regioisomers are contemplated, e.g., 2-pyridyl, 3-pyridyl and 4-pyridyl. Typical 5-membered heteroaryl rings are furyl, imidazolyl, oxazolyl, isoxazolyl, isothiazolyl, oxadiazolyl, pyrrolyl, 1,3,4-thiadiazolyl, thiazolyl, thienyl, triazolyl, and silole. All regioisomers are contemplated, e.g., 2-thienyl and 3-thienyl. Bicyclic groups typically are benzo-fused ring systems derived from the heteroaryl groups named above, e.g., benzofuryl, benzimidazolyl, benzothiazolyl, indolyl, indolizinyl, isoquinolyl, quinazolinyl, quinolyl and benzothienyl; or, (ii) an optionally substituted partially saturated polycyclic heteroaryl ring system in which a heteroaryl and a cycloalkyl or cycloalkenyl group are fused together to form a cyclic structure such as a tetrahydroquinolyl or pyrindinyl ring. It will be appreciated that the polycyclic ring system includes bicyclic and tricyclic ring systems.

The term "optionally fused" means that a group is either fused by another ring system or unfused, and "fused" refers to one or more rings that share at least two common ring atoms with one or more other rings. Fusing may be provided by one or more carbocyclic, heterocyclic, aryl or heteroaryl rings, as defined herein, or be provided by substituents of rings being joined together to form a further ring system. The fused ring may be a 5, 6 or 7 membered ring of between 5 and 10 ring atoms in size. The fused ring may be fused to one or more other rings, and may for example contain 1 to 4 rings.

The term "optionally substituted" means that a functional group is either substituted or unsubstituted, at any available position. Substitution can be with one or more functional groups selected from, e.g., alkyl, alkenyl, alkynyl, cycloalkyl, cycloalkenyl, aryl, heterocyclyl, heteroaryl, formyl, alkanoyl, cycloalkanoyl, aroyl, heteroaroyl, carboxyl, alkoxycarbonyl, cycloalkyloxycarbonyl, aryloxycarbonyl, heterocyclyloxycarbonyl, heteroaryloxycarbonyl, alkylaminocarbonyl, cycloalkylaminocarbonyl, arylaminocarbonyl, heterocyclylaminocarbonyl, heteroarylaminocarbonyl, cyano, alkoxy, cycloalkoxy, aryloxy, heterocyclyloxy, heteroaryloxy, alkanoate, cycloalkanoate, aryloate, heterocyclyloate, heteroaryloate, alkylcarbonylamino, cycloalkylcarbonylamino, arylcarbonylamino, heterocyclylcarbonylamino, heteroarylcarbonylamino, nitro, alkylthio, cycloalkylthio, arylthio, heterocyclylthio, heteroarylthio, alkylsulfonyl, cycloalkylsulfonyl, arylsulfonyl, heterocyclylsulfonyl, heteroarylsulfonyl, hydroxyl, halo, haloalkyl, haloaryl, haloheterocyclyl, haloheteroaryl, haloalkoxy, haloalkylsulfonyl, silylalkyl, alkenylsilylalkyl, and alkynylsilylalkyl. It will be appreciated that other groups not specifically described may also be used.

The term "halo" or "halogen" whether employed alone or in compound words such as haloalkyl, haloalkoxy or haloalkylsulfonyl, represents fluorine, chlorine, bromine or iodine. Further, when used in compound words such as haloalkyl, haloalkoxy or haloalkylsulfonyl, the alkyl may be partially halogenated or fully substituted with halogen atoms which may be independently the same or different. Examples of haloalkyl include, without limitation, —$CH_2CH_2F$, —$CF_2CF_3$ and —$CH_2CHFCl$. Examples of haloalkoxy include, without limitation, —$OCHF_2$, —$OCF_3$, —$OCH_2CCl_3$, —$OCH_2CF_3$ and -$OCH_2CH_2CF_3$. Examples of haloalkylsulfonyl include, without limitation, —$SO_2CF_3$, —$SO_2CO_3$, —$SO_2CH_2CF_3$ and —$SO_2CF_2CF_3$.

"Alkyl" whether used alone, or in compound words such as alkoxy, alkylthio, alkylamino, dialkylamino or haloalkyl, represents straight or branched chain hydrocarbons ranging in size from one to about 20 carbon atoms, or more. Thus alkyl moieties include, unless explicitly limited to smaller groups, moieties ranging in size, for example, from one to about 6 carbon atoms or greater, such as, methyl, ethyl, n-propyl, iso-propyl and/or butyl, pentyl, hexyl, and higher isomers, including, e.g., those straight or branched chain hydrocarbons ranging in size from about 6 to about 20 carbon atoms, or greater.

"Alkenyl" whether used alone, or in compound words such as alkenyloxy or haloalkenyl, represents straight or branched chain hydrocarbons containing at least one carbon-carbon double bond, including, unless explicitly limited to smaller groups, moieties ranging in size from two to about 6 carbon atoms or greater, such as, methylene, ethylene, 1-propenyl, 2-propenyl, and/or butenyl, pentenyl, hexenyl, and higher isomers, including, e.g., those straight or branched chain hydrocarbons ranging in size, for example, from about 6 to about 20 carbon atoms, or greater.

"Alkynyl" whether used alone, or in compound words such as alkynyloxy, represents straight or branched chain hydrocarbons containing at least one carbon-carbon triple bond, including, unless explicitly limited to smaller groups, moieties ranging in size from, e.g., two to about 6 carbon atoms or greater, such as, ethynyl, 1-propynyl, 2-propynyl, and/or butynyl, pentynyl, hexynyl, and higher isomers, including, e.g., those straight or branched chain hydrocarbons ranging in size from, e.g., about 6 to about 20 carbon atoms, or greater.

"Cycloalkyl" represents a mono- or polycarbocyclic ring system of varying sizes, e.g., from about 3 to about 20 carbon atoms, e.g., cyclopropyl, cyclobutyl, cyclopentyl, cyclohexyl or cycloheptyl. The term cycloalkyloxy represents the same groups linked through an oxygen atom such as cyclopentyloxy and cyclohexyloxy. The term cycloalkylthio represents the same groups linked through a sulfur atom such as cyclopentylthio and cyclohexylthio.

"Cycloalkenyl" represents a non-aromatic mono- or polycarbocyclic ring system, e.g., of about 3 to about 20 carbon atoms containing at least one carbon-carbon double bond, e.g., cyclopentenyl, cyclohexenyl or cycloheptenyl. The term "cycloalkenyloxy" represents the same groups linked through an oxygen atom such as cyclopentenyloxy and cyclohexenyloxy. The term "cycloalkenylthio" represents the same groups linked through a sulfur atom such as cyclopentenylthio and cyclohexenylthio.

"Cycloalkynyl" represents a non-aromatic mono- or polycarbocyclic ring system, e.g., of about 3 to about 20 carbon atoms containing at least one carbon-carbon double bond, e.g., cyclopentenyl, cyclohexenyl or cycloheptenyl. The term "cycloalkenyloxy" represents the same groups linked through an oxygen atom such as cyclopentenyloxy and cyclohexenyloxy. The term "cycloalkenylthio" represents the same groups linked through a sulfur atom such as cyclopentenylthio and cyclohexenylthio.

"Formyl" represents a —CHO moiety.

"Alkanoyl" represents a —C(=O)-alkyl group in which the alkyl group is as defined supra. In a particular embodiment, an alkanoyl ranges in size from about $C_2$-$C_{20}$. One example is acyl.

"Aroyl" represents a —C(=O)-aryl group in which the aryl group is as defined supra. In a particular embodiment, an aroyl ranges in size from about $C_7$-$C_{20}$. Examples include benzoyl and 1-naphthoyl and 2-naphthoyl.

"Heterocycloyl" represents a —C(=O)-heterocyclyl group in which the heterolicyc group is as defined supra. In a particular embodiment, an heterocycloyl ranges in size from about $C_4$-$C_{20}$.

"Heteroaroyl" represents a —C(=O)-heteroaryl group in which the heteroaryl group is as defined supra. In a particular embodiment, a heteroaroyl ranges in size from about $C_6$-$C_{20}$. An example is pyridylcarbonyl.

"Carboxyl" represents a —$CO_2$H moiety.

"Oxycarbonyl" represents a carboxylic acid ester group —$CO_2$R which is linked to the rest of the molecule through a carbon atom.

"Alkoxycarbonyl" represents an —$CO_2$-alkyl group in which the alkyl group is as defined supra. In a particular embodiment, an alkoxycarbonyl ranges in size from about $C_2$-$C_{20}$. Examples include methoxycarbonyl and ethoxycarbonyl.

"Aryloxycarbonyl" represents an —$CO_2$-aryl group in which the aryl group is as defined supra. Examples include phenoxycarbonyl and naphthoxycarbonyl.

"Heterocyclyloxycarbonyl" represents a —$CO_2$-heterocyclyl group in which the heterocyclic group is as defined supra.

"Heteroaryloxycarbonyl" represents a —CO-heteroaryl group in which the heteroaryl group is as defined supra.

"Aminocarbonyl" represents a carboxylic acid amide group —C(=O)NHR or —C(=O)$NR_2$ which is linked to the rest of the molecule through a carbon atom.

"Alkylaminocarbonyl" represents a —C(=O)NHR or —C(=O)$NR_2$ group in which R is an alkyl group as defined supra.

"Arylaminocarbonyl" represents a —C(=O)NHR or —C(=O)$NR_2$ group in which R is an aryl group as defined supra.

"Heterocyclylaminocarbonyl" represents a —C(=O)NHR or —C(=O)$NR_2$ group in which R is a heterocyclic group as defined supra. In certain embodiments, $NR_2$ is a heterocyclic ring, which is optionally substituted.

"Heteroarylaminocarbonyl" represents a —C(=O)NHR or —C(=O)$NR_2$ group in which R is a heteroaryl group as defined supra. In certain embodiments, $NR_2$ is a heteroaryl ring, which is optionally substituted.

"Cyano" represents a —CN moiety.

"Hydroxyl" represents a OH moiety.

"Alkoxy" represents an —O-alkyl group in which the alkyl group is as defined supra. Examples include methoxy, ethoxy, n-propoxy, iso-propoxy, and the different butoxy, pentoxy, hexyloxy and higher isomers.

"Aryloxy" represents an —O-aryl group in which the aryl group is as defined supra. Examples include, without limitation, phenoxy and naphthoxy.

"Alkenyloxy" represents an —O-alkenyl group in which the alkenyl group is as defined supra. An example is allyloxy.

"Heterocyclyloxy" represents an —O-heterocyclyl group in which the heterocyclic group is as defined supra.

"Heteroaryloxy" represents an —O-heteroaryl group in which the heteroaryl group is as defined supra. An example is pyridyloxy.

"Alkanoate" represents an —OC(=O)—R group in which R is an alkyl group as defined supra.

"Aryloate" represents a —OC(=O)—R group in which R is an aryl group as defined supra.

"Heterocycloate" represents an —OC(=O)—R group in which R is a heterocyclic group as defined supra.

"Heteroaryloate" represents an —OC(=O)—R group in which P is a heteroaryl group as defined supra.

"Amino" represents an —$NH_2$ moiety.

"Alkylamino" represents an —NHR or —$NR_2$ group in which R is an alkyl group as defined supra. Examples include, without limitation, methylamino, ethylamino, n-propylamino, isopropylamino, and the different butylamino, pentylamino, hexylamino and higher isomers.

"Arylamino" represents an —NHR or —$NR_2$ group in which R is an aryl group as defined supra. An example is phenylamino. "Heterocyclylamino" represents an —NHR or —$NR_2$ group in which R is a heterocyclic group as defined supra. In certain embodiments, $NR_2$ is a heterocyclic ring, which is optionally substituted.

"Heteroarylamino" represents a —NHR or —NR₂ group in which R is a heteroaryl group as defined supra. In certain embodiments, NR₂ is a heteroaryl ring, which is optionally substituted.

"Carbonylamino" represents a carboxylic acid amide group —NHC(=O)R that is linked to the rest of the molecule through a nitrogen atom.

"Alkylcarbonylamino" represents a —NHC(=O)R group in which R is an alkyl group as defined supra.

"Arylcarbonylamino" represents an —NHC(=O)R group in which R is an aryl group as defined supra.

"Heterocyclylcarbonylamino" represents an —NHC(=O)R group in which R is a heterocyclic group as defined supra.

"Heteroarylcarbonylamino" represents an —NHC(=O)R group in which R is a heteroaryl group as defined supra.

"Nitro" represents a —NO₂ moiety.

"Alkylthio" represents an —S-alkyl group in which the alkyl group is as defined supra. Examples include, without limitation, methylthio, ethylthio, n-propylthio, iso propylthio, and the different butylthio, pentylthio, hexylthio and higher isomers.

"Arylthio" represents an —S-aryl group in which the aryl group is as defined supra. Examples include phenylthio and naphthylthio.

"Heterocyclylthio" represents an —S-heterocyclyl group in which the heterocyclic group is as defined supra.

"Heteroarylthio" represents an —S-heteroaryl group in which the heteroaryl group is as defined supra.

"Sulfonyl" represents an —SO₂R group that is linked to the rest of the molecule through a sulfur atom.

"Alkylsulfonyl" represents an —SO₂-alkyl group in which the alkyl group is as defined supra.

"Arylsulfonyl" represents an —SO₂-aryl group in which the aryl group is as defined supra.

"Heterocyclylsulfonyl" represents an —SO₂-heterocyclyl group in which the heterocyclic group is as defined supra.

"Heteoarylsulfonyl" presents an —SO₂-heteroaryl group in which the heteroaryl group is as defined supra.

"Aldehyde" represents a —C(=O)H group.

"Alkanal" represents an alkyl-(C=O)H group in which the alkyl group is as defined supra.

"Alkylsilyl" presents an alkyl group that is linked to the rest of the molecule through the silicon atom, which may be substituted with up to three independently selected alkyl groups in which each alkyl group is as defined supra.

"Alkenylsilyl" presents an alkenyl group that is linked to the rest of the molecule through the silicon atom, which may be substituted with up to three independently selected alkenyl groups in which each alkenyl group is as defined supra.

"Alkynylsilyl" presents an alkynyl group that is linked to the rest of the molecule through the silicon atom, which may be substituted with up to three independently selected alkynyl groups in which each alkenyl group is as defined supra.

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —C₁-C₈ alkyl, —O—(C₁-C₈ alkyl), -aryl, —C(O)R', —OC(O)R', —C(O)OR', —C(O)NH₂, —C(O)NHR', —C(O)N(R')₂—NHC(O)R', —S(O)₂R', —S(O)R', —OH, —halogen, —N₃, —NH₂, —NH(R'), —N(R')₂ and —CN; wherein each R' is independently selected from H, —C₁-C₈ alkyl and aryl.

The term "C₁-₁₀alkyl" as used herein refers to a straight chain or branched, saturated or unsaturated hydrocarbon having from 1 to 10 carbon atoms. Representative "C₁-₁₀alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched C₁-C₈ alkyls include, but are not limited to, -isopropyl, -sec-butyl, -isobutyl, -tert-butyl, -isopentyl, 2-methylbutyl, unsaturated C₁-C₈ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl, methyl, ethyl, propyl, isopropyl, n-butyl, isobutyl, sec-butyl, tert-butyl, n-pentyl, isopentyl, neopentyl, n-hexyl, isohexyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A C₁-C₈ alkyl group can be unsubstituted or substituted with one or more groups including, but not limited to, —C₁-C₈ alkyl, —O—(C₁-C₈ alkyl), -aryl, —C(O)R', —OC(O)R', —C(O)OR', —C(O)NH₂, —C(O)NHR', —C(O)N(R')₂—NHC(O)R', —SO₃R', —S(O)₂R', —S(O)R', —OH, -halogen, —N₃, —NH₂, —NH(R'), —N(R')₂ and —CN; where each R' is independently selected from H, —C₁-C₈alkyl and aryl.

A "C₃-₁₂carbocyclyl" is a 3-, 4-, 5-, 6-, 7- or 8-membered saturated or unsaturated non-aromatic carbocyclic ring. Representative C₃-₁₂carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A C₃-C₈ carbocycle group can be unsubstituted or substituted with one or more groups including, but not limited to, —C₁-₁₂alkyl, —O—(C₁-₁₂alkyl), -aryl, —C(O)R', —OC(O)R', —C(O)OR', —C(O)NH₂, —C(O)NHR', —C(O)N(R')₂—NHC(O)R', —S(O)₂R', —S(O)R', —OH, -halogen, —N₃, —NH₂, —NH(R'), —N(R')₂ and —CN; where each R' is independently selected from H, —C₁-₁₂alkyl and aryl.

A "C₃-₁₂ carbocyclo" refers to a C₃-C₈ carbocycle group defined above wherein one of the carbocycle groups' hydrogen atoms is replaced with a bond.

A "C₁-₁₀alkylene" is a straight chain, saturated hydrocarbon group of the formula (CH₂)₁-₁₀—. Examples of a C₁-C₁₀ alkylene include methylene, ethylene, propylene, butylene, pentylene, hexylene, heptylene, ocytylene, nonylene and decalene.

An "arylene" is an aryl group which has two covalent bonds and can be in the ortho, meta, or para configurations as shown in the following structures:

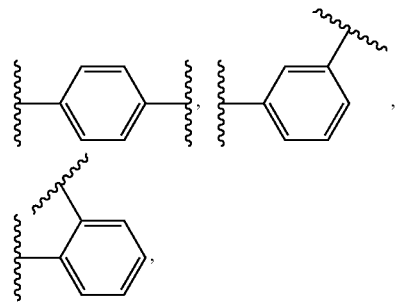

in which the phenyl group can be unsubstituted or substituted with up to four groups including, but not limited to, —$C_1$-$C_8$ alkyl, —O($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$alkyl and aryl.

A "$C_{3-12}$heterocyclyl" refers to an aromatic or non-aromatic $C_{3-12}$carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_{12}$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$alkyl and aryl.

"$C_{3-12}$heterocyclo" refers to a $C_{3-12}$heterocycle group defined above wherein one of the heterocycle group's hydrogen atoms is replaced with a bond. A $C_3$-$C_{12}$ heterocyclo can be unsubstituted or substituted with up to six groups including, but not limited to, —$C_1$-$C_{12}$alkyl, —O—($C_1$-$C_{12}$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_{12}$alkyl and aryl.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—CH$_2$C≡C—), and 4-pentynyl (—CH$_2$CH$_2$CH$_2$C≡CH—).

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or sp$^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g., the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl", "substituted aryl", and "substituted arylalkyl" mean alkyl, aryl, and arylalkyl respectively, in which one or more hydrogen atoms are each independently replaced with a substituent. Typical substituents include, but are not limited to, —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$^-_3$, —PO$_3$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, —C(=NR)NR$_2$, where each X is independently a halogen: F, Cl, Br, or I; and each R is independently —H, $C_2$-$C_{20}$ alkyl, $C_6$-$C_{20}$ aryl, $C_3$-$C_{14}$ heterocycle, protecting group or prodrug moiety. Alkylene, alkenylene, and alkynylene groups as described above may also be similarly substituted.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, B-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Linker", "Linker Unit", or "link" means a chemical moiety comprising a covalent bond or a chain of atoms that covalently attaches an antibody to a drug moiety. In various embodiments, a linker may be specified as LU. Linkers include a divalent radical such as an alkyldiyl, an aryldiyl, a heteroaryldiyl, moieties such as: —$(CR_2)_nO(CR_2)_n$—, repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

"Polyethylene glycol" or "PEG" refers to oligomers and polymers of ethylene glycol (O—$(CH_2CH_2O)_n$R where n is typically in the range of 1 to 200 and R=H or $CH_3$. In an embodiment, the repeating units defined by n may be any number or range of numbers between 1 and 200, for example about 2 to about 50, or about 3 to about 30. PEG may have an average molecular weight between 300 and 60,000 Daltons. In an embodiment, PEG as disclosed herein may have an average molecular weight between about 180 and 10,000 Daltons, for example between about 300 and 5,000 Daltons. It will be appreciated that "PEG" is also known as polyoxyethylene, polyglycol, and polyether glycol. The polymer can be homopolymer or block co-polymer, straight chain or branched, unsubstituted or substituted, typically with lower alkyl, lower hydroxy alkyl, and lower alkoxy group. In some embodiments, "PEG" is also meant to include water-soluble polyoxyethylated polyols such as polyoxyethylated sorbitol, polyoxyethylated glucose, polyoxyethylated glycerol, etc. As used herein, the term "mPEG" refers to a PEG, which is capped at one end with a methyl group. It will be appreciated that the PEG groups may also be optionally substituted as herein described.

"Saccharide" refers to a carbohydrate moiety from monosaccharides derived from D-glucose, D-galactose, D-mannose, D-ribose, D-arabinose, L-arabinose, D-xylose, D-glucuronic acid, L-guluronic acid, D-glucosamine, D-galactosamine, D-mannosamine, and to oligo- and polysaccharides made up of repeating units of monosaccharides. The saccharide can be, for example, an aldehyde-containing saccharide (glucose, mannose, arabinose, galactose, xylose); a ketone-containing saccharide (fructose, xylulose, sorbose); a saccharide alcohol (sorbitol, inositol, xylitol, mannitol); a saccharide acid (glucuronic acid, neuramiaic acid, mannuronic acid); a deoxysaccharide (deoxy-ribose, rhamnose, fructose); an aminosaccharide (glucosamine, galactosamine); or a derivatized saccharide (alkyl, alkoxyl, amino acids, thiol). Higher order saccharides being covalently linked in any of a number of ways to form different isomeric structures include for example disaccharides such as maltose, cellobiose, sucrose and lactose, trisaccharides such as raffinose, and polysaccharides such as starch, modified starch, dextran and modified dextrans. It will be appreciated that the saccharides may be optionally protected (e.g. hydroxyl groups protected with acetyl protecting groups) and/or optionally substituted as herein described.

The term "amino acid" means an L- or D-amino acid, amino acid analogue (eg. naphthylalanine) or amino acid mimetic which may be naturally occurring or of purely synthetic origin, and may be optically pure, i.e. a single enantiomer and hence chiral, or a mixture of enantiomers. Conventional 3-letter or single letter abbreviations for amino acids can be used herein. The amino acids may be optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retro-inverso peptides, thioamides, cycloalkanes or 1,5-disubstituted tetrazoles[6]. It will be appreciated that the amino acid(s) may be optionally substituted as herein described.

The term "peptide" means a compound comprising two or more amino acids, as defined below, linked by a peptide bond (ie. an amide bond linking the amine of one amino acid to the carboxyl of another). The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. The term "peptide analogue" refers to peptides comprising one or more amino acid analogues, as described herein.

General Terms

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Those skilled in the art will appreciate that the disclosure herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

Each example of the present disclosure described herein is to be applied mutatis mutandis to each and every other example unless specifically stated otherwise. The present disclosure is not to be limited in scope by the specific examples described herein, which are intended for the purpose of exemplification only. Functionally-equivalent products, compositions and methods are clearly within the scope of the disclosure as described herein.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be clearly understood that, although a number of prior art publications are referred to herein, this reference does not constitute an admission that any of these documents forms part of the common general knowledge in the art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropyl silyl ether, t-butyldimethyl silyl ether, triphenylmethyl silyl ether, acetate ester, substituted acetate esters, pivaloate, benzoate, methanesulfonate and p-toluenesulfonate.

Examples of an "amino protecting group" include, but are not limited to, 9-fluorenylmethyl carbamate (Fmoc), t-Butyl carbamate (Boc), benzyl carbamate, trifluoroacetamide, phthalimide, benzylamine, benzylideneamine, p-toluenesulfonamide, and triphenylmethylamine.

"Leaving group" refers to a functional group that can undergo an elimination reaction to form a double bond. Such leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The phrase "pharmaceutically acceptable salt" as used herein, refers to pharmaceutically acceptable organic or inorganic salts of a compound according to the present invention. The compounds contain at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" or "solvate" refer to an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and ethanolamine.

"Pharamceutically acceptable excipient" or "pharmaceutically acceptable carrier", "Biologically acceptable excipient" or "Biologically acceptable carrier" means pharmacologically or biologically inactive compounds that are added to compositions or formulations as bulking agents and as active compound stabilisers as well as facilitators of absorption. This claim can utilise a variety of established pharmaceutical and sterile biological excepients according to the delivery method and target cell, tissue or organ structure. Example of such excepients that may be utilised with these agents include chitosan for both oral and topical applications, organ storage and perfusion solutions such as: STEEN solution, Perfadex, UW solution, etc for organ or tissue preservation. Biological excepients include cell culture media such as the various modifications of Eagle's minimum essential media.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow Parker.[7, 8] Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "subject" is intented to cover mammals and includes human, and non-human mammals such as cats, dogs, horses, cows, sheep, deer, mice, rats, primates (including gorillas, rhesus monkeys and chimpanzees), possums and other domestic farm or zoo animals. Thus, inventions described herein have application to both human and non-human animals, in particular, and without limitation, humans, primates, farm animals including cattle, sheep, goats, pigs, deer, alpacas, llamas, buffalo, companion and/or pure bred animals including cats, dogs and horses. In many examples according to the present invention, "subjects"

refer to living humans who may receive or are receiving medical care or assessment for a disease or condition.

The terms "prevent", "preventing" and "prevention" in the context of the administration of a therapy to a subject refers to the prevention or inhibition of the recurrence, onset, and/or development of a cancer or a symptom thereof in a subject resulting from the administration of a therapy (e.g., a prophylactic or therapeutic agent), or a combination of therapies (e.g., a combination of prophylactic or therapeutic agents).

The terms "treat", "treatment" and "treating" in the context of the administration of a therapy to a subject refer to the reduction or inhibition of the progression and/or duration of cancer, the reduction or amelioration of the severity of cancer, and/or the amelioration of one or more symptoms thereof resulting from the administration of one or more therapies.

The term "ischaemic injury" means the deprivation of oxygen (hypoxia or anoxia) to a cell, tissue or organ resulting in cell damage and death. "Ischaemia-reperfusion injury" refers to the deprivation of oxygen to the cell, tissue or organ for a period of time prior to the subsequent restoration of oxygen supply. Depending upon the duration of the ischaemic episode, this restoration of oxygen can result in a cascade of cellular inflammatory and oxidative signalling events with catastrophic consequences to the neighbouring tissues.

Norbornenone Compounds

The norbornenone compounds of Formula 1 as described herein may be generally described by the following structure:

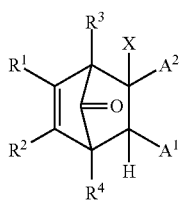

Formula 1

Substituents $R^1$, $R^2$, $R^3$, and $R^4$ $R^1$, $R^2$, $R^3$ and $R^4$, may each be independently selected from hydrogen, halo, CN, $NO_2$, $OC(O)R^5$, $C(O)R^5$, $C(O)OR^5$, $OR^5$, $OS(O)_2R^5$, $NR^5R^6$, $SR^5$, $C_{1-20}$alkyl, $C_{2-20}$alkenyl, $C_{2-20}$alkynyl, monocyclic and polycyclic carbocyclyl or heterocyclyl, polyethylene glycol, amino acid, and saccharide; wherein the $C_{1-20}$alkyl, $C_{2-20}$alkenyl, $C_{2-20}$alkynyl, are each optionally interrupted with one or more heteroatoms selected from O, N and S; and wherein the $C_{1-20}$alkyl, $C_{2-20}$alkenyl, $C_{2-20}$alkynyl, carbocycle, and heterocycle, are each optionally substituted with 1-3 substituents independently selected from halo, CN, $NO_2$, $OC(O)R^5$, $C(O)R^5$, $C(O)OR^5$, $OR^5$, $OS(O)_2R^5$, $NR^5R^6$, $SR^5$, polyethylene glycol, amino acid, and saccharide; and $R^5$ and $R^6$ may be each independently selected from hydrogen, $C_{1-10}$alkyl, and $C_{1-10}$haloalkyl; and wherein two or more of $R^1$, $R^2$, $R^3$ and $R^4$, may together form an optionally substituted monocyclic or polycyclic carbocyclyl or heterocyclyl.

The monocyclic or polycyclic carbocyclyl or heterocyclyl may be aromatic, for example may be a monocyclic or polycyclic aryl or heteroaryl. In one embodiment, the monocyclic or polycyclic carbocyclyl is phenyl, which may be optionally substituted and optionally fused.

$R^1$, $R^2$, $R^3$ and $R^4$, may be each independently selected from hydrogen, halo, $C_{1-10}$alkyl, $C_{2-10}$alkenyl, $C_{2-10}$alkynyl, monocyclic or bicyclic $C_{3-12}$carbocyclyl, and monocyclic or bicyclic $C_{3-12}$heterocyclyl, polyethylene glycol, and a mono, di or tri-saccharide; wherein the alkyl, alkenyl, alkynyl, carbocyclyl, and heterocyclyl group, are each optionally substituted with 1-3 substituents independently selected from halo, CN, $NO_2$, $OC(O)R^5$, $C(O)R^5$, $C(O)OR^5$, $OR^5$, $OS(O)_2R^5$, $NR^5R^6$, $SR^5$, polyethylene glycol, and -saccharide; and $R^5$ and $R^6$ may be each independently selected from hydrogen, $C_{1-4}$alkyl, and $C_{1-4}$haloalkyl.

$R^1$, $R^2$, $R^3$ and $R^4$, may be each independently selected from $C_{1-10}$alkyl, $C_{2-10}$alkenyl, $C_{2-10}$alkynyl, monocyclic or bicyclic $C_{3-12}$carbocyclyl, and monocyclic or bicyclic $C_{3-12}$heterocyclyl, polyethylene glycol, and a mono, di or tri-saccharide; wherein the alkyl, alkenyl, alkynyl, carbocyclyl, and heterocyclyl group, are each optionally substituted with 1-3 substituents independently selected from halo, CN, $NO_2$, $OC(O)R^5$, $C(O)R^5$, $C(O)OR^5$, $OR^5$, $OS(O)_2R^5$, $NR^5R^6$, $SR^5$, polyethylene glycol, and saccharide; and $R^5$ and $R^6$ may be each independently selected from hydrogen, $C_{1-4}$alkyl, and $C_{1-4}$haloalkyl.

$R^1$, $R^2$, $R^3$ and $R^4$, may be each independently selected from $C_{1-6}$alkyl and monocyclic aryl or hetaryl; wherein the alkyl, aryl and hetaryl group, are each optionally substituted with 1-3 substituents independently selected from halo, CN, $NO_2$, $OC(O)R^5$, $C(O)R^5$, $C(O)OR^5$, $OR^5$, $OS(O)_2R^5$, $NR^5R^6$, $SR^5$, polyethylene glycol, and saccharide; and $R^5$ and $R^6$ may be each independently selected from hydrogen, $C_{1-4}$alkyl, and $C_{1-4}$haloalkyl.

$R^1$, $R^2$, $R^3$ and $R^4$, may be each independently selected from $C_{1-6}$alkyl and phenyl, wherein each may be optionally substituted with 1-3 substituents independently selected from halo, CN, $NO_2$, $OC(O)R^5$, $C(O)R^5$, $C(O)OR^5$, $OR^5$, $OS(O)_2R^5$, $NR^5R^6$, $SR^5$, polyethylene glycol, and saccharide; and $R^5$ and $R^6$ may be each independently selected from hydrogen, $C_{1-4}$alkyl, and $C_{1-4}$haloalkyl.

$R^1$, $R^2$, $R^3$ and $R^4$, may be each independently selected from optionally substituted $C_{1-6}$alkyl and phenyl.

In one embodiment, $R^3$ and $R^4$ are selected from optionally substituted $C_{1-6}$alkyl.

It will be appreciated that any susbtituents for $R^1$, $R^2$, $R^3$, $R^4$, $R^5$ and $R^6$, may be provided by any one or more substituents listed from any of the above groups of substituents.

Leaving Group X

X is a leaving group, which can be selected to provide a leaving group that is capable of an elimination reaction under various physiological or biological environments or conditions to form, in situ, a norbornadienone compound that may spontaneously release carbon monoxide as previously described.

In an embodiment, X is selected from halo, $NO_2$, $ONO_2$, $OP(O)(OR^7)$, $OC(O)R^7$, $OS(O)_2R^7$, $OS(O)_2OR^7$, $SR^7$, $S(O)R^7$, $S(O)_2R^7$, $OR^7$, and $NR^7R^8$; and $R^7$ and $R^8$ are each independently selected from hydrogen, $C_{1-10}$alkyl, $C_{1-10}$haloalkyl, aryl, arylalkyl and arylhaloalkyl.

X may be selected from halo, $ONO_2$, $OP(O)(OR^7)$, $OC(O)R^7$, $OS(O)_2R^7$, $OS(O)_2OR^7$, $SR^7$, $S(O)R^7$, $S(O)_2R^7$, $OR^7$, and $NR^7R^8$; and $R^7$ and $R^8$ are each independently selected from hydrogen, $C_{1-10}$alkyl, $C_{1-10}$haloalkyl, aryl, arylalkyl and arylhaloalkyl.

X may be selected from halo, $S(O)_2R^7$, $OS(O)_2R^7$, and $OS(O)_2OR^7$; and $R^7$ is independently selected from hydrogen, $C_{1-10}$alkyl, $C_{1-10}$haloalkyl, aryl, arylalkyl and arylhaloalkyl.

X may be selected from iodo, bromo, chloro, $SR^7$, $S(O)R^7$, $S(O)_2R^7$, $OS(O)_2R^7$, and $OS(O)_2OR^7$; and $R^7$ is independently selected from hydrogen, $C_{1-4}$alkyl, $C_{1-4}$haloalkyl, phenyl, phenylalkyl and phenylhaloalkyl.

It will be appreciated that X, or $R^7$, $R^8$ or $R^9$, may be provided by any one or more substituents listed from any of the above groups of substituents.

Substituents $A^1$, $A^2$, $R^9$, $R^{10}$ and $R^{11}$ $A^1$ and $A^2$ may be each independently selected from hydrogen, halo, CN, $NO_2$, $S(O)R^9$, $S(O)_2R^9$, $S(O)_2OR^9$, $SR^9$, $NR^9R^{10}$, $C(=O)R^9$, $C(=S)R^9$, $C(=CR^{10}R^{11})R^9$, or $A^1$ and $A^2$ together may form an optionally substituted monocyclic or polycyclic carbocyclyl or heterocyclyl. $R^9$ may be selected from hydrogen, hydroxyl, $C_{1-20}$alkyl, $C_{1-20}$haloalkyl, aryl, arylalkyl and arylhaloalkyl. $R^{10}$ and $R^{11}$ may be each independently selected from hydrogen, $C_{1-10}$alkyl, and $C_{1-10}$haloalkyl.

$A^1$ and $A^2$ may be each independently selected from halo, CN, $NO_2$, $S(O)R^9$, $S(O)_2R^9$, $S(O)_2OR^9$, $SR^9$, $NR^9R^{10}$, $C(=O)R^9$, $C(=S)R^9$, $C(=CR^{10}R^{11})R^9$, or $A^1$ and $A^2$ together form an optionally substituted monocyclic or polycyclic carbocyclyl or heterocyclyl. $R^9$ may be selected from hydrogen, $C_{1-6}$alkyl, $C_{1-6}$haloalkyl, phenyl, phenylalkyl, phenylhaloalkyl, polyethyleneglycol and saccharide substituted variations thereof. $R^{10}$ and $R^{11}$ may be each independently selected from hydrogen, $C_{1-4}$alkyl, and $C_{1-4}$haloalkyl.

$A^1$ and $A^2$ may be each independently selected from halo, $C(=O)R^9$, $C(=O)OR^9$, $C(=O)NHR^9$, $C(=S)R^9$, $C(=CR^{10}R^{11})R^9$, or $A^1$ and $A^2$ together form an optionally substituted monocyclic carbocyclyl or heterocyclyl. $R^9$, $R^{10}$ and $R^{11}$, may be any embodiments as previously described for these substituents herein.

It will be appreciated that any susbtituents for $A^1$, $A^2$, $R^9$, $R^{10}$, and $R^{11}$, may be provided by any one or more substituents listed from any of the above groups of substituents.

Compounds of Formula 1a and Formula 1b

A compound of Formula 1 may be selected from a compound of Formula 1a or Formula 1b as described below:

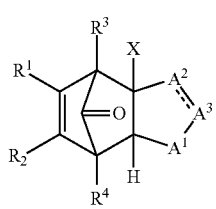

Formula 1a

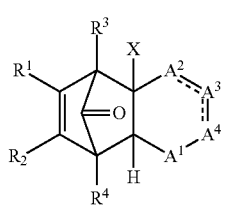

Formula 1b wherein $R^1$, $R^2$, $R^3$, $R^4$, and X, are as defined according to any one or more embodiments as described herein;

each $A^1$ is independently selected from C=O, C=S, $C=CR^{12}R^{13}$, S=O, $S(=O)_2$, S, $NR^{14}$;

each $A^2$, $A^3$ and $A^4$, are independently selected from $CR^{14}R^{15}$, $CR^{14}$, C=O, C=S, $C=CR^{12}R^{13}$, S=O, $S(=O)_2$, O, S, N, $NR^{14}$; and the dotted lines denote optional double bonds;

$R^{12}$ and $R^{13}$ are each independently selected from hydrogen, $C_{1-10}$alkyl, and $C_{1-10}$haloalkyl;

$R^{14}$ and $R^{15}$ are each independently selected from hydrogen, halo, CN, $NO_2$, $OC(O)R^5$, $C(O)R^5$, $C(O)OR^5$, $OR^5$, $OS(O)_2R^5$, $NR^5R^6$, $SR^5$, $C_{1-20}$alkyl, $C_{2-20}$alkenyl, $C_{2-20}$alkynyl, monocyclic and polycyclic carbocyclyl or heterocyclyl, polyethylene glycol, amino acid, and mono- or poly-saccharide; wherein the $C_{1-20}$alkyl, $C_{2-20}$alkenyl, $C_{2-20}$alkynyl, are each optionally interrupted with one or more heteroatoms selected from O, N and S; and wherein the $C_{1-20}$alkyl, $C_{2-20}$alkenyl, $C_{2-20}$alkynyl, carbocycle, and heterocycle, are each optionally substituted with one or more substituents independently selected from halo, CN, $NO_2$, $OC(O)R^5$, C=O, $C(O)R^5$, $C(O)OR^5$, $OR^5$, $OS(O)_2R^5$, $NR^5R^6$, $SR^5$, monocyclic and polycyclic heterocyclyl, polyethylene glycol, amino acid, and saccharide; and $R^5$ and $R^6$ are each independently selected from hydrogen, $C_{1-10}$alkyl, and $C_{1-10}$haloalkyl.

In an embodiment of Formula 1a or Formula 1b, each $A^1$ and $A^2$ may be independently selected from C=O, C=S, $C=CR^{12}R^{13}$, S=O, $S(=O)_2$, S, $NR^{14}$. In another embodiment, each $A^3$ and $A^4$ may be independently selected from $CR^{14}R^{15}$, $CR^{14}$, C=O, C=S, $C=CR^{12}R^{13}$, S=O, $S(=O)_2$, O, S, $NR^{14}$. It will be appreciated that $R^{12}$, $R^{13}$, $R^{14}$, and $R^{15}$, may be provided by any embodiment as previously described for these substituents.

In an embodiment of Formula 1a or Formula 1b, each $A^1$ may be selected from C=O. In another embodiment, each $A^1$ and $A^2$ may be C=O.

It will be appreciated that any susbtituents for $A^1$, $A^2$, $A^3$, $A^4$, $R^{12}$, $R^{13}$, $R^{14}$, and $R^{15}$, may be provided by any one or more substituents listed from any of the above groups of substituents.

Compounds of Formula 1a(i)

A compound of Formula 1 or Formula 1a may be selected from a compound of Formula 1a(i) as described below:

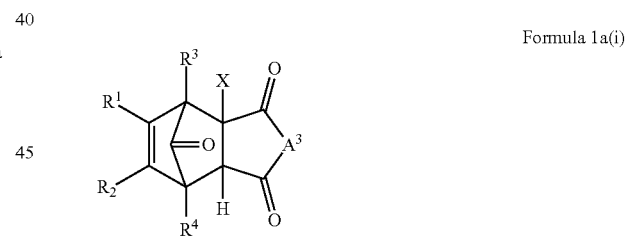

Formula 1a(i)

wherein $R^1$, $R^2$, $R^3$, $R^4$, and X, may be selected according to any one or more embodiments as described herein;

$A^3$ is selected from O, S, $CR^{14}R^{15}$ and $NR^{14}$;

$R^{14}$ and $R^{15}$ are each independently selected from hydrogen, halo, CN, $NO_2$, —$OC(O)R^5$, $C(O)R^5$, $C(O)OR^5$, $OR^5$, $OS(O)_2R^5$, $NR^5R^6$, $SR^5$, $C_{1-20}$alkyl, $C_{2-20}$alkenyl, $C_{2-20}$alkynyl, monocyclic and polycyclic carbocyclyl or heterocyclyl, polyethylene glycol, amino acid, and saccharide; wherein the $C_{1-20}$alkyl, $C_{2-20}$alkenyl, $C_{2-20}$alkynyl, are each optionally interrupted with one or more heteroatoms selected from O, N and S; and wherein the $C_{1-20}$alkyl, $C_{2-20}$alkenyl, $C_{2-20}$alkynyl, carbocycle, and heterocycle, are each optionally substituted with one or more substituents independently selected from halo, CN, $NO_2$, $OC(O)R^5$, C=O, $C(O)R^5$, $C(O)OR^5$, $OR^5$, $OS(O)_2R^5$, $NR^5R^6$, $SR^5$, monocyclic and polycyclic heterocyclyl, polyethylene glycol, amino acid, and -saccharide. $R^5$ and $R^6$ are each independently selected from hydrogen, $C_{1-10}$alkyl, and $C_{1-10}$haloalkyl.

$R^{14}$ and $R^{15}$ may be each independently be selected from $C_{1-20}$alkyl, $C_{2-20}$alkenyl, $C_{2-20}$alkynyl, monocyclic and polycyclic carbocyclyl or heterocyclyl, polyethylene glycol, amino acid, and mono- or poly-saccharide; wherein the $C_{1-20}$alkyl, $C_{2-20}$alkenyl, $C_{2-20}$alkynyl, are each optionally interrupted with one or more heteroatoms selected from O, N and S; and wherein the $C_{1-20}$alkyl, $C_{2-20}$alkenyl, $C_{2-20}$alkynyl, carbocycle, and heterocycle, are each optionally substituted with one or more substituents independently selected from halo, CN, $NO_2$, $OC(O)R^5$, $C=O$, $C(O)R^5$, $C(O)OR^5$, $OR^5$, $OS(O)_2R^5$, $NR^5R^6$, $SR^5$, monocyclic and polycyclic heterocyclyl, polyethylene glycol, amino acid, and saccharide. $R^5$ and $R^6$ may be each independently selected from hydrogen, $C_{1-10}$alkyl, and $C_{1-10}$haloalkyl.

$R^{14}$ and $R^{15}$ may be each independently selected from $C_{1-20}$alkyl, $C_{2-20}$alkenyl, $C_{2-20}$alkynyl, phenyl; wherein the $C_{1-20}$alkyl, $C_{2-20}$alkenyl, $C_{2-20}$alkynyl, are each optionally interrupted with one or more heteroatoms selected from O, N and S; and wherein the $C_{1-20}$alkyl, $C_{2-20}$alkenyl, $C_{2-20}$alkynyl, phenyl, are each optionally substituted with one to four substituents independently selected from halo, CN, $NO_2$, $OC(O)R^5$, $C=O$, $C(O)R^5$, $C(O)OR^5$, $OR^5$, $OS(O)_2 R^5$, $NR^5R^6$, $SR^5$, monocyclic and polycyclic heterocyclyl, polyethylene glycol, amino acid, and mono-, di- or tri-saccharide. $R^5$ and $R^6$ may be each independently selected from hydrogen, $C_{1-10}$alkyl, and $C_{1-10}$haloalkyl, polyethyleneglycol and saccharide substituted variations thereof.

In another example, $A^3$ is $NR^{14}$, and $R^{14}$ is selected from $C_{1-20}$alkyl, $C_{2-20}$alkenyl, $C_{2-20}$alkynyl, and phenyl; wherein the $C_{1-20}$alkyl, $C_{2-20}$alkenyl, $C_{2-20}$alkynyl, are each optionally interrupted with one to four heteroatoms selected from O, N and S, and optionally interrupted with one to four groups, in either orientation, selected from $—NR^5—$, $—NR^5—C(O)—$, $—C(O)—O—$, and $—NR^5—C(O)—O—$; and wherein the $C_{1-20}$alkyl, $C_{2-20}$alkenyl, $C_{2-20}$alkynyl, phenyl, are each optionally substituted or terminated with one to four substituents independently selected from halo, CN, $NO_2$, $OC(O)R^5$, $C=O$, $C(O)R^5$, $C(O)OR^5$, $OR^5$, $OS(O)_2R^5$, $NR^5R^6$, $SR^5$, monocyclic and polycyclic heterocyclyl, polyethylene glycol, amino acid, and saccharide; and $R^5$ and $R^6$ are each independently selected from hydrogen, $C_{1-10}$alkyl, and $C_{1-10}$haloalkyl.

Compounds of Formula 1a(ii)

A compound of Formula 1, Formula 1a or Formula 1a(i) may be selected from a compound of Formula 1a(ii) as described below:

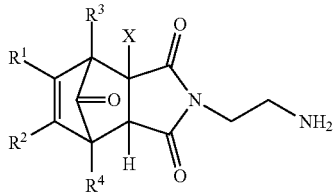

Formula 1a(ii)

wherein
$R^1$, $R^2$, $R^3$, $R^4$, and X, are each selected from one or more examples as described above or herein.

Water Solubilising Groups

The selection of any substituent group, for example groups $R^1$ to $R^6$, $R^9$, $R^{10}$, $R^{14}$ and $R^{15}$, or any substituent of those groups, may be selected to enhance the water solubility of the compounds or may be used to modify the biodistribution of the compounds. For example, the introduction of polar groups such as ether groups or charged species such as ammonium groups, as a substituent will enhance water solubility or hydrophilicity. A polyethyleneglycol (PEG) group, an amino acid group such as a peptide chain of 1 to 10 amino acid residues, saccharide group, or ammonium ion containing group, can function to modify the water solubility or pharmacokinetics of the agent or compound. In one embodiment, $R^{14}$ and $R^{15}$ of Formula 1a and 1b compounds, or substituents of those groups are selected to include water solubilising groups as described below and herein.

The water solubilising groups may be selected from polar groups, for example groups selected from $NO_2$, $OC(O)R^5$, $C(O)R^5$, $C(O)OR^5$, $OR^5$, $OS(O)_2R^5$, $NR^5R^6$, $SR^5$, monocyclic and polycyclic carbocyclyl or heterocyclyl, polyethylene glycol, amino acid, and mono- or poly-saccharide. The polar groups may be linked to the norbornenone core through a linker group such as $C_{1-20}$alkyl, $C_{2-20}$alkenyl, $C_{2-20}$alkynyl, which may each be optionally interrupted with one or more heteroatoms selected from O, N and S, ethers, esters, amines, amides, amino acids, or ammonium salts. The linker may be a monocyclic or polycyclic carbocyclyl or heterocyclyl, for example a hetaryl or aryl group. It will be appreciated that $R^5$ and $R^6$ may be each independently selected from hydrogen, $C_{1-10}$alkyl, and $C_{1-10}$haloalkyl, which may be optionally substituted. In one embodiment, the water solubilising group is an ammonium salt, for example a trifluoroacetic acid salt of a primary amine group.

In one embodiment, $R^{14}$ and $R^{15}$ are each independently selected from a $C_{1-20}$alkyl substituted with one or more groups selected from an amine, ammonium salt, amide, amino acid, ester, ether, polyethylene glycol, and saccharide. In another embodiment, $R^{14}$ and $R^{15}$ are each independently selected from a $C_{1-20}$alkyl substituted with one or more groups selected from an ammonium salt, amino acid, polyethylene glycol and saccharide.

The polyethylene glycol, which is also referred to as "PEG", is an oligomer or polymer of ethylene glycol (O—$(CH_2CH_2O)nR$ where n is typically in the range of 1 to 200 and R=H or $CH_3$. In an example, the repeating units defined by n may be any number or range of numbers between 1 and 200, for example about 2 to about 50, or about 3 to about 30. PEG may be a homopolymer or block co-polymer, straight chain or branched, unsubstituted or substituted, typically with $C_{1-10}$ alkyl, $C_{1-10}$alkylhydroxy, and $C_{1-10}$alkoxy group. PEG may be selected from water-soluble polyoxyethylated polyols such as polyoxyethylated sorbitol, polyoxyethylated glucose, polyoxyethylated glycerol, etc. PEG may be an "mPEG" group, which is a PEG group capped at one end with a methyl group. It will be appreciated that the PEG groups may also be optionally substituted as herein described.

In some embodiments, the water solubilising group may be selected from polyethers or polyols, such as polyethylene glycol (PEG) as described herein, a polyalkyloxazoline such as polyethyloxazoline (PEOX), polyvinylpyrolidone and polypropylene glycol.

The saccharide group refers to a carbohydrate moiety from monosaccharides derived from D-glucose, D-galactose, and D-mannose to oligo- and poly-saccharides made up of repeating units of monosaccharides. The saccharide can be, for example, an aldehyde-containing saccharide (glucose, mannose, arabinose, galactose, xylose); a ketone-containing saccharide (fructose, xylulose, sorbose); a saccharide alcohol (sorbitol, inositol, xylitol, mannitol); a saccharide acid (glucuronic acid, neuramiaic acid, mannuronic acid); a deoxysaccharide (deoxy-ribose, rhamnose, fructose); an aminosaccharide (glucosamine, galactosamine); or a derivatized saccharide (alkyl, alkoxyl, amino acids, thiol). Higher order saccharides being covalently linked in any of a number of ways to form different isomeric structures include for example disaccharides such as maltose, cellobiose, sucrose and lactose and trisaccharides, such as raffinose. It will be appreciated that the saccharides may be optionally protected (e.g. hydroxyl groups protected with acetyl protecting groups) and/or optionally substituted as herein described.

The amino acid may be an L- or D-amino acid, amino acid analogue (eg. naphthylalanine) or amino acid mimetic which may be naturally occurring or of purely synthetic origin, and may be optically pure, i.e. a single enantiomer and hence chiral, or a mixture of enantiomers. Conventional 3-letter or single letter abbreviations for amino acids can be used herein. It will be appreciated that the amino acid(s) may be optionally substituted as herein described.

It will be appreciated that the peptide group refers to a compound comprising two or more amino acids, as defined below, linked by a peptide bond (ie. an amide bond linking the amine of one amino acid to the carboxyl of another). The peptide may be a peptide mimetic, which refers to biologically active compounds that mimic the biological activity of a peptide or a protein but are no longer peptidic in chemical nature, that is, they no longer contain any peptide bonds (that is, amide bonds between amino acids).

The norbornenone compounds described herein may include salts, solvates, hydrates, isomers, tautomers, racemates, stereoisomers, enantiomers or diastereoisomers of those complexes. Asymmetric centers may exist in the complexes disclosed herein. These centers can be designated by the symbols "R" or "S," depending on the configuration of substituents around the chiral carbon atom. It should be understood that the present disclosure encompasses all stereochemical isomeric forms, including diastereomeric, enantiomeric, and epimeric forms, as well as D-isomers and L-isomers, and mixtures thereof. Additionally, the complexes disclosed herein may exist as geometric isomers. The present invention includes all cis, trans, syn (e.g. endo), anti (e.g. exo), entgegen (E), and zusammen (Z) isomers as well as the appropriate mixtures thereof. Additionally, complexes may exist as tautomers; all tautomeric isomers are provided by this invention.

It will also be appreciated that the compounds may comprise groups that have been suitably protected, for example amine groups that have been protected by using BOC groups. Suitable protecting groups, methods for their introduction and removal are described in Protective Groups in Organic Chemistry[9].

Where the norbornenone compound has a net overall charge, for example where there is a substituent such as an amino group, the norbornenone compound may be present in the form of a salt. In principle the counterion may be any organic or inorganic moiety that stabilizes the charge on the norbornenone compound.

Additionally, the norbornenone compounds disclosed herein may exist in unsolvated as well as solvated forms. Polymorphic forms of the complexes are also encompassed.

Example Compounds of Formulae 1, 1a, 1b, 1a(i) and 1a(ii)

Norbornenone compounds of Formulae 1, 1a, 1b, 1a(i) and 1a(ii), as exemplified in the present disclosure include the following compounds:

Norbornenone Compounds of Formula 1

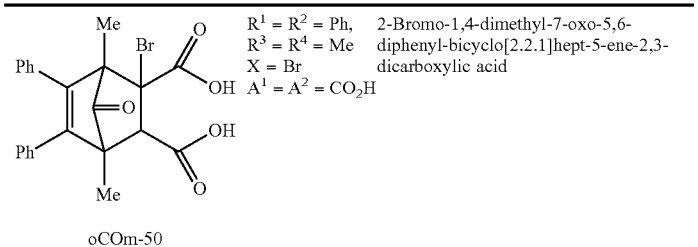

oCOm-50

$R^1 = R^2 = Ph$, $R^3 = R^4 = Me$, $X = Br$, $A^1 = A^2 = CO_2H$

2-Bromo-1,4-dimethyl-7-oxo-5,6-diphenyl-bicyclo[2.2.1]hept-5-ene-2,3-dicarboxylic acid Norbornenone Compounds of Formula 1a(i)

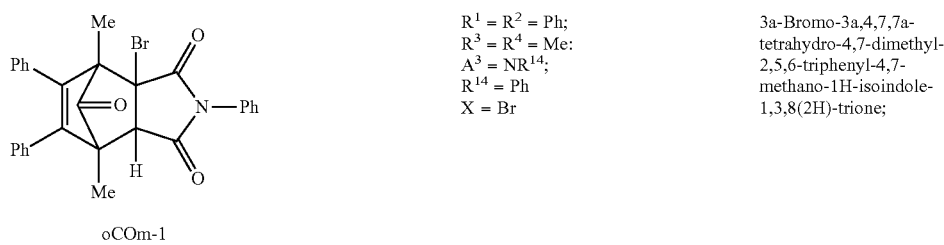

oCOm-1

$R^1 = R^2 = Ph$; $R^3 = R^4 = Me$; $A^3 = NR^{14}$; $R^{14} = Ph$; $X = Br$

3a-Bromo-3a,4,7,7a-tetrahydro-4,7-dimethyl-2,5,6-triphenyl-4,7-methano-1H-isoindole-1,3,8(2H)-trione;

-continued

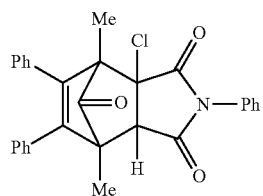

oCOm-2

$R^1 = R^2 = $ Ph;
$R^3 = R^4 = $ Me;
$A^3 = NR^{14}$;
$R^{14} = $ Ph
X = Cl

3a-Chloro-3a,4,7,7a-tetrahydro-4,7-dimethyl-2,5,6-triphenyl-4,7-methano-1H-isoindole-1,3,8(2H)-trione

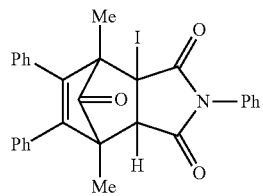

oCOm-3

$R^1 = R^2 = $ Ph;
$R^3 = R^4 = $ Me;
$A^3 = NR^{14}$;
$R^{14} = $ Ph
X = I

3a-Iodo-3a,4,7,7a-tetrahydro-4,7-dimethyl-2,5,6-triphenyl-4,7-methano-1H-isoindole-1,3,8(2H)-trione

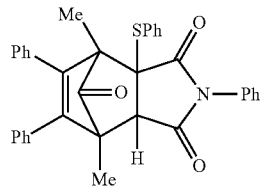

oCOm-4

$R^1 = R^2 = $ Ph;
$R^3 = R^4 = $ Me;
$A^3 = NR^{14}$;
$NR^{14} = $ Ph
X = SPh

3a-Phenylthio-3a,4,7,7a-tetrahydro-4,7-dimethyl-2,5,6-triphenyl-4,7-methano-1H-isoindole-1,3,8(2H)-trione

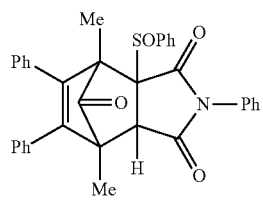

oCOm-5

$R^1 = R^2 = $ Ph;
$R^3 = R^4 = $ Me;
$A^3 = NR^{14}$;
$R^{14} = $ Ph
X = SOPh

3a-Phenylsulfinyl-3a,4,7,7a-tetrahydro-4,7-dimethyl-2,5,6-triphenyl-4,7-methano-1H-isoindole-1,3,8(2H)-trione

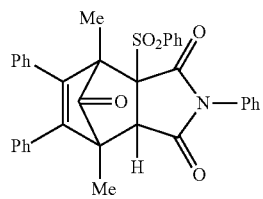

oCOm-6

$R^1 = R^2 = $ Ph;
$R^3 = R^4 = $ Me;
$A^3 = NR^{14}$;
$R^{14} = $ Ph
X = SO$_2$Ph

3a-Phenylsulfonyl-3a,4,7,7a-tetrahydro-4,7-dimethyl-2,5,6-triphenyl-4,7-methano-1H-isoindole-1,3,8(2H)-trione

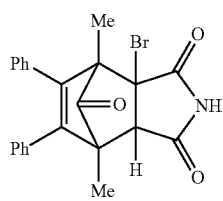

oCOm-7

$R^1 = R^2 = $ Ph;
$R^3 = R^4 = $ Me;
$A^3 = NR^{14}$;
$R^{14} = $ H
X = Br

3a-Bromo-4,7-dimethyl-5,6-diphenyl-3a,4,7,7a-tetrahydro-1H-4,7-methanoisoindole-1,3,8(2H)-trione -continued

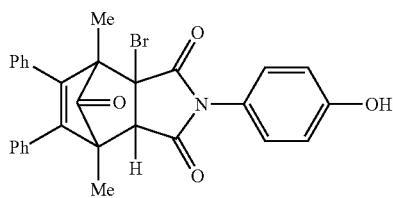

oCOM-8

$R^1 = R^2 = Ph$;
$R^3 = R^4 = Me$;
$A^3 = NR^{14}$;
$R^{14} = pC_6H_4OH$
$X = Br$

3a-Bromo-3a,4,7,7a-tetrahydro-4,7-dimethyl-2-(4-hydroxyphenyl)-5,6-diphenyl-4,7-methano-1H-isoindole-1,3,8(2H)-trione

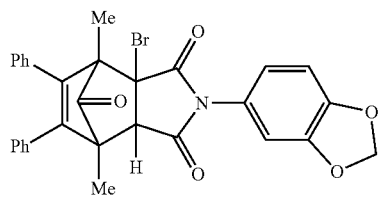

oCOm-9

$R^1 = R^2 = Ph$;
$R^3 = R^4 = Me$:
$A^3 = NR^{14}$;
$R^{14} = 3,4\text{-}C_6H_3(OCH_2O)$
$X = Br$ 3a-Bromo-3a,4,7,7a-tetrahydro-4,7-dimethyl-5,6-diphenyl-2-tri-(3,4-methylenedioxyphenyl)-4,7-methano-1H-isoindole-1,3,8(2H)-trione

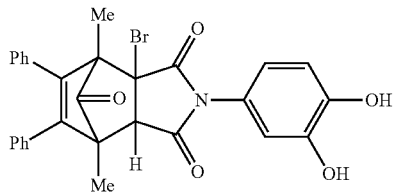

oCOm-10

$R^1 = R^2 = Ph$;
$R^3 = R^4 = Me$:
$A^3 = NR^{14}$;
$R^{14} = 3,4\text{-}C_6H_3(OH)_2$
$X = Br$ 3a-Bromo-3a,4,7,7a-tetrahydro-4,7-dimethyl-2-(3,4-dihydroxyphenyl)-5,6-diphenyl-4,7-methano-1H-isoindole-1,3,8(2H)-trione

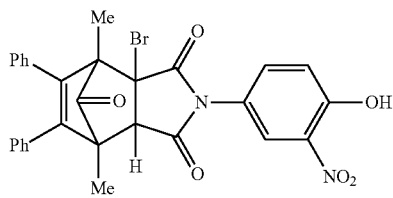

oCOm-11

$R^1 = R^2 = Ph$;
$R^3 = R^4 = Me$:
$A^3 = NR^{14}$;
$R^{14} = C_6H_3\text{-}3\text{-}(NO_2)\text{-}4\text{-}(OH)$
$X = Br$ 3a-Bromo-3a,4,7,7a-tetrahydro-4,7-dimethyl-2-(4-hydroxy-3-nitrophenyl)-5,6-diphenyl-4,7-methano-1H-isoindole-1,3,8(2H)-trione

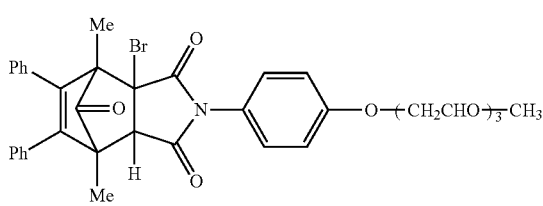

oCOm-12

$R^1 = R^2 = Ph$;
$R^3 = R^4 = Me$:
$A^3 = NR^{14}$;
$R^{14} = p\text{-}C_6H_4O(CH_2CH_2O)_3CH_3$
$X = Br$ 3a-Bromo-3a,4,7,7a-tetrahydro-4,7-dimethyl-2-(4-(2-(2-(2-methoxyethoxy)ethoxy)ethoxy)phenyl)-5,6-diphenyl-4,7-methano-1H-isoindole-1,3,8(2H)-trione -continued

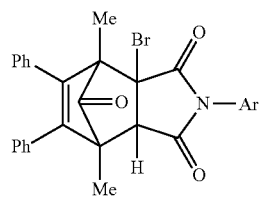

oCOm-13

$R^1 = R^2 = Ph$;
$R^3 = R^4 = Me$;
$A^3 = NR^{14}$;
$R^{14} = p\text{-}C_6H_4O(CH_2CH_2O)_nCH_3$
$X = Br$ 3a-Bromo-3a,4,7,7a-tetrahydro-4,7-dimethyl-2-(4-(2-methoxy(2-polyethoxy)phenyl)-5,6-diphenyl-4,7-methano-1H-isoindole-1,3,8(2H)-trione

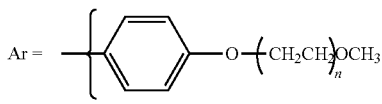

average for n = 16

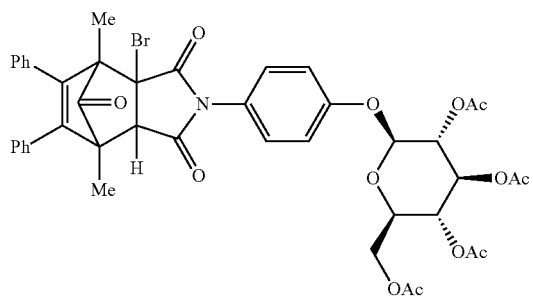

oCOm-14

$R^1 = R^2 = Ph$;
$R^3 = R^4 = Me$;
$A^3 = NR^{14}$;
$R^{14} = pC_6H_4O\text{-}\beta\text{-}D\text{-}Glc(OAc)_4$
$X = Br$ 3a-Bromo-3a,4,7,7a-tetrahydro-4,7-dimethyl-2-(4-(2,3,4,6-tetra-O-acetyl-β-D-glucopyranosyloxy)phenyl)-5,6-diphenyl-4,7-methano-1H-isoindole-1,3,8(2H)-trione

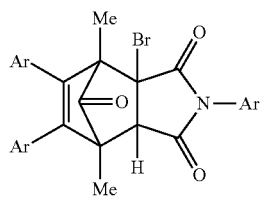

oCOm-15

$R^1 = R^2 = p\text{-}C_6H_4O(CH_2CH_2O)_3OCH_3$;
$R^3 = R^4 = Me$;
$A^3 = NR^{14}$;
$R^{14} = p\text{-}C_6H_4O(CH_2CH_2O)_3CH_3$
$X = Br$ 3a-Bromo-3a,4,7,7a-tetrahydro-4,7-dimethyl-2,5,6-tri-(4-(2-(2-(2-methoxyethoxy)ethoxy)ethoxy)phenyl)-4,7-methano-1H-isoindole-1,3,8(2H)-trione

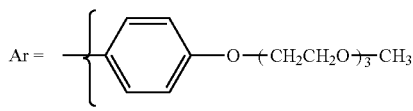

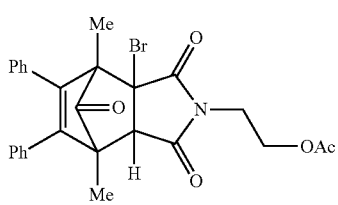

oCOm-16

$R^1 = R^2 = Ph$;
$R^3 = R^4 = Me$;
$A^3 = NR^{14}$;
$R^{14} = CH_2CH_2OCOCH_3$
$X = Br$

3a-Bromo-3a,4,7,7a-tetrahydro-4,7-dimethyl-2-(2-acetoxyethyl)-5,6-diphenyl-4,7-methano-1H-isoindole-1,3,8(2H)-trione -continued

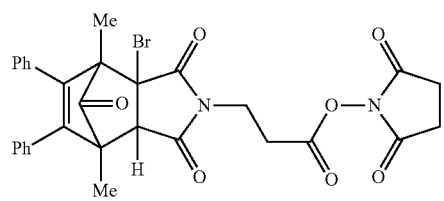

oCOm-17

$R^1 = R^2 = Ph$;
$R^3 = R^4 = Me$:
$A^3 = NR^{14}$; $R^{14} =$
$CH_2CH_2COOSuc$-
cinimidyl
X = Br 2,5-Dioxopyrrolidin-1-yl
3-(3a-bromo-4,7-
dimethyl-1,3,8-trioxo-5,6-
diphenyl-1,3,3a,4,7,7a-
hexahydro-2H-4,7-
methanoisoindol-2-
yl)propanoate

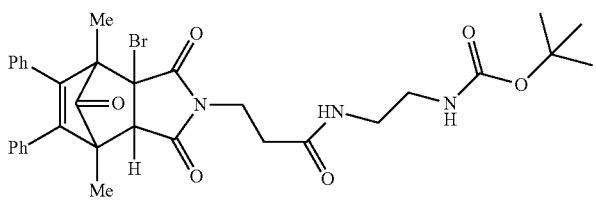

oCOm-18

$R^1 = R^2 = Ph$;
$R^3 = R^4 = Me$:
$A^3 = NR^{14}$; $R^{14} =$
$CH_2CH_2CONHCH_2CH_2NHBoc$
X = Br tert-Butyl (2-(3-((4S,7R)-
3a-bromo-4,7-dimethyl-
1,3,8-trioxo-5,6-diphenyl-
3a,4,7,7a-tetrahydro-1H-
4,7-methanoisoindol-
2(2H)-
yl)propanamido)eth-
yl)carbamate

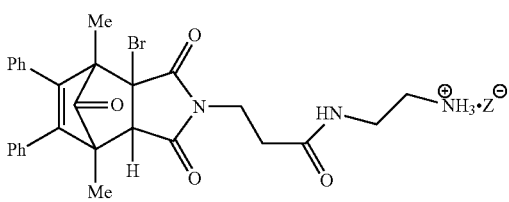

oCOm-19

$R^1 = R^2 = Ph$;
$R^3 = R^4 = Me$:
$A^3 = NR^{14}$; $R^{14} =$
$CH_2CH_2CONHCH_2CH_2NH_3 \cdot Z$
where Z = Cl$^-$ and
$CF_3CO_2^-$
X = Br 2-(3-(3a-Bromo-4,7-
dimethyl-1,3,8-trioxo-5,6-
diphenyl-1,3,3a,4,7,7a-
hexahydro-2H-4,7-
methanoisoindol-2-
yl)propanamido)ethan-1-
aminium trifluoroacetate
and chloride

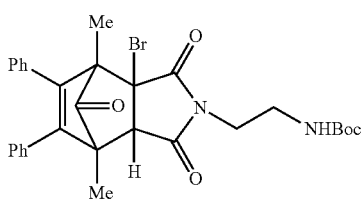

oCOm-20

$R^1 = R^2 = Ph$;
$R^3 = R^4 = Me$:
$A^3 = NR^{14}$; $R^{14} =$
$CH_2CH_2NHBoc$
X = Br tert-Butyl (2-(3a-bromo-
4,7-dimethyl-1,3,8-trioxo-
5,6-diphenyl-3a,4,7,7a-
tetrahydro-2H-4,7-
methanoisoindol-2-
yl)ethyl)carbamate

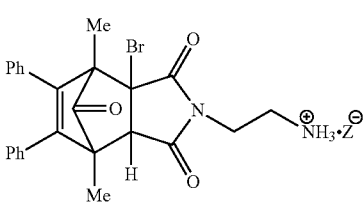

oCOm-21

$R^1 = R^2 = Ph$;
$R^3 = R^4 = Me$:
$A^3 = NR^{14}$; $R^{14} =$
$CH_2CH_2NH_3 \cdot Z$
where Z = Cl$^-$,
Br$^-$, and $CF_3CO_2^-$
X = Br 2-(3a-Bromo-4,7-
dimethyl-1,3,8-trioxo-5,6-
diphenyl-2H-4,7-
methanoisoindolin-2-
yl)ethan-1-aminium 2,2,2-
trifluoroacetate, chloride,
and bromide

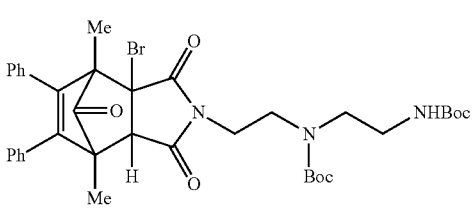

oCOm-22

$R^1 = R^2 = Ph$;
$R^3 = R^4 = Me$:
$A^3 = NR^{14}$; $R^{14} =$
$CH_2CH_2N(Boc)CH_2CH_2NHBoc$
X = Br tert-Butyl (2-(3a-bromo-
4,7-dimethyl-1,3,8-trioxo-
5,6-diphenyl-3a,4,7,7a-
tetrahydro-1H-4,7-
methanoisoindol-2(2H)-
yl)ethyl)(2-((tert-
butoxycarbonyl)amino)eth-
yl)carbamate -continued

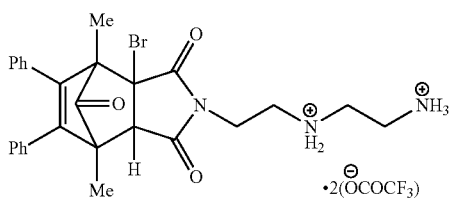

oCOm-23

$R^1 = R^2 = Ph$;
$R^3 = R^4 = Me$;
$A^3 = NR^{14}$; $R^{14} =$
$CH_2CH_2NHCH_2CH_2NH_2 \cdot 2CF_3CO_2H$
X = Br 2-(2-(2-Aminoethyl)aminoethyl)-3a-bromo-3a,4,7,7a-tetrahydro-4,7-dimethyl--5,6-diphenyl-4,7-methano-1H-isoindole-1,3,8(2H)-trione bis-trifluoroacetate salt

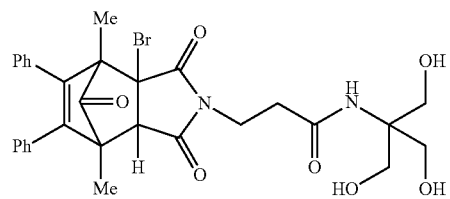

oCOm-24

$R^1 = R^2 = Ph$;
$R^3 = R^4 = Me$;
$A^3 = NR^{14}$; $R^{14} =$
$CH_2CH_2CONHC(CH_2OH)_3$
X = Br

N-(2-Hydroxy-1,1-bis(hydroxymethyl)ethyl)-3-(3a-bromo-4,7-dimethyl-1,3,8-trioxo-5,6-diphenyl-3a,4,7,7a-tetrahydro-1H-4,7-methanoisoindol-2(2H)-yl)propanamide

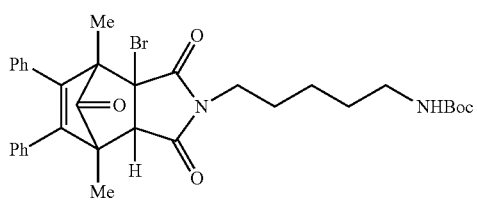

oCOm-25

$R^1 = R^2 = Ph$;
$R^3 = R^4 = Me$;
$A^3 = NR^{14}$; $R^{14} =$
$(CH_2)_5NHBoc$
X = Br tert-Btuyl (5-(3a-bromo-4,7-dimethyl-1,3,8-trioxo-5,6-diphenyl-3a,4,7,7a-tetrahydro-2H-4,7-methanoisoindol-2-yl)pentyl)carbamate

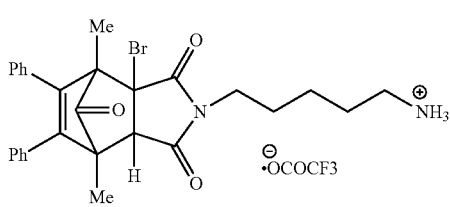

oCOm-26

$R^1 = R^2 = Ph$;
$R^3 = R^4 = Me$;
$A^3 = NR^{14}$; $R^{14} =$
$(CH_2)_5NH_2 \cdot CF_3CO_2H$
X = Br 5-(3a-Bromo-4,7-dimethyl-1,3,8-trioxo-5,6-diphenyl-2H-4,7-methanoisoindolin-2-yl)pentan-1-aminium 2,2,2-trifluoroacetate

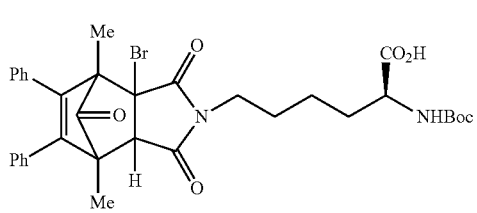

oCOm-27

$R^1 = R^2 = Ph$;
$R^3 = R^4 = Me$;
$A^3 = NR^{14}$; $R^{14} =$
$(CH_2)_4CH(NHBoc)CO_2H$ X = Br (2S)-2-tert-butoxycarbonylamino-6-(3a-bromo-4,7-dimethyl-1,3,8-trioxo-5,6-diphenyl-1,3,3a,4,7,7a-hexahydro-2H-4,7-methanoisoindol-2-yl)hexanoic acid

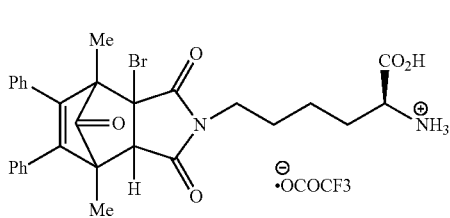

oCOm-28

$R^1 = R^2 = Ph$;
$R^3 = R^4 = Me$;
$A^3 = NR^{14}$; $R^{14} =$
$(CH_2)_4CH(NH_2 \cdot HOCOCF_3)CO_2H$
X = Br (2S)-2-Amino-6-(3a-bromo-4,7-dimethyl-1,3,8-trioxo-5,6-diphenyl-1,3,3a,4,7,7a-hexahydro-2H-4,7-methanoisoindol-2-yl)hexanoic acid trifluoroacetic acid salt -continued

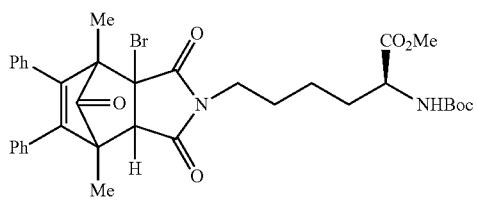

oCOm-29

$R^1 = R^2 = Ph$;
$R^3 = R^4 = Me$;
$A^3 = NR^{14}$;
$R^{14} =$
$(CH_2)_4CH(NHBoc)CO_2Me$
$X = Br$

Methyl (2S)-2-tert-butoxycarbonylamino-6-(3a-bromo-4,7-dimethyl-1,3,8-trioxo-5,6-diphenyl-1,3,3a,4,7,7a-hexahydro-2H-4,7-methanoisoindol-2-yl)hexanoate

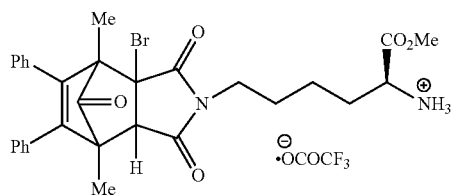

oCOm-30

$R^1 = R^2 = Ph$;
$R^3 = R^4 = Me$;
$A^3 = NR^{14}$; $R^{14} =$
$(CH_2)_4CH(NH_2 \cdot HOCOCF_3)CO_2Me$
$X = Br$ Methyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)hexanoate trifluoroacetic acid salt

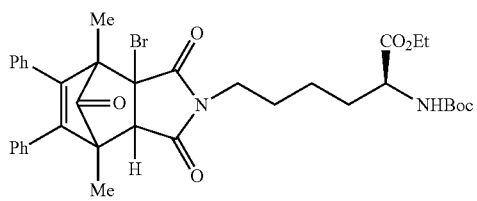

oCOm-31

$R^1 = R^2 = Ph$;
$R^3 = R^4 = Me$;
$A^3 = NR^{14}$;
$R^{14} =$
$(CH_2)_4CH(NHBoc)CO_2Et$
$X = Br$

Ethyl (2S)-2-tert-butoxycarbonylamino-6-(3a-bromo-4,7-dimethyl-1,3,8-trioxo-5,6-diphenyl-1,3,3a,4,7,7a-hexahydro-2H-4,7-methanoisoindol-2-yl)hexanoate

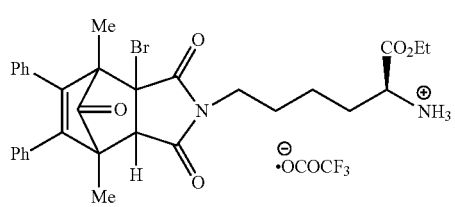

oCOm-32

$R^1 = R^2 = Ph$;
$R^3 = R^4 = Me$;
$A^3 = NR^{14}$;
$R^{14} =$
$(CH_2)_4CH(NH_2 \cdot HOCOCF_3)CO_2Et$
$X = Br$ Ethyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)hexanoate trifluoroacetic acid salt

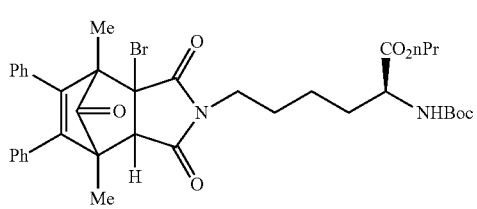

oCOm-33

$R^1 = R^2 = Ph$;
$R^3 = R^4 = Me$;
$A^3 = NR^{14}$;
$R^{14} =$
$(CH_2)_4CH(NHBoc)CO_2nPr$
$X = Br$ nPropyl (2S)-2-tert-butoxycarbonylamino-6-(3a-bromo-4,7-dimethyl-1,3,8-trioxo-5,6-diphenyl-1,3,3a,4,7,7a-hexahydro-2H-4,7-methanoisoindol-2-yl)hexanoate

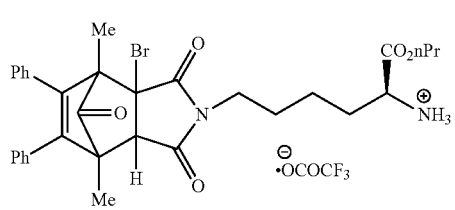

oCOm-34

$R^1 = R^2 = Ph$;
$R^3 = R^4 = Me$;
$A^3 = NR^{14}$;
$R^{14} =$
$(CH_2)_4CH(NH_2 \cdot HOCOCF_3)CO_2nPr$
$X = Br$ nPropyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)hexanoate trifluoroacetic acid salt -continued

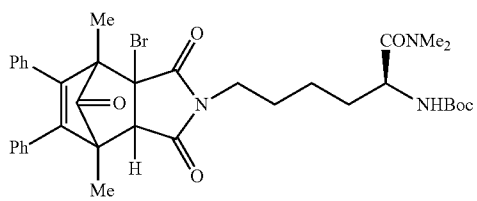

oCOm-35

$R^1 = R^2 = Ph$;
$R^3 = R^4 = Me$;
$A^3 = NR^{14}$;
$R^{14} =$
$(CH_2)_4CH(NHBoc)CONMe_2$
$X = Br$

N,N-Dimethyl (2S)-2-tert-butoxycarbonylamino-6-(3a-bromo-4,7-dimethyl-1,3,8-trioxo-5,6-diphenyl-1,3,3a,4,7,7a-hexahydro-2H-4,7-methanoisoindol-2-yl)hexanamide

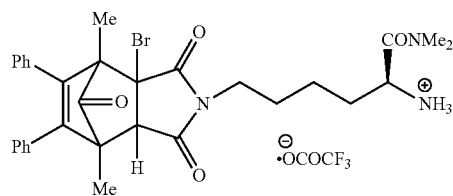

oCOm-36

$R^1 = R^2 = Ph$;
$R^3 = R^4 = Me$;
$A^3 = NR^{14}$;
$R^{14} =$
$(CH_2)_4CH(NH_2 \cdot HOCOCF_3)CONMe_2$
$X = Br$ N,N-Dimethyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)hexanamide trifluoroacetic acid salt

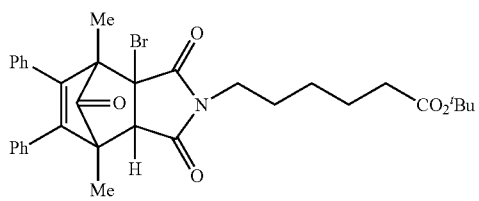

oCOm-37

$R^1 = R^2 = Ph$;
$R^3 = R^4 = Me$;
$A^3 = NR^{14}$;
$R^{14} =$
$(CH_2)_5CO_2tBu$
$X = Br$ tert-Butyl 6-(3a-bromo-4,7-dimethyl-1,3,8-trioxo-5,6-diphenyl-1,3,3a,4,7,7a-hexahydro-2H-4,7-methanoisoindol-2-yl)hexanoate

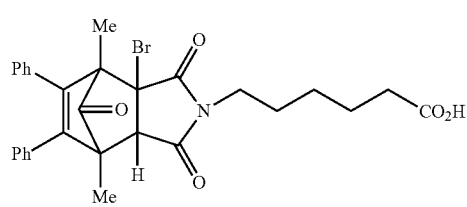

oCOm-38

$R^1 = R^2 = Ph$;
$R^3 = R^4 = Me$;
$A^3 = NR^{14}$;
$R^{14} =$
$(CH_2)_5CO_2H$
$X = Br$ 6-(3a-bromo-4,7-dimethyl-1,3,8-trioxo-5,6-diphenyl-1,3,3a,4,7,7a-hexahydro-2H-4,7-methanoisoindol-2-yl)hexanoic acid

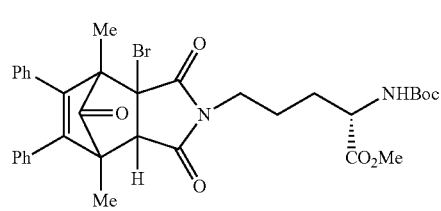

oCOm-39

$R^1 = R^2 = Ph$;
$R^3 = R^4 = Me$;
$A^3 = NR^{14}$;
$R^{14} =$
$(CH_2)_3CH(NHBoc)CO_2Me$
$X = Br$

Methyl (2S)-2-tert-butoxycarbonylamino-5-(3a-bromo-4,7-dimethyl-1,3,8-trioxo-5,6-diphenyl-1,3,3a,4,7,7a-hexahydro-2H-4,7-methanoisoindol-2-yl)pentanoate

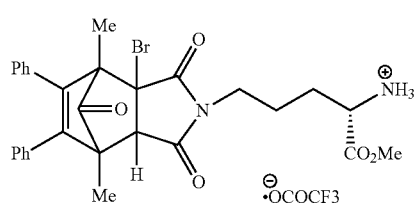

oCOm-40

$R^1 = R^2 = Ph$;
$R^3 = R^4 = Me$;
$A^3 = NR^{14}$; $R^{14} =$
$(CH_2)_3CH(NH_2 \cdot HOCOCF_3)CO_2Me$
$X = Br$ Methyl (2S)-2-amino-5-(3a-bromo-4,7-dimethyl-1,3,8-trioxo-5,6-diphenyl-1,3,3a,4,7,7a-hexahydro-2H-4,7-methanoisoindol-2-yl)pentanoate trifluoroacetic acid salt

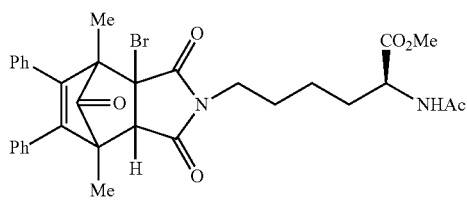

oCOm-41

| R¹ = R² = Ph; | Methyl (2S)-2-acetamido- |
| R³ = R⁴ = Me; | 6-(3a-bromo-4,7- |
| A³ = NR¹⁴; | dimethyl-1,3,8-trioxo-5,6- |
| R¹⁴ = | diphenyl-1,3,3a,4,7,7a- |
| (CH₂)₄CH(NHAc)CO₂Me | hexahydro-2H-4,7- |
| X = Br | methanoisoindol-2- |
|  | yl)hexanoate |

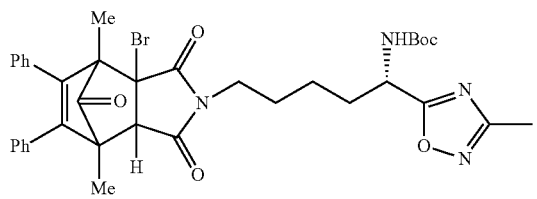

oCOm-42

R¹ = R² = Ph;
R³ = R⁴ = Me;
A³ = NR¹⁴;
R¹⁴ = (CH₂)₄CH(NHBoc)-5-(3-Me-(1,2,4-oxadiazolyl)yl)
X = Br (1S)-1-tert-butoxycarbonylamino-5-(3a-bromo-4,7-dimethyl-1,3,8-trioxo-5,6-diphenyl-1,3,3a,4,7,7a-hexahydro-2H-4,7-methanoisoindol-2-yl)-1-(3-methyl-1,2,4-oxadiazol-5'-yl)pentane

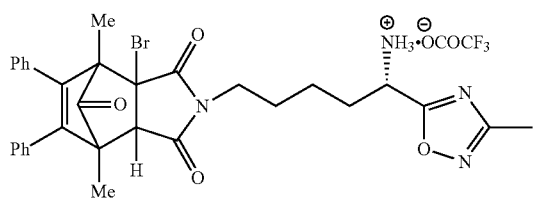

oCOm-43

R¹ = R² = Ph;
R³ = R⁴ = Me;
A³ = NR¹⁴;
R¹⁴ = (CH₂)₄CH(NH₂•HOCOCF₃)-5-(3-Me-(1,2,4-oxadiazolyl)yl)
X = Br (1S)-1-amino-5-(3a-bromo-4,7-dimethyl-1,3,8-trioxo-5,6-diphenyl-1,3,3a,4,7,7a-hexahydro-2H-4,7-methanoisoindol-2-yl)-1-(3-methyl-1,2,4-oxadiazol-5-yl)pentane trifluoroacetic acid salt

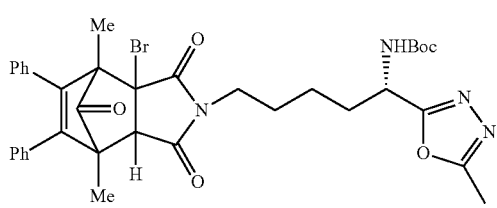

oCOm-44

R¹ = R² = Ph;
R³ = R⁴ = Me;
A³ = NR¹⁴;
R¹⁴ = (CH₂)₄CH(NHBoc)-2-(5-Me-(1,3,4-oxadiazolyl)yl)
X = Br (1S)-1-tert-butoxycarbonylamino-5-(3a-bromo-4,7-dimethyl-1,3,8-trioxo-5,6-diphenyl-1,3,3a,4,7,7a-hexahydro-2H-4,7-methanoisoindol-2-yl)-1-(5-methyl-1,3,4-oxadiazol-2-yl)pentane

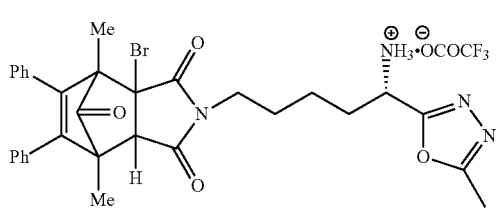

oCOm-45

R¹ = R² = Ph;
R³ = R⁴ = Me;
A³ = NR¹⁴;
R¹⁴ = (CH₂)₄CH(NH₂•HOCOCF₃)-2-(5-Me-(1,3,4-oxadiazolyl)yl)
X = Br (1S)-1-Amino-5-(3a-bromo-4,7-dimethyl-1,3,8-trioxo-5,6-diphenyl-1,3,3a,4,7,7a-hexahydro-2H-4,7-methanoisoindol-2-yl)-1-(5-methyl-1,3,4-oxadiazol-2-yl)pentane trifluoroacetic acid salt

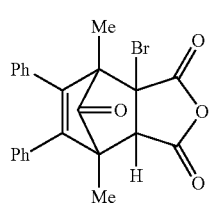

oCOm-46

R¹ = R² = Ph;
R³ = R⁴ = Me;
A³ = O;
X = Br 3a,4,7,7a-Tetrahydro-7a-bromo-4,7-dimethyl-5,6-diphenyl-1H-4,7-methanoisobenzofuran-1,3,8(2H)-trione

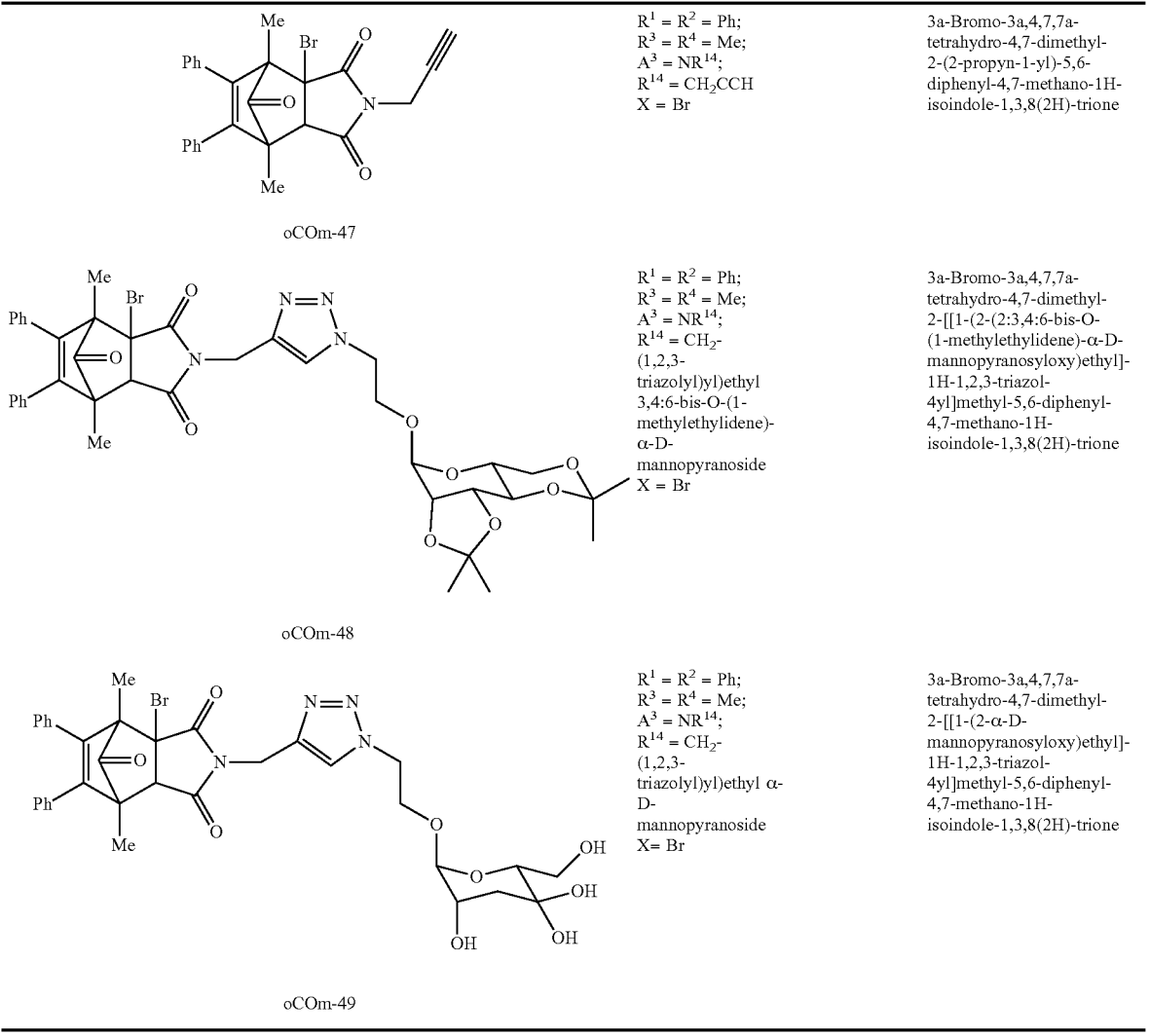

Norbornenone Compounds of Formula 1b

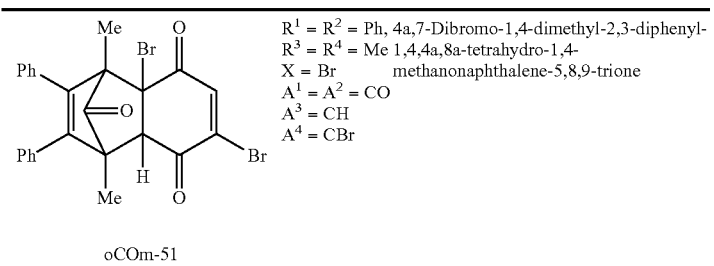

Release of Carbon Monoxide by Norbornenone Compounds

Release of carbon monoxide by norbornenone compounds according to the present disclosure may be characterised directly (e.g.) quantifying the amount of carbon monoxide released using an electrode, or indirectly (e.g.) by quantifying the amount of reaction byproduct through NMR and/or HPLC analysis.

In the experimental examples which follow, the characterisation of reaction byproducts is documented. In the case of oCOm-1, oCOm-2, oCOm-3, oCOm-4, oCOm-5, oCOm-6, oCOm-7, oCOm-8, under optimal pH (i.e. pH=7.4) these compounds release carbon monoxide forming the byproduct designated "BP-1". By way of illustration only, refer to Examples 1-3. These byproduct compounds were characterised by $^1H$ and $^{13}C$ NMR, as well as mass spectrometry. Similarly, under optimal pH conditions (e.g. pH=7.4) oCOm-8 releases CO forming BP-8, oCOm-9 releases CO forming BP-9, oCOm-10 releases CO forming BP-10, oCOm-11 releases CO forming BP-11, oCOm-12 releases CO forming BP-12, oCOm-13 releases CO forming BP-13, oCOm-14 releases CO forming BP-14, oCOm-15 releases CO forming BP-15, oCOm-16 releases CO forming BP-16, oCOm-17 releases CO forming BP-17, oCOm-18 releases CO forming BP-18, oCOm-19 releases CO forming BP-19, oCOm-20 releases CO forming BP-20, oCOm-21 releases CO forming BP-21, oCOm-22 releases CO forming BP-22, oCOm-23 releases CO forming BP-23 and oCOm-24 releases CO forming BP-24. Again, these byproduct compounds (designated BP-X, where X=the oCOm compound number interrogated) were characterised by $^{1}$H and $^{13}$C NMR, as well as mass spectrometry.

For those compounds that are water soluble (e.g. oCOm-19, oCOm-21, oCOm-23, oCOm-28, oCOm-30, oCOm-32, oCOm-34, oCOm-40), CO release was demonstrated using a CO electrode, in addition to characterisation by way of carboxymyoglobin assay (oCOm-19 and oCOm-21) and BODIPY (oCOm-21, oCOm-23, oCOm-28 and oCOm-30), data not currently shown.

With respect to oCOm-25 to oCOm-45, inclusive, release of carbon monoxide was demonstrated indirectly by characterising the reaction byproduct using HPLC analysis, data also not currently shown.

Biological Methods and Uses for the Norbornenone Compounds

In certain aspects, the present disclosure provides methods of delivering a physiologically effective amount of carbon monoxide to a physiological target comprising providing a norbornenone compound of Formula 1 as described herein, or a composition or formulation as described herein, to the physiological target. In one example, the physiological target is a subject, for example a human subject. In other examples, the physiological target may be a cell, tissue or organ obtained from the subject.

A person skilled in the art will recognise that the methods according to the present invention may optionally comprise providing a pH trigger sufficient to trigger release of carbon monoxide thereby delivering carbon monoxide to the physiological target. Release of carbon monoxide by the norborneone compounds according to the present invention, and defined by Formula 1, will occur at pH greater than or equal to 7.0 (i.e. pH≥7.0). In certain examples the pH trigger will adjust the pH to a pH of between 7.0 and 8.5, namely pH=7.0, 7.1, 7.2, 7.3, 7.4, 7.5, 7.6, 7.7, 7.8, 7.9, 8.0, 8.1, 8.2, 8.3, 8.4 and 8.5.

Alternatively, a person skilled in the art will recognise that the pH environment of the physiological target will be sufficient to trigger release of carbon monoxide when the norborneone compound is delivered or administered to the target. A physiological pH range comprises a pH of about 7.0 to about 8.5, and in particular a pH selected from pH=7.0, 7.1, 7.2, 7.3, 7.4, 7.5, 7.6, 7.7, 7.8, 7.9, 8.0, 8.1, 8.2, 8.3, 8.4 and 8.5.

Where the physiological target is a subject, delivery may be achieved by administration. Administration may be via one or more of oral, parenteral, topical, intravenous, subcutaneous, nasal, inhalatory, intramuscular, intraperitoneal and suppository routes. In one example, the administration is oral administration.

Where the physiological target is a cell, tissue or organ obtained from a subject, delivery may be achieved by conditioning the cell, tissue or organ in a composition, pharmaceutical composition or formulation including perfusion formulation as described herein. A person skilled in the art will recognise that the cell, tissue or organ may be conditioned prior to removal from the subject, during transport and/or storage following removal from the subject, following transplantation into the desired host, or any combination thereof. That is to say conditioning comprises pre-conditioning, peri-conditioning and/or post-conditioning of the cell, tissue or organ, or any combination thereof.

The methods according to the present invention may be for stimulating at least one of a neurotransmission, vasodilatory, antiapoptotic, antithrombic, anti-inflammatory and immunomodulatory response in a subject, or cell, tissue or organ obtained from the subject.

In an example, the methods according to the present invention are for the prevention or treatment of at least one of transplant organ injury, cell and tissue transplantation, ischaemic and ischaemia-reperfusion organ injury, hyperoxia-induced injury, transplant rejection, apoptosis, arteriosclerosis, myocardial infarction, angina, stroke, oxidative stress, hypertension, endotoxic shock, inflammation, inflammation-related disease, haemorrhagic shock, sepsis, adult respiratory disease syndrome, chronic obstructive pulmonary disease, pre-eclampsia, cancer, radiation damage, neuropathic pain, hepatosteatosis, platelet activation, attenuation of venom-mediated catalysis of fibrinogen, cerebral malaria, acute liver failure and acute kidney injury.

In a related example, the methods according to the present invention are for protecting a cell, tissue or organ from ischaemic injury either before, during or after transplantation surgery. In other examples, the methods according to the present invention comprise ex-vivo methods for protecting a cell, tissue or organ from ischaemic injury during transportation or storage of the cell, tissue or organ undergoing transplantation, for example by using a perfusion formulation as described herein.

In one example, the norborneone compounds according to the present invention, and as defined by Formula 1, are added to organ transplant perfusion solutions or flush solution (e.g. STEEN solution, UW Solution, etc.,) for a defined period of time prior to and/or during organ storage/transportation to reduce ischaemia-reperfusion injury and improve organ function.

The organ may be a whole organ or part thereof, selected from a kidney, liver, heart, lungs, skin, large or small intestine, pancreas and vasculature.

In another example, the norborneone compounds according to the present invention, and as defined by Formula 1, can be used as an additive to improve viability and outcomes in cell implantation conducted in autogenic-, syngenic-, allogenic-, and xeno-transplant procedures. The compounds are added to tissue or cell storage media for a defined period of time prior to or during tissue or cell storage, transportation or implantation to reduce tissue or cell damage, and to increase cell or tissue take rates.

In yet another example, the norborneone compounds according to the present invention, and as defined by Formula 1, may be administered to a subject intravenously as an additive to infusion solutions (e.g.) physiological solution (e.g. normal saline) or in a drug delivery system (i.e. polymer conjugate, liposome, micellular formulation, solid nanoparticles, or hydrogel) administered to patients prior to surgical/intervention procedures involving coronary artery by-pass or cardiac arrest in order to reduce the resulting ischaemia-reperfusion injury inherent to the surgical intervention.

Compositions and Formulations

The present disclosure provides pharmaceutical formulations or compositions, both for veterinary and for human medical use, which comprise one or more compounds of Formula 1, or any embodiments thereof as described herein or any pharmaceutically acceptable salts thereof, with one or more pharmaceutically acceptable carriers and/or excipients, and optionally any other therapeutic actives, stabilisers, or the like.

The carrier(s) or excipients must be biologically or pharmaceutically acceptable in the sense of being compatible with the other ingredients of the composition or formulation and not unduly deleterious to the recipient, cell, tissue or organ thereof.

The compositions may also include polymeric excipients/additives or carriers, e.g., polyvinylpyrrolidones, derivatised celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-(β-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions are listed in "Remington: The Science & Practice of Pharmacy", 19.sup.th ed.,[10] Williams & Williams, (1995), and in the "Physician's Desk Reference", 52.sup.nd ed., Medical Economics, Montvale, N.J. (1998),[11] and in "Handbook of Pharmaceutical Excipients", Third Ed., Ed. A. H. Kibbe, Pharmaceutical Press, 2000.[12]

The compounds of Formula 1, or any embodiments thereof as described herein or any pharmaceutically acceptable salts thereof, may also be formulated in the presence of an appropriate formulation carrier or excipient, for example carriers and excipients that are suitable for use in perfusion formulations.

The compounds of Formula 1, or any embodiments thereof as described herein or any pharmaceutically acceptable salts thereof, may be formulated in compositions including those suitable for oral, rectal, topical, nasal, inhalation to the lung, by aerosol, ophthalmic, or parenteral (including intraperitoneal, intravenous, subcutaneous, or intramuscular injection) administration. In an example, the composition is adapted for oral or parenteral administration. The compositions may conveniently be presented in unit dosage form and may be prepared by any of the methods well known in the art of pharmacy. All methods include the step of bringing the norbornenone compounds into association with a carrier that constitutes one or more accessory ingredients. In general, the compositions are prepared by bringing the norbornenone compounds into association with a liquid carrier to form a solution or a suspension, or alternatively, bring the norbornenone compounds into association with formulation components suitable for forming a solid, optionally a particulate product, and then, if warranted, shaping the product into a desired delivery form. Solid formulation, when particulate, will typically comprise particles with sizes ranging from about 1 nanometer to about 500 microns. In general, for solid formulations intended for intravenous administration, particles will typically range from about 1 nm to about 10 microns in diameter. The composition may contain norbornenone compounds that are nanoparticulate having a particulate diameter of below 1000 nm, for example, between 5 and 1000 nm, 5 and 500 nm, 5 to 400 nm, such as 5 to 50 nm and for example between 5 and 20 nm. In particular embodiments, the composition contains norbornenone compounds with a mean size of between 5 and 20 nm. In some embodiments, the norbornenone compound is polydispersed in the composition, with PDI of between 1.01 and 1.8, especially between 1.01 and 1.5, and more especially between 1.01 and 1.2. In particular embodiments, the norbornenone compounds is monodispersed in the composition. Particularly preferred are sterile, lyophilized compositions that are reconstituted in an aqueous vehicle prior to injection.

Compositions of the present disclosure suitable for oral administration may be presented as discrete units such as capsules, cachets, tablets, lozenges, and the like, each containing a predetermined amount of the active agent as a powder or granules; or a suspension in an aqueous liquor or non-aqueous liquid such as a syrup, an elixir, an emulsion, a draught, and the like.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised with a suitable carrier may be made by molding in a suitable machine.

A syrup may be made by adding the active compound to a concentrated aqueous solution of a sugar, for example sucrose, to which may also be added any accessory ingredient(s). Such accessory ingredients may include flavorings, suitable preservatives, an agent to retard crystallization of the sugar, and an agent to increase the solubility of any other ingredient, such as polyhydric alcohol, for example, glycerol or sorbitol.

Formulations suitable for parenteral administration conveniently comprise a sterile aqueous preparation of the norbornenone compound(s), which can be formulated to be isotonic with the blood of the recipient.

Nasal spray formulations comprise purified aqueous solutions of the active agent with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical formulations. The addition of other accessory ingredients as noted above may be desirable.

Pharmaceutical formulations are also provided which are suitable for administration as an aerosol, by inhalation. These formulations comprise a solution or suspension of the desired norbornenone compound or a salt thereof. The desired formulation may be placed in a small chamber and nebulized. Nebulization may be accomplished by compressed air or by ultrasonic energy to form a plurality of liquid droplets or solid particles comprising the macromolecules or salts thereof.

Often drugs are co-administered with other drugs in combination therapy. The norbornenone compounds may therefore be administered as combination therapies. For example, the norbornenone compounds may be administered with other medications such as corticosteroids, antihistamines, analgesics and drugs that aid in recovery or protect from ischaemia, for example.

In some examples, the norbornenone compounds may be formulated for transdermal delivery such as an ointment, a lotion or in a transdermal patch or use of microneedle technology. High drug loading and aqueous solubility allows small volumes to carry sufficient drug for patch and microneedle technologies to provide a therapeutically effective amount.

The norbornenone compounds may also be used to provide controlled-release of the pharmaceutically active agents and/or slow-release formulations.

In slow-release formulations, the formulation ingredients are selected to release the norbornenone compounds from the formulation over a prolonged period of time, such as days, weeks or months. This type of formulation includes transdermal patches or in implantable devices that may be deposited subcutaneously or by injection intraveneously, subcutaneously, intramuscularly, intraepidurally or intracranially.

Perfusion Formulations

The present disclosure provides a formulation comprising a norbornenone compound as described herein and at least one biologically or pharmaceutically acceptable excipient or carrier.

It will be appreciated that the formulations comprise at least one norbornenone compound, and may comprise two or more norbornenone compounds. The formulations may also include one or more additives and/or additional active agents.

In one example, the formulation is a perfusion formulation.

The perfusion formulation may comprise Ringer's lactate (RL), Marshall's hypertonic citrate (HOC), Bretschneider's histidine-tryptophan-ketoglutarate (HTK), EuroCollins solution, Belzer UW, Viaspan, KPS-1, STEEN Solution, Perfadex, IGL-1, Celsior, Polysol, SCOT15, Aedesta, Lifor, Custodial HTK, Renograf, Hypothermosol, HBS Solution, siRNA Transplant Solution, Ross-Marshall Citrate Solutions, Celsior Solution, Phosphate-Buffered Sucrose Solution, ET-Kyoto, TranSend, HetaFreeze, MaPersol and CryoStor.

It will be appreciated that the perfusion formulations may comprise a carrier such as water or DMSO. The carrier may also be provided by other solutions, such as phosphate buffered saline (PBS), Tris-sucrose buffer, University of Wisconsin solution, HTK solution, DMEM solution, or foetal bovine serum. In an example, the perfusion formulation comprises UW machine perfusion solution.

The formulations may comprise concentrations of a norbornenone compound of Formula 1 in the range of 1-1000 uM, although 10-100 uM range is most likely used in the formulations according to the present invention. For the avoidance of doubt, a concentration range of 1-1000 uM means the norborneone compounds may be present at a concentration of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999 or 1000 uM, or any part integer thereof.

In one example, the perfusion formulation comprises a compound of Formula 1 defined by oCOm-21 at a concentration of between 1-30 uM, or more specifically, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 uM.

The compound of Formula 1 may be formulated in any number of transplant perfusion and storage solutions including, but not limited to, Ringer's lactate (RL), Marshall's hypertonic citrate (HOC), Bretschneider's histidine-tryptophan-ketoglutarate (HTK), EuroCollins solution, Belzer UW, Viaspan, KPS-1, STEEN Solution, Perfadex, IGL-1, Celsior, Polysol, SCOT15, Aedesta, Lifor, Custodial HTK, Renograf, Hypothermosol, HBS Solution, and siRNA Transplant Solution, Ross-Marshall Citrate Solutions, Celsior Solution, Phosphate-Buffered Sucrose Solution, ET-Kyoto, TranSend, HetaFreeze, MaPersol and CryoStor.

These solutions have been adapted over the years to produce an array of transplant organ flushing, storage and perfusion solutions, examples of which are summarised below. Despite decades of adaptations, the advantages of one solution over another remain marginal.[6]

EuroCollins has evolved from Collins solution, a simple crystalloid solution developed in the 1970s, high in potassium and low in sodium to mimic intracellular concentration with high glucose levels. The main modification in Euro-Collins has been the removal of magnesium from its original formulation.

Belzer UW® also known as University of Wisconsin solution or UW solution (Wisconsin Alumni Research Foundation, Madison, Wis., USA) is available as both a cold storage solution for hypothermic flushing and storage of organs or as a machine perfusion solution. Developed in the late 1980s by Folkert Belzer and James Southard for pancreas preservation, the solution soon displaced EuroCollins solution as the preferred medium for cold storage of livers and kidneys, as well as pancreas. Its use resulted in less tissue damage, longer storage times and improved transplant outcomes and it had long been considered the gold standard solution for most organ transplants. The main innovation in UW compared to previous physiological buffer solutions was the inclusion of hydroxyethyl starch (HES) used to prevent oedema. ViaSpan™ (DuPont Merck Pharmaceutical Company, Wilmington, Del., USA) is the trademark under which the UW cold storage solution was marketed. KPS-1® (Lifeline Scientific, Itasca, Ill., USA) is the same composition as the UW Machine Perfusion Solution and is used for flushing and continuous hypothermic machine perfusion of kidneys.

STEEN Solution™ (XVIVO, Göteborg Sweden) is designed to facilitate prolonged evaluation and promote stability of isolated lungs ex vivo. STEEN Solution™ is a buffered extracellular solution that includes both human albumin to provide an optimal colloid osmotic pressure and dextran 40 to coat and protect the endothelium from excessive leukocyte interaction.

Perfadex® (XVIVO, Göteborg Sweden) is a colloid containing, lightly buffered 'extracellular' low K⁺ electrolyte solution for rapid cooling, perfusion and storage of organs in connection with transplantation.

IGL-1® (Institut Georges Lopez, Civrieux d'Azergues, France) is a preservation solution with lower potassium and lower viscosity than University Wisconsin solution (UW) developed for liver preservation.

Celsior® (Genzyme Corporation, Cambridge, Mass., USA) is a low viscosity preservation solution originally developed to preserve hearts but is also used for liver, kidney and pancreas.

Polysol® (Doorzand Medical Innovations B.V., Amsterdam, The Netherlands) is a colloid-based low-viscosity organ preservation solution with an extracellular electrolyte composition. However, a recent clinical trial for kidney transplantation was ended prematurely due to an increased incidence of acute organ rejection.

SCOT15® (MacoPharma, Tourcoing, France) is an extracellular ionic composition which includes PEG 20 kD (15 g/L) as a colloid. It is claimed as a better preservation solution for pancreatic islet cell isolation than UW.

Lifor™ (Lifeblood Medical, Freehold, N.J., USA); is a proprietary solution for use with animal organs with a number of unique characteristics compared to the standard solutions. It is a non-animal protein solution with the capabilities to carry oxygen and promote metabolism over a wide range of temperature gradients including room temperature. Lifor® acts at the cellular level preventing organ and tissue damage and also reversing harvesting damage. This is claimed as a major advance over current technology and significantly extends organ and tissue viability for transplant.

Aedesta™ Organ Perfusion Medium (Lifeblood Medical, Freehold, N.J., USA) is a proprietary solution used for perfusion or static storage of human organs and tissues with its own proprietary oxygen and nutrient carrying properties.

Transplant Solution Additives

A number of compounds are either added routinely to transplant solutions or are being investigated for use.

Prostacyclin and prostaglandin E1 have both been studied as additives to transplant solutions with limited benefit demonstrated.

Insulin and dexamethasone are routinely added to UW solution immediately prior to use to promote glucose utilisation and reduce inflammatory reactions. However their routine addition is no longer recommended by the UK NHS National organ retrieval group (November 2014).

Bridge to Life are investigating a fusogenic liposomal ATP (FL-ATP) technology to increase the amount of time an organ can be stored and improve the overall number of viable organs that can be procured.

A review[13] provides an overview of the emerging strategies to prevent ischaemia-reperfusion injuries in donor kidneys and describes strategies that are aimed at the donor, organ or recipient to improve graft outcome. These approaches include management of donors, preconditioning of the kidney, improvements in organ preservation solutions, post-conditioning, machine perfusion and regenerative therapies of the kidney graft following transplantation.

As an additive to transplant solutions, the compounds of the present invention are particularly well suited to preconditioning and preservation of a cell, tissue or organ subjected to normothermic or hypothermic ex vivo ischaemia. In one example, the cell is a stem cell.

Processes for Preparing the Norbornenone Compounds

The norbornenone compounds may be prepared by Diels-Alder reactions of a diene and dienophile, for example where the diene is an optionally substituted cyclopentadienone and the dienophile is an optionally substituted maleimide or anhydride. It will be appreciated that the processes may include additional steps such as the use of directing and/or protecting groups, and deprotection or substitution thereof. For example, the following process shown in Scheme 2 can be used to prepare norbornenone compounds of the present disclosure.

Scheme 2: Procedure for preparing Norbornenone Compound with the Formula 1a(i)

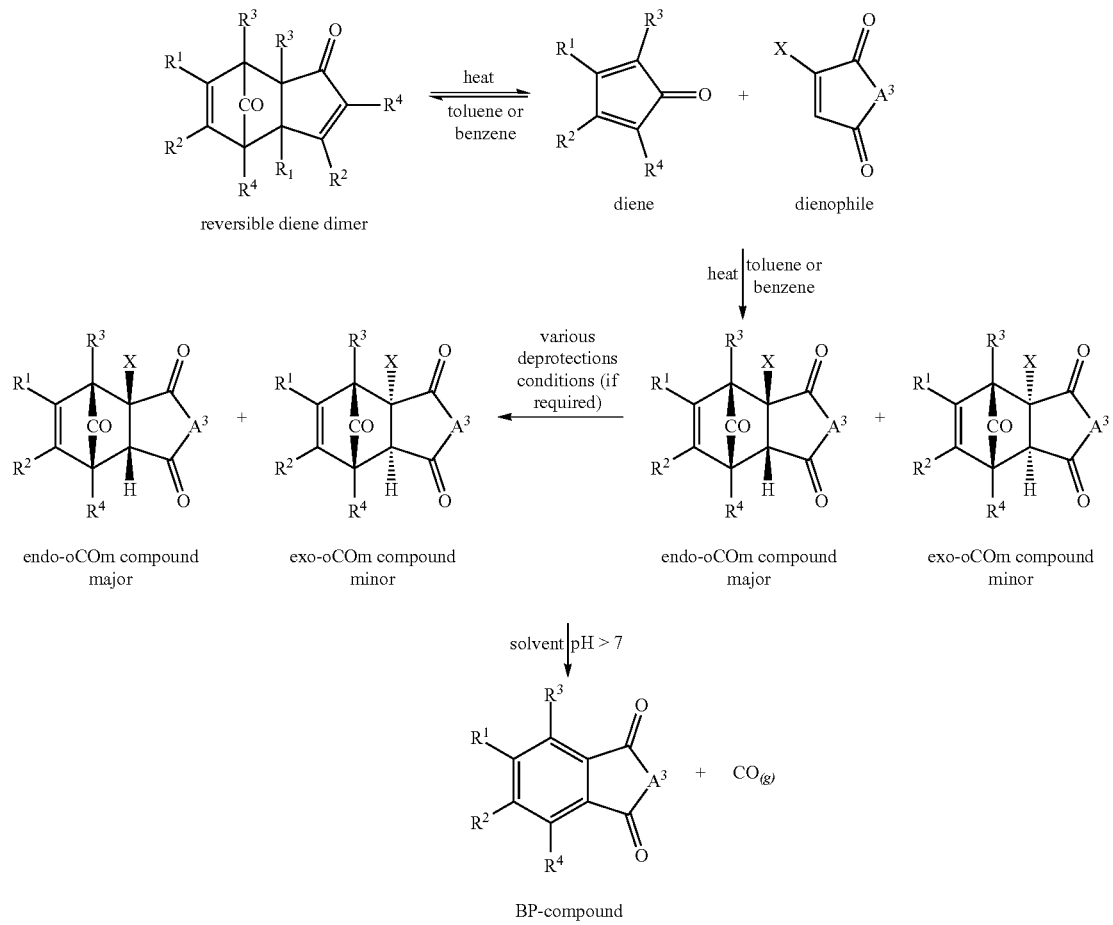

The norbornenone compounds COm-1 to oCOm-46 as described herein were prepared by the thermally promoted Diels-Alder reaction of a reversible diene dimer and either an N-substituted halomaleimide or haloanhydride as a dienophile to give the norbornenone compounds as mixtures of endo- (major) and exo- (minor) isomers. The substituents; $R^1$, $R^2$, $R^3$, $R^4$, and $A^3$; for compounds where $A^3$ had tert-butyloxycarbonyl protected amines (oCOm-18,-20,-22,-25,-27,-29,-31,-33,-35,-39,-42,-44) were treated with acidic solution such as HCl in aqueous dioxane, HBr in aqueous dioxane, or TFA in dichloromethane, to give the corresponding amines as their hydrochloride, hydrobromide or trifluoroacetic acid salts. oCOm-9 was treated with boron tribromide to provide oCOm-10. tert-Butyl ester oCOm-37 was treated with trifluoroacetic acid to give carboxylic acid oCOm-38. Solutions of the oCOm adduct were treated with either of the bases, triethylamine or 1,8-diazabicyclo[5.4.0]undecene, or dissolved in a buffer with pH=7.4 to provide the BP-compounds and carbon monoxide.

The norbornenone compound oCOm-50, which accords with Formula 1, was prepared by the acid hydrolysis of oCOm-46 with aqueous acetic acid.

The norbornenone compound oCOm-51, which accords with of Formula 1b, was prepared from the Diels-Alder reaction of diene dimer 17 with 2,5-dibromobenzoquinone (Scheme 3)

Scheme 3: Preparation of oCOm-51

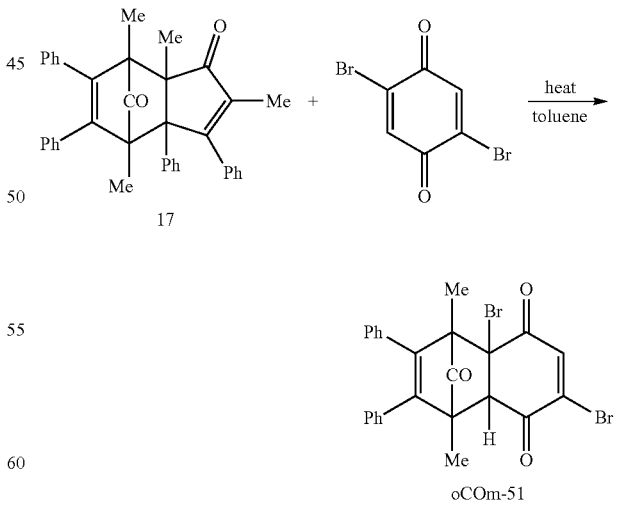

It will be appreciated that processes, reagents and conditions described above are examples only, and other processes, reagents and conditions, may be used to prepare the norbornenone compounds of the present disclosure.

EXAMPLES

The present disclosure is further described by the following examples. It is to be understood that the following description is for the purpose of describing particular examples only and is not intended to be limiting with respect to the above description.

General Experimental

Experiments requiring anhydrous conditions were performed under a dry nitrogen or argon atmosphere using apparatus heated and dried under vacuum, unless stated otherwise.

Anhydrous dichloromethane ($CH_2Cl_2$), tetrahydrofuran (THF), toluene, acetonitrile ($CH_3CN$) and methanol ($CH_3OH$) were dried using the PURE SOLV MD-6 solvent purification system. All other reagents were purchased as analytical or reagent grade and used without further purification. Aqueous solutions of sodium chloride (NaCl), sodium bicarbonate ($NaHCO_3$) and ammonium chloride ($NH_4Cl$) were saturated. Reactions performed at room temperature (rt) were carried out at approximately 20° C. and reaction temperatures from −78° C. to 0° C. were obtained using the following cooling bath mixtures: acetone/dry ice, −78° C.; acetonitrile/dry ice, −40° C.; NaCl/ice, −15° C.; water/ice, 0° C.

Reactions were monitored by thin layer chromatography (TLC) carried out on 0.2 mm Kieselgel F254 (Merck) silica gel plates using UV light as a visualising agent and then stained and developed with heat using either vanillin in ethanolic sulfuric acid, ammonium heptamolybdate and cerium sulfate in aqueous sulfuric acid, or potassium permanganate and potassium carbonate in aqueous sodium hydroxide. Separation of mixtures was performed by flash chromatography using 0.063-0.1 mm silica gel with the indicated eluent.

Infrared spectra were recorded on a Bruker Optics Alpha FT-IR spectrometer with a diamond Attenuated Total Reflectance (ATR) top plate. No sample preparation was required. Absorption peaks are reported as wavenumbers (v, cm$^{-1}$).

NMR spectra were recorded on a Varian 400-MR spectrometer operating at 400 MHz for $^1H$ nuclei and 100 MHz for $^{13}C$ nuclei at 25° C., or a Varian 500 MHz AR Premium Shielded Spectrometer at operating at 500 MHz for $^1H$ nuclei and 125 MHz for $^{13}C$ nuclei at 25° C. $^1H$ NMR chemical shifts are reported in parts per million (ppm) relative to the chloroform (CDCl$_3$, δ 7.26), or dimethylsulfoxide (DMSO-d6, δ 2.50) peak. $^1H$ NMR values are reported as chemical shifts δ, relative integral, multiplicity (s, singlet; d, doublet; t, triplet; q, quartet; dd, doublet of doublets; m, multiplet), coupling constant (J, Hz) and assignment. Coupling constants were taken directly from the spectra. $^{13}C$ NMR chemical shifts are reported in ppm relative to the chloroform (CDCl$_3$, δ 77.0), or dimethylsulfoxide (DMSO-d6, δ 39.5) peak. $^{13}C$ NMR values are reported as chemical shifts δ and assignment. Decoupled $^{19}F$ NMR spectra were recorded on a Varian 400-MR spectrometer operating at 376 MHz at 25° C. and data are expressed in ppm. Assignments were made with the aid of DEPT, gCOSY, gHSQC, and gHMBC experiments.

Mass spectra were recorded on a Bruker micrOTOF-Q II mass spectrometer by electrospray ionisation in positive and negative mode. High-resolution mass spectra (HRMS) were obtained with a nominal resolution of 5,000 to 10,000.

Microanalyses were performed by the Campbell Microanalytical Laboratory, University of Otago. The accuracy of the results is within±0.4%.

HPLC Analysis

HPLC grade acetonitrile ($CH_3CN$) was purchased from Merck Chemicals. MilliQ grade $H_2O$ was obtained from a Millipore purification system. HPLC grade trifluoroacetic acid (TFA) was purchased from Scharlau. HPLC analyses were conducted on an analytical RP-HPLC (Shimadzu LC-20AD equipped with an SPD-20A UV detector [210 and 254 nm]) using a Phenomenex Prodigy column (C-18, 5 μm, 3.00×250 mm) at 0.5 mL/min and heated to 40° C. Unless otherwise stated, the solvent system for all LC purposes was a mixture of A (0.05% TFA in $H_2O$) and B ($CH_3CN$). The method used was 10% to 100% B over 12.5 min, then 100% B for 2.5 min, unless otherwise stated.

A. Preparation of Norbornenone Compounds of Formula 1

The following compounds exemplify compounds according to Formula 1 as described herein:

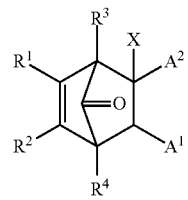

Formula 1

Example 32 oCOm-50

2-Bromo-1,4-dimethyl-7-oxo-5,6-diphenyl-bicyclo[2.2.1]hept-5-ene-2,3-dicarboxylic add: Where $R^1=R^2=Ph$; $R^3=R^4=Me$; $X=Br$; $A^1=A^2=CO_2H$

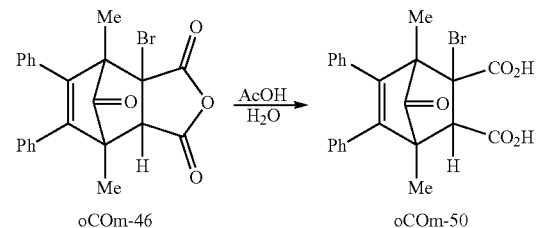

oCOm-46 (100 mg, 0.23 mmol) was suspended in acetic acid (1.5 mL) and water (1.5 mL) then heated with stirring to 110° C. for 4 h. The mixture was cooled to rt, the solvents were removed in vacuo to afford the title compound oCOm-50 (95 mg, 91%) as a white solid. $^1H$ NMR (400 MHz, (CD$_3$)$_2$CO) δ 0.88 (3H, s, CH$_3$), 1.61 (3H, s, CH$_3$), 3.77 (1H, s, H-2), 6.65 (1H, s), 7.00-7.40 (10H, m, Ph), 8.00 (1H, s); $^{13}C$ NMR (100 MHz, (CD$_3$)$_2$CO) δ 5.5, 5.9, 40.3, 43.4, 55.5 (C-3), 58.1 (C-2), 126.1, 127.4, 129.1, 129.2, 129.5, 129.6, 131.8, 132.5, 164.1, 164.6, 167.7, 172.4, 204.5 (C-7); HRMS (ESI-TOF) m/z: Calcd for $C_{23}H_{19}{}^{79}BrO_5$; Found. [M+Na—HBr]$^+$ Calcd for $C_{23}H_{18}{}_0NaO_5{}^+$ 397.1046, found 397.1025; RP-HPLC (10% to 100% B over 12.5 min, then 100% B for 2.5 min), $t_R$=11.35 min.

B. Preparation of Norbornenone Compounds of Formulae 1a

The following compounds exemplify compounds according to Formula 1a, and in particular compounds according to Formula 1a(i), as described herein:

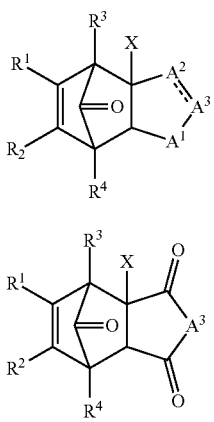

Formula 1a

Formula 1a(i)

Example 1 oCOm-1

3a-Bromo-3a,4,7,7a-tetrahydro-4,7-dimethyl-2,5,6-triphenyl-4,7-methano-1H-isoindole-1,3,8(2H)-trione; Where $R^1=R^2=Ph$; $R^3=R^4=Me$; $A^3=NR^{14}$; $R^{14}=Ph$; $X=Br$ Scheme 4: Synthesis of oCOm-1 and base promoted release of carbon monoxide forming BP-1

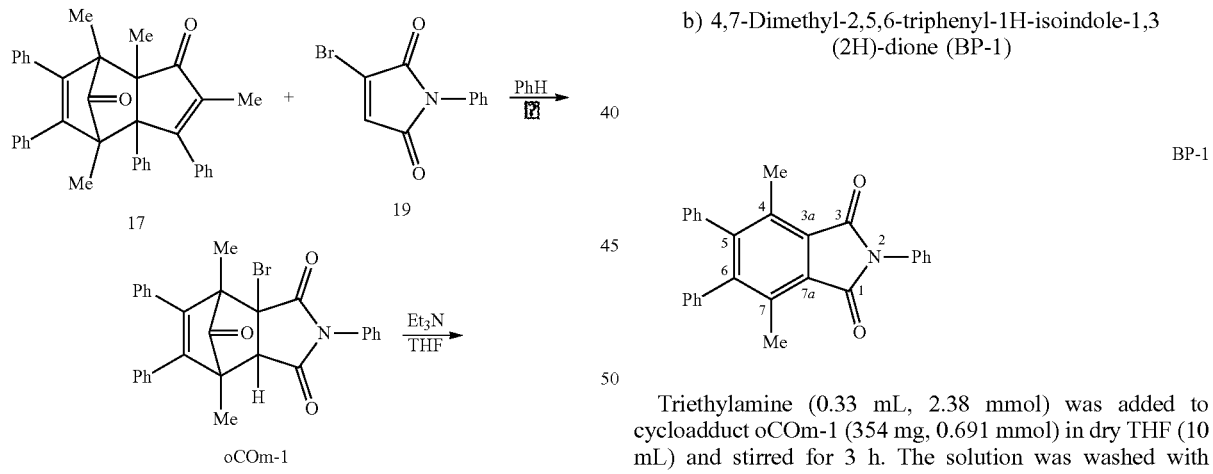

a) 3a-Bromo-3a,4,7,7a-tetrahydro-4,7-dimethyl-2,5,6-triphenyl-4,7-methano-1H-isoindole-1,3,8(2H)-trione (oCOm-1)

The dimer of 2,5-dimethyl-3,4-diphenylcyclopentadien-1-one (17)[14] (393 mg, 1.51 mmol) and 3-bromo-1-phenyl-1H-pyrrole-2,5-dione (19)[15, 16] (418 mg, 1.66 mmol) were refluxed in benzene (20 mL) for 6 h. The solution was concentrated in vacuo to a brown solid which was recrystallised from diethyl ether to afford the title compound oCOm-1 (551 mg, 71%) as white crystals. m.p. 180° C. $^1$H NMR (500 MHz, CDCl$_3$) δ 1.67 (3H, s, Me-7), 1.69 (3H, s, Me-4), 3.69 (1H, s, H-7a), 6.93-7.00 (4H, m, 4×Ph-H), 7.13-7.28 (8H, m, 8×Ph-H), 7.40-7.50 (3H, m, 3×Ph-H). $^{13}$C NMR (500 MHz, CDCl$_3$) δ 11.66 (C-Me), 12.49 (C-Me), 56.82 q (C-7a), 58.95 q (C-3a), 60.34 q (C-7), 60.01 q (C-4), 126.12, 128.23, 128.28, 128.35, 128.41, 129.21, 129.41, 129.47, 129.75, 131.19 q (C-1'), 132.46 q (C-5-ipso), 132.55 q (C-6-ipso), 140.54 q (C-6), 144.62 q (C-5), 171.34 q (C-1), 171.89 q (C-3), 196.76 q (C-8); $v_{max}$ (cm$^{-1}$) 1781 (C=O), 1719 (C=O), 1367 (C—N); HRMS-ESI [M+Na]$^+$ Calcd. for $C_{29}H_{22}{}^{81}BrNO_3Na^+$ 536.0655, found 536.0673.

b) 4,7-Dimethyl-2,5,6-triphenyl-1H-isoindole-1,3(2H)-dione (BP-1)

Triethylamine (0.33 mL, 2.38 mmol) was added to cycloadduct oCOm-1 (354 mg, 0.691 mmol) in dry THF (10 mL) and stirred for 3 h. The solution was washed with aqueous 1M HCl, dried over anhydrous magnesium sulfate and concentrated in vacuo to afford a white solid. The crude product was purified by column chromatography (DCM/Petrol 2:1) to afford the title compound BP-1 (258 mg, 93%) as a white solid. m.p. 260° C. $^1$H NMR (500 MHz, CDCl$_3$) δ 2.47 (6H, s, Me-4, Me-7), 6.90-6.94 (4H, m, 4×Ph-H), 7.11-7.21 (6H, m, 6×Ph-H), 7.38-7.48 (3H, m, 3×Ph-H), 7.49-7.54 (2H, m, 2×Ph-H); $^{13}$C NMR (500 MHz, CDCl$_3$) δ 15.85 (C-Me), 126.93, 126.96, 127.87, 127.99, 129.07, 129.58, 132.06 q (C-1'), 134.99 q (C-5), 138.74 (q), 148.93 (q), 168.17 q (C-1, C-3); $v_{max}$ (cm$^{-1}$) 1706 (C=O), 1375 (C—N); HRMS-ESI [M+Na]$^+$ Calcd. for $C_{28}H_{21}NO_2Na^+$ 426.1446, found 426.1449; Anal. Calcd. for $C_{28}H_{21}NO_2$: C, 83.35; H, 5.25; N, 3.47. Found: C, 83.20; H, 5.30; N, 3.46.

Example 2 oCOm-2

3a-Chloro-3a,4,7,7a-tetrahydro-4,7-dimethyl-2,5,6-triphenyl-4,7-methano-1H-isoindole-1,3,8(2H)-trione; Where $R^1=R^2=Ph$; $R^3=R^4=Me$; $A^3=NR^{14}$; $R^{14}=Ph$; $X=Cl$ Scheme 5: Synthesis of oCOm-2 and base promoted release of carbon monoxide forming BP-1

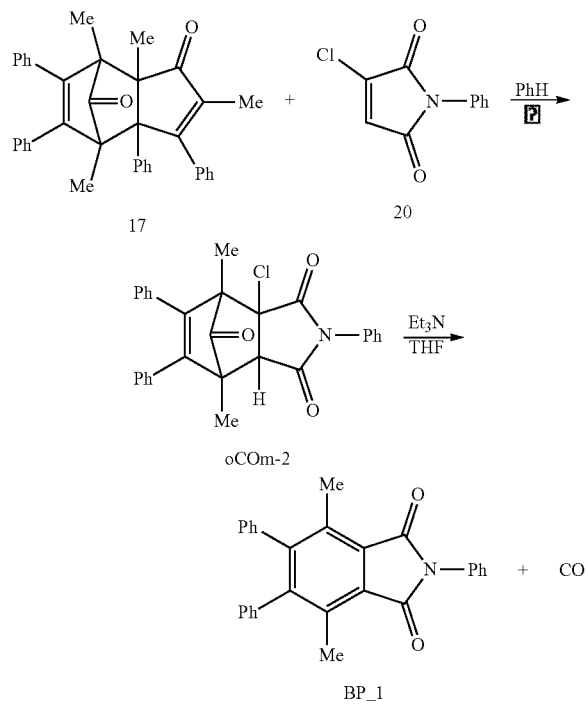

a) 3-Chloro-1-phenyl-1H-pyrrole-2,5-dione (20)

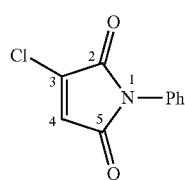

A solution of 3-bromo-1-phenyl-1H-pyrrole-2,5-dione (19) (119 mg, 0.492 mmol) and n-Bu$_4$NCl (652 mg, 2.35 mmol) in acetone (3 mL) was heated at reflux overnight. The reaction was cooled to room temperature. The solvent was removed under reduced pressure and the residue was extracted into EtOAc. The organic extract was washed with water and brine, and dried over anhydrous Na$_2$SO$_4$. The organic layer was concentrated in vacuo and the residue was purified by column chromatography (EtOAc/Pet. ether 1:9) to give the title compound 20 (84 mg, 86%) as a white powder. m.p 160-161° C. (EtOAc/Pet. ether 1:9) (lit.[17] m.p.=160° C.). $^1$H NMR (500 MHz, CDCl$_3$) δ 6.78 (1H, s, H-4), 7.33-7.35 (2H, m, Ph-H), 7.38-7.41 (1H, m, Ph-H), 7.46-7.50 (2H, m, Ph-H); $^{13}$C NMR (125 MHz, CDCl$_3$) δ 126.16, 126.94 (C-4), 128.48, 129.39, 131.04 (C-6), 141.37 (C-3), 163.95 (C-5), 166.77 (C-2); ν$_{max}$ (cm$^{-1}$) 1602 (C=O); HRMS-ESI [M+Na]$^+$ Calcd. for C$_{11}$H$_{10}$$^{35}$ClNO$_2$Na$^+$ 262.0241, found 262.0226; Anal. Calcd. for C$_{10}$H$_6$ClNO$_2$: C, 57.85; H, 2.91; N, 6.75. Found: C, 57.96; H, 2.99; N, 6.55.

b) 3a-Chloro-3a,4,7,7a-tetrahydro-4,7-dimethyl-2,5,6-triphenyl-4,7-methano-1H-isoindole-1,3,8(2H)-trione (oCOm-2)

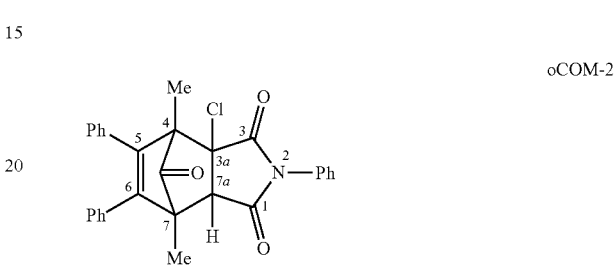

The dimer of 2,5-dimethyl-3,4-diphenylcyclopentadien-1-one (17) (307 mg, 1.18 mmol) and chloromaleimide 20 (202 mg, 0.97 mmol) were refluxed in toluene (12 mL) overnight. The solvent was concentrated in vacuo to give a brown oil which was purified by column chromatography (EtOAc/Pet.ether 1:9) to give the title compound oCOm-2 (439 mg, 96%) as a white solid in a 3.3:1 ratio of endo and exo isomers respectively. m.p. 182-184° C. (EtOAc/Pet.ether 1:9); ν$_{max}$ (cm$^{-1}$) 1783 (C=O), 1722 (C=O); HRMS-ESI [M+Na]$^+$ Calcd. for C$_{29}$H$_{22}$$^{35}$ClNO$_3$Na$^+$: 490.1191, found: 490.1180; Anal. Calcd. For C$_{29}$H$_{22}$ClNO$_3$: C, 74.43; H, 4.74; N, 2.99. Found: C, 74.64; H, 5.03; N, 3.20.

For the endo isomer; $^1$H NMR (500 MHz, CDCl$_3$) inter alia δ 1.66 (3H, s, Me-4), 1.68 (3H, s, Me-7), 3.55 (1H, s, H-7a), 6.96-6.98 (4H, m, Ph-H), 7.11-7.31 (8H, m, Ph-H), 7.41-7.53 (3H, m, Ph-H); $^{13}$C NMR (125 MHz, CDCl$_3$) δ 9.48 (Me-4), 12.53 (Me-7), 56.68 q (C-7), 59.35 (C-7a), 61.59 q (C-4), 67.62 (C-3a), 126.20, 128.32, 128.45, 128.48, 129.31, 129.46, 129.55, 129.78, 131.18, 132.43, 132.63, 140.97 (C-5), 144.67 (C-6), 171.11 (C-3), 171.68 (C-1), 196.86 (C-8);

For the exo isomer; $^1$H NMR (500 MHz, CDCl$_3$) inter alia δ 1.47 (3H, s, Me-7), 1.53 (3H, s, Me-4), 3.39 (1H, s, H-7a), 6.96-6.98 (4H, m, Ph-H), 7.10-7.35 (8H, m, Ph-H), 7.42-7.53 (3H, m, Ph-H); $^{13}$C NMR (125 MHz, CDCl$_3$) δ 7.85 (Me-4), 9.48 (Me-7), 57.58 q (C-7), 58.73 (C-7a), 62.12 (C-4), 71.26 (C-3a), 126.68, 128.17, 128.40, 128.62, 129.44, 129.52, 130.40, 131.03, 132.91, 132.99, 144.21 (C-5), 144.87 (C-6), 169.71 (C-3), 169.91 (C-1), 198.91 (C-8).

c) 4,7-Dimethyl-2,5,6-triphenyl-1H-isoindole-1,3 (2H)-dione (BP-1)

To a solution of oCOm-2 (44 mg, 0.094 mmol) in anhydrous THF (2 mL) at 0° C. was added DBU (50 μL) with stirring. The mixture was allowed to warm to rt and stirred for 3 h. Saturated ammonium chloride (10 mL) was added and the product extracted into DCM (3×10 mL). Purification by column chromatography (DCM) gave the title compound BP-1 (37 mg, 97%) as a white solid.

Example 3 oCOm-3

3a-Iodo-3a,4,7,7a-tetrahydro-4,7-dimethyl-2,5,6-triphenyl-4,7-methano-1H-isoindole-1,3,8(2H)-trione; Where $R^1=R^2=Ph$; $R^3=R^4=Me$; $A^3=NR^{14}$; $R^{14}=Ph$; X=I Scheme 6: Synthesis of oCOm-3 and base promoted release of carbon monoxide forming BP-1

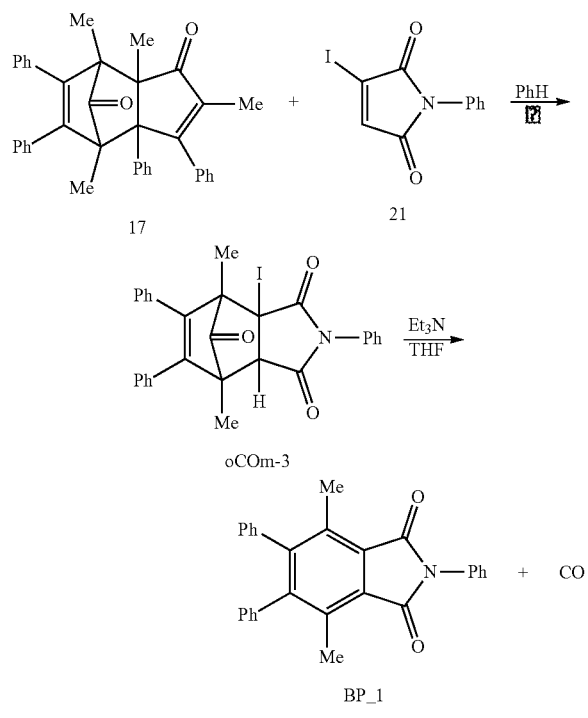

a) 3-Iodo-1-phenyl-1H-pyrrole-2,5-dione (21)

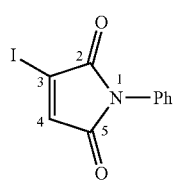

A solution of 3-bromo-1-phenyl-1H-pyrrole-2,5-dione (19) (545 mg, 2.16 mmol) and sodium iodide (1.84 mg, 12.3 mmol) in acetone (15 mL) was heated at reflux for 16 hours. The reaction was cooled to room temperature. The solvent was removed under reduced pressure, and the residue was extracted into EtOAc. The organic extract was washed with water and brine, and dried over anhydrous $Na_2SO_4$. The organic layer was concentrated in vacuo to give a brown residue which was purified by column chromatography (EtOAc/Pet. ether 1:3) to give the title compound 21 (569 mg, 88%) as a pale yellow solid. m.p. 158-159° C. (EtOAc/Pet. ether 1:3). $^1$H NMR (500 MHz, $CDCl_3$) δ 7.31-7.34 (2H, m, Ph-H), 7.32 (1H, s, H-4), 7.37-7.40 (1H, m, Ph-H), 7.45-7.49 (2H, m, Ph-H). $^{13}$C NMR (125 MHz, $CDCl_3$), δ 108.12 (C-3), 126.15, 128.40, 129.33), 131.37 (C-6), 140.67 (C-4), 165.64 (C-5), 168.75 (C-2); $v_{max}$ (cm$^{-1}$) 1701 (C=O); HRMS-ESI [M+Na]$^+$ Calcd. for $C_{10}H_7INO_2$ 299.9516, found 299.9490; Anal. Calcd. for $C_{10}H_6INO_2$: C, 40.16; H, 2.02; N, 4.69. Found: C, 40.39; H, 1.97; N, 4.68.

b) 3a-Iodo-3a,4,7,7a-tetrahydro-4,7-dimethyl-2,5,6-triphenyl-4,7-methano-1H-isoindole-1,3,8(2H)-trione (oCOm-3)

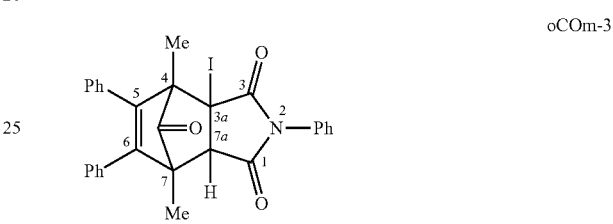

The dimer of 2,5-dimethyl-3,4-diphenylcyclopentadien-1-one (17) (287 mg, 1.10 mmol) and iodomaleimide 21 (270 mg, 0.90 mmol) were refluxed in toluene (12 mL) overnight. The solvent was concentrated in vacuo to give a brown oil which was purified by column chromatography (1:9 EtOAc/Pet. ether) to give the endo isomer of the title compound oCOm-3 (502 mg, 0.90 mmol, 99%) as a white foam. $^1$H NMR (500 MHz, $CDCl_3$) δ 1.66 (3H, s, Me-7), 1.71 (3H, s, Me-4), 3.81 (1H, s, H-7a), 6.94-6.98 (4H, m, Ph-H), 7.13-7.24 (8H, m, Ph-H), 7.40-7.48 (3H, m, Ph-H); $^{13}$C NMR (125 MHz, $CDCl_3$) δ 12.65 (Me-7), 15.88 (Me-4), 38.69 (C-3a), 57.19 q (C-7), 60.92 q (C-4), 63.08 (C-7a), 126.15, 128.27, 128.36, 128.39, 128.49, 129.21, 129.53, 129.55, 129.89, 131.43, 132.71, 132.81, 139.50 (C-5), 144.56 (C-6), 172.44 (C-1), 173.21 (C-3), 196.94 (C-8); $v_{max}$ (cm$^{-1}$) 1774 (C=O), 1712 (C=O); HRMS-ESI [M+Na]$^+$ Calcd. for $C_{29}H_{22}INO_3Na^+$ 582.0512, found 582.0537; Anal. Calcd. for $C_{29}H_{22}INO_3$: C, 62.27; H, 3.96; N, 2.50. Found: C, 62.53; H, 4.12; N, 2.35.

c) 4,7-Dimethyl-2,5,6-triphenyl-1H-isoindole-1,3(2H)-dione (BP-1)

The procedure used for oCOm-2 was repeated using the cycloadduct oCOm-3 (55 mg, 0.098 mmol) and triethylamine (48 μl, 0.344 mmol) in toluene (1.51 ml) to give 17 (36 mg, 0.089 mmol, 91%).

Similarly, oCOm-3 (16 mg, 0.029 mmol) in THF (1 mL) with DBU (20 μL) gave the title compound BP-1 (11 mg, 96%) as a white solid.

Example 4 oCOm-4

3a-Phenylthio-3a,4,7,7a-tetrahydro-4,7-dimethyl-2,5,6-triphenyl-4,7-methano-1H-isoindole-1,3,8(2H)-trione; Where $R^1=R^2=Ph$; $R^3=R^4=Me$; $A^3=NR^{14}$; $R^{14}=Ph$; $X=SPh$ Scheme 7: Synthesis of oCOm-4

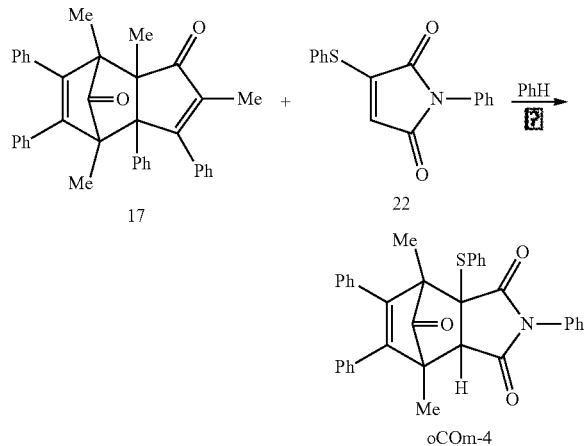

a) 3-Phenylthio-1-phenyl-1H-pyrrole-2,5-dione (22)[18]

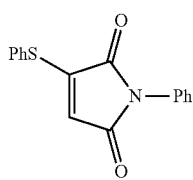

A solution of 3-bromo-1-phenyl-1H-pyrrole-2,5-dione (19) (400 mg, 1.59 mmol), benzenethiol (179 µL, 1.75 mmol) and triethylamine (332 µl, 2.38 mmol) in CH$_2$Cl$_2$ (20 ml) was stirred for 1 hour at 0° C. The solvent was removed under reduced pressure, and the residue was extracted into EtOAc. The organic extract was washed with water and brine, and dried over anhydrous Na$_2$SO$_4$. The organic layer was concentrated in vacuo and the residue was recrystallised in EtOAc/Pet. ether to give the title compound 22 (428 mg, 96%) as yellow crystals. m.p. 168-170° C. (EtOAc/Pet. ether) (lit.[18] m.p.=162-164° C.). $^1$H NMR (500 MHz, CDCl$_3$) δ 5.80 (1H, s, H-4), 7.34-7.37 (4H, m, Ph-H), 7.44-7.53 (7H, m, Ph-H), 7.60-7.62 (4H, m, Ph-H); $^{13}$C NMR (125 MHz, CDCl$_3$) δ 118.91 (C-4), 125.98, 127.23, 127.89, 129.16, 130.39, 130.66, 131.45, 134.49, 153.08 (C-3), 166.75 (C-5), 168.27 (C-2); $v_{max}$ (cm$^{-1}$) 1700 (C=O); HRMS-ESI [M+Na]$^+$ Calcd. for C$_{16}$H$_{11}$NO$_2$SNa$^+$ 304.0403, found 304.0411; Anal. Calcd. for C$_{16}$H$_{11}$NO$_2$S: C, 68.31; H, 3.84; N, 4.98. Found: C, 68.33; H, 3.87; N, 5.01.

b) 3a-Phenylthio-3a,4,7,7a-tetrahydro-4,7-dimethyl-2,5,6-triphenyl-4,7-methano-1H-isoindole-1,3,8(2H)-trione (oCOm-4)

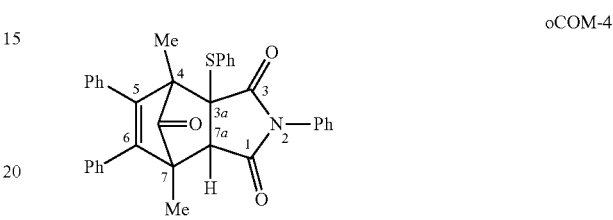

The dimer of 2,5-dimethyl-3,4-diphenylcyclopentadien-1-one (17) (389 mg, 1.49 mmol) and 3-phenylthio-1-phenyl-1H-pyrrole-2,5-dione (22) (350 mg, 1.24 mmol) were refluxed in toluene (20 mL) overnight. The solution was concentrated in vacuo to give a yellow oil which was purified by column chromatography (EtOAc/Pet. ether 1:9) to give the title compound oCOm-4 (602 mg, 89%) as a yellow solid in a 5:1 ratio of endo and exo isomers respectively. m.p. 193° C. (EtOAc/Pet. Ether 1:9); $v_{max}$ (cm$^{-1}$) 1781 (C=O), 1710 (C=O); HRMS-ESI [M+Na]$^+$ Calcd. for C$_{35}$H$_{28}$NO$_3$S 542.1813, found 542.1784; Anal. Calcd. For C$_{35}$H$_{27}$NO$_3$S: C, 77.61; H, 5.02; N, 2.59. Found: C, 77.40; H, 5.01; N, 2.61.

For the endo isomer; $^1$H NMR (500 MHz, CDCl$_3$) inter alia δ 1.61 (3H, s, Me-7), 1.67 (3H, s, Me-4), 3.27 (1H, s, H-7a), 6.72-6.90 (4H, m, Ph-H), 7.02-7.04 (2H, m, Ph-H), 7.11-7.20 (5H, m, Ph-H), 7.29-7.60 (9H, m, Ph-H); $^{13}$C NMR (125 MHz, CDCl$_3$) inter alia δ 9.60 (Me-4), 12.86 (Me-7), 56.61 (C-7a), 56.76 (C-7), 60.78 (C-4), 61.82 (C-3a), 126.21, 128.04, 128.11, 128.36, 128.40, 129.02, 129.40, 129.44, 129.97, 130.01, 130.76, 131.55, 132.76, 133.08, 136.94, 142.67 (C-5), 143.96 (C-6), 172.74 (C-1), 174.53 (C-3), 197.68 (C-8);

For the exo isomer; $^1$H NMR (500 MHz, CDCl$_3$) inter alia δ 1.56 (3H, s, Me-7), 1.61 (3H, s, Me-4), 3.31 (1H, s, H-7a), 6.72-6.90 (4H, m, Ph-H), 7.02-7.04 (2H, m, Ph-H), 7.11-7.20 (5H, m, Ph-H), 7.29-7.60 (9H, m, Ph-H); $^{13}$C NMR (125 MHz, CDCl$_3$) inter alia δ 8.69 (Me-4), 9.68 (Me-7), 56.53 (C-7a), 56.73 (C-7), 60.34 (C-4), 65.65 (C-3a), 126.70, 127.61, 128.15, 128.26, 128.65, 129.03, 129.20, 129.26, 129.55, 129.93, 130.73, 130.86, 131.28, 133.34, 133.49, 137.36, 144.04 (C-5), 144.40 (C-6), 171.31 (C-1), 172.24 (C-3), 200.20 (C-8).

Example 5 oCOm-5

3a-Phenylsulfinyl-3a,4,7,7a-tetrahydro-4,7-dimethyl-2,5,6-triphenyl-4,7-methano-1H-isoindole-1,3,8 (2H)-trione; Where $R^1=R^2=Ph$; $R^3=R^4=Me$; $A^3=NR^{14}$; $R^{14}=Ph$; X=SOPh

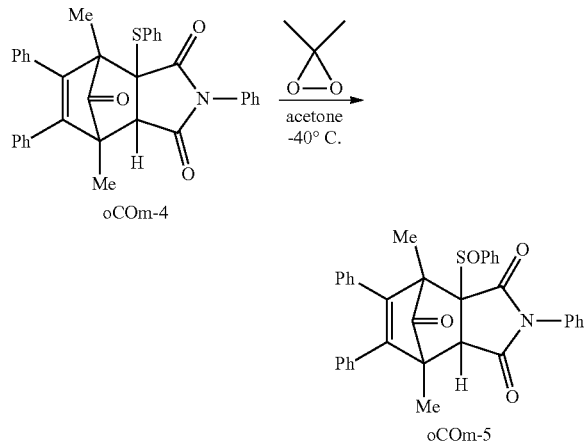

3a-Phenylsulfinyl-3a,4,7,7a-tetrahydro-4,7-dimethyl-2,5,6-triphenyl-4,7-methano-1H-isoindole-1,3,8 (2H)-trione (oCOm-5)

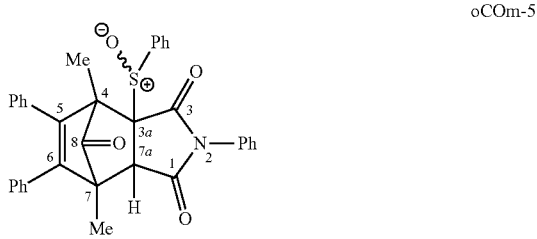 [SMILES: CC12C(=O)C(C)(C(c3ccccc3)=C1c1ccccc1)C1([S+]([O-])c3ccccc3)C(=O)N(c3ccccc3)C(=O)C21]

A solution of dimethyldioxirane (ca. 0.1 M) in acetone at −40° C. was added slowly to a solution of cycloadduct oCOm-4 (300 mg, 0.092 mmol) in acetone (12 ml) at −40° C. and stirred at this temperature. The reaction was monitored by TLC and no trace of starting material was evident after the addition of 1.9 ml of dimethyldioxirane. The reaction was quenched with 10% aqueous solution of sodium thiosulfate and extracted into EtOAc (×2). The combined organic extract was washed with water and brine, and dried over anhydrous $Na_2SO_4$. The organic layer was concentrated in vacuo to give a yellow oil which was purified by column chromatography (EtOAc/Pet. ether 1:4) to give the major endo isomer of oCOm-5 (156 mg, 51%) and the minor endo isomer of oCOm-5 (40 mg, 13%) as a white solid and colourless oil respectively and exo isomer of oCOm-5 (60 mg, 19%) as a colourless oil.

For the major endo isomer; m.p. 186° C. (EtOAc/Pet. ether 1:4). $^1H$ NMR (500 MHz, $CDCl_3$) δ 1.66 (3H, s, Me-7), 2.00 (3H, s, Me-4), 3.75 (1H, s, H-7a), 6.56-6.58 (2H, m, Ph-H), 6.87-7.89 (2H, m, Ph-H), 7.02-7.04 (2H, m, Ph-H), 7.10-7.22 (6H, m, Ph-H), 7.28-7.33 (3H, m, Ph-H), 7.54-7.63 (3H, m, Ph-H), 7.69-7.70 (2H, m, Ph-H); $^{13}C$ NMR (125 MHz, $CDCl_3$) δ 10.04 (Me-4), 12.18 (Me-7), 46.96 (C-7a), 57.70 q (C-7), 59.32 q (C-4), 77.29 (C-3a), 125.78, 125.93, 128.16, 128.27, 128.45, 129.16, 129.31, 129.36, 129.87, 129.92, 130.61, 132.54, 132.87, 132.99, 138.66, 142.28 (C-5), 143.85 (C-6), 170.84 (C-3), 172.61 (C-1), 195.43 (C-8); $v_{max}$ (cm$^{-1}$) 1795 (C=O), 1709 (C=O), 1050 (S=O); HRMS-ESI [M+Na]$^+$ Calcd. for $C_{35}H_{27}NO_4SNa^+$ 580.1553, found 580.1589; Anal. Calcd. For $C_{35}H_{27}NO_4S$: C, 75.38; H, 4.88; N, 2.51. Found: C, 75.44; H, 5.17; N, 2.37.

For the minor endo isomer; $^1H$ NMR (500 MHz, $CDCl_3$) δ 1.44 (3H, s, Me-7), 1.85 (3H, s, Me-4), 3.33 (1H, s, H-7a), 6.88-6.90 (2H, m, Ph-H), 7.00-7.02 (4H, m, Ph-H), 7.12-7.20 (6H, m, Ph-H), 7.35-7.41 (3H, m, Ph-H), 7.60-7.67 (3H, m, Ph-H), 7.84-7.86 (2H, m, Ph-H); $^{13}C$ NMR (125 MHz, $CDCl_3$) δ 10.85 (Me-4), 12.35 (Me-7), 49.72 (C-7a), 56.90 q (C-7), 59.46 q (C-4), 74.76 (C-3a), 126.20, 126.80, 129.29, 128.33, 128.45, 128.47, 129.14, 129.39, 129.43, 129.80, 130.05, 131.22, 132.26, 132.67, 133.57, 138.49, 143.80 (C-5), 143.85 (C-6), 170.50 (C-3), 172.52 (C-1), 196.09 (C-8); HRMS-ESI [M+Na]$^+$ Calcd. for $C_{35}H_{27}NO_4SNa^+$ 580.1553, found 580.1540; Anal. Calcd. For $C_{35}H_{27}NO_4S$: C, 75.38; H, 4.88; N, 2.51. Found: C, 75.37; H, 4.82; N, 2.49.

For the exo isomer; $^1H$ NMR (500 MHz, $CDCl_3$) inter alia δ 1.46 (3H, s, Me-7), 1.77 (3H, s, Me-4), 3.89 (1H, s, H-7a), 6.46-6.48 (2H, m, Ph-H), 7.23-7.37 (13H, m, Ph-H), 7.52-7.56 (2H, t, J=7.7 Hz, Ph-H), 7.61-7.65 (1H, m, Ph-H), 7.71-7.72 (2H, d, J=8.0 Hz, Ph-H); $^{13}C$ NMR (125 MHz, $CDCl_3$) δ 9.52 (Me-4), 9.66 (Me-7), 43.62 (C-7a), 57.10 q (C-7), 59.54 q (C-4), 72.28 (C-3a), 126.47, 128.06, 128.17, 128.51, 129.18, 129.31, 129.58, 129.71, 130.48 (C-1'), 130.60, 133.07 (C-6-ipso), 133.11, 133.40 (C-5-ipso), 138.96 (C-1''), 141.51 (C-5), 142.11 (C-6), 169.41 (C-3), 170.83 (C-1), 198.28 (C-8); HRMS-ESI [M+Na]$^+$ Calcd. for $C_{35}H_{27}NO_4SNa^+$: 580.1553, found: 580.1526; Anal. Calcd. For $C_{35}H_{27}NO_4S$: C, 75.38; H, 4.88; N, 2.51. Found: C, 75.41; H, 4.93.01; N, 2.45.

Example 6 oCOm-6

3a-Phenylsulfonyl-3a,4,7,7a-tetrahydro-4,7-dimethyl-2,5,6-triphenyl-4,7-methano-1H-isoindole-1,3, 8(2H)-trione: Where $R^1=R^2=Ph$; $R^3=R^4=Me$; $A^3=NR^{14}$; $R^{14}=Ph$; X=$SO_2Ph$ Method A: Oxidation of oCOm-4

Scheme 9a: Synthesis of oCOm-6

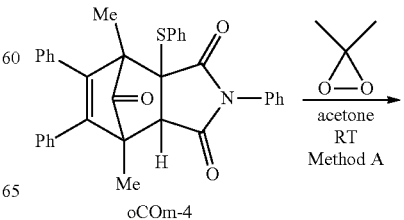

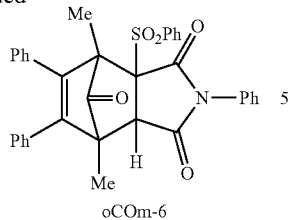

oCOm-6

A solution of ca. 0.1 M dimethyldioxirane (9.23 ml, 0.923 mmol) in acetone was added slowly to an acetone solution (2 ml) of cycloadduct oCOm-4 (50 mg, 0.092 mmol) and stirred for 30 minutes at room temperature. The solvent was concentrated in vacuo to give an orange solid which was purified by column chromatography (EtOAc/Pet. ether 1:4) to give the endo isomer of the title compound oCOm-6 (42 mg, 79%) as a white foam and the exo isomer of the title compound oCOm-6 (5 mg, 9%) as a white solid. For the endo isomer of oCOm-6; $^1$H NMR (500 MHz, CDCl$_3$) δ 1.69 (3H, s, Me-7), 1.79 (3H, s, Me-4), 3.79 (1H, s, H-7a), 6.86-6.91 (4H, m, Ph-H), 6.99-7.01 (2H, m, Ph-H), 7.12-7.20 (6H, m, Ph-H), 7.38-7.42 (3H, m, Ph-H), 7.60-7.63 (2H, t, J=7.8 Hz, Ph-H), 7.73-7.76 (1H, m, Ph-H), 7.98-7.99 (2H, m, Ph-H); $^{13}$C NMR (125 MHz, CDCl$_3$) δ 11.21 (Me-4), 12.56 (Me-7), 53.68 (C-7a), 57.06 (C-7), 60.34 (C-4), 76.00 (C-3a), 125.94, 128.35, 128.39, 128.52, 129.32, 129.39, 129.52, 129.79, 130.06, 130.38, 130.98 (C-1'), 132.10, 132.64, 135.40, 137.28, 142.72 (C-5), 144.23 (C-6), 169.25 (C-3), 171.50 (C-1), 195.15 (C-8); $v_{max}$ (cm$^{-1}$) 1786 (C=O), 1716 (C=O), 1333 (S=O), 1157 (S=O); HRMS-ESI [M+Na]$^+$ Calcd. for C$_{35}$H$_{27}$NO$_5$SNa$^+$ 596.1490, found 596.1502; Anal. Calcd. For C$_{35}$H$_{27}$NO$_5$S: C, 73.28; H, 4.74; N, 2.44. Found: C, 73.21; H, 4.80; N, 2.41.

For the exo isomer of oCOm-6; m.p. 106° C. (EtOAc/Pet. ether 1:4). $^1$H NMR (500 MHz, CDCl$_3$) δ 1.43 (3H, s, Me-7), 1.64 (3H, s, Me-4), 3.86 (1H, s, H-7a), 6.71-6.73 (2H, m, Ph-H), 7.21-7.27 (6H, m, Ph-H), 7.29-7.34 (3H, m, Ph-H), 7.37-7.39 (2H, m, Ph-H), 7.43-7.45 (2H, m, Ph-H), 7.48-7.51 (2H, m, Ph-H), 7.69-7.72 (1H, m, Ph-H), 7.76-7.78 (2H, m, Ph-H); $^{13}$C NMR (125 MHz, CDCl$_3$) δ 9.33 (Me-4), 9.74 (Me-7), 53.33 (C-7a), 56.90 (C-7), 60.83 (C-4), 76.62 (C-3a), 126.52, 128.04, 128.13, 128.38, 128.64, 129.40, 129.55, 129.60, 129.62, 130.53, 130.76 (C-1'), 131.15, 133.05, 133.22, 135.32, 136.79, 141.85 (C-5), 142.68 (C-6), 167.96 (C-3), 170.13 (C-1), 196.95 (C-8); $v_{max}$ (cm$^{-1}$) 1781 (C=O), 1717 (C=O), 1329 (S=O), 1155 (S=O); HRMS-ESI [M+Na]$^+$ Calcd. for C$_{35}$H$_{28}$NO$_5$S 574.1687, found 574.1683; Anal. Calcd. For C$_{35}$H$_{27}$NO$_5$S: C, 73.28; H, 4.74; N, 2.44. Found: C, 73.37; H, 5.02; N, 2.50.

Method B: Oxidation of oCOm-5

Scheme 9b: Synthesis of oCOm-6

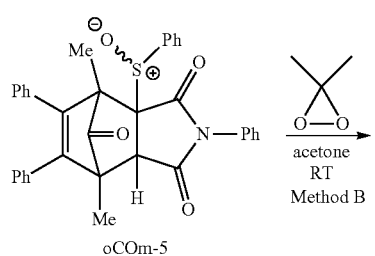

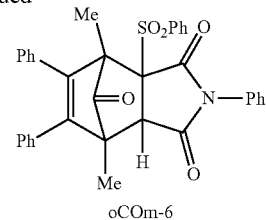

oCOm-6

1. Oxidation of Major Endo Isomer of oCOm-5

A solution of ca. 0.1 M dimethyldioxirane (1.3 ml, 0.130 mmol) in acetone was added slowly to a solution of the major endo isomer of oCOm-5 (36 mg, 0.065 mmol) in acetone (1.5 ml) and stirred for 1 hour at room temperature. The solvent was concentrated in vacuo and the residue was purified by column chromatography (EtOAc/Pet. ether 1:4) to give compound endo-oCOm-6 (30 mg, 83%) as a white foam.

2. Oxidation of Minor Endo Isomer of oCOm-5

The above procedure was repeated using the minor endo isomer of oCOm-5 (36 mg, 0.065 mmol) and ca. 0.1 M dimethyldioxirane (1.3 ml, 0.130 mmol) in acetone to give endo oCOm-6 (27 mg, 74%) as a white foam.

3. Oxidation of Exo Isomer of oCOm-5

Once again following the procedure above with the exo isomer of oCOm-5 (36 mg, 0.065 mmol) and a solution of ca. 0.1 M dimethyldioxirane (1.3 ml, 0.130 mmol) in acetone, endo-oCOm-6 (31 mg, 86%) was obtained as a white solid.

Example 7 oCOm-7

3a-Bromo-4,7-dimethyl-5,6-diphenyl-3a,4,7,7a-tetrahydro-1H-4,7-methanoisoindole-1,3,8(2H)-trione: Where R$^1$=R$^2$=Ph; R$^3$=R$^4$=Me; A$^3$=NR$^{14}$; R$^{14}$=H; X=Br Scheme 10: Synthesis of oCOm-7

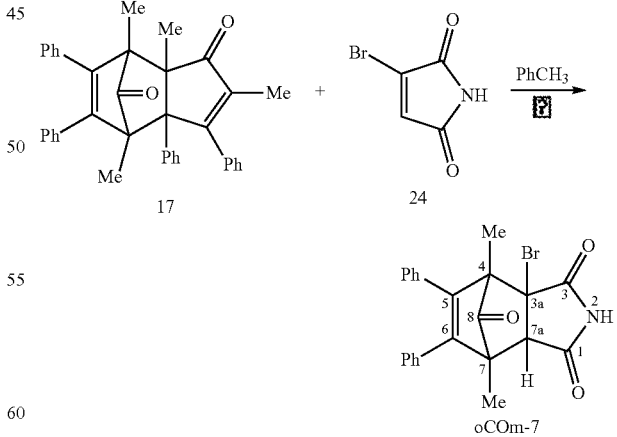

oCOm-7

4-Bromo-2H-pyrrole-1,3-dione (24)[19]

To a solution of maleimide (2.0 g, 20.6 mmol) in CHCl$_3$ (20 mL) was added a solution of Br$_2$ (1.1 mL, 21.33 mmol)

in CHCl$_3$ (15 mL). The mixture was heated to reflux for 2 h and then cooled to rt. The precipitate formed was collected by Buchner filtration (Whatman number 5 paper) and washed with cold CHCl$_3$ (2×50 mL) to afford the crude dibromo-maleimide as a pale yellow powder that was used without further purification. Crude dibromo-maleimide was dissolved in anhydrous THF (50 mL) and cooled to 0° C. A solution of anhydrous NEt$_3$ (2.9 mL) in anhydrous THF (10 mL) was then added over 5 mins and the resulting pale pink suspension stirred at 0° C. for 2 h. Without warming, the suspension was filtered and the filtrate concentrated in vacuo to afford the title compound 24 (2.30 g, 63%) as a light yellow solid. $^1$H NMR (400 MHz, CDCl$_3$) δ 6.89 (1H, s, 5-H), 7.68 (1H, br s, 2-H); $^{13}$C NMR (100 MHz, CDCl$_3$) δ 132.2, 132.8, 164.8, 167.8. The $^1$H and $^{13}$C NMR data obtained was in agreement with that reported from literature.[20]

3a-Bromo-4,7-dimethyl-5,6-diphenyl-3a,4,7,7a-tetrahydro-1H-4,7-methanoisoindole-1,3,8(2H)-trione (oCOm-7)

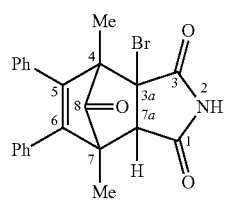

oCOm-7

A mixture of bromomaleimide 24 (200 mg, 1.13 mmol) and diene dimer 17 (355 mg, 0.68 mmol) in anhydrous toluene (6.6 mL) was heated to reflux under an argon atmosphere for 4.5 h. The reaction mixture was allowed to cool to rt and then concentrated in vacuo to obtain a brown oil. Purification by flash chromatography (0%, then 20%, then 30% EtOAc in petroleum ether) gave a 19:1 endo:exo mixture of title compound oCOm-7 (397 mg, 80%) as a pale yellow solid. R$_f$ (20% EtOAc in petroleum ether) 0.19; IR (ATR) v$_{max}$/cm$^{-1}$ 3247, 1780 (C=O), 1716 (C=O), 1442, 1327, 1201, 751, 698; HRMS (ESI-TOF) m/z: [M−H]$^-$ Calcd for C$_{23}$H$_{17}$$^{79}$BrNO$_3^-$ 434.0397, found 434.0405; RP-HPLC (10% to 100% B over 12.5 min, then 100% B for 2.5 min), t$_R$=13.14 min, endo- and exo-isomers co-elute as a single peak.

Endo-oCOm-7 NMR data: $^1$H NMR (500 MHz, CDCl$_3$) δ inter alia 1.60 (3H, s, CH$_3$), 1.62 (3H, s, CH$_3$), 3.54 (1H, s, H-7a), 6.91-6.95 (4H, m, Ph), 7.09-7.18 (6H, m, Ph), 8.93 (1H, br s, 2-H); $^{13}$C NMR (125 MHz, CDCl$_3$) δ inter alia 11.4, 12.2, 56.3, 59.6, 60.5, 61.5, 128.2, 128.3, 128.5, 129.3, 129.7, 132.3, 132.4, 140.4, 144.7, 172.3, 172.9, 196.7.

Exo-oCOm-7 NMR data: $^1$H NMR (500 MHz, CDCl$_3$) δ inter alia 1.38 (3H, s, CH$_3$), 1.49 (3H, s, CH$_3$), 3.39 (1H, s, H-7a), 7.04-7.06 (4H, m, Ph), 7.22-7.27 (6H, m, Ph), 8.44 (1H, br s); $^{13}$C NMR (125 MHz, CDCl$_3$) δ inter alia 8.0, 9.3, 60.3, 128.0, 128.2, 129.2, 129.4, 130.5, 197.1.

Example 8 oCOm-8

3a-Bromo-3a,4,7,7a-tetrahydro-4,7-dimethyl-2-(4-hydroxyphenyl)-5,6-di phenyl-4,7-methano-1H-isoindole-1,3,8(2H)-trione: Where R$^1$=R$^2$=Ph; R$^3$=R$^4$=Me; A$^3$=NR$^{14}$; R$^{14}$=pC$_6$H$_4$OH; X=Br Scheme 11: Synthesis of oCOm-8 and base promoted release of carbon monoxide forming BP-8

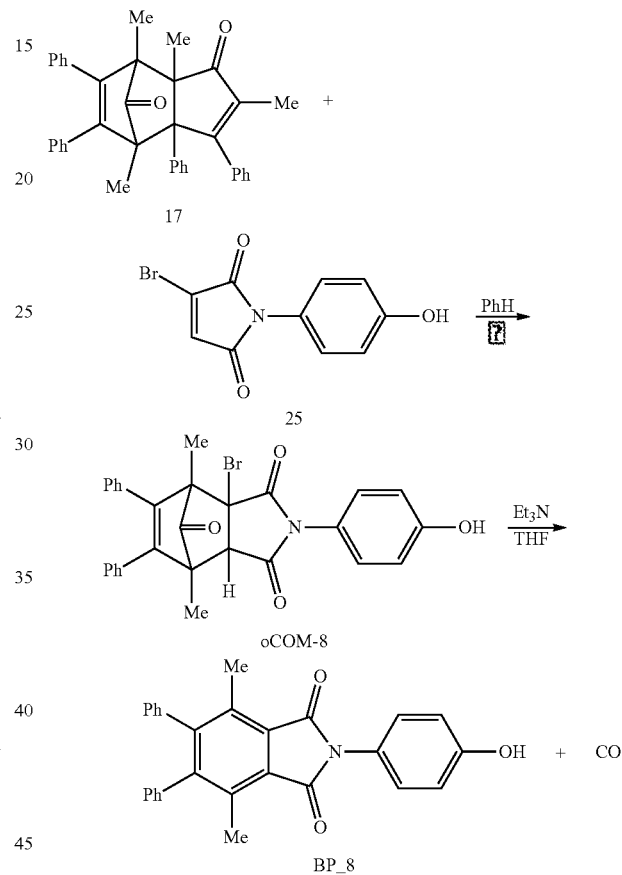

a) 1-(4-Hydroxyphenyl)-3-bromo-1H-pyrrole-2,5-dione (17) (Alternative Name: 2-Bromo-N-(4-hydroxyphenyl)-maleimide)

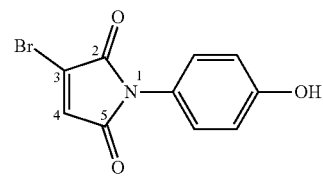

Bromomaleic anhydride (0.56 mL, 6.0 mmol) and p-aminophenol (927 mg, 1.12 mmol) were dissolved in acetic acid (10 mL), and stirred at r.t. overnight. The reaction mixture was then heated to reflux for 3 hours and concentrated to remove a portion of the acetic acid. Crystallisation of the product occurred, providing the title compound 25 (940 mg, 58%) as a yellow powder.

$R_f$=0.2 (4:1 petroleum ether:ethyl acetate); m.p. 229-233° C.; $^1$H NMR (500 MHz, CDCl$_3$,δ 4.90 (1H, s), 6.91 (2H, d, J=9.1 Hz), 7.01 (1H, s), 7.18 (2H, d, J=9.1 Hz); $^{13}$C NMR (125 MHz, CDCl$_3$): δ 116.1, 123.9, 127.9, 131.8, 131.9, 155.6, 164.5167.7; IR: $v_{max}$ 3367, 3109, 1705, 1597, 1516, 1452, 1248, 1151, 1047, 846, 824 cm$^{-1}$; HRMS-ESI: [M−H]$^-$ Calcd for C$_{10}$H$_5$$^{79}$BrNO$_3$$^-$ 265.9458, found 265.9499.

b) 3a-Bromo-3a,4,7,7a-tetrahydro-4,7-dimethyl-5,6-diphenyl-2-(4-hydroxyphenyl)-4,7-methano-1H-isoindole-1,3,8(2H)-trione (oCOm-8)

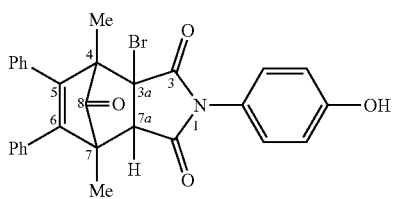

oCOM-8

Maleimide 25 (203 mg, 0.757 mmol) and diene 17 (199 mg, 0.764 mmol) were dissolved in toluene (10 mL), and refluxed for 3 hours. The reaction mixture was then concentrated and the residue purified by column chromatography (4:1 petroleum ether:ethyl acetate), to provide the title compound oCOm-8 (304 mg, 76%) an inseparable 3.5:1 mixture of endo- and exo-isomers in the form of a white solid. A portion of this material was recrystallised from ethanol to provide endo-oCOm-8 exclusively; all characterization was performed on this sample.

$R_f$=0.2 (4:1 petroleum ether:ethyl acetate); $^1$H NMR (500 MHz, CDCl$_3$): δ 1.65 (3H, s), 1.67 (3H, s), 3.65 (1H, s), 5.06 (1H, s), 6.87 (2H, dt, J=8.9, 2.8 Hz), 6.93-6.95 (4H, m), 7.09 (2H, dt, J=8.8, 2.8 Hz), 7.20-7.14 (6H, complex m); $^{13}$C NMR (125 MHz, CDCl$_3$): δ 11.7, 12.5, 56.8, 58.9, 60.3, 61.0, 116.3, 123.9, 127.6, 128.26, 128.31, 128.38, 128.44, 129.4, 129.8, 132.5, 132.6, 140.6, 144.7, 156.1, 171.6, 172.2, 196.8; IR: $v_{max}$ 3446, 3057, 2982, 2936, 1785, 1713, 1514, 1445, 1384, 1204, 755, 700 cm$^{-1}$; HRMS-ESI: [M+Na]$^+$ Calcd for C$_{29}$H$_{22}$$^{79}$BrNO$_4$Na$^+$ 550.0624, found 550.0583.

c) 2-(4-Hydroxyphenyl)-4,7-dimethyl-5,6-diphenyl-1H-isoindole-1,3(2H)-dione (BP-8) Alternative name: N-(4-Hydroxyphenyl)-3,6-dimethyl-4,5-diphenyl-phthalimide (67) (BP-8)

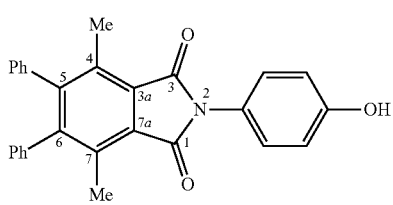

BP_8 oCOm-8 (117 mg, 0.221 mmol) was dissolved in THF (10 mL), treated with DBU (100 μL, 0.66 mmol) and the reaction mixture was stirred for 1 hour. After separation between ethyl acetate and 2 molL$^{-1}$ hydrochloric acid the organic fraction was concentrated to provide the title compound BP-8 (73 mg, 79%) as a white solid.

$R_f$=0.25 (4:1 petroleum ether:ethyl acetate); $^1$H NMR (500 MHz, CDCl$_3$): δ 2.46 (6H, s), 5.32 (1H, br s), 6.88-6.93 (6H, m), 7.12-7.20 (6H, m), 7.27 (2H, d, J=8.4 Hz); $^{13}$C NMR (125 MHz, CDCl$_3$): δ 15.9, 116.1, 124.6, 126.9, 127.9, 128.5, 129.6, 135.0, 138.7, 148.9, 155.5, 168.6S; IR: $v_{max}$ 3410, 3058, 3026, 2972, 2927, 1702, 1515, 1389, 759 cm$^{-1}$; HRMS-ESI: [M+Na]$^+$Calcd for C$_{28}$H$_{21}$NO$_3$Na$^+$ 442.1414, found 442.1430.

Example 9 oCOm-9 and oCOm-10 oCOm-10 3a-Bromo-3a,4,7,7a-tetrahydro-4,7-dimethyl-2-(3,4-dihydroxyphenyl)-5,6-diphenyl-4,7-methano-1H-isoindole-1,3,8(2H)-trione (oCOm-10): Where R$^1$=R$^2$=Ph; R$^3$=R$^4$=Me; A$^3$=NR$^{14}$; R$^{14}$=3,4-C$_6$H$_3$(OH)$_2$; X=Br Scheme 12: Synthesis of oCOm-10 and base promoted release of carbon monoxide forming BP-10

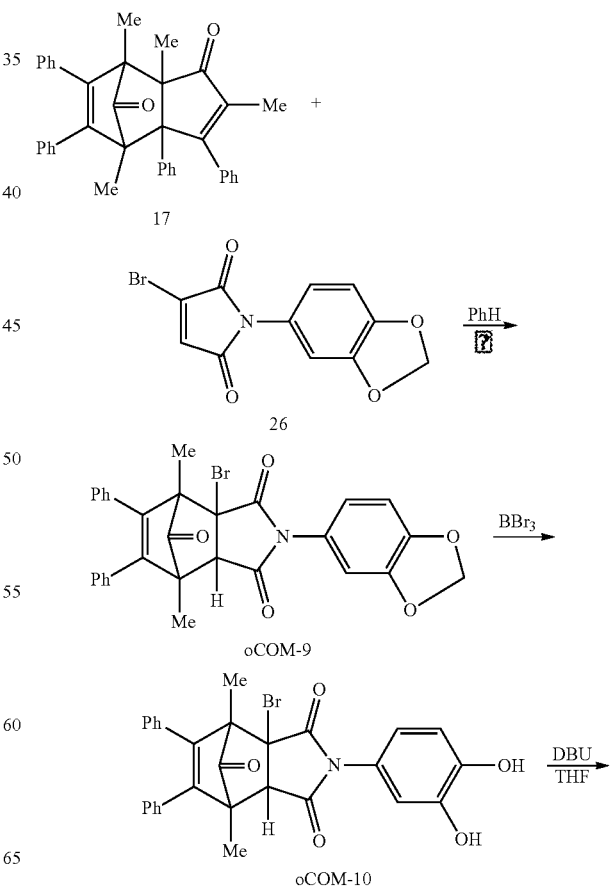

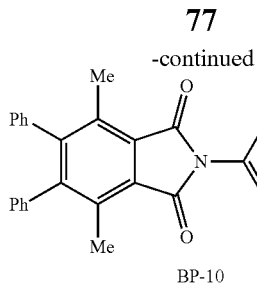

BP-10 a) 1-(3,4-(methylenedioxy)phenyl)-3-bromo-1H-pyrrole-2,5-dione (26) (Alternative Name: 2-Bromo-N-(3,4-(methylenedioxy)phenyl)-maleimide)

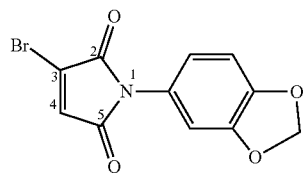

26

Bromomaleic anhydride (0.33 mL, 3.6 mmol) and 3,4-(methylenedioxy)aniline (515 mg, 3.76 mmol) were dissolved in acetic acid (40 mL), and stirred at r.t. overnight. The reaction mixture was then heated to reflux for 3 hours and concentrated. The residue was purified by column chromatography (5:1 to 2:1 petroleum ether:ethyl acetate), to afford the title compound 26 (726 mg, 68%) as a yellow powder.

$R_f$=0.4 (5:1 petroleum ether:ethyl acetate); m.p. 133-135° C.; $^1$H NMR (500 MHz, CDCl$_3$): δ 6.02 (2H, s), 6.76 (2H, dd, J=7.9, 2.0 Hz), 6.77 (1H, s), 6.87 (2H, dd, J=8.8, 1.7 Hz), 7.00 (1H, s); $^{13}$C NMR (125 MHz, CDCl$_3$): δ 101.9, 107.7, 108.5, 120.3, 124.8, 131.8, 131.9, 147.8, 148.2, 164.4, 167.6; IR: $v_{max}$ 3096, 2991, 2906, 2794, 1703, 1501, 1489, 1248, 1231, 990, 777 cm$^{-1}$; HRMS-ESI: [M–H]$^-$ Calcd for C$_{11}$H$_6$$^{79}$BrNO$_4$Na$^+$ 317.9372, found 317.9346. Anal. Calcd for C$_{11}$H$_6$BrNO$_4$: C, 44.62; H, 2.04; N, 4.73; Br, 26.99. Found: C, 44.90; H, 2.00; N, 4.69; Br, 26.93.

b) 3a-Bromo-3a,4,7,7a-tetrahydro-4,7-dimethyl-5,6-diphenyl-2-tri-(3,4-methylenedioxyphenyl)-4,7-methano-1H-isoindole-1,3,8(2H)-trione (oCOm-9)

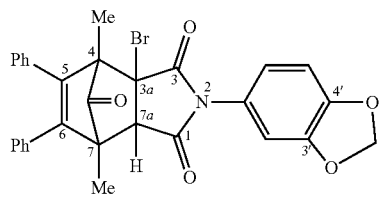

oCOm-9

Maleimide 26 (505 mg, 1.71 mmol) and diene dimer 17 (448 mg, 1.72 mmol) were dissolved in toluene (20 mL), and refluxed for 20 hours. The reaction mixture was then concentrated and the residue purified by column chromatography (5:1 petroleum ether:ethyl acetate), to provide the title compound oCOm-9 an inseparable 3:1 mixture of endo- and exo-isomers (676 mg, 71%) in the form of a pale-brown gum.

$R_f$=0.4 (5:1 petroleum ether:ethyl acetate); IR: $v_{max}$ 3061, 2982, 2894, 1782, 1716, 1487, 1241, 1035, 698 cm$^{-1}$; HRMS-ESI: [M+Na]$^+$ calcd for C$_{30}$H$_{22}$$^{79}$BrNO$_5$Na$^+$ 578.0574; found 578.0585.

NMR data for endo-oCOm-9: $^1$H NMR (500 MHz, CDCl$_3$): δ 1.65 (3H, s), 1.66 (3H, s), 3.65 (1H, s), 6.02 (2H, s), 6.67 (1H, s), 6.68 (1H, m), 6.85 (1H, d, J=8.9 Hz), 6.92-6.96 (4H, m), 7.15-7.21 (6H, m); $^{13}$C NMR (125 MHz, CDCl$_3$): δ 11.6, 12.5, 56.8, 58.9, 60.3, 61.0, 102.0, 107.3, 108.7, 120.2, 124.6, 128.30, 128.34, 128.4, 128.5, 129.4, 129.7, 132.46, 132.53, 140.5, 144.7, 148.30, 148.33, 171.5, 172.1, 196.8;

NMR data for exo-oCOm-9: $^1$H NMR (500 MHz, CDCl$_3$): δ inter alia 1.42 (3H, s), 1.52 (3H, s), 3.49 (1H, s); $^{13}$C NMR (125 MHz, CDCl$_3$): δ inter alia 8.3, 9.5, 59.1;

c) 3a-Bromo-3a,4,7,7a-tetrahydro-4,7-dimethyl-5,6-diphenyl-2-tri-(3,4-dihydoxyphenyl)-4,7-methano-1H-isoindole-1,3,8(2H)-trione (oCOm-10)

oCOm-9 (355 mg, 0.638 mmol) was dissolved in a freshly prepared solution of boron tribromide in dichloromethane (0.5 molL$^{-1}$, 4 mL) and stirred at 0° C. for 3 hours. The reaction mixture was quenched with methanol (1 mL), and stirred for 30 minutes, then diluted with water and extracted with dichloromethane. The organic fractions were concentrated, and the residue purified by column chromatography (3:1 to 1:1 petroleum ether:ethyl acetate), to provide the title compound oCOm-10 (273 mg, 79%) as an 8:1 mixture of endo- and exo-isomers in the form of a pale-brown solid.

$R_f$=0.25 (2:1 petroleum ether:ethyl acetate); IR: $v_{max}$ 3502, 3058, 2982, 2935, 1779, 1707, 1282, 1187, 739, 698 cm$^{-1}$; HRMS-ESI: [M+Na]$^+$ Calcd for C$_{29}$H$_{22}$$^{79}$BrNO$_5$Na$^+$ 566.0574, found 566.0597.

NMR data for endo-oCOm-10: $^1$H NMR (500 MHz, DMSO-d$_6$): δ 1.48 (3H, s), 1.51 (3H, s), 4.16 (1H, s), 6.44 (1H, d, J=8.5, 2.1 Hz), 6.60 (1H, d, J=2.8 Hz), 6.83 (1H, d, J=8.5 Hz), 6.93-6.94 (4H, m), 7.20-7.23 (6H, m), 9.42 (2H, d, J=6.3 Hz); $^{13}$C NMR (125 MHz, DMSO-d$_6$): δ 11.3, 11.8, 55.9, 58.3, 59.1, 60.4, 113.8, 115.6, 117.3, 122.1, 128.1, 128.2, 128.3, 129.1, 129.3, 132.3132.4, 139.6, 144.7, 145.7, 146.3, 171.6, 171.9, 196.5.

NMR data for exo-oCOm-10: $^1$H NMR (500 MHz, DMSO-d$_6$): δ inter alia 1.22 (3H, s), 1.35 (3H, s), 4.04 (1H, s).

d) 2-(4-Hydroxyphenyl)-4,7-dimethyl-5,6-diphenyl-1H-isoindole-1,3(2H)-dione (BP-10) (Alternative Name: N-(3,4-dihydroxyphenyl)-3,6-dimethyl-4,5-diphenyl-phthalimide)

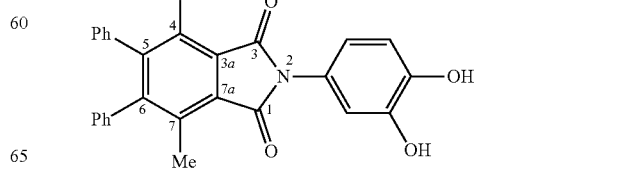

BP_10 oCOm-10 (167 mg, 0.307 mmol) was dissolved in THF (10 mL), then treated with DBU (100 µL, 0.66 mmol) and the reaction mixture was stirred for 1 hour. After separation between ethyl acetate and a solution of 2 molL$^{-1}$ aqueous hydrochloric acid the organic fraction was concentrated to provide the title compound BP-10 (71 mg, 53%) as a white solid.

$R_f$=0.3 (2:1 petroleum ether:ethyl acetate); $^1$H NMR (500 MHz, DMSO-$d_6$): δ2.33 (6H, s), 6.66 (2H, dd, J=8.3, 2.4 Hz), 6.79 (2H, d, J=2.4 Hz), 6.84 (2H, d, J=8.3 Hz), 6.99 (4H, d, J=7.0 Hz), 7.14 (2H, t, J=7.4 Hz), 7.21 (4H, t, J=7.4 Hz), 9.21 (2H, s); $^{13}$C NMR (125 MHz, DMSO-$d_6$): δ 15.3, 115.2, 115.4, 118.9, 123.1, 126.9, 127.6, 127.8, 129.3, 133.5, 138.4, 145.2, 145.4, 148.0, 167.8; IR: $v_{max}$ 3337, 2969, 2932, 2885, 1160, 1127, 1105, 950, 815 cm$^{-1}$; HRMS-ESI: [M−H]$^-$ Calcd for $C_{28}H_{20}NO_4^-$ 434.1398, found 434.1424.

Example 10 oCOm-11

3a-Bromo-3a,4,7,7a-tetrahydro-4,7-dimethyl-2-(4-hydroxy-3-nitrophenyl)-5,6-diphenyl-4,7-methano-1H-isoindole-1,3,8(2H)-trione: Where R$^1$=R$^2$=Ph; R$^3$=R$^4$=Me; A$^3$=NR$^{14}$; R$^{14}$=3,4-C$_6$H$_3$-(NO$_2$)-4-(OH); X=Br Scheme 13: Synthesis of oCOm-11 and base promoted release of carbon monoxide forming BP-11

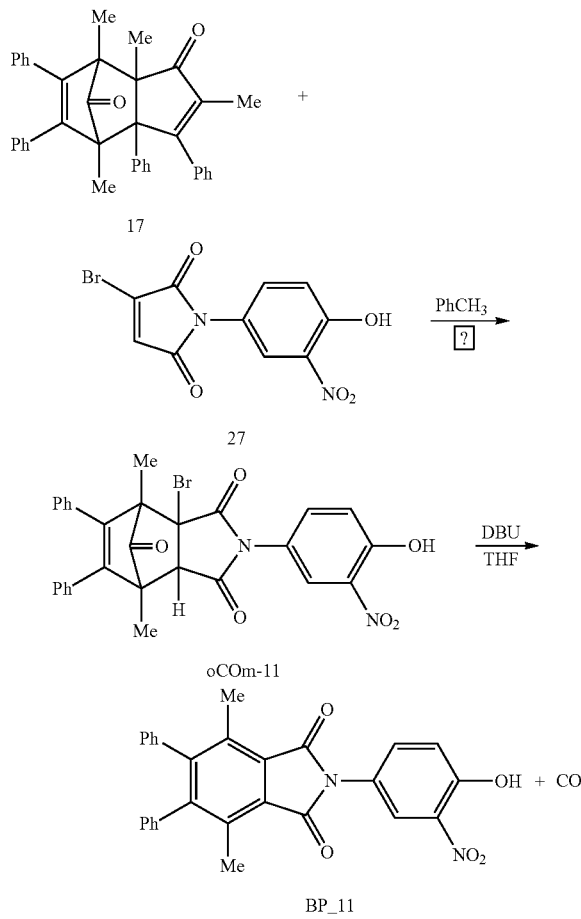

a) 3-Bromo-1-(4-hydroxy-3-nitrophenyl)-1H-pyrrole-2,5-dione (27) (Alternative Name: 2-Bromo-N-(4-hydroxy-3-nitrophenyl)maleimide)

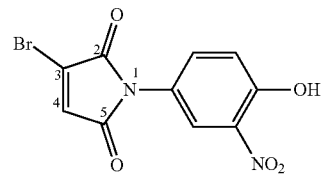

Bromomaleic anhydride (0.34 mL, 3.7 mmol) and 4-amino-2-nitrophenol (564 mg, 3.66 mmol) were dissolved in acetic acid (25 mL), and stirred at r.t. overnight. The reaction mixture was then heated to reflux for 3 hours and concentrated. Recrystallisation of the residue from ethanol provided the title compound 27 (729 mg, 64%) as a brown solid.

$R_f$=0.3 (5:1 petroleum ether:ethyl acetate); m.p. 138-140° C.; $^1$H NMR (500 MHz, CDCl$_3$): δ 7.06 (1H, s), 7.28 (1H, d, J=9.0 Hz), 7.61 (1H, dd, J=9.0, 2.6 Hz), 8.17 (1H, d, J=2.6 Hz), 10.63 (1H, s); $^{13}$C NMR (125 MHz, CDCl$_3$): δ 121.0, 122.6, 123.4, 132.1, 132.2, 133.4, 135.0, 154.6, 163.8, 166.8; IR: $v_{max}$ 3272, 3095, 1708, 1541, 1489, 1243, 1143, 1052, 787, 718, 641, 554 cm$^{-1}$; HRMS-ESI: [M−H]$^-$ Calcd for $C_{10}H_4^{79}BrN_2O_5^-$ 310.9309, found 310.9329.

b) 3a-Bromo-3a,4,7,7a-tetrahydro-4,7-dimethyl-5,6-diphenyl-2-tri-(4-hydoxy-3-nitrophenyl)-4,7-methano-1H-isoindole-1,3,8(2H)-trione (oCOm-11)

Maleimide 27 (365 mg, 1.17 mmol) and diene dimer 17 (312 mg, 1.20 mmol) were dissolved in toluene (50 mL), and refluxed for 5 hours. The reaction mixture was then concentrated and the residue purified by column chromatography (9:1 to 6:1 petroleum ether:ethyl acetate), to provide the title compound oCOm-11(540 mg, 81%) an 2.5:1 mixture of endo- and exo-isomers in the form of a bright yellow solid. A portion of this material was recrystallised from ethanol to provide endo-oCOm-11 exclusively; all characterization was performed on this sample.

$R_f$=0.4 (5:1 petroleum ether:ethyl acetate); m.p. 207° C. (decomposes); $^1$H NMR (500 MHz, CDCl$_3$): δ 1.695 (3H, s), 1.701 (3H, s), 3.70 (1H, s), 6.91 (4H, d, J=7.2 Hz), 7.17-7.23 (6H, m), 7.26 (1H, d, J=9.0 Hz), 7.52 (1H, d, J=9.0, 2.6 Hz), 8.12 (1H, d, J=2.6 Hz), 10.66 (1H, s); $^{13}$C NMR (125 MHz, CDCl$_3$): δ 11.7, 12.5, 56.9, 58.6, 60.4, 61.0, 121.2, 122.9, 123.3,128.49, 128.53, 128.54, 128.6, 129.3, 129.7, 132.2, 132.4, 133.4, 134.7, 140.5, 144.6, 155.0, 171.1, 171.5, 196.5; IR: $v_{max}$ 3492, 3211, 3053, 2982, 2934, 1793, 1721, 1174, 698 cm$^{-1}$; HRMS-ESI: [M−H]$^-$ Calcd for $C_{29}H_{20}^{79}BrN_2O_6^-$ 571.0510, found 571.0536.

Anal. Calcd for $C_{29}H_{21}BrN_2O_6$: C, 60.75; H, 3.69; N, 4.89; Br, 13.94. Found: C, 60.86; H, 3.70; N, 4.68; Br, 14.60.

c) 2-(4-Hydroxy-3-nitrophenyl)-4,7-dimethyl-5,6-diphenyl-1H-isoindole-1,3(2H)-dione (BP-11) (Alternative Name: N-(4-hydroxy-3-nitrophenyl)-3,6-dimethyl-4,5-diphenyl-phthalimide)

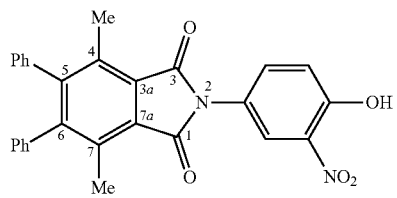

BP_11 oCOm-11 (161 mg, 0.281 mmol) was dissolved in THF (10 mL), then treated with DBU (100 µL, 0.66 mmol) and the reaction mixture was stirred for 1 hour. The reaction mixture was concentrated, then purified by filtration through a silica plug with chloroform elution, to provide the title compound BP-11 (77 mg, 59%) as a yellow solid.

$R_f$=0.55 (5:1 petroleum ether:ethyl acetate); m.p. >250° C.; $^1$H NMR (500 MHz, CDCl$_3$): δ 2.46 (6H, s), 6.91 (1H, d, J=7.0 Hz), 7.14 (2H, m), 7.19 (4H, apparent t, J=7.0 Hz), 7.31 (1H, d, J=8.5 Hz), 7.74 (1H, dd, J=8.9, 2.6 Hz), 8.29 (1H, d, J=2.1 Hz), 10.66 (1H, s); $^{13}$C NMR (125 MHz, CDCl$_3$): δ 15.9, 120.6, 123.2, 124.5, 127.1, 127.5, 127.9, 129.5, 133.4, 135.4, 136.0, 138.5, 149.4, 154.3, 167.7; IR: $v_{max}$ 3287, 3097, 3030, 2919, 1707, 1537, 1488, 1396, 1316, 1251, 1162, 1115, 759, 698 cm$^{-1}$; HRMS-ESI: [M–H]$^-$ Calcd for $C_{28}H_{19}N_2O_5^-$ 463.1299, found 463.1264.

Example 11 oCOm-12

3a-Bromo-3a,4,7,7a-tetrahydro-4,7-dimethyl-2-(4-(2-(2-(2-methoxyethoxy)ethoxy)ethoxy)phenyl)-5,6-diphenyl-4,7-methano-1H-isoindole-1,3,8(2H)-trione: Where $R^1$=$R^2$=Ph; $R^3$=$R^4$=Me; $A^3$=NR$^{14}$; $R^{14}$=p-$C_6H_4O(CH_2CH_2O)_3CH_3$; X=Br Scheme 14: Synthesis of oCOm-12 and base promoted release of carbon monoxide forming BP-12

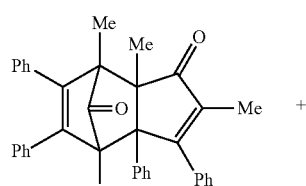

17

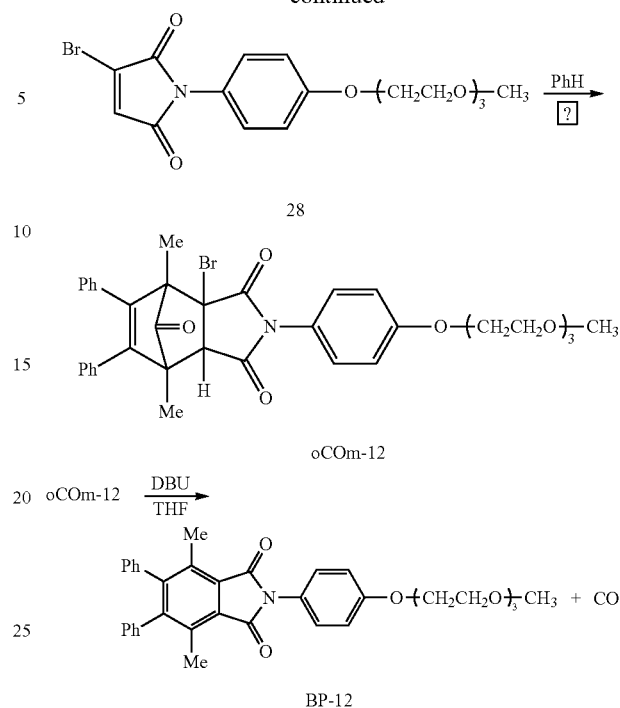

a) 1-(4-(2-(2-(2-Methoxyethoxy)-ethoxy)ethoxy)phenyl)-3-bromo-1H-pyrrole-2,5-dione (28) (Alternative Name: 2-Bromo-N-(4-(2-(2-(2-methoxyethoxy)ethoxy)ethoxy)phenyl)maleimide)

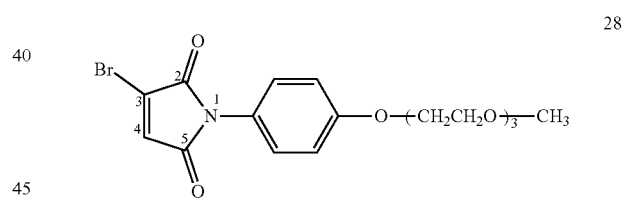

28

A solution of bromomaleic anhydride (0.23 mL, 2.5 mmol) and 4-(2-(2-(2-methoxyethoxy)ethoxy)ethoxy)aniline$^{21}$ (588 mg, 2.30 mmol) in acetic acid (6 mL), was stirred at r.t. overnight. The reaction mixture was then heated to reflux for 3 hours and concentrated. The residue was purified by column chromatography (1:1 petroleum ether:ethyl acetate), to provide maleimide 28 (691 mg, 72%) as a yellow oil.

$R_f$=0.25 (1:1 petroleum ether:ethyl acetate); $^1$H NMR (500 MHz, CDCl$_3$): δ 3.37 (3H, s), 3.54 (2H, m), 3.64-3.69 (4H, m), 3.73 (2H, t, J=4.7 Hz), 3.86 (2H, t, J=4.7 Hz), 4.14 (2H, t, J=4.9 Hz), 6.98 (2H, d, J=9.3 Hz), 6.99 (1H, s), 7.20 (2H, d, J=9.3 Hz); $^{13}$C NMR (125 MHz, CDCl$_3$): δ 59.1, 67.8, 69.6, 70.6, 70.7, 70.9, 72.0, 115.3, 123.8, 127.6, 131.7, 131.9, 158.7, 164.5, 167.7; IR: $v_{max}$ 2874, 1708, 1519, 1145, 1105, 1048 cm$^{-1}$; HRMS-ESI: [M+Na]$^+$ calcd for $C_{17}H_{20}^{79}BrNO_6Na^+$ 436.0366, found 436.0372. Anal. Calcd for $C_{17}H_{20}BrNO_6$: C, 49.29; H, 4.87; N, 3.38; Br, 19.29. Found: C, 49.59; H, 5.00; N, 3.47; Br, 18.75.

b) 3a-Bromo-3a,4,7,7a-tetrahydro-4,7-dimethyl-2-(4-(2-(2-(2-methoxyethoxy)ethoxy)ethoxy)phenyl)-5,6-diphenyl-4,7-methano-1H-isoindole-1,3,8(2H)-trione (oCOm-12) (Alternative Name: 2a-Bromo-N-(4-(2-(2-(2-methoxyethoxy)ethoxy)ethoxy)phenyl)-3,6-dimethyl-4,5-diphenyl-2a,3,6,6a-tetrahydro-3,6-methanophthalimide-8-one)

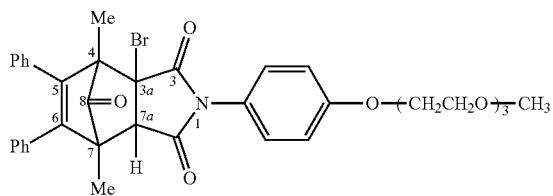

oCOm-12

Maleimide 28 (220 mg, 0.53 mmol) and diene dimer 17 (150 mg, 0.58 mmol) were dissolved in toluene (2 mL), and refluxed for 1.5 hours. The reaction mixture was then concentrated and the residue purified by column chromatography (1:1 petroleum ether:ethyl acetate), to provide the title compound oCOm-12 (312 mg, 87%) as a 5:1 inseparable mixture of endo- and exo-isomers in the form of a pale-yellow oil.

$R_f$=0.25 (1:1 petroleum ether:ethyl acetate); IR: $v_{max}$ 2932, 2874, 1784, 1717, 1509, 1251, 1196, 1167, 1105, 699 cm$^{-1}$; HRMS-ESI: [M+Na]$^+$ calcd for $C_{36}H_{36}{}^{79}BrNO_7Na^+$ 696.1653; found 696.1617. Anal. Calcd for $C_{36}H_{36}BrNO_7$: C, 64.10; H, 5.38; N, 2.08; Br, 11.85. Found: C, 64.30; H, 5.22; N, 1.97; Br, 12.32.

NMR data for endo-oCOm-12: $^1$H NMR (500 MHz, CDCl$_3$): δ 1.65 (3H, s), 1.66 (3H, s), 3.37 (3H, s), 3.55 (2H, m), 3.65 (1H, s), 3.64-3.69 (4H, m), 3.73 (2H, m), 3.86 (2H, t, J=4.8 Hz), 4.14 (2H, t, J=4.9 Hz), 6.92-7.33 (14H, m); $^{13}$C NMR (125 MHz, CDCl$_3$): δ 11.6, 12.5, 56.8, 59.0, 59.1, 60.3, 61.0, 67.8, 69.6, 70.65, 70.72, 70.9, 72.0, 115.4, 123.9, 127.3, 128.2, 128.3, 128.36, 128.42, 129.4, 129.8, 132.5, 132.6, 140.6, 144.7, 159.1, 171.5, 172.1, 196.9.

NMR data for exo-oCOm-12: $^1$H NMR (500 MHz, CDCl$_3$): δ inter alia 1.42 (3H, s), 1.52 (3H, s),3.50 (1H, s); $^{13}$C NMR (125 MHz, CDCl$_3$): δ inter alia 8.3, 9.5, 59.1.

c) 2-(4-(2-(2-(2-Methoxyethoxy)ethoxy)ethoxy)phenyl)-4,7-dimethyl-5,6-diphenyl-1H-isoindole-1,3(2H)-dione (BP-12) N-(4-(2-(2-(2-Methoxyethoxy)ethoxy)ethoxy)phenyl)-3,6-dimethyl-4,5-diphenyl-phthalimide (BP-12)

BP-12

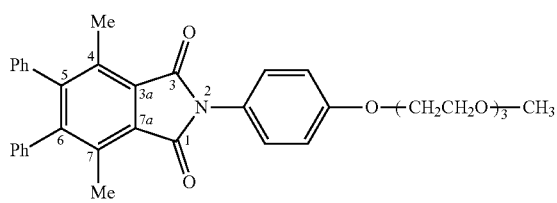

triethylamine (18 µL, 0.19 mmol), and stirred at r.t. for 30 minutes. The reaction was accelerated via addition of DBU (20 µL, 0.13 mmol), in which full completion was observed after 15 minutes stirring at r.t. The reaction mixture was separated between ethyl acetate and 2 molL$^{-1}$ hydrochloric acid, then the organic phase was dried, filtered and concentrated. The residue was purified by column chromatography (1:1 petroleum ether:ethyl acetate), to provide the title compound BP-12 (42 mg, 70%) as an off-white solid.

$R_f$=0.3 (1:1 petroleum ether:ethyl acetate); m.p. 127-129° C.; $^1$H NMR (500 MHz, CDCl$_3$): δ 2.45 (6H, s), 3.39 (3H, s), 3.56 (2H, m), 3.66-3.71 (4H, m), 3.75 (2H, m), 3.89 (2H, t, J=4.9 Hz), 4.18 (2H, t, J=4.9 Hz), 6.92 (2H, d, J=8.3 Hz), 7.04 (2H, d, J=8.8 Hz), 7.11-7.19 (6H, m), 7.34 (2H, d, J=8.8 Hz); $^{13}$C NMR (125 MHz, CDCl$_3$): δ 15.8, 59.1, 67.8, 69.7, 70.65, 70.73, 70.9, 72.0, 115.1, 124.9, 126.9, 127.8, 127.9, 128.2, 129.6, 134.9, 138.8, 148.8, 158.4, 168.4; IR: $v_{max}$ 2874, 1702, 1512, 1382, 1248, 1118, 1104, 760, 702 cm$^{-1}$; HRMS-ESI: [M+Na]$^+$ calcd for $C_{35}H_{35}NO_6Na^+$ 588.2357, found 588.2369. Anal. Calcd for $C_{35}H_{35}NO_6$: C, 74.32; H, 6.24; N, 2.48. Found: C, 74.11; H, 6.21; N, 2.36.

Example 12 oCOm-13

Pegylated CO Releasing Compound Where $R^1$=$R^2$=Ph; $R^3$=$R^4$=Me; $A^3$=NR$^{14}$; $R^{14}$=p-$C_6H_4$O(CH$_2$CH$_2$O)$_n$CH$_3$ (n$_{average}$=16); X=Br Scheme 15: Synthesis of oCOm-13 and base promoted release of carbon monoxide forming BP-13

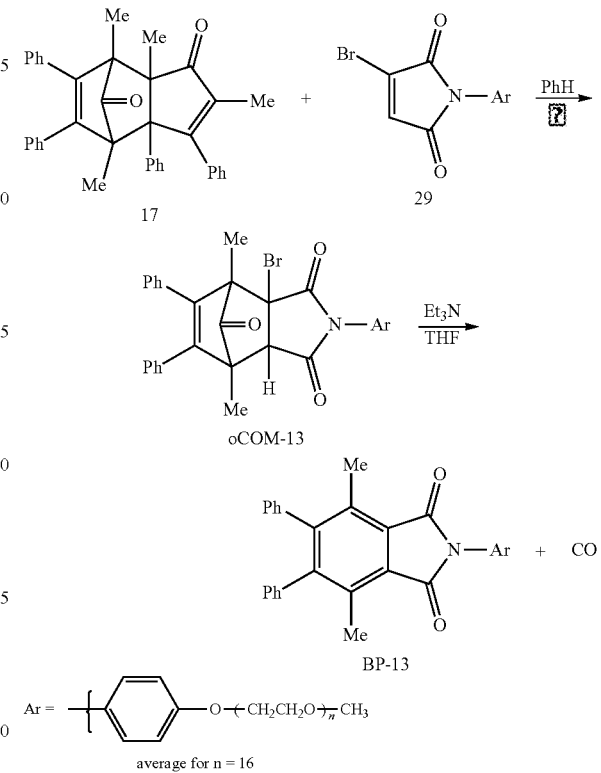

average for n = 16 a) Poly(ethylene glycol) tosylate (30)

TsO—(CH$_2$CH$_2$O)$_n$CH$_3$ average for n=16     (30)

A solution of poly(ethylene glycol) monomethyl ether (CAS #9004-74-4 average MW=750 g mol$^{-1}$, 7.95 g, 10.8 mmol) and triethylamine (4.2 mL, 30 mmol) in dichloromethane (100 mL) was cooled to 0° C., then treated with tosyl chloride (2.47 g, 13.0 mmol) and stirred for one day at r.t. Diethyl ether was added (100 mL), then the solution was filtered to remove the precipitated triethylammonium salt. Concentration of the solution and purification by column chromatography (ethyl acetate) provided tosylate 30 (5.05 g, 53%) as a pale yellow oil.

$R_f$=0.6 (1:9 methanol:chloroform); $^1$H NMR (500 MHz, CDCl$_3$): δ 2.45 (3H, s), 3.38 (3H, s), 3.55 (2H, dd, J=5.9, 3.9 Hz), 3.58 (4H, s), 3.61-3.66 (54H, m), 3.68 (2H, t, J=4.9 Hz), 4.16 (2H, t, J=5.0 Hz), 7.34 (2H, d, J=8.4 Hz), 7.80 (2H, d, J=7.8 Hz); $^{13}$C NMR (125 MHz, CDCl$_3$): δ 21.7, 59.1, 68.8, 69.3, 70.59, 70.64, 70.7, 70.8, 72.0, 128.1, 129.9, 133.1, 144.8; IR: $v_{max}$ 2897, 2861, 1341, 1086, 1059 cm$^{-1}$; HRMS-ESI: [M+Na]$^+$ Calcd for C$_{40}$H$_{74}$O$_{19}$SNa$^+$ 913.4437, found 913.4454. Anal. Calcd for C$_{40}$H$_{74}$O$_{19}$S: C, 53.92; H, 8.37. Found: C, 53.65; H, 8.53.

b) 1-Nitro-4-O-(Poly(ethylene glycol))benzene (31)

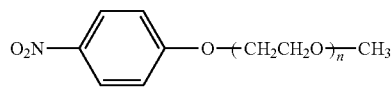

average for n = 16

A solution of tosylate 30 (7.72 g, 8.66 mmol) and p-nitrophenol (1.40 g, 10.1 mmol) in acetonitrile (120 mL) was treated with potassium carbonate (1.88 g, 13.6 mmol) then refluxed overnight. The reaction mixture was concentrated, then separated between dichloromethane (120 mL) and water (120 mL), then the aqueous phase was extracted further with dichloromethane (2×120 mL). The combined organic fractions were concentrated, then purified by column chromatography (10:1 to 1:3 petroleum ether:ethyl acetate to 1:9 methanol:chloroform) to provide nitrobenzene derivative 31 (4.62 g, 54%) as a pale yellow oil.

$R_f$=0.6 (1:9 methanol:chloroform); $^1$H NMR (500 MHz, CDCl$_3$): δ 3.37 (3H, s), 3.58 (2H, m), 3.64-3.68 (56H, m), 3.72 (2H, m), 3.89 (2H, t, J=4.7 Hz), 4.22 (2H, t, J=4.8 Hz), 6.98 (2H, dd, J=7.1, 2.1 Hz), 8.19 (2H, dd, J=7.1, 2.2 Hz); $^{13}$C NMR (125 MHz, CDCl$_3$): δ 59.1, 68.1, 68.3, 69.4, 70.58, 70.64, 70.67, 70.70, 71.0, 72.0, 114.7, 125.9, 141.7, 163.9; IR: $v_{max}$ 2917, 2851, 1592, 1512, 1462, 1341, 1258, 1104, 1027, 859 cm$^{-1}$; HRMS-ESI: [M+Na]$^+$ Calcd for C$_{39}$H$_{71}$NO$_{19}$Na$^+$ 880.4513, found 880.4520. Anal. Calcd for C$_{39}$H$_{71}$NO$_{19}$: C, 54.60; H, 8.34; N, 1.63. Found: C, 54.72; H, 8.51; N, 1.57.

c) 4-O-(Poly(ethylene glycol))aniline (32)

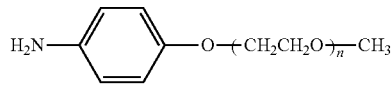

average for n = 16

A solution of nitrobenzene derivative 31 (4.60 g, 5.36 mmol) in ethyl acetate (80 mL) was treated with 5% (w/w) palladium on carbon (300 mg, 0.141 mmol) then charged with an atmosphere of hydrogen and stirred for 3 hours. The reaction mixture was filtered through a pad of Celite®, and concentrated, then purified by column chromatography (1:9 methanol:chloroform) to provide amine 32 (4.26 g, 80%) as a pale yellow oil.

$R_f$=0.5 (1:9 methanol:chloroform); $^1$H NMR (500 MHz, CDCl$_3$): δ 3.38 (3H, s), 3.55 (2H, m), 3.64-3.68 (56H, m), 3.71 (2H, m), 3.81 (2H, t, J=4.8 Hz), 4.05 (2H, t, J=4.9 Hz), 6.64-6.67 (4H, m), 6.76 (2H, d, J=8.8 Hz); $^{13}$C NMR (125 MHz, CDCl$_3$): δ 59.1, 68.2, 70.0, 70.59, 70.64, 70.68, 70.70, 70.9, 72.0, 116.0, 116.2, 116.7, 117.0; IR: $v_{max}$ 2866, 1511, 1455, 1345, 1281, 1238, 1096, 947 841 cm$^{-1}$; HRMS-ESI: [M+Na]$^+$ Calcd for C$_{39}$H$_{73}$NO$_{17}$Na$^+$ 850.4771, found 850.4792. Anal. Calcd for C$_{39}$H$_{73}$NO$_{17}$: C, 56.57; H, 8.89; N, 1.69. Found: C, 55.99; H, 8.81; N, 1.72.

d) 1-(4-(methoxy-polyetheneglycyloxy)phenyl)-3-bromo-1H-pyrrole-2,5-dione (29) (Alternative Name: 2-Bromo-N-(4-0-(poly(ethylene glycol methyl ether))phenyl)-maleimide)

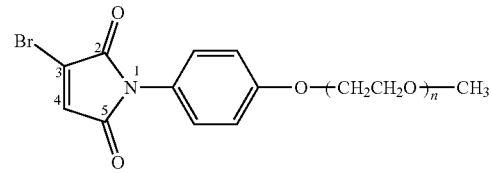

average for n = 16

Bromomaleic anhydride (0.15 mL, 1.6 mmol) and aniline 32 (927 mg, 1.12 mmol) were dissolved in acetic acid (10 mL), and stirred at r.t. overnight. The reaction mixture was then heated to reflux for 3 hours and concentrated. The residue was purified by column chromatography (0% to 4% methanol in chloroform) to provide the title compound 29 (818 mg, 74%) as a pale yellow oil.

$R_f$=0.6 (1:9 methanol:chloroform); $^1$H NMR (500 MHz, CDCl$_3$): δ 3.37 (3H, s), 3.54 (2H, t, J=4.7 Hz), 3.63-3.68 (56H, m), 3.72 (2H, m), 3.86 (2H, t, J=4.9 Hz), 4.14 (2H, t, J=4.9 Hz), 6.99 (2H, d, J=9.2 Hz), 7.00 (1H, s), 7.21 (2H, d, J=9.2 Hz); $^{13}$C NMR (125 MHz, CDCl$_3$): δ 59.1, 67.8, 69.7, 70.57, 70.63, 70.67, 70.70, 70.9, 72.0, 115.3, 123.8, 127.6, 131.8, 131.9, 158.7, 164.5, 167.7; IR: $v_{max}$ 2868, 1721, 1513, 1455, 1392, 1250, 1104, 948 848 cm$^{-1}$; HRMS-ESI: [M+Na]$^+$ Calcd for C$_{43}$H$_{72}$$^{79}$BrNO$_{19}$Na$^+$ 1008.3774, found 1008.3793. Anal. Calcd for C$_{43}$H$_{72}$BrNO$_{19}$: C, 52.33; H, 7.35; N, 1.42; Br, 8.10. Found: C, 52.18; H, 7.18; N, 1.67; Br, 8.40.

e) 3a-Bromo-3a,4,7,7a-tetrahydro-4,7-dimethyl-5,6-diphenyl-2-tri-(4-(poly(ethylene glycol methyl ether)phenyl)-4,7-methano-1H-isoindole-1,3,8(2H)-trione (oCOm-13)

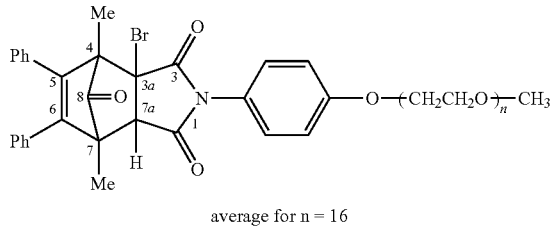

average for n = 16

Maleimide 29 (113 mg, 0.114 mmol) and diene 7 (51 mg, 0.196 mmol) were dissolved in toluene (3 mL), and refluxed for 4 hours. The reaction mixture was then concentrated and the residue purified by column chromatography (0% to 10% methanol in chloroform), to provide the title compound oCOm-13 (103 mg, 72%) as a 4:1 mixture of endo- and exo-isomers in the form of a pale-yellow oil.

$R_f$=0.6 (1:9 methanol:chloroform); NMR data for endo-oCOm-13: $^1$H NMR (500 MHz, CDCl$_3$): δ 1.64 (3H, s), 1.66 (3H, s), 3.37 (3H, s), 3.54 (2H, t, J=4.9 Hz), 3.60-3.68 (57H, m), 3.72 (2H, m), 3.85 (2H, t, J=4.7 Hz), 4.13 (2H, t, J=4.9 Hz), 6.92-7.01 (7H, m), 7.11-7.20 (7H, m), 4; $^{13}$C NMR (125 MHz, CDCl$_3$): δ 11.6, 12.5, 56.8, 58.9, 59.1, 60.3, 61.0, 67.8, 69.6, 70.59, 70.64, 70.68, 70.70, 70.9, 72.0, 115.4, 123.9, 127.3, 128.2, 128.3, 128.35, 128.41, 129.4, 129.8, 132.5, 132.6, 140.6, 144.7, 159.1, 171.5, 172.1, 196.9; IR: $v_{max}$ 2866, 1785, 1720, 1511, 1251, 1099, 947, 701 cm$^{-1}$; NMR data for exo-oCOm-13: $^1$H NMR (500 MHz, CDCl$_3$): δ inter alia 3.49 (1H, s), 1.52 (3H, s), 1.42 (3H, s); $^{13}$C NMR (125 MHz, CDCl$_3$): δ inter alia 9.5, 8.3; HRMS-ESI: [M+Na]$^+$ Calcd for C$_{62}$H$_{88}$$^{79}$BrNO$_{20}$Na$^+$ 1268.4975, found 1268.5019. Anal. Calcd for C$_{62}$H$_{88}$BrNO$_{20}$: C, 59.70; H, 7.11; N, 1.12; Br, 6.41. Found: C, 59.17; H, 7.31; N, 1.08; Br, 5.07.

f) 2-(4-(2-(2-(2-Methoxyethoxy)ethoxy)ethoxy)phenyl)-4,7-dimethyl-5,6-diphenyl-1H-isoindole-1,3 (2H)-dione (BP-13) (Alternative Name: N-(4-O-(poly(ethylene glycol))phenyl)-3,6-dimethyl-4,5-diphenyl-phthalimide)

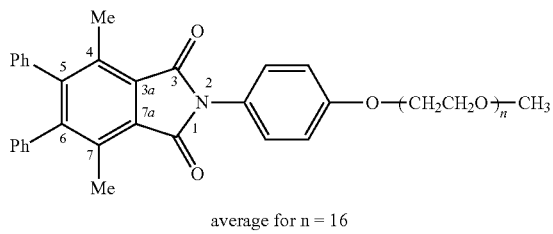

average for n = 16 oCOm-13 (136 mg, 0.109 mmol) was dissolved in THF (3 mL), then treated with DBU (50 µL, 0.33 mmol) and the reaction mixture was stirred for 2 hours. After separation between ethyl acetate and 2 molL$^{-1}$ hydrochloric acid, the organic fraction was concentrated, then purified by column chromatography (1:9 methanol:chloroform), to provide the title compound BP-13 (106 mg, 85%) as a pale yellow oil.

$R_f$=0.6 (1:9 methanol:chloroform); $^1$H NMR (500 MHz, CDCl$_3$): δ 2.45 (6H, s), 3.37 (3H, s), 3.54 (2H, m), 3.63-3.70 (56H, m), 3.74 (2H, m), 3.88 (2H, t, J=4.9 Hz), 4.18 (2H, t, J=4.4 Hz), 6.91 (4H, dt, J=6.9, 1.5 Hz), 7.04 (2H, dt, J=8.8, 2.0 Hz), 7.13 (2H, dt, J=7.3, 1.8 Hz), 7.15-7.19 (4H, m), 7.33 (2H, dt, J=8.8, 2.0 Hz); $^{13}$C NMR (125 MHz, CDCl$_3$): δ 15.8, 59.1, 67.8, 69.7, 70.58, 70.63, 70.67, 70.70, 70.9, 72.0, 115.1, 124.9, 126.9, 127.8, 127.9, 128.2, 129.6, 134.9, 138.8, 148.8, 158.4, 168.4; IR: $v_{max}$ 2866, 1707, 1512, 1249, 1097 cm$^{-1}$; HRMS-ESI: [M+Na]$^+$ Calcd for C$_{61}$H$_{87}$NO$_{19}$Na$^+$ 1160.5765, found 1160.5726. Anal. Calcd for C$_{61}$H$_{87}$NO$_{19}$: C, 64.36; H, 7.70; N, 1.23. Found: C, 64.34; H, 7.80; N, 1.28.

Example 13 oCOm-14

3a-Bromo-3a,4,7,7a-tetrahydro-4,7-dimethyl-2-(4-(2,3,4,6-tetra-O-acetyl-β-D-glucopyranosyloxy)phenyl)-5,6-diphenyl-4,7-methano-1H-isoindole-1,3,8 (2H)-trione: R$^1$=R$^2$=Ph; R$^3$=R$^4$=Me; A$^3$=NR$^{14}$; R$^{14}$=pC$_6$H$_4$-O-β-D-Glc(OAc)$_4$; X=Br Scheme 16: Synthesis of oCOm-14 and base promoted release of carbon monoxide forming BP-14

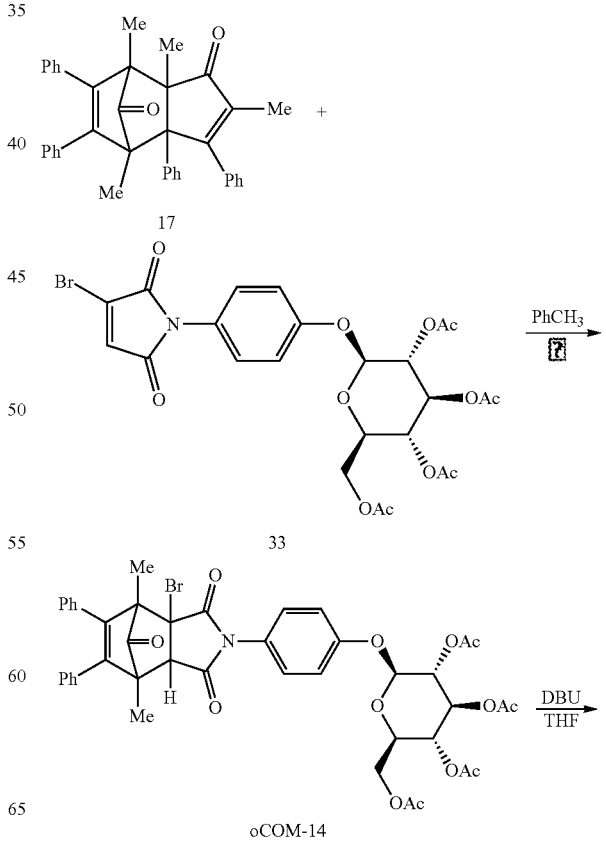

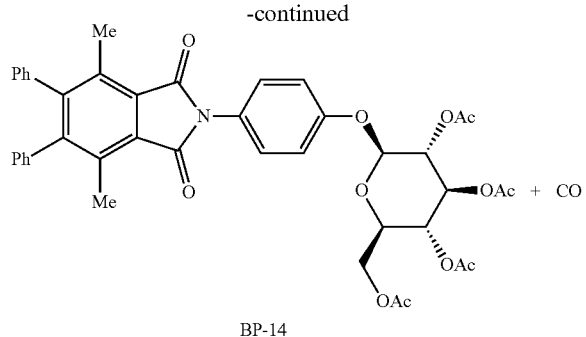

BP-14 a) 3-Bromo-1-(-(2,3,4,6-tetra-O-acetyl-β-D-glucopyranosyloxy)phenyl)-1H-pyrrole-2,5-dione (33) (Alternative Name: 2-Bromo-N-(4-(2,3,4,6-tetra-O-acetyl-β-D-glucopyranosyloxy)phenyl)-maleimide)

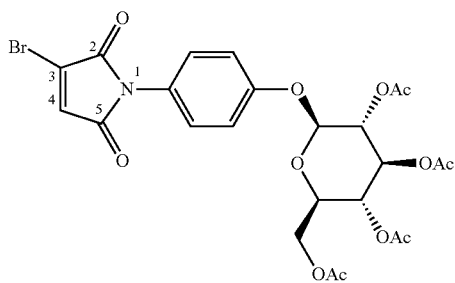

33

4-(2,3,4,6-Tetra-O-acetyl-β-D-glucopyranosyloxy)aniline[22] (120 mg, 0.273 mmol) was dissolved in acetic acid (10 mL) then treated with bromomaleic anhydride (30 μL, 0.32 mmol) and stirred at r.t. overnight. The mixture was then refluxed for 3 hours, then concentrated. The residue was passed through a silica plug, which was eluted with chloroform to provide the title compound 33 (154 mg, 94%) as a pale-brown solid.

$R_f$=0.3 (2:1 petroleum ether:ethyl acetate); m.p. 203-204° C.; $[\alpha]_D^{22}$-10.2 (c 1.0 CHCl$_3$); $^1$H NMR (500 MHz, CDCl$_3$): δ 2.04 (3H, s), 2.05 (3H, s), 2.06 (3H, s), 2.07 (3H, s), 3.87 (1H, ddd, J=9.8, 5.4, 2.5 Hz), 4.17 (1H, dd, J=12.2, 2.4 Hz), 4.29 (1H, dd, J=12.5, 5.4 Hz), 5.10 (1H, d, J=7.8 Hz), 5.17 (1H, t, J=9.7 Hz), 5.26-5.32 (2H, m), 7.02 (1H, s), 7.08 (2H, dd, J=9.0, 2.3 Hz), 7.26 (2H, dd, J=9.3, 2.3 Hz); $^{13}$C NMR (125 MHz, CDCl$_3$): δ 20.65, 20.67, 20.69, 20.8, 62.0, 68.3, 71.2, 72.2, 72.7, 99.0, 117.7, 126.2, 127.6, 131.91, 131.94, 156.5, 164.3, 167.5, 169.3, 169.4, 170.3, 170.6; IR: $v_{max}$ 3089, 2963, 1748, 1736, 1713, 1513, 1222, 1070, 1042, 844, 782 cm$^{-1}$; HRMS-ESI: [M+Na]$^+$ Calcd for C$_{24}$H$_{24}$BrNO$_{12}$Na$^+$ 620.0360, found 620.0374. Anal. Calcd for C$_{24}$H$_{24}$BrNO$_{12}$: C, 48.18; H, 4.04; N, 2.34; Br, 13.35. Found: C, 48.46; H, 4.08; N, 2.46; Br, 12.99.

b) 3a-Bromo-3a,4,7,7a-tetrahydro-4,7-dimethyl-2-(4-(2,3,4,6-tetra-O-acetyl-b-D-glucopyranosyloxy)phenyl)-5,6-diphenyl-4,7-methano-1H-isoindole-1,3,8(2H)-trione (oCOm-14) (Alternative Name: 2a-Bromo-N-(4-O-(2,3,4,6-tetra-O-acetyl-β-D-glucopyranosyl)phenyl)-3,6-dimethyl-4,5-diphenyl-2a, 3,6,6a-tetrahydro-3,6-methanophthalimide-8-one)

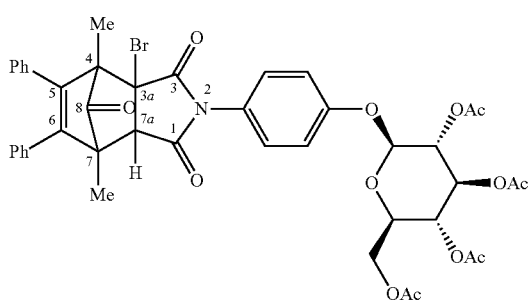

oCOm-14

Maleimide 33 (383 mg, 0.640 mmol) and diene dimer 17 (160 mg, 0.615 mmol) were dissolved in toluene (20 mL) and refluxed for 4 hours. The reaction mixture was concentrated, and the residue purified by column chromatography (2:1 petroleum ether:ethyl acetate), to provide the title compound oCOm-14 (361 mg, 68%) as a 3.5:1 mixture of endo- and exo-isomers in the form of a pale-brown solid.

$R_f$=0.4 (2:1 petroleum ether:ethyl acetate); m.p. 116-119° C.; NMR data for endo-98: $^1$H NMR (500 MHz, CDCl$_3$): δ 1.65 (3H, s), 1.67 (3H, s), 2.02 (3H, d, J=3.0 Hz), 2.04 (3H, s), 2.05 (3H, s), 2.06 (3H, s), 3.66 (1H, s), 3.86 (1H, d, J=10.0, 5.4, 2.4 Hz), 4.16 (1H, dd, J=12.2, 2.2 Hz), 4.28 (1H, dt, J=12.2, 4.9 Hz), 5.10 (1H, d, J=5.4 Hz), 5.17 (1H, apparent t, J=9.4 Hz), 5.32-5.26 (2H, complex m), 6.91-6.93 (4H, m), 7.06 (2H, d, J=9.0 Hz), 7.14-7.20 (8H, m); $^{13}$C NMR (125 MHz, CDCl$_3$): δ 11.6, 12.5, 20.64, 20.67, 20.69, 20.71, 56.8, 58.9, 60.3, 61.0, 61.9, 68.2, 71.1, 72.2, 72.7, 98.8, 117.7, 126.2, 127.6, 128.39, 128.45, 129.4, 129.7, 132.4, 132.5, 140.5, 144.6, 156.9, 169.3, 169.4, 170.3, 170.6, 171.4, 172.0, 196.7; NMR data for exo-98: $^1$H NMR (500 MHz, CDCl$_3$): δ inter alia 1.42 (3H, s), 1.52 (3H, s), 3.51 (1H, s); $^{13}$C NMR (125 MHz, CDCl$_3$): δ inter alia 8.3, 9.5; IR: $v_{max}$ 2937, 1785, 1748, 1719, 1509, 1368, 1213, 1033, 699 cm$^{-1}$; HRMS-ESI: [M+Na]$^+$ calcd for C$_{43}$H$_{40}$BrNO$_{13}$Na$^+$ 880.1575, found 880.1541. Anal. Calcd for C$_{43}$H$_{40}$BrNO$_{13}$: C, 60.15; H, 4.70; N, 1.63; Br, 9.31. Found: C, 60.20; H, 4.75; N, 1.82; Br, 8.84.

c) 2-(4-Hydroxy-3-nitrophenyl)-4,7-dimethyl-5,6-diphenyl-1H-isoindole-1,3(2H)-dione (BP-14) (Alternative Name: N-(4-O-(2,3,4,6-tetra-O-acetyl-β-D-glucopyranosyl)phenyl)-3,6-dimethyl-4,5-diphenyl-3,6-phthalimide)

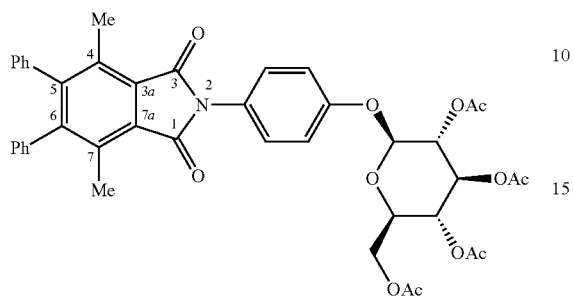

BP-14 oCOm-14 (214 mg, 0.249 mmol) was dissolved in THF (20 mL), treated with DBU (40 μL, 0.27 mmol) and the reaction mixture was stirred for 1 hour. After separation between ethyl acetate and 2 molL$^{-1}$ hydrochloric acid, the organic fraction was concentrated, then purified by filtration through a silica plug with chloroform elution, to provide the title compound BP-14 (154 mg, 82%) as a white solid.

$R_f$=0.25 (2:1 petroleum ether:ethyl acetate); m.p. 113-115° C.; $[\alpha]_D^{27}$-20.6 (c 0.8 CHCl$_3$); $^1$H NMR (500 MHz, CDCl$_3$): δ 2.05 (3H, s), 2.06 (3H, s), 2.08 (3H, s), 2.10 (3H, s), 2.45 (6H, s), 3.88 (1H, ddd, J=10.4, 5.5, 2.4 Hz), 4.18 (1H, dd, J=12.5, 2.4 Hz), 4.31 (1H, dd, J=12.5, 5.5 Hz), 5.13 (1H, m), 5.19 (1H, m), 5.29-5.34 (2H, m), 6.91 (4H, dd, J=6.8, 1.2 Hz), 7.11-7.19 (8H, m), 7.39 (2H, d, J=9.2 Hz); $^{13}$C NMR (125 MHz, CDCl$_3$): δ 170.7, 170.3, 169.5, 169.4, 168.2, 156.3, 149.0, 138.7, 135.0, 129.5, 128.3, 127.9, 127.8, 127.3, 127.0, 117.6, 99.3, 72.8, 72.2, 71.2, 68.3, 62.0, 20.8, 20.72, 20.70, 20.67, 15.9; IR: ν$_{max}$ 2975, 1743, 1707, 1509, 1376, 1230, 1211, 1170, 1119, 1078, 1034, 759, 700 cm$^{-1}$; HRMS-ESI: [M+Na]$^+$ calcd for C$_{42}$H$_{39}$NO$_{12}$Na$^+$ 772.2364, found 772.2355. Anal. Calcd for C$_{42}$H$_{39}$NO$_{12}$: C, 67.28; H, 5.24; N, 1.87. Found: C, 66.24; H, 5.33; N, 1.93.

Example 14 oCOm-15

3a-Bromo-3a,4,7,7a-tetrahydro-4,7-dimethyl-2,5,6-tri-(4-(2-(2-(2-methoxyethoxy)ethoxy)ethoxy)phenyl)-4,7-methano-1H-isoindole-1,3,8(2H)-trione:
Where R$^1$=R$^2$=pC$_6$H$_5$—O(CH$_2$CH$_2$O)$_3$CH$_3$; R$^3$=R$^4$=Me; A$^3$=NR$^{14}$; R$^{14}$=pC$_6$H$_5$—O(CH$_2$CH$_2$O)$_3$CH$_3$; X=Br Scheme 17a: Synthesis of oCOm-15 and base promoted release of carbon monoxide forming BP-15

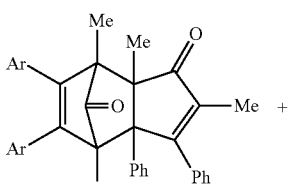

34

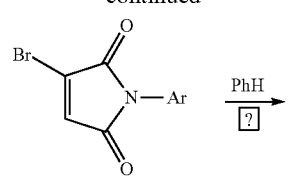

28

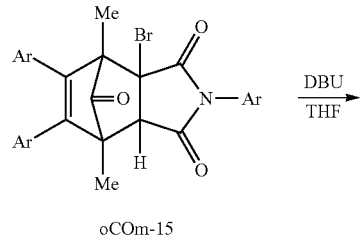

oCOm-15

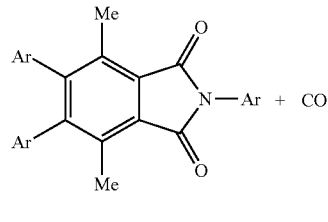

BP-15

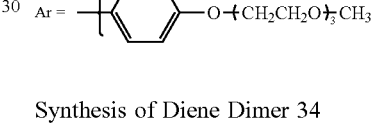

Synthesis of Diene Dimer 34

Scheme 17b: Synthesis of diene 34 from dihydroxybenzil 35

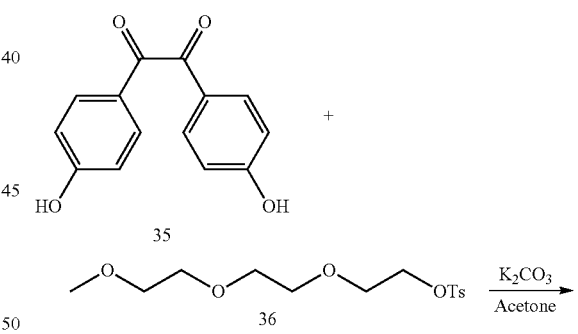

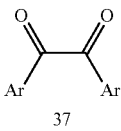

37 i. ↓ [ethyl ketone structure] and KOH
ii. Ac$_2$O and H$_2$SO$_4$

93

-continued

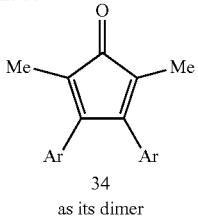

34
as its dimer

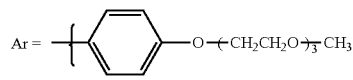

a) Bis-4,4'-(2-(2-(2-Methoxyethoxy)ethoxy)ethoxy)benzil (35)

A solution of tosylated PEG group 36[21] (6.63 g, 20.8 mmol) and 4,4'-dihydroxybenzl[23] (2.34 g, 10.1 mmol) in acetonitrile (60 mL) was treated with potassium carbonate (5.63 g, 40.7 mmol), then refluxed for 24 hours. The reaction mixture was filtered through a small plug of silica, which was eluted further with diethyl ether (100 mL). After concentration of the solvent fractions, the residue was purified by column chromatography (1:1 petroleum ether:ethyl acetate), to provide bis-PEGylated benzil 37 (4.51 g, 84%) as a yellow solid.

$R_f$=0.2 (ethyl acetate); m.p. 37-39° C.; $^1$H NMR (500 MHz, CDCl$_3$): δ 3.36 (3H, s), 3.53 (2H, m), 3.63 (2H, m), 3.66 (2H, m), 3.72 (2H, m), 3.89 (2H, t, J=4.9 Hz), 4.20 (2H, t, J=4.4 Hz), 6.97 (4H, d, J=9.1, 1.2 Hz), 7.92 (4H, dd, J=7.1, 1.7 Hz); $^{13}$C NMR (125 MHz, CDCl$_3$): δ 59.1, 67.8, 69.5, 70.6, 70.7, 71.0, 72.0, 114.9, 126.4, 132.3, 164.2, 193.5; IR: $v_{max}$ 2979, 2870, 1660, 1594, 1509, 1258, 1000, 848, 753, 618 cm$^{-1}$; HRMS-ESI: [M+Na]$^+$ Calcd for $C_{28}H_{38}O_{10}Na^+$ 557.2357, found 557.2345.

b) 2,5-Dimethyl-3,4-bis(4-(2-(2-(2-methoxyethoxy)ethoxy)ethoxy)phenyl)-cyclopenta-2,4-dien-1-one (34)

A solution of bis-PEGylated benzil 37 (282 mg, 0.53 mmol) and 3-pentanone (0.11 mL, 1.0 mmol) in isopropanol (5 mL) was combined with a solution of potassium hydroxide (31 mg, 0.55 mmol) in isopropanol (5 mL), then diluted with additional isopropanol (10 mL). The mixture was stirred at r.t. for 24 hours, then the mixture was concentrated to remove isopropanol, then acidified with 5% hydrochloric acid; extracted with ethyl acetate (2×20 mL), then dried and concentrated to afford the aldol adduct. This intermediate was then diluted with acetic anhydride (4 mL), and treated with sulfuric acid (ca. 5 µL, 0.09 mmol); then stirred for six hours at r.t. The mixture was diluted with water (50 mL), then upon hydrolysis of the anhydride, extracted with ethyl acetate (50 mL). Concentration of the organic phase provided crude diene 34, which was used without further purification.

94 c) 3a-Bromo-3a,4,7,7a-tetrahydro-4,7-dimethyl-2,5,6-tri-(4-(2-(2-(2-methoxyethoxy)ethoxy)ethoxy)phenyl)-4,7-methano-1H-isoindole-1,3,8(2H)-trione (oCOm-15) (Alternative Name: 2a-Bromo-N-(4-(2-(2-(2-methoxyethoxy)ethoxy)ethoxy)phenyl)-3,6-dimethyl-4,5-bis(4-(2-(2-(2-methoxyethoxy)ethoxy)ethoxy)phenyl)-2a,3,6,6a-tetrahydro-3,6-methanophthalimide-8-one)

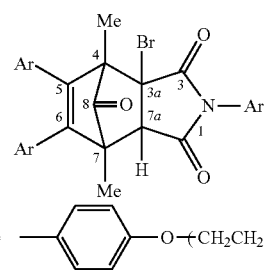

Ar = <img>—C$_6$H$_4$—O—(CH$_2$CH$_2$O)$_n$—CH$_3$</img>

Diene 34 (101 mg, 0.173 mmol) and dienophile 28 (114 mg, 0.275 mmol) were dissolved in toluene (2 mL), then stirred at reflux for four hours. The reaction mixture was concentrated, then purified by column chromatography (1:1 petroleum ether:ethyl acetate), then further purified by column chromatography (5% methanol in dichloromethane), to obtain the title compound oCOm-15 (62 mg, 36%) as a 6:1 mixture of endo- and exo-isomers in the form of a brown oil.

$R_f$=0.15 (ethyl acetate); IR: $v_{max}$ 2927, 2874, 1782, 1719, 1512, 1250, 1202, 1097, 1058, 842, 811 cm$^{-1}$; HRMS-ESI: [M+Na]$^+$ Calcd for $C_{50}H_{64}^{79}BrNO_{15}Na^+$ 1020.3352, found 1020.3367.

NMR data for endo-oCOm-15: $^1$H NMR (500 MHz, CDCl$_3$): δ 1.63 (3H, s), 1.65 (3H, s), 3.365 (3H, s), 3.367 (3H, s), 3.38 (3H, s), 3.56-3.53 (6H, m), 3.61 (1H, s), 3.63-3.75 (18H, m), 3.81 (4H, dd, J=9.3, 3.9 Hz), 3.86 (2H, t, J=4.7 Hz), 4.04 (4H, apparent q, J=4.9 Hz), 4.14 (2H, t, J=4.7 Hz), 6.67-6.71 (4H, m), 6.83-6.86 (4H, m), 6.96 (2H, d, J=9.3 Hz), 7.09 (2H, d, J=9.3 Hz); $^{13}$C NMR (125 MHz, CDCl$_3$): δ 11.7, 12.6, 56.7, 59.08, 59.11, 60.3, 60.9, 67.4, 67.8, 69.66, 69.7, 70.65, 70.68, 70.73, 70.75, 70.9, 71.0, 72.0, 114.47, 114.53, 115.4, 123.9, 125.0, 125.1, 127.3, 130.8, 131.1, 139.3, 143.6, 158.5, 158.6, 159.1, 171.6, 172.3, 197.2.

NMR data for exo-oCOm-15: $^1$H NMR (500 MHz, CDCl$_3$): δ inter alia 1.41 (3H, s), 1.49 (3H, s).

d) 2,5,6-Tri-(4-(2-(2-(2-methoxyethoxy)ethoxy)ethoxy)phenyl)-4,7-dimethyl-1H-isoindole-1,3(2H)-dione (BP-15) (Alternative Name: N-(4-(2-(2-(2-Methoxyethoxy)ethoxy)ethoxy)phenyl)-3,6-dimethyl-4,5-bis(4-(2-(2-(2-methoxyethoxy)ethoxy)ethoxy)phenyl)-phthalimide)

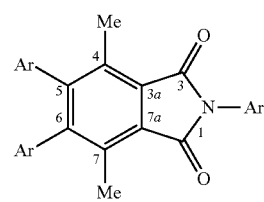

BP_15

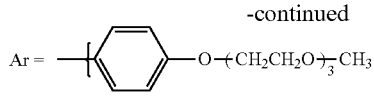

oCOm-15 (65 mg, 0.065 mmol) was dissolved in THF (1 mL), then treated with triethylamine (15 μL, 0.11 mmol) at r.t. No reaction was observed after 30 minutes, therefore DBU (15 μL, 0.10 mmol) was added and the reaction mixture was stirred for 30 minutes. After separation between ethyl acetate and 2 molL$^{-1}$ hydrochloric acid, the organic fraction was concentrated, then purified by column chromatography (0% to 1% methanol in chloroform), to provide BP-15 (11 mg, 19%) as a pale yellow oil.

$R_f$=0.15 (ethyl acetate); $^1$H NMR (500 MHz, CDCl$_3$): δ 2.44 (6H, s), 3.38 (6H, s), 3.39 (3H, s), 3.54-3.57 (6H, m), 3.65-3.76 (18H, m), 3.84 (4H, t, J=4.9 Hz), 3.88 (2H, t, J=4.9 Hz), 4.06 (4H, t, J=4.9 Hz), 4.18 (2H, t, J=4.9 Hz), 6.73 (4H, d, J=8.8 Hz), 6.79 (4H, d, J=8.4 Hz), 7.03 (2H, d, J=8.8 Hz), 7.32 (2H, d, J=8.8 Hz); $^{13}$C NMR (125 MHz, CDCl$_3$): δ 15.9, 59.1, 67.3, 67.8, 69.7, 69.8, 70.6, 70.67, 70.72, 70.8, 70.9, 71.0, 72.01, 72.02, 114.0, 115.1, 124.9, 127.7, 128.2, 130.6, 131.3, 135.2, 148.9, 157.5, 158.4, 168.5; IR: $v_{max}$ 2871, 1705, 1512, 1453, 1379, 1284, 1244, 1104, 1061, 833 cm$^{-1}$; HRMS-ESI: [M+Na]$^+$ Calcd for C$_{49}$H$_{63}$NO$_{14}$Na$^+$ 912.4141, found 912.4140.

Example 15 oCOm-16

3a-Bromo-3a,4,7,7a-tetrahydro-4,7-dimethyl-2-(2-acetoxyethyl)-5,6-diphenyl-4,7-methano-1H-isoindole-1,3,8(2H)-trione: Where R$^1$=R$^2$=Ph; R$^3$=R$^4$=Me; A$^3$=NR$^{14}$; R$^{14}$=CH$_2$CH$_2$OCOCH$_3$; X=Br Scheme 18: Synthesis of oCOM-16 and base promoted release of carbon monoxide forming BP-16

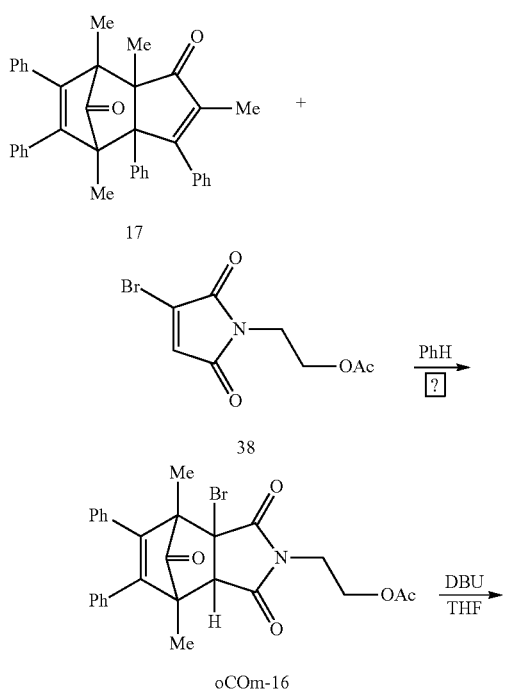

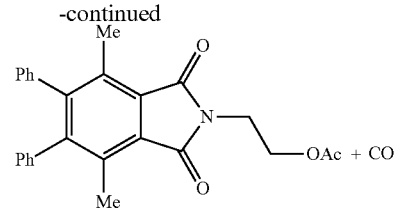

a) 1-(2-Acetoxyethyl)-1H-pyrrole-2,5-dione (39) (Alternative Name: N-(2-Acetoxyethyl)maleimide)

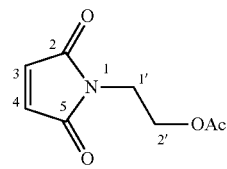 [SMILES: CC(=O)OCCN1C(=O)C=CC1=O]

Maleic anhydride (2.25 mg, 22.9 mmol) was added to a solution of ethanolamine (1.38 ml, 22.9 mmol) in glacial acetic acid (80 mL). The reaction was refluxed for 16 h under argon. After return to ambient temperature, the reaction mixture was evaporated under reduced pressure. The residue obtained was taken up with a solution of sodium acetate (302 mg, 3.69 mmol) in acetic acid (70 mL). The solution was refluxed for 2 h then washed with water (230 mL) and ether (120 mL) and the aqueous phase was extracted with ether (50 ml). The combined organic phases were washed with a solution of saturated sodium chloride (2×70 mL), water (2×120 mL), was dried over anhydrous magnesium sulfate, and concentrated in vacuo. The residue was purified by flash chromatography (hexane: EA, 4:1) to afford the title compound 39 (951 mg, 30%) as a white solid m.p. 79° C. (lit.$^{24,\ 25}$ m.p.=79° C.). $^1$H NMR (500 MHz, CDCl$_3$) δ 2.02 (3H, s, Ac), 3.79 (2H, t, J 5 Hz, H-1'), 4.22 (2H, t, J 5 Hz, H-2'), 6.72 (2H, s, H-3 and -4).

b) 3-Bromo-1-(2-acetoxyethyl)-1H-pyrrole-2,5-dione (38) (Alternative Name: 1-Bromo-N-(2-acetoxyethyl)maleimide)

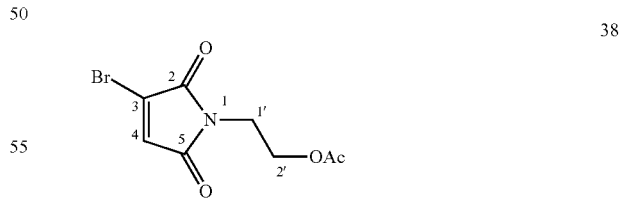

A solution of 1-(2-acetoxyethyl)-1H-pyrrole-2,5-dione (39) (564 mg, 3.08 mmol) in CCl$_4$ (15 ml) was added drop wise to a solution of bromine (0.17 ml, 3.38 mmol) in CCl$_4$ (10 ml). The reaction mixture was refluxed for 1 h, and then concentrated in vacuo. The residue was dissolved in dry THF (30 ml) and added to a solution of Et$_3$N (1.4 ml, 9.90 mmol) in dry THF (5 ml) at 0° C. The reaction mixture was stirred for 2 h and concentrated in vacuo. The residue was dissolved in EtOAc and washed with H$_2$O and brine and dried over anhydrous sodium sulfate. The organic layer was concentrated in vacuo and the crude product was purified by column chromatography (DCM: petrol 1:1) to afford the title compound 38(6.22 mg, 77%) as a white solid. m.p. 62° C.; $^1$H NMR (500 MHz, CDCl$_3$) δ 2.02 (3H, s, Ac), 3.83 (2H, t, J=5 Hz, 2×H-1'), 4.22 (2H, t, J=5 Hz, H-2'), 6.90 (1H, s, H-4); $^{13}$C NMR (500 MHz, CDCl$_3$) δ 20.80, 38.04, 61.26, 131.53 (C-3), 132.04 (C-4), 165.173, 168.29, 170.84; $v_{max}$ (cm$^{-1}$) 1712 (C=O) 660 (C-Br); HRMS-ESI [M+Na]$^+$ Calcd. for C$_8$H$_8$$^{81}$BrNO$_4$Na$^+$ 285.0589, found 285.9503.

c) 3a-Bromo-3a,4,7,7a-tetrahydro-4,7-dimethyl-2-(2-acetoxyethyl)-5,6-diphenyl-4,7-methano-1H-isoindole-1,3,8(2H)-trione (oCOm-16)

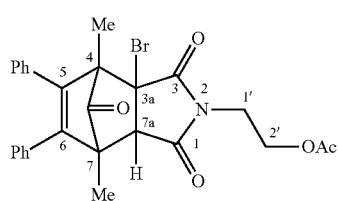

oCOm-16

Diene dimer 1 (563 mg, 2.16 mmol) and bromo-N-(2-acetoxyethyl)maleimide 38 (624 mg, 2.38 mmol) were refluxed in benzene (20 ml) for 6 h. The solution was concentrated in vacuo to afford a brown oil which was purified by column chromatography (EA:petrol 1:2) to afford the title compound oCOm-16 (947 mg, 84%) as an off white solid. m.p. 133° C. $v_{max}$ (cm$^{-1}$) 1784 (C=O), 1745 (C=O), 1709 (C=O); HRMS-ESI [M+Na]$^+$ Calcd. for C$_{27}$H$_{24}$$^{81}$BrNO$_5$Na$^+$ 544.0730, found 544.0687.

For the endo isomer; $^1$H NMR (500 MHz, CDCl$_3$) inter alia δ 1.61 (3H, s, Me-7), 1.63 (3H, s, Me-4), 1.86 (3H, s, Ac-Me), 3.53 (1H, s, H-7a), 3.79-3.927 (2H, m, H-9), 4.19-4.34 (2H, m, H-10), 6.85-7.30 (10H, m, Ph-H); $^{13}$C NMR (500 MHz, CDCl$_3$) inter alia δ 11.60 (C-7 Me), 12.44 (C-4 Me), 20.59 (Ac), 39.16 (C-9), 60.23, 60.44 (C-7a), 128.07-130.55 (C-Ph), 140.44 (C-6), 144.59 (C-5), 170.84 (Ac), 172.33 (C-1), 172.59 (C-3), 196.82 (C-8). For the exo isomer; $^1$H NMR (500 MHz, CDCl$_3$) inter alia δ 1.37 (3H, s, Me-7), 1.48 (3H, s, Me-4), 2.08 (3H, s, Ac-Me), 3.39 (1H, s, H-7a), 3.79-3.923 (2H, m, H-1'), 4.19-4.34 (2H, m, H-2'), 6.85-7.30 (10H, m, Ph-H); $^{13}$C NMR (500 MHz, CDCl$_3$) inter alia δ 8.18 (C-7 Me), 9.37 (C-4 Me), 20.73 (Ac), 37.95 (C-9), 58.90 (C-7a), 60.78 (C-10), 128.07-130.55 (C-Ph), 145.06 (C-5), 170.63 (C-Ac), 172.96 (C-3), 197.02 (C-8).

d) 4,7-Dimethyl-2-(2-acetoxyethyl)-5,6-diphenyl-1H-isoindole-1,3(2H)-dione (BP-16)

BP-16

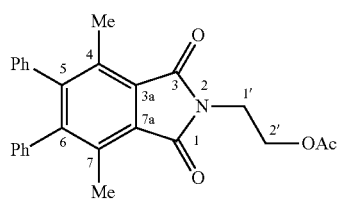

oCOm-16 (257 mg, 0.492 mmol) was dissolved in dry THF (10 ml). DBU (0.6 ml, 4.01 mmol) was added and the mixture was stirred for 3 h. The solution was washed with dilute acid (1M HCl), dried over anhydrous magnesium sulfate and concentrated in vacuo. The crude product was purified by column chromatography (CH$_2$Cl$_2$/petrol 2:1) to afford the title compound BP-16 (161 mg, 0.390 mmol, 79%) as an off white solid. m.p. 155° C. $^1$H NMR (500 MHz, CDCl$_3$) δ 2.06 (3H, s, Ac), 2.41 (6H, s, Me-4, Me-7), 3.97 (2H, t, J=5.5 Hz), 4.35 (2H, t, J=5.5 Hz,), 6.88-6.91 (4H, m, 4×Ph-H), 7.09-7.19 (6H, m, 6×Ph-H); $^{13}$C NMR (500 MHz, CDCl$_3$) δ 15.76 (Me), 21.01 (Ac), 36.82 (C-8), 61.73 (C-9), 126.88, 127.84, 128.12, 129.59, 134.56 (C-5, C-6), 138.72, 148.59 (C-3a, C-7a), 168.98, 170.98 (C-1, C-3); $v_{max}$ (cm$^{-1}$) 1692 (C=O); HRMS-ESI [M+Na]$^+$ Calcd. for C$_{26}$H$_{23}$NO$_4$Na$^+$ 436.1519, found 436.1497; Anal. Calcd. for C$_{26}$H$_{23}$NO$_4$: C, 75.53; H, 5.61; N, 3.39. Found: C, 75.27; H, 5.66; N, 3.27.

Example 16 oCOm-17

2,5-Dioxopyrrolidin-1-yl 3-(3a-bromo-4,7-dimethyl-1,3,8-trioxo-5,6-diphenyl-1,3,3a,4,7,7a-hexahydro-2H-4,7-methanoisoindol-2-yl)propanoate: Where R$^1$=R$^2$=Ph; R$^3$=R$^4$=Me; A$^3$=NR$^{14}$; R$^{14}$=CH$_2$CH$_2$COOSuccinimidyl; X=Br Scheme 19: Synthesis of oCOm-17 and base promoted release of carbon monoxide forming BP-17

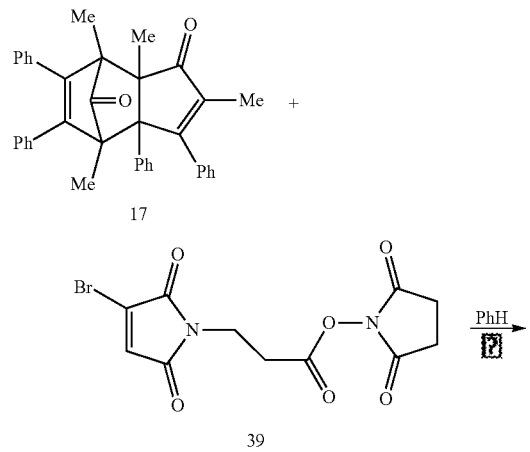

oCOM-17 $\xrightarrow{\text{DBU}}{\text{THF}}$

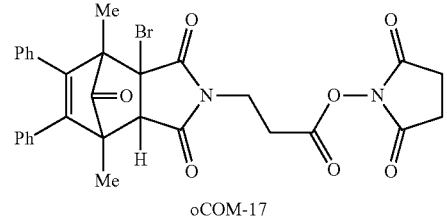

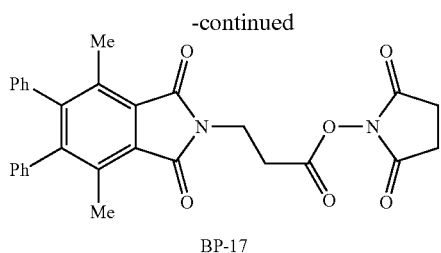

BP-17 a) 2,5-Dihydro-2,5-dioxo-1-pyrrolidinyl 3-bromo-1H-pyrrole-2,5-dione-1-propanoate (39) (Alternative Names: 2,5-dihydro-2,5-dioxo-1-pyrrolidinyl 3-bromo-1H-pyrrole-1-propanoate, or N-Succinimidyl 3-(N-(2-bromo)maleimido) propionate)

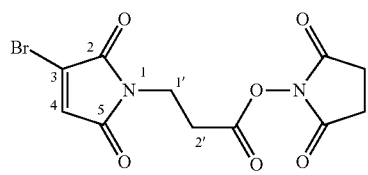

2,5-Dioxo-pyrrolidinyl 2,5-dihydro-2,5-dioxo-1H-pyrrole-1-propanoate (40)[21] (1.60 g, 6.01 mmol) was dissolved in carbon tetrachloride (25 mL), then treated with bromine (0.35 mL, 6.8 mmol) and refluxed for 1 hour. The reaction mixture was then cooled, the precipitate was collected, then dissolved in THF (30 mL) and treated with triethylamine (0.85 mL, 6.1 mmol), then stirred at 0° C. for 2 hours. The mixture was concentrated, then dissolved in ethyl acetate (50 mL), and washed with water (50 mL), then brine (50 mL). Upon concentration of the organic fraction, title compound 39 (1.28 g, 62%) was obtained as a light-brown solid. $R_f$=0.6 (1:1 petroleum ether:ethyl acetate); $^1$H NMR (500 MHz, CDCl$_3$): δ 2.81 (4H, br s), 3.02 (2H, t, J=6.9 Hz), 3.97 (2H, t, J=6.9 Hz), 6.90 (1H, s); $^{13}$C NMR (125 MHz, CDCl$_3$): δ 25.6, 29.7, 34.0, 131.6, 132.1, 164.9, 165.9, 167.9, 168.7; HRMS-ESI: [M+Na]$^+$ calcd for C$_{11}$H$_9$$^{79}$BrN$_2$O$_6$Na$^+$ 366.9536, found 366.9516.

b) 2,5-Dioxopyrrolidin-1-yl 3-(3a-bromo-4,7-dimethyl-1,3,8-trioxo-5,6-diphenyl-1,3,3a,4,7,7a-hexahydro-2H-4,7-methanoisoindol-2-yl)propanoate

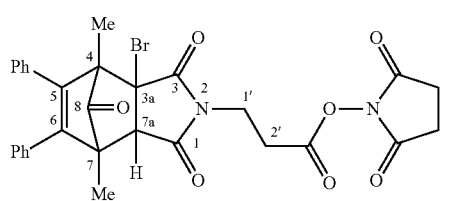

oCOm-17

A solution of diene dimer 17 (200 mg, 0.77 mmol) and dienophile 39 (256 mg, 0.74 mmol) in toluene (5 mL) was refluxed for seven hours, then concentrated. The crude residue was purified by column chromatography (1:1 petroleum ether:ethyl acetate), to provide the title compound oCOm-17 (386 mg, 83%) as an inseparable 6:1 mixture of endo- and exo-cycloadducts in the form of a pale-yellow oil.

$R_f$=0.7 (1:1 petroleum ether:ethyl acetate); HRMS-ESI: [M+Na] calcd for C$_{30}$H$_{25}$$^{79}$BrN$_2$O$_7$Na$^+$ 627.0737; found 627.0735.

NMR data for endo-oCOm-17: $^1$H NMR (500 MHz, CDCl$_3$): δ inter alia 1.61 (3H, s), 1.63 (3H, s), 2.84 (4H, br s), 2.94-3.09 (2H, m), 3.59 (1H, s), 3.89 (1H, m), 4.04 (1H, m), 6.83-6.73 (4H, m), 7.16-7.22 (6H, m); $^{13}$C NMR (125 MHz, CDCl$_3$): δ inter alia 11.6, 12.4, 56.4, 58.5, 60.4, 60.8, 128.3, 128.40, 128.44, 129.3, 129.7, 132.4, 132.5, 140.4, 144.7, 165.6, 168.7, 171.9, 172.1, 196.9.

NMR data for exo-oCOm-17: $^1$H NMR (500 MHz, CDCl$_3$): δ inter alia 1.37 (3H, s), 1.48 (3H, s), 3.42 (1H, s); $^{13}$C NMR (125 MHz, CDCl$_3$): δ inter alia 8.2, 9.4, 59.1.

c) 2,5-Dioxo-1-pyrrolidinyl 4,7-dimethyl-5,6-diphenyl-1H-isoindole-1,3(2H)-dione-2-propanoate (BP-17) (Alternative Name: Succinimidyl 3-(N-(3,6-dimethyl-4,5-diphenyl-)phthalimido)propionate)

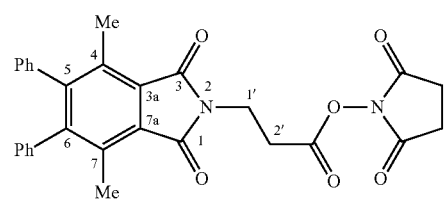

BP_2 oCOm-17 (261 mg, 0.43 mmol) was dissolved in THF (5 mL), then treated with triethylamine (60 μL, 0.43 mmol). The mixture was stirred for 30 minutes, however no reaction was observed. DBU (60 μL, 0.40 mmol) was added, and after 15 minutes reaction, had proceeded to completion. The reaction mixture was separated between ethyl acetate and 2 mmolL$^{-1}$ hydrochloric acid, then the organic fraction was concentrated to provide crude byproduct. After purification by column chromatography (1:1 petroleum ether:ethyl acetate), the title compound BP-17 (55 mg, 26%) was obtained as a clear oil.

$^1$H NMR (500 MHz, CDCl$_3$): δ 2.41 (6H, s), 2.83 (4H, br s), 3.12 (2H, t, J=7.3 Hz), 4.11 (2H, t, J=7.1 Hz), 6.90-6.88 (4H, xm), 7.18-7.10 (6H, m); $^{13}$C NMR (125 MHz, CDCl$_3$): δ 15.7, 25.6, 29.8, 32.7, 126.8, 127.7, 127.9, 129.5, 134.6, 138.6, 148.5, 166.2, 168.5, 168.8; HRMS-ESI: [M+Na]$^+$ calcd for C$_{29}$H$_{24}$N$_2$O$_6$Na$^+$ 519.1527, found 519.1496.

Example 17 oCOm-18 and -19

2-(3-(3a-Bromo-4,7-dimethyl-1,3,8-trioxo-5,6-diphenyl-1,3,3a,4,7,7a-hexahydro-2H-4,7-methanoisoindol-2-yl)propanamido)ethan-1-aminium trifluoroacetate and chloride (oCOm-19) Where $R^1=R^2=Ph$; $R^3=R^4=Me$; $A^3=NR^{14}$; $R^{14}=CH_2CH_2CONHCH_2CH_2NH_3 \cdot Z$ where $Z=Cl$ and $CF_3CO_2$; $X=Br$ Scheme 20: Synthesis of oCOm-19 as the hydrochloride and trifluoroacetic acid salts.

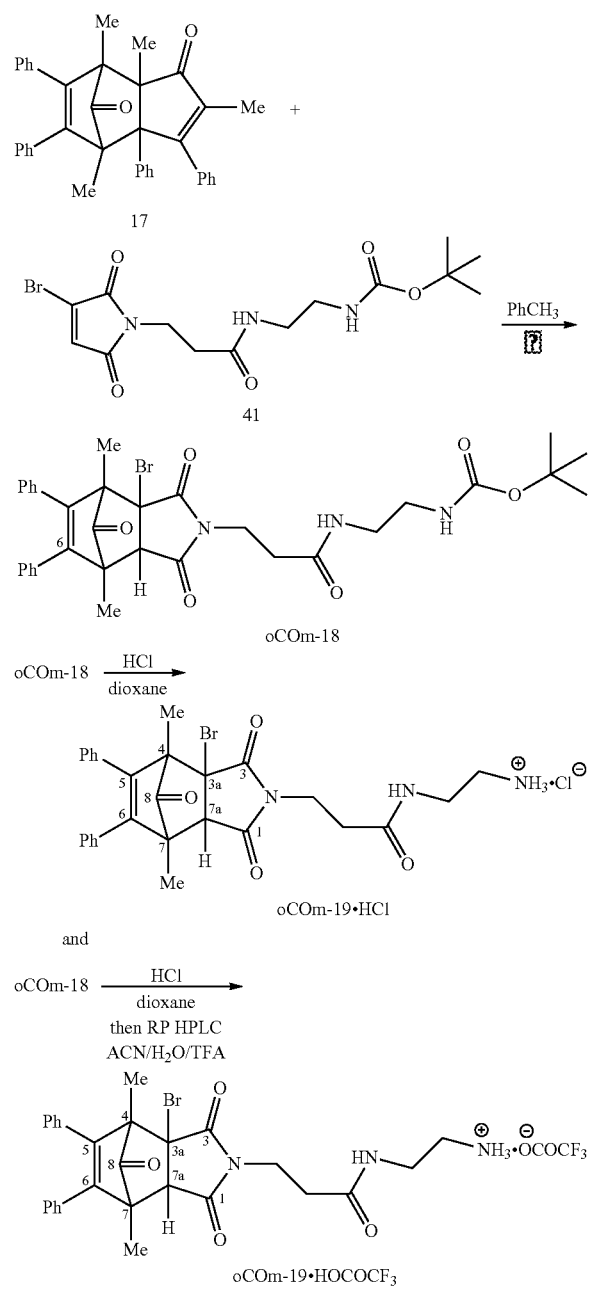

a) tert-Butyl (2-(3-(2,5-dioxo-2,5-dihydro-1H-pyrrol-1-yl)propanamido)ethyl)carbamate (43)

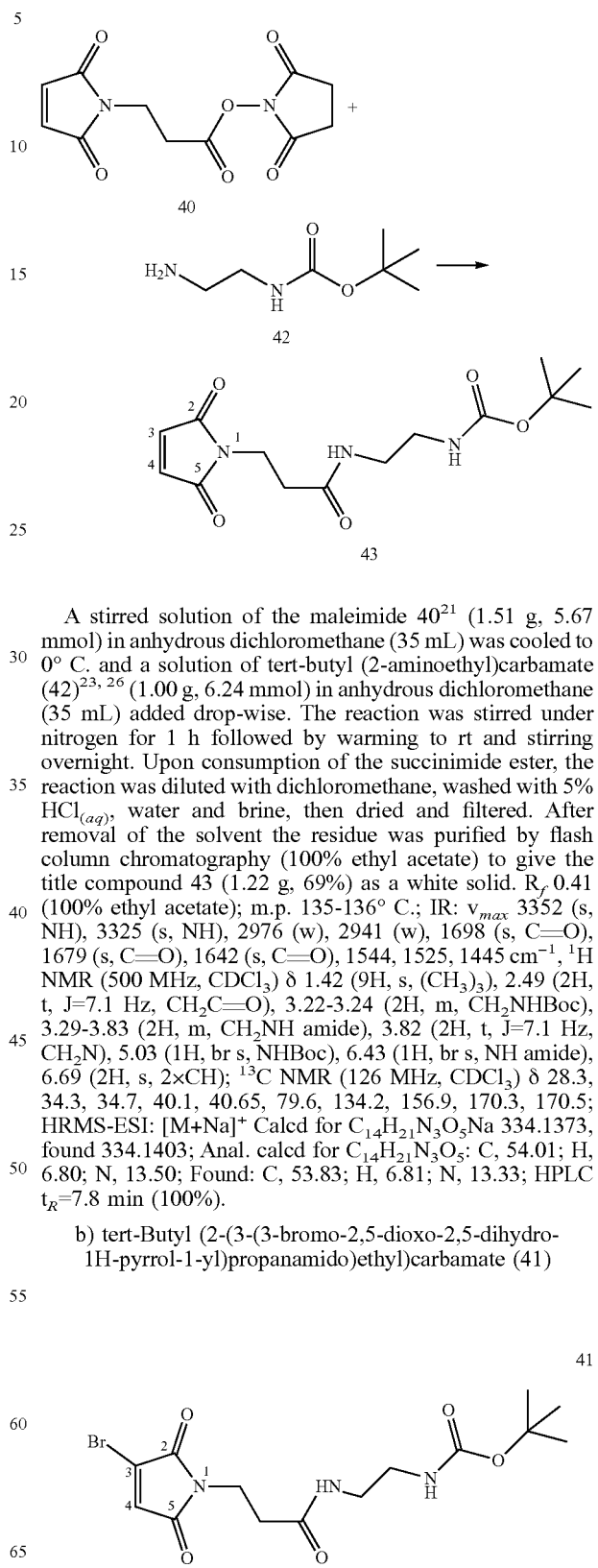

A stirred solution of the maleimide $40^{21}$ (1.51 g, 5.67 mmol) in anhydrous dichloromethane (35 mL) was cooled to 0° C. and a solution of tert-butyl (2-aminoethyl)carbamate $(42)^{23,\ 26}$ (1.00 g, 6.24 mmol) in anhydrous dichloromethane (35 mL) added drop-wise. The reaction was stirred under nitrogen for 1 h followed by warming to rt and stirring overnight. Upon consumption of the succinimide ester, the reaction was diluted with dichloromethane, washed with 5% $HCl_{(aq)}$, water and brine, then dried and filtered. After removal of the solvent the residue was purified by flash column chromatography (100% ethyl acetate) to give the title compound 43 (1.22 g, 69%) as a white solid. $R_f$ 0.41 (100% ethyl acetate); m.p. 135-136° C.; IR: $v_{max}$ 3352 (s, NH), 3325 (s, NH), 2976 (w), 2941 (w), 1698 (s, C=O), 1679 (s, C=O), 1642 (s, C=O), 1544, 1525, 1445 cm$^{-1}$, $^1$H NMR (500 MHz, CDCl$_3$) δ 1.42 (9H, s, (CH$_3$)$_3$), 2.49 (2H, t, J=7.1 Hz, CH$_2$C=O), 3.22-3.24 (2H, m, CH$_2$NHBoc), 3.29-3.83 (2H, m, CH$_2$NH amide), 3.82 (2H, t, J=7.1 Hz, CH$_2$N), 5.03 (1H, br s, NHBoc), 6.43 (1H, br s, NH amide), 6.69 (2H, s, 2×CH); $^{13}$C NMR (126 MHz, CDCl$_3$) δ 28.3, 34.3, 34.7, 40.1, 40.65, 79.6, 134.2, 156.9, 170.3, 170.5; HRMS-ESI: [M+Na]$^+$ Calcd for C$_{14}$H$_{21}$N$_3$O$_5$Na 334.1373, found 334.1403; Anal. calcd for C$_{14}$H$_{21}$N$_3$O$_5$: C, 54.01; H, 6.80; N, 13.50; Found: C, 53.83; H, 6.81; N, 13.33; HPLC $t_R$=7.8 min (100%).

b) tert-Butyl (2-(3-(3-bromo-2,5-dioxo-2,5-dihydro-1H-pyrrol-1-yl)propanamido)ethyl)carbamate (41)

Maleimide 43 (1.00 g, 3.21 mmol) was dissolved in carbon tetrachloride (12.5 mL) and treated with bromine (0.18 mL, 3.53 mmol) then heated at reflux for 1 h. Upon cooling the precipitate was collected by vacuum filtration and re-dissolved in anhydrous THF (15 mL). The solution was cooled to 0° C. and anhydrous triethylamine (0.45 mL, 3.21 mmol) added dropwise followed by stirring for 2 h. Volatiles were removed in vacuo and the residue partitioned between ethyl acetate and water. The organic extracts were washed with brine, dried and filtered. Removal of solvent under vacuum gave the crude bromomaleimide which was purified by flash column chromatography (100% ethyl acetate) to provide the title compound 41 (708 mg, 57%) as an off-white solid. $R_f$ 0.50 (100% ethyl acetate); m.p. 156158° C. (decomposition); IR: $v_{max}$ 3343, 3323, 3095, 2984, 2941, 1712, 1678, 1645 cm$^{-1}$; $^1$H NMR (500 MHz, CDCl$_3$) δ 1.44 (s, 9H, (CH$_3$)$_3$), 2.51 (t, J=7.1 Hz, 2H, CH$_2$C=O), 3.22-3.25 (m, 2H, CH$_2$NHBoc), 3.31-3.34 (m, 2H, CH$_2$NH amide), 3.87 (t, J=7.1 Hz, 2H, CH$_2$N), 4.93 (s, 1H, NHBoc), 6.33 (s, 1H, NH amide), 6.86 (s, 1H, 2×CH); $^{13}$C NMR (126 MHz, CDCl$_3$) δ 28.4, 34.5, 35.2, 40.1, 40.9, 79.8, 131.4, 132.0, 157.0, 165.1, 168.2, 169.9; HRMS-ESI: [M+Na]$^+$ Calcd for C$_{14}$H$_{20}$$^{79}$BrN$_3$O$_5$Na$^+$ 412.0479, found 412.0498; HPLC $t_R$=9.1 min (100%).

c) tert-Butyl (2-(3-((4S,7R)-3a-bromo-4,7-dimethyl-1,3,8-trioxo-5,6-diphenyl-3a,4,7,7a-tetrahydro-1H-4,7-methanoisoindol-2(2H)-yl)propanamido)ethyl)carbamate (oCOm-18)

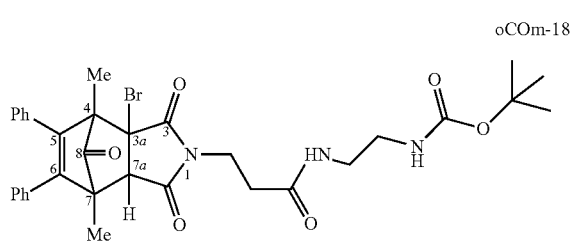 [SMILES: CC(C)(C)OC(=O)NCCNC(=O)CCN1C(=O)C2C3(C)C(=O)C(C)(C(c4ccccc4)=C3c3ccccc3)C2(Br)C1=O]

oCOm-18

Bromomaleimide 21 (200 mg, 0.51 mmol) and diene dimer 17 (140 mg, 0.54 mmol) were dissolved in toluene (5 mL) and heated at reflux for 4 h under nitrogen. The solvent was removed under vacuum and the crude residue purified by flash column chromatography (50% ethyl acetate/petroleum spirit) to give the title compound oCOm-18 (310 mg, 93%) as an 3:1 mixture of endo- and exo-isomers in the form of a white solid. M.p. 97-100° C.; IR: $v_{max}$ 3325 (br), 3293 (br), 2978, 2935, 2873, 1782, 1709 (s), 1655, 1514 (br), 1443 cm$^{-1}$. HRMS-ESI: [M+Na]$^+$ calcd for C$_{33}$H$_{36}$$^{79}$BrN$_3$O$_6$Na 672.1680, found 672.1726; HPLC $t_R$=13.5 min (100%).

NMR data for endo-oCOm-18: $^1$H NMR (500 MHz, CDCl$_3$) δ inter alia 1.42 (9H, s), 1.59 (3H, s), 1.61 (3H, s), 2.51 (2H, td, J=7.9, 2.2 Hz), 3.18-3.28 (2H, m,), 3.28-3.36 (2H, m), 3.51 (1H, s), 3.76-3.97 (2H, m), 4.95 (1H, br s), 6.32 (1H, br s), 6.80-6.90 (4H, m), 7.12-7.29 (6H, m); $^{13}$C NMR (126 MHz, CDCl$_3$) δ inter alia 11.5, 12.3, 28.3, 33.4, 36.1, 40.0, 40.9, 56.7, 57.1, 58.8, 59.0, 60.2, 60.7, 79.8, 126.8, 127.7, 128.0, 128.1, 128.2, 128.3, 128.4, 129.2, 129.2, 129.4, 129.6, 130.4, 132.3, 132.4, 140.3, 144.6, 156.9, 169.5, 172.1, 172.3, 196.8.

NMR data for exo-oCOm-18: $^1$H NMR (500 MHz, CDCl$_3$) δ inter alia 1.35 (3H, s), 1.43 (9H, s), 1.46 (3H, s), 2.44 (2H, t, J=6.9 Hz), 3.37 (1H, s), 5.06 (1H, br s), 6.16 (1H, br s), 7.02-7.06 (4H, m); $^{13}$C NMR (126 MHz, CDCl$_3$) δ inter alia 8.1, 9.3, 57.1, 58.8, 61.51, 132.6, 132.8, 144.9, 170.3, 170.6.

d) N-(2-Aminoethyl)-3-(3a-bromo-4,7-dimethyl-1,3,8-trioxo-5,6-diphenyl-3a,4,7,7a-tetrahydro-1H-4,7-methanoisoindol-2(2H)-yl)propanamide hydrochloride (OCOm-19. HCl)

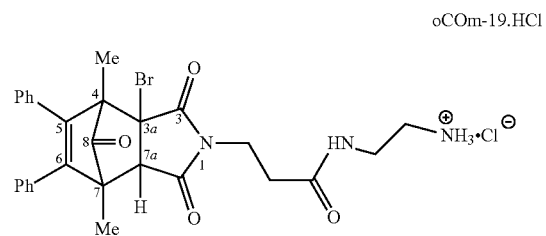

oCOm-19.HCl

The Boc-protected amino CO compound oCOm-18 (230 mg, 0.35 mmol) was dissolved in anhydrous dioxane (1 mL) and cooled to 0° C. under nitrogen. A solution of 6M HCl in dioxane (3 mL) was added dropwise and the reaction allowed to warm to rt and stirred overnight. Removal of volatiles under vacuum provided the amine hydrochloride salt which was lyophilized to provide the title compound oCOm-19.HCl (205 mg, 99%) as a 3:1 mixture of endo- and exo-isomers in the form of a white solid. M.p. 142-148° C. (decomposition); IR: $v_{max}$ 3378 (br), 2979, 2937, 2873, 1781, 1711, 1676, 1520 (br), 1444 cm$^{-1}$; HRMS-ESI: [M–Cl]$^+$ Calcd for C$_{28}$H$_{29}$$^{79}$BrN$_3$O$_4$ 550.1336, found 550.1355; Anal. Calcd for C$_{28}$H$_{29}$BrClN$_3$O$_4$.H$_2$O: C, 55.59; H, 5.17; N, 6.95; Found: C, 55.61; H, 5.19; N, 6.92; HPLC $t_R$=8.8 min.

NMR data for endo-oCOm-19.HCl: $^1$H NMR (500 MHz, d$_6$-DMSO) δ inter alia 1.45 (3H, s, CH$_3$), 1.48 (3H, s, CH$_3$), 2.38-2.45 (2H, m, NCH$_2$), 2.84 (2H, q, J=6.1 Hz, CH$_2$NH$_3$), 3.28 (2H, q, J=6.2 Hz, O=CNHCH$_2$), 3.75 (2H, td, J=13.5, 6.4 Hz, CH$_2$C=O), 4.00 (1H, s), 6.91-6.82 (4H, m), 7.19-7.26 (6H, m,), 8.03 (3H, br s, NH$_3$), 8.37 (1H, t, J=5.6 Hz, NH); $^{13}$C NMR (126 MHz, d$_6$-DMSO) δ inter alia 11.2, 11.7, 32.7, 36.0, 36.4, 38.5, 55.7, 58.3, 58.9, 60.1, 128.0, 128.1, 128.3, 129.1, 129.4, 132.3, 132.4, 139.6, 144.6, 169.5, 171.8, 172.3, 196.7.

NMR data for exo oCOm-19: $^1$H NMR (500 MHz, d$_6$-DMSO) δ inter alia 1.18 (3H, s), 1.32 (3H, s), 2.34 (2H, t, J=7.5 Hz), 3.91 (1H, s,), 8.26 (1H, t, J=5.6 Hz); $^{13}$C NMR (126 MHz, d$_6$-DMSO) δ inter alia 169.4, 197.1.

tert-Butyl (2-(3-(4,7-dimethyl-1,3-dioxo-5,6-diphenylisoindolin-2-yl)propanamido)ethyl)carbamate (BP-18)

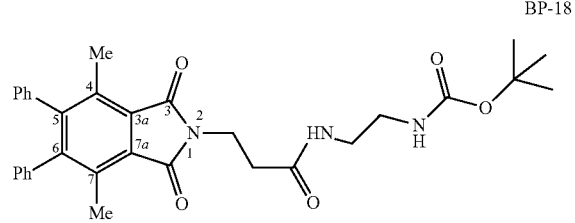 [SMILES: Cc1c2c(c(C)c(-c3ccccc3)c1-c1ccccc1)C(=O)N(CCC(=O)NCCNC(=O)OC(C)(C)C)C2=O]

BP-18 oCOm-18 (200 mg, 0.31 mmol) was dissolved in anhydrous THF (5 mL) and DBU (0.09 mL, 0.62 mmol) added dropwise. The reaction was stirred and monitored by TLC until no starting material remained (1 h). Volatiles were removed under vacuum and the residue taken up in ethyl acetate and washed with 5% HCl$_{(aq)}$. After drying and filtering the organic extracts, removal of volatiles under vacuum gave the crude aromatized material. Purification by flash column chromatography (60% ethyl acetate/petroleum spirit) provided the title compound BP-18 (147 mg, 88%) as a white solid. R$_f$ 0.21 (50% ethyl acetate/petroleum spirit); m.p. 183-185° C.; IR: ν$_{max}$ 3312 (br), 2974, 2932, 1761, 1700, 1646, 1523 (br), 1443 cm$^{-1}$, $^1$H NMR (500 MHz, CDCl$_3$) δ 1.43 (9H, s), 2.39 (6H, s), 2.63 (2H, t, J=7.0 Hz), 3.20-3.32 (2H, m), 3.32-3.43 (2H, m), 4.01 (2H, t, J=7.0 Hz), 5.09 (1H, br s), 6.44 (1H, br s), 6.82-6.95 (3H, m), 7.05-7.22 (5H, m); $^{13}$C NMR (126 MHz, CDCl$_3$) δ 15.6, 28.4, 34.1, 35.2, 40.2, 40.6, 79.6, 126.8, 127.7, 128.0, 129.5, 134.5, 138.6, 148.5, 156.7, 169.0, 170.6; HRMS-ESI: [M+Na]$^+$ Calcd for C$_{32}$H$_{35}$N$_3$O$_5$Na 564.2469, found 564.2455.

e) N-(2-aminoethyl)-3-(4,7-dimethyl-1,3-dioxo-5,6-diphenylisoindolin-2-yl)propanamide hydrochloride (BP-19)

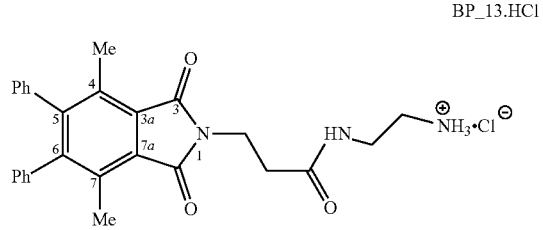

BP_13.HCl

Boc-protected amine BP-18 (139 mg, 0.26 mmol) was dissolved in anhydrous dioxane (1 mL) with cooling to 0° C. under nitrogen and 6M HCl in anhydrous dioxane (3 mL) added dropwise. The reaction allowed to warm to rt and stirred overnight. Removal of volatiles under vacuum followed by lyophilization provided the title compound (117 mg, 95%) BP-19 as its HCl salt in the form of a white solid. M.p. 185-187° C.; IR: ν$_{max}$ 3274 (br), 3057, 3024, 2939 (br), 1760, 1695, 1645, 1549, 1495, 1441 cm$^{-1}$, $^1$H NMR (500 MHz, d$_6$-DMSO) δ 2.30 (6H, s, 2×CH$_3$), 2.49 (2H, t, J=5.0 Hz), 2.78-2.91 (2H, m), 3.25-3.32 (2H, m), 3.82 (2H, t, J=7.3 Hz), 6.90-7.04 (3H, m), 7.07-7.17 (2H, m), 7.17-7.27 (3H, m), 7.99 (3H, s), 8.30 (1H, t, J=5.6 Hz); $^{13}$C NMR (126 MHz, d$_6$-DMSO) δ 15.2, 34.0, 34.0, 36.4, 38.5, 126.9, 127.7, 127.8, 129.3, 133.2, 138.3, 147.8, 168.1, 170.5; HRMS-ESI: [M−Cl]$^+$ Calcd for C$_{27}$H$_{28}$N$_3$O$_3$ 442.2125, found 442.2116. HPLC t$_R$=9.2 min (100%).

f) N-(2-Aminoethyl)-3-(3a-bromo-1H-4,7-dimethyl-1,3,8-trioxo-5,6-diphenyl-isoindolin-2(2H)-yl) propanamide 2,2,2-trifluoroacetate (oCOm-19.CF$_3$CO$_2$H)

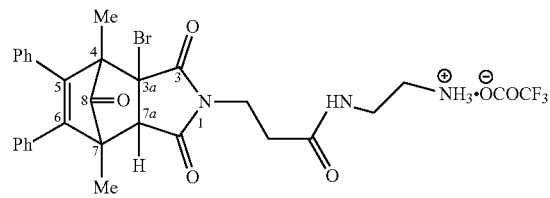

oCOm-19.HOCOCF$_3$

A solution of Boc-protected oCOm-19 (305 mg, 0.47 mmol) in 1,4-dioxane (1.4 mL) was prepared under an ambient atmosphere. In a separate vessel, concentrated aqueous HCl (2.1 mL, 36%=11.65 M) was diluted with 1,4-dioxane (2 mL) to afford a solution of 6 M HCl in dioxane. The solution of Boc-protected oCOm-18 was placed in an ice bath prior to the addition of the 6 M HCl solution. The reaction mixture was allowed to warm to rt and monitored by RP-HPLC (10% to 100% B over 12.5 min, then 100% B for 2.5 min, 0.5 mL/min). Upon consumption of the starting material (4-5 h), the solvent was removed in vacuo. The residue was dissolved in a mixture of approximately 50% H$_2$O in 1,4-dioxane (50 mL) and then lyophilised. The crude off-white solid obtained was dissolved in approximately 20% CH$_3$CN in H$_2$O (2×5 mL) and then loaded onto a pre-washed C-18 solid phase extraction cartridge (100% CH$_3$CN [2×10 mL]), then 90%, then 50% CH$_3$CN in H$_2$O [1×10 mL each], 20% CH$_3$CN in H$_2$O [2×10 mL]). The compound was eluted from the C-18 cartridge (20% to 40% CH$_3$CN in H$_2$O [10% increments, 2×10 mL each], then 50% to 100% CH$_3$CN in H$_2$O [10% increments, 10 mL each]). The fractions collected were analysed by RP-HPLC (10% to 100% B over 12.5 min, then 100% B for 2.5 min, t$_R$=8.99 min) and lyophilised to afford the title compound oCOm-19.CF$_3$CO$_2$H as a white powder (106.9 mg, 34%, >97% purity, inseparable 10:1 mixture of endo: exo isomers) and a mixture of oCOm-19 and BP-19 (112.4 mg, 3:1 oCOm-19:BP-19). Mp. 142-148° C.; IR (ATR) ν$_{max}$/cm$^{-1}$ 3378 (br), 2979, 1937, 2873, 1781 (C=O), 1711 (C=O), 1676, 1520 (br), 1444; HRMS (ESI-TOF) m/z: [M−$^-$O$_2$CCF$_3$]$^+$ calcd for C$_{28}$H$_{29}$$^{79}$BrN$_3$O$_4$$^+$ 550.1336, found 550.1355; RP-HPLC (10% to 100% B over 12.5 min, then 100% B for 2.5 min), t$_R$=8.99 min, endo- and exo-isomers co-elute as a single peak.

Endo-oCOm-19 NMR data: $^1$H NMR (400 MHz, DMSO-d6) δ inter alia 1.45 (3H, s, CH$_3$), 1.49 (3H, s, CH$_3$), 2.41 (2H, t, J=8.0 Hz), 2.84 (2H, q, J=6.0 Hz), 3.25 (2H, q, J=6.0 Hz), 3.71-3.79 (2H, m), 4.00 (1H, s, H-7a), 6.85-6.88 (4H, m, Ph), 7.17-7.29 (6H, m, Ph), 7.68 (3H, br s), 8.21 (1H, t, J=6.0 Hz); $^{13}$C NMR (125 MHz, DMSO-d6) δ inter alia 11.2 (CH$_3$), 11.7 (CH$_3$), 32.7, 36.0, 36.4, 38.7, 55.7, 58.3, 58.9, 60.0, 128.0, 128.1, 128.3, 129.1, 129.4, 132.3, 132.4, 139.5, 144.6, 169.8, 171.9, 172.3, 196.7; $^{19}$F NMR (376 MHz, DMSO-d6) δ −73.74.

Exo-oCOm-19 NMR data: $^1$H NMR (400 MHz, DMSO-d6) δ inter alia 1.19 (3H, s, CH$_3$), 1.32 (3H, s, CH$_3$), 3.92 (1H, s, H-7a).

Example 18 oCOm-21

2-(3a-Bromo-4,7-dimethyl-1,3,8-trioxo-5,6-diphenyl-2H-4,7-methanoisoindolin-2-yl)ethan-1-aminium 2,2,2-trifluoroacetate, chloride, and bromide: Where $R^1=R^2=Ph$; $R^3=R^4=Me$; $A^3=NR^{14}$; $R^{14}=CH_2CH_2NH_3 \cdot Z$ where $Z=Cl$, Br, and $CF_3CO_2$; $X=Br$ Scheme 21a: Synthesis of oCOm-21 as its trifluoroacetic acid salt.

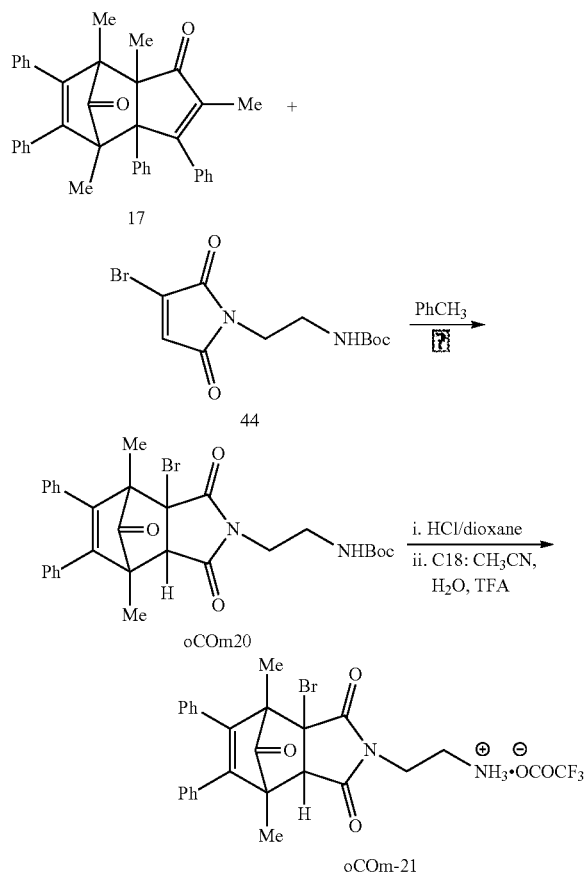

a) tert-Butyl N-(2,5-dioxo-2,5-dihydro-1H-pyrrol-1-yl)ethylcarbamate (46)

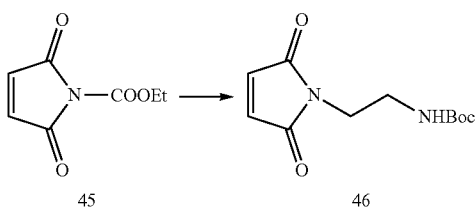 [SMILES: CCOC(=O)N1C(=O)C=CC1=O ; CC(C)(C)OC(=O)NCCN1C(=O)C=CC1=O]

To a solution of 1-((tert-butoxycarbonyl)amino)-2-aminoethane (42)[23, 26, 27] (1.13 g, 7.1 mmol) in saturated NaHCO₃ (35 mL) at 0° C. was added N-(ethoxycarbonyl) maleimide[22] (45) (1.1 g, 7.1 mmol). The reaction mixture was warmed to rt and stirred for 15 min. THF (55 mL) was then added and the reaction mixture stirred for a further 45 min. H₂O (50 mL) was added and the aqueous phase extracted with EtOAc (3×75 mL). The combined organic extracts were washed with saturated NaCl (100 mL) and dried over MgSO₄. Removal of the solvent in vacuo gave an off-white solid that was purified by flash chromatography (0%, then 5%, then 10% EtOAc in CH₂Cl₂) to yield the title compound 46 (1.1 g 58%) as a white solid. Mp. 126-128° C.; $R_f$(10% EtOAc in CH₂Cl₂) 0.28; IR (ATR) $v_{max}$/cm⁻¹ 3350 (C—H), 3089 (C—H), 2977, 1701 (C=O), 1678 (C=O), 1516, 1434, 1288, 1256, 1167, 944, 844, 692, 623; ¹H NMR (400 MHz, CDCl₃) δ 1.40 (9H, s), 3.30-3.35 (2H, m), 3.66 (2H, t, J=6.0 Hz), 4.74 (1H, br s), 6.71 (2H, s); ¹³C NMR (100 MHz, CDCl₃) δ 28.3, 38.0, 39.4, 79.5, 131.1, 155.9, 170.8. The ¹H and ¹³C NMR data obtained was in agreement with that reported from literature.[23]

b) tert-Butyl 3-(3-bromo-2,5-dioxo-2,5-dihydro-1H-pyrrol-1-yl)ethylcarbamate (28)

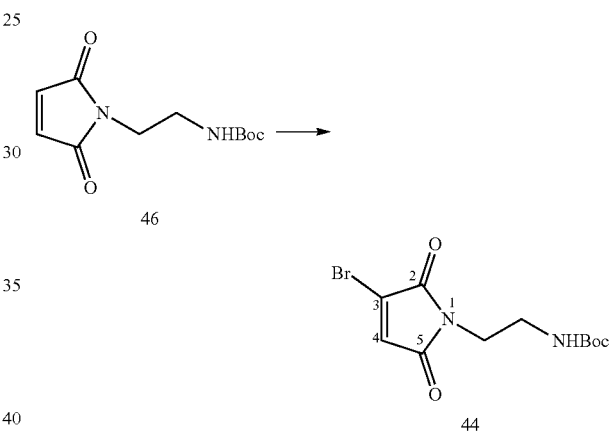

A solution of Boc-maleimide 46 (2.0 g, 8.32 mmol) in CH₂Cl₂ (12.4 mL) was treated with Br₂ (470 µL, 9.13 mmol) and heated to reflux for 1 h. The reaction was cooled to rt and concentrated in vacuo to give the dibrominated intermediate as a thick orange oil which was then diluted in anhydrous THF (39.6 mL) and cooled to 0° C. Anhydrous NEt₃ (1.16 mL, 8.32 mmol) was added drop-wise and the reaction mixture stirred for 2 h at 0° C. The resulting thick off-white suspension was diluted in H₂O (20 mL) and the aqueous phase extracted with EtOAc (3×20 mL). The combined organic extracts were dried over MgSO₄ and concentrated in vacuo to give a dark brown oil that was purified by flash chromatography (0%, then 5%, then 10% EtOAc in CH₂Cl₂) to afford the title compound 44 (1.944 g, 73%) as a pale yellow solid. Mp. 90-93° C.; $R_f$ (2% EtOAc in CH₂Cl₂) 0.05; $R_f$(10% EtOAc in CH₂Cl₂) 0.30; IR (ATR) $v_{max}$/cm⁻¹ 3354 (C—H), 2970, 1702 (C=O), 1681 (C=O), 1523, 1406, 1284, 1246, 1160, 957, 625; ¹H NMR (400 MHz, CDCl₃) δ 1.40 (9H, s), 3.32-3.36 (2H, m), 3.70 (2H, t, J=6.0 Hz,), 4.70 (1H, br s), 6.88 (1H, s); ¹³C NMR (100 MHz, CDCl₃) δ 28.3, 39.1, 39.2, 79.7, 131.4, 131.9, 156.0, 165.4, 168.6; HRMS (ESI-TOF) m/z: [M+Na]⁺ Calcd for $C_{11}H_{15}^{79}BrN_2NaO_4^+$ 341.010, found 341.0102. Anal. Calcd for $C_{11}H_{15}BrN_2O_4$: C, 41.40; H, 4.74; N, 8.78; Br, 25.04. Found: C, 41.41; H, 4.51; N, 8.76; Br, 25.23.

c) tert-Butyl (2-(3a-bromo-4,7-dimethyl-1,3,8-tri-oxo-5,6-diphenyl-3a,4,7,7a-tetrahydro-2H-4,7-methanoisoindol-2-yl)ethyl)carbamate (oCOm-20)

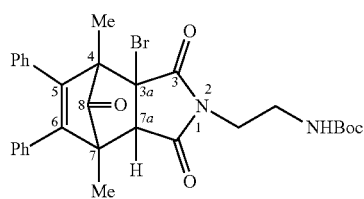

oCOm-20

Boc-bromomaleimide 46 (355.6 mg, 1.11 mmol) and diene dimer 17 (305 mg, 0.59 mmol) was dissolved in anhydrous toluene (6.5 mL) and placed under argon. The mixture was then heated to reflux for 4 h. After cooling to rt, the solvent was removed in vacuo to afford a brown oil containing cycloadduct oCOm-20 as a mixture of endo- and exo-isomers (~2.5:1). Purification by flash chromatography (0%, then 2%, then 10% EtOAc in CH$_2$Cl$_2$) afforded the title compound oCOm-20 as a white foamy solid in two fractions: the pure endo-isomer (204 mg, 32%) and a ~1:1 mixture of endo- and exo-isomers (333 mg, 52%). Endo-oCOm-20 data: Mp. 107-109° C.; R$_f$(2% EtOAc in CH$_2$Cl$_2$) 0.11; IR (ATR) v$_{max}$/cm$^{-1}$ 2984, 2937, 1790 (C=O), 1713 (C=O), 1390, 1366, 1248, 1201, 737, 699; $^1$H NMR (400 MHz, CDCl$_3$) δ 1.42 (9H, s, C(CH$_3$)$_3$), 1.61 (3H, s, CH$_3$), 1.62 (3H, s, CH$_3$), 3.37-3.39 (2H, m), 3.52 (1H, s, H-7a), 3.73 (2H, t, J=5.8 Hz), 4.72 (1H, br s), 6.83-6.88 (4H, m, Ph), 7.15-7.19 (6H, m, Ph); $^{13}$C NMR (125 MHz, CDCl$_3$) δ 11.5, 12.4, 28.4, 38.7, 40.0, 56.3, 58.7, 60.4 (C-7a), 60.8 (C-3a), 79.8, 128.1, 128.3, 128.3, 129.3, 129.6, 132.4, 132.5, 140.4 (C-5), 144.5 (C-6), 155.8, 172.4 (C-1), 172.7 (C-3), 196.9 (C-8); HRMS (ESI-TOF) m/z: [M−Boc+H]$^+$ Calcd for C$_{25}$H$_{24}$$^{79}$BrN$_2$O$_3$$^+$ 479.0965; Found 479.0949. [M+Na]$^+$ Calcd for C$_{30}$H$_{31}$$^{79}$BrN$_2$NaO$_5$$^+$ 601.1309, found 601.1303; Anal. Calcd for C$_{30}$H$_{31}$BrN$_2$O$_5$: C, 62.18; H, 5.39; N, 4.83; Br, 13.79. Found: C, 62.16; H, 5.39; N, 4.89; Br, 13.89; RP-HPLC (10% to 100% B over 12.5 min, then 100% B for 2.5 min), t$_R$=14.56 min.

Exo-oCOm-20 data: RP-HPLC (10% to 100% B over 12.5 min, then 100% B for 2.5 min), t$_R$=14.97 min.

d) 2-(3a-Bromo-4,7-dimethyl-1,3,8-trioxo-5,6-diphenyl-2H-4,7-methanoisoindolin-2-yl)ethan-1-aminium 2,2,2-trifluoroacetate (oCOm-21)

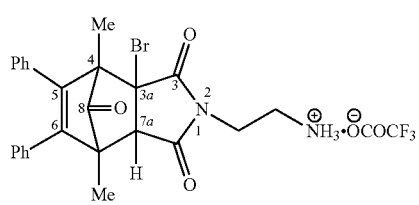

oCOm-21

A solution of Boc-protected endo-oCOm-20 (400.1 mg, 0.69 mmol) in 1,4-dioxane (2 mL) was prepared under an ambient atmosphere the cooled in an ice bath. In a separate vessel, concentrated aqueous HCl (3.1 mL) was diluted with 1,4-dioxane (2.9 mL) to afford a solution of 6 M HCl in dioxane. The two solutions were mixed, allowed to warm to rt and monitored by RP-HPLC (10% to 100% B over 12.5 min, then 100% B for 2.5 min, 0.5 mL/min). Upon consumption of the starting material (4-5 h), the solvent was removed in vacuo. The residue was dissolved in a mixture of approximately 75% H$_2$O in 1,4-dioxane (40 mL) and lyophilised. The crude off-white solid obtained was dissolved in approximately 16% CH$_3$CN in H$_2$O (12 mL) and loaded onto a pre-washed C-18 solid phase extraction cartridge (100% CH$_3$CN [2×10 mL]), then 90%, then 50% CH$_3$CN in H$_2$O [1×10 mL each], 10% CH$_3$CN in H$_2$O [2×10 mL]). The product was eluted from the C-18 cartridge (20% to 40% CH$_3$CN in H$_2$O [10% increments, 2×10 mL each], then 50% to 100% CH$_3$CN in H$_2$O [10% increments, 10 mL each]). The fractions collected were analysed by RP-HPLC (10% to 100% B over 12.5 min, then 100% B for 2.5 min, t$_R$=9.00 min) and lyophilised to afford the title compound oCOm-21.TFA (259 mg, 63%) as a white powder. IR (ATR) v$_{max}$/cl1$^{-1}$ 2937, 1781 (C=O), 1711 (C=O), 1664, 1648, 1443, 1388, 1203, 1180, 1134, 798, 723, 697; $^1$H NMR (400 MHz, DMSO-d6) δ 1.46 (3H, s, CH$_3$), 1.52 (3H, s, CH$_3$), 2.95-3.07 (2H, m), 3.77-3.81 (2H, m), 3.93 (1H, s, H-7a), 6.83-6.87 (4H, m, Ph), 7.20-7.24 (6H, m, Ph), 7.90 (3H, br s); $^{13}$C NMR (125 MHz, DMSO-d6) δ 11.3, 11.8, 36.5, 37.0, 55.6, 58.5, 58.7, 60.5, 128.1, 128.2, 128.2, 128.3, 129.1, 129.3, 132.2, 132.3, 139.5, 144.5, 172.0, 172.6, 196.5; $^{19}$F NMR (376 MHz, DMSO-d6) δ −73.97 (3F, $^-$O$_2$CCF$_3$); HRMS (ESI-TOF) m/z: [M−$^-$O$_2$CCF$_3$]$^+$ Calcd for C$_{25}$H$_{24}$$^{79}$BrN$_2$O$_3$$^+$ 479.0965, found 479.0978; RP-HPLC (10% to 100% B over 12.5 min, then 100% B for 2.5 min), t$_R$=9.00 min.

e) 2-(3a-Bromo-4,7-dimethyl-1,3,8-trioxo-5,6-diphenyl-2H-4,7-methanoisoindolin-2-yl)ethan-1-aminium chloride

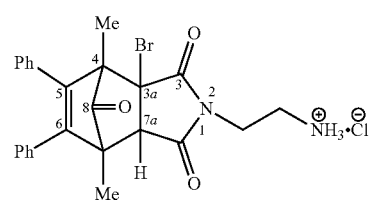

oCOM-21.HCl

A solution of Boc-protected endo-29 (200 mg, 0.35 mmol) in 1,4-dioxane (1 mL) was prepared under an ambient atmosphere. In a separate vessel, concentrated aqueous HCl (1.55 mL) was diluted with 1,4-dioxane (1.45 mL) to afford a solution of 6 M HCl in dioxane. The solution of Boc-protected endo-27 was placed in an ice bath prior to the addition of the 6 M HCl solution. The reaction mixture was allowed to warm to rt and monitored by RP-HPLC (10% to 100% B over 12.5 min, then 100% B for 2.5 min, 0.5 mL/min). Upon consumption of the starting material (4 h), the solvent was removed in vacuo. The residue was dissolved in a mixture of approximately 75% H$_2$O in 1,4-dioxane (40 mL) and lyophilised to give the title compound oCOm-21.HCl as a pale brown powder (175 mg, 98%).

$^1$H NMR (500 MHz, DMSO-d6) δ 1.45 (3H, s, CH$_3$), 1.52 (3H, s, CH$_3$), 2.90-3.05 (2H, m), 3.78-3.83 (2H, m), 3.93 (1H, s, H-7a), 6.83-6.87 (4H, m, Ph), 7.20-7.24 (6H, m, Ph), 8.18 (3H, br s); $^{13}$C NMR (125 MHz, DMSO-d6) δ 11.3, 11.8, 36.4, 36.9, 55.5, 58.6, 58.7, 60.5, 128.1, 128.1, 128.2, 128.3, 129.1, 129.3, 132.2, 132.3, 139.5, 144.5, 172.0, 172.6, 196.5; HRMS (ESI-TOF) m/z: [M−$^-$O$_2$CCF$_3$]$^+$ Calcd for C$_{25}$H$_{24}$$^{79}$BrN$_2$O$_3$$^+$ 479.0965, found 479.0932; RP-HPLC (10% to 100% B over 12.5 min, then 100% B for 2.5 min), $t_R$=9.00 min.

f) 2-(3a-Bromo-4,7-dimethyl-1,3,8-trioxo-5,6-diphenyl-2H-4,7-methanoisoindolin-2-yl)ethan-1-aminium bromide

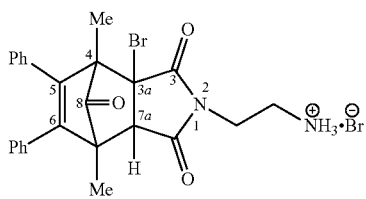

A solution of Boc-protected endo-29 (96 mg, 0.17 mmol) in 1,4-dioxane (0.5 mL) was prepared under an ambient atmosphere. In a separate vessel, concentrated aqueous HBr (1.55 mL) was diluted with 1,4-dioxane (1.45 mL) to afford a solution of 6 M HBr in dioxane. The solution of Boc-protected endo-27 was placed in an ice bath prior to the addition of the 6 M HBr solution. The reaction mixture was allowed to warm to rt and monitored by RP-HPLC (10% to 100% B over 12.5 min, then 100% B for 2.5 min, 0.5 mL/min). Upon consumption of the starting material (4 h), the solvent was removed in vacuo. The residue was dissolved in a mixture of approximately 75% H$_2$O in 1,4-dioxane (40 mL) and lyophilised to give the title compound oCOm-21.HBr as a pale brown powder (90 mg, 97%).

$^1$H NMR (400 MHz, DMSO-d6) δ 1.45 (3H, s, CH$_3$), 1.52 (3H, s, CH$_3$), 2.90-3.05 (2H, m), 3.78-3.83 (2H, m), 3.93 (1H, s, H-7a), 6.83-6.87 (4H, m, Ph), 7.20-7.24 (6H, m, Ph), 7.97 (3H, br s); $^{13}$C NMR (100 MHz, DMSO-d6) δ 11.3, 11.9, 36.4, 36.9, 55.6, 58.6, 58.7, 60.6, 128.1, 128.2, 128.3, 128.4, 129.1, 129.3, 132.3, 132.3, 139.5, 144.6, 172.0, 172.6, 196.5; HRMS (ESI-TOF) m/z: [M−$^-$O$_2$CCF$_3$]$^+$ Calcd for C$_{25}$H$_{24}$$^{79}$BrN$_2$O$_3$$^+$ 479.0965, found 479.0940; RP-HPLC (10% to 100% B over 12.5 min, then 100% B for 2.5 min), $t_R$=9.00 min.

g) tert-Butyl (2-(4,7-dimethyl-1,3-dioxo-5,6-diphenylisoindolin-2-yl)ethyl)carbamate (BP-20)

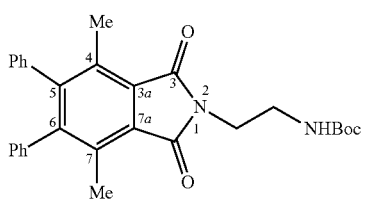

To a solution of oCOm-20 (414 mg, 0.71 mmol, endo:exo 2.6:1) in anhydrous THF (11.5 mL) at 0° C. was added 1,8-diazabicyclo[5.4.0]undec-7-ene (210 μL, 1.40 mmol) dropwise. The reaction mixture was allowed to warm to rt. Upon consumption of starting material by TLC (approximately 10 min), saturated NH$_4$Cl (7 mL) was added and the aqueous phase was extracted with EtOAc (3×20 mL). The combined organic extracts were dried over MgSO$_4$ and concentrated in vacuo to afford a brown crystalline solid. Purification by flash chromatography (0%, then 5%, then 10% EtOAc in CH$_2$Cl$_2$) furnished the title compound BP-20 (205 mg, 61%) as white crystals. Mp. 181-182° C.; $R_f$ (10% EtOAc in CH$_2$Cl$_2$) 0.37; IR (ATR) $v_{max}$/cm$^{-1}$ 3431, 2981, 2944, 1758 (C=O), 1725 (C=O), 1698 (C=O), 1504, 1431, 1401, 1391, 1365, 1284, 1246, 1180, 1153, 991, 751, 699; $^1$H NMR (400 MHz, CDCl$_3$) δ 1.40 (9H, s, C(CH$_3$)$_3$), 2.41 (6H, s, CH$_3$), 3.42-3.47 (2H, m, 2'-H), 3.85 (2H, t, J=5.6 Hz), 4.89 (1H, br s), 6.87-6.89 (4H, m, Ph), 7.10-7.18 (6H, m, Ph); $^{13}$C NMR (100 MHz, CDCl$_3$) δ 15.7, 28.3, 37.6), 39.9, 79.4 ($C_{quat}$), 126.8, 127.8), 128.1, 129.5, 134.4, 138.7, 148.4, 155.9, 169.3; HRMS (ESI-TOF) m/z: [M+Na]$^+$ Calcd for C$_{29}$H$_{30}$N$_2$NaO$_4$$^+$ 493.2098, found 493.2097; Anal. Calcd for C$_{29}$H$_{30}$N$_2$O$_4$: C, 74.02; H, 6.43; N, 5.95. Found: C, 74.00; H, 6.52; N, 5.91; RP-HPLC (10% to 100% B over 12.5 min, then 100% B for 4.5 min), $t_R$=15.21 min.

h) 2-(4,7-Dimethyl-1,3-dioxo-5,6-diphenylisoindohn-2-yl)ethanaminium 2,2,2-trifluoroacetate (BP-21)

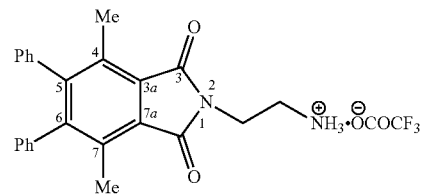

A solution of BP-20 (204 mg, 0.43 mmol) in 1,4-dioxane (9 mL) was prepared under an ambient atmosphere. In a separate vessel, concentrated HCl (2 mL) was diluted with 1,4-dioxane (1.8 mL) to afford a solution of 6 M HCl in dioxane which was then added dropwise to the solution of Boc-protected 29 at rt. The reaction mixture was monitored by RP-HPLC (10% to 100% B over 12.5 min, then 100% B for 2.5 min, 0.5 mL/min). Upon consumption of the starting material (4-5 h), the solvent was removed in vacuo. The residue was dissolved in a mixture of approximately 60% H$_2$O in 1,4-dioxane (20 mL) and lyophilised. The crude off-white solid obtained was dissolved in approximately 10% CH$_3$CN in H$_2$O (2×5 mL) and loaded onto a pre-washed C-18 solid phase extraction cartridge (100% CH$_3$CN [2×10 mL]), then 90%, then 50% CH$_3$CN in H$_2$O [1×10 mL each], 20% CH$_3$CN in H$_2$O [2×10 mL]). The product was eluted from the C-18 cartridge (20% to 40% CH$_3$CN in H$_2$O [10% increments, 2×10 mL each], then 50% to 100% CH$_3$CN in H$_2$O [10% increments, 10 mL each]). The fractions collected were analysed by RP-HPLC (10% to 100% B over 12.5 min, then 100% CH$_3$CN for 2.5 min, $t_R$=9.22 min) and lyophilised to afford the title compound BP-21 (1634 mg, 78%) as a white powder. IR (ATR) $v_{max}$/cm$^{-1}$ 1763 (C=O), 1697 (C=O), 1664, 1430, 1403, 1364, 1203, 1174, 1136, 761, 699; $^1$H NMR (400 MHz, DMSO-d6) δ 2.32 (6H, s, CH$_3$), 3.11 (2H, apparent q, J=6.0 Hz), 3.86 (2H, t, J=6.0 Hz), 6.95-6.97 (4H, m, Ph), 7.13-7.17 (2H, m, Ph), 7.20-7.24 (4H, m, Ph), 7.85 (3H, br s); $^{13}$C NMR (100 MHz, DMSO-d6) δ 15.2, 35.1, 37.7, 126.9, 127.8, 128.0, 129.3, 133.3, 138.2, 147.8, 168.4; $^{19}$F NMR (376 MHz, DMSO-d6) δ −73.78; HRMS (ESI-TOF) m/z: [M−⁻O₂CCF₃]⁺ Calcd for C₂₄H₂₃N₂O₂⁺ 371.1754, found 371.1741; RP-HPLC (10% to 100% B over 12.5 min, then 100% B for 2.5 min), $t_R$=9.22 min.

Synthesis of desbromo-oCOm-21 (DB-oCOm-21) as a Control Compound.

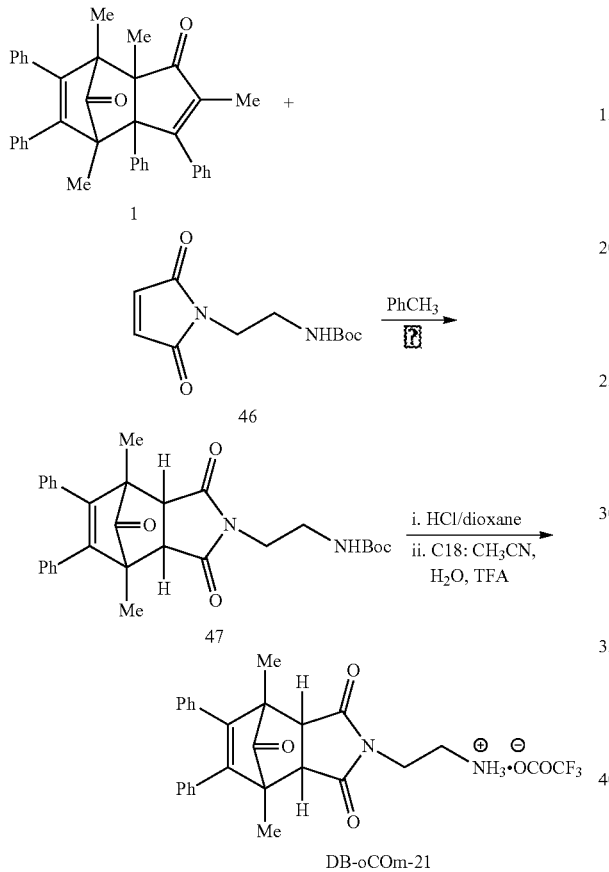

Scheme 21b: Synthesis of control compound DB-oCOm-21 as the hydrochloride and trifluoroacetic acid salts.

a) tert-Butyl (2-(4,7-dimethyl-1,3,8-trioxo-5,6-diphenyl-3a,4,7,7a-tetrahydro-1H-4,7-methanoisoindol-2(2H)-yl)ethyl)carbamate (47)

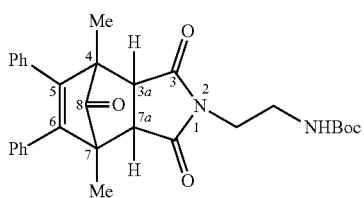

Maleimide 46 (150 mg, 0.62 mmol) and diene dimer 17 (171 mg, 0.66 mmol) were dissolved in anhydrous toluene (3.6 mL) and placed under argon. The mixture was then heated to reflux for 4 h. After cooling to rt, the solvent was removed in vacuo to afford an orange oil that was purified by flash chromatography (0%, then 5%, then 7%, then 20% EtOAc in CH₂Cl₂) to afford an inseparable ~4.2:1 mixture (endo:exo) of the title compound 47 (300 mg, 52%) as a white foam. IR (ATR) $v_{max}$/cm⁻¹ 3411, 2977, 2933, 1788 (C=O), 1770 (C=O), 1704 (C=O), 1698 (C=O), 1693 (C=O), 1509, 1392, 1168, 1164, 768, 698; HRMS (ESI-TOF) m/z: [M+Na]⁺ Calcd for C₃₀H₃₂N₂NaO₅⁺ 523.2203, found 523.2173; RP-HPLC (10% to 100% B over 12.5 min, then 100% B for 2.5 min), $t_R$=14.56 min, endo- and exo-isomers co-elute as a single peak.

Endo-47 NMR data: ¹H NMR (500 MHz, CDCl₃) δ inter alia 1.40 (9H, s, C(CH₃)₃), 1.57 (6H, s, CH₃), 3.23 (2H, s, 3a-H and 7a-H), 3.32-3.35 (2H, m), 3.64 (2H, t, J=5.0 Hz), 4.78 (1H, br s), 6.87-6.91 (4H, m, Ph), 7.15-7.17 (6H, m, Ph); ¹³C NMR (125 MHz, CDCl₃) δ inter alia 12.2, 28.3 (CH₃, C(CH₃)₃), 38.9, 39.6), 48.0, 56.5, 79.5, 127.7, 128.2, 129.5, 133.0, 141.6, 156.1, 175.7, 199.7.

Exo-47 NMR data: ¹H NMR (500 MHz, CDCl₃) δ inter alia 1.40 (6H, s, CH₃), 1.45 (9H, s, C(CH₃)₃), 3.20-3.22 (2H, m), 3.23 (2H, s, H-3a and -7a), 3.68 (2H, t, J=5.0 Hz, 3'-H), 4.78 (1H, br s), 7.03-7.05 (4H, m, Ph), 7.23-7.25 (6H, m, Ph); ¹³C NMR (125 MHz, CDCl₃) δ inter alia 9.1, 28.3, 38.1, 38.7, 49.8, 55.7, 79.4, 128.0, 128.3, 129.0, 133.0, 144.4, 155.8, 173.4, 204.7.

b) 2-(4,7-Dimethyl-1,3,8-trioxo-5,6-diphenyl-3a,4,7,7a-tetrahydro-1H-4,7-methanoisoindol-2(2H)-yl)ethanaminium 2,2,2-trifluoroacetate (DB-oCOm-21)

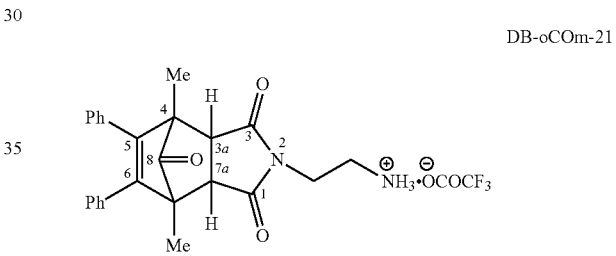

A solution of Boc-protected 47 (512.6 mg, 1.02 mmol) in 1,4-dioxane (3 mL) was prepared under an ambient atmosphere. In a separate vessel, concentrated HCl (4.6 mL) was diluted with 1,4-dioxane (4.3 mL) to afford a solution of 6 M HCl in dioxane. The solution of Boc-protected 31 was placed in an ice bath prior to the addition of the 6 M HCl solution. The reaction mixture was allowed to warm to rt and monitored by RP-HPLC (10% to 100% B over 12.5 min, then 100% B for 2.5 min, 0.5 mL/min). Upon consumption of the starting material (2-3 h) as indicated by the formation of a white precipitate, the solvent was removed in vacuo to afford an off-white solid that was dissolved in 16% CH₃CN in H₂O (15 mL) and loaded onto a pre-washed C-18 solid phase extraction cartridge (100% CH₃CN [2×10 mL]), then 90%, then 50% CH₃CN in H₂O [1×10 mL each], 20% CH₃CN in H₂O [2×10 mL]). The product was eluted from the C-18 cartridge (20% to 40% CH₃CN in H₂O [10% increments, 2×10 mL each], then 50% to 100% CH₃CN in H₂O [10% increments, 10 mL each]). The fractions collected were analysed by RP-HPLC (10% to 100% B over 12.5 min, then 100% B for 2.5 min, $t_R$=8.60 min, endo- and exo-isomers co-elute as a single peak) and lyophilised to afford an inseparable ~4.1:1 mixture (endo:exo) of the title compound DB-oCOm-21 (407 mg, 73%, as a white powder that rapidly collapsed to a thick pale yellow oil. IR (ATR) $v_{max}$/cm⁻¹ 2984, 2933, 1790 (C=O), 1774 (C=O), 1736 (C=O), 1702 (C=O), 1697 (C=O), 1670, 1394, 1374, 1239, 1203, 1177, 1137, 1046, 713, 698; HRMS (ESI-TOF) m/z: [M−$^−$O$_2$CCF$_3$]$^+$ Calcd for C$_{25}$H$_{25}$N$_2$O$_3^+$ 401.1860, found 401.1840; RP-HPLC (10% to 100% B over 12.5 min, then 100% B for 2.5 min), $t_R$=8.60 min, endo- and exo-isomers co-elute as a single peak.

Endo-DB-oCOm-21 NMR data: $^1$H NMR (400 MHz, DMSO-d6) δ inter alia 1.43 (6H, s, 2×CH$_3$), 2.93-2.97 (2H, m), 3.51 (2H, s, H-3a and -7a), 3.67 (2H, t, J=8.0 Hz, 3'-H), 6.84-6.87 (4H, m, Ph), 7.17-7.28 (6H, m, Ph), 7.81 (3H, br); $^{13}$C NMR (125 MHz, DMSO-d6) δ inter alia 11.8, 36.1, 36.7, 47.7, 55.8, 127.6, 128.1, 129.2, 133.1, 141.3, 176.1, 199.0 (C=O, C-8); $^{19}$F NMR (376 MHz, DMSO-d6) δ −73.77.

Exo-DB-oCOm-21 NMR data: $^1$H NMR (400 MHz, DMSO-d6) δ inter alia 1.19 (2×CH$_3$).

Example 19 oCOm-23

2-(2-(2-Aminoethyl)aminoethyl)-3a-bromo-3a,4,7,7a-tetrahydro-4,7-dimethyl-5,6-diphenyl-4,7-methano-1H-isoindole-1,3,8(2H)-trione bis-trifluoroacetate salt: Where R$^1$=R$^2$=Ph; R$^3$=R$^4$=Me; A$^3$=NR$^{14}$; R$^{14}$=CH$_2$CH$_2$NHCH$_2$CH$_2$NH$_2$.2CF$_3$CO$_2$H; X=Br Scheme 22a: Synthesis of oCOm-23 as its trifluoroacetic acid salt.

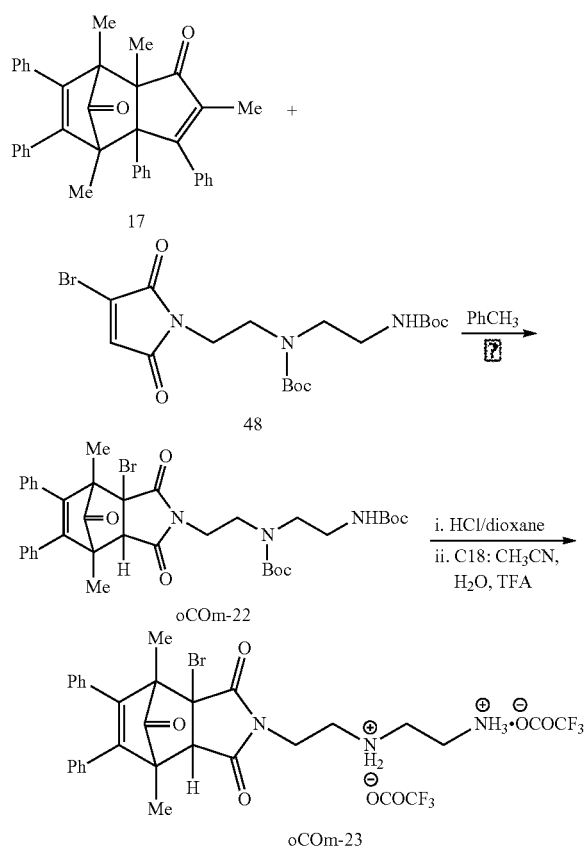

a) tert-Butyl (2-aminoethyl)(2-((tert-butoxycarbonyl)amino)ethyl)carbamate (49)

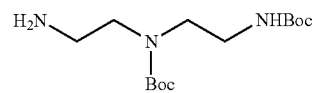

49

A solution of ethyl trifluoroacetate (4 mL, 33.6 mmol) in anhydrous CH$_2$Cl$_2$ (39 mL) was slowly added to a solution of diethyltriamine (3.6 mL, 33.6 mmol) in anhydrous CH$_2$Cl$_2$ (39 mL) at 0° C. The reaction mixture was stirred at 0° C. for 2 h and then rt for a further 2 h. The solvent was removed in vacuo to obtain a crude yellow oil that was re-dissolved in anhydrous CH$_2$Cl$_2$ (66 mL) and cooled to 0° C. A solution of Boc$_2$O (14.8 g, 68 mmol) in anhydrous CH$_2$Cl$_2$ (66 mL) was added over 1 h by dropping funnel and the reaction mixture was allowed to stir at rt for 48 h. Removal of the solvent in vacuo gave a thick yellow oil that was taken up in a solution of 5% H$_2$O in CH$_3$OH (75 mL). K$_2$CO$_3$ $_{(s)}$ (26 g, 188 mmol) was added and the suspension refluxed for 2.5 h. Upon cooling, the CH$_3$OH was removed in vacuo and the residue diluted in distilled H$_2$O (100 mL). The pH was adjusted to ~13 using 15% (w/v) aqueous NaOH and the aqueous phase extracted with CHCl$_3$ (3×100 mL). The solvent was removed in vacuo to obtain an approximate 3:1 mixture of the title compound 49 and the tri-Boc protected amine as a thick yellow oil (6.9 g). This crude mixture could be used directly or purified by flash chromatography (0%, then 5% EtOAc in CH$_2$Cl$_2$ with 5% NEt$_3$, then 10% CH$_3$OH in CHCl$_3$ with 5% NEt$_3$) to yield the title compound 32 (4.2 g, 41%) as a yellow oil that solidified upon cooling to form a waxy yellow solid. Mp. 77-80° C.; R$_f$ (10% EtOAc in CH$_2$Cl$_2$ and 5% NEt$_3$) 0.11; R$_f$ (10% CH$_3$OH in CHCl$_3$ and 5% NEt$_3$) 0.31; $^1$H NMR (400 MHz, CDCl$_3$) δ inter alia 1.41-1.44 (18H, m, 2×C(CH$_3$)$_3$), 2.90-2.93 (2H, m), 3.23-3.26 (4H, m), 3.29-3.33 (4H, m), 5.28-5.45 (1H, m); $^{13}$C NMR (100 MHz, CDCl$_3$) δ inter alia 28.3, 28.4, 39.2, 39.6, 40.2, 40.4, 47.6, 48.2, 49.6, 50.3, 79.2, 80.3, 156.2. The $^1$H and $^{13}$C NMR data obtained was in agreement with that reported from literature.[28]

b) tert-Butyl (2-((tert-butoxycarbonyl)amino)ethyl)(2-(2,5-dioxo-2,5-dihydro-1H-pyrrol-1-yl)ethyl)carbamate (50)

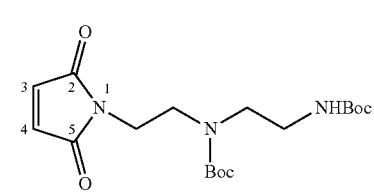

50

To a suspension of crude di-Boc triamine 49 (11.1 g, 36.6 mmol) in saturated NaHCO$_3$ (183 mL) at rt was added powdered N-(ethoxycarbonyl)maleimide (45)[22] (6.2 g, 36.7 mmol). After stirring the reaction mixture for 15 min, THF was added (281 mL) and the resulting biphasic suspension was stirred vigorously at rt for 2 h. H$_2$O (100 mL) was then added and the aqueous phase extracted with EtOAc (3×100 mL). The combined organic extracts were washed with saturated NaCl (150 mL), dried over MgSO₄ and then concentrated in vacuo to afford an orange oil. Purification by flash chromatography (0%, then 5%, then 10%, then 50% EtOAc in CH₂Cl₂) gave a mixture of the title compound 50 and ethyl carbamate (3.7 g) as a yellow oil.

An analytically pure sample of 501 was obtain by re-purification by flash chromatography (0%, then 5%, then 20% EtOAc in CH₂Cl₂, then 100% EtOAc) to afford the title compound 33 as a pale yellow oil that forms colourless crystals upon cooling. Mp. 105-107° C.; $R_f$ (5% EtOAc in CH₂Cl₂) 0.11, $R_f$ (20% EtOAc in CH₂Cl₂) 0.38; IR (ATR) $v_{max}$/cm⁻¹ 2976, 2929, 1708 (C=O), 1671 (C=O), 1508, 1404, 1364, 1251, 1155, 824, 696: ¹H NMR (500 MHz, CDCl₃) δ inter alia 1.37-1.40 (18H, m), 3.21-3.29 (4H, m), 3.38-3.40 (2H, m), 3.62-3.67 (2H, m), 5.07 (1H, br s), 6.65-6.69 (2H, m); ¹³C NMR (125 MHz, CDCl₃) δ inter alia 28.2, 28.3, 35.9, 36.2, 39.4, 45.6, 45.9), 46.5, 47.7, 79.1, 80.1, 80.3), 134.1, 134.1, 134.2, 155.6, 155.8, 156.0), 170.3, 170.7; HRMS (ESI-TOF) m/z: [M+Na]⁺ Calcd for $C_{18}H_{29}N_3NaO_6^+$ 406.1949; Found 406.1968.

c) tert-Butyl (3-(4-bromo-1,3-dioxo-1,3-dihydro-1H-pyrrol-1-yl)ethyl)(4-((tert-butoxycarbonyl)amino)ethyl)carbamate (48)

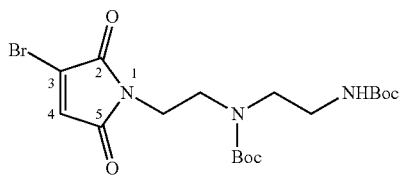

To a solution containing an approximate 1:1 mixture of maleimide 50 and ethyl carbamate (1.81 g, 4.7 mmol) in CH₂Cl₂ (23.6 mL) was added bromine (270 μL, 5.2 mmol) at rt. The dark brown solution was heated to reflux for 1.5 h and then cooled to rt. Removal of the solvent in vacuo gave a thick orange gum that was dissolved in anhydrous THF (23.6 mL) and cooled to 0° C. under argon. Anhydrous NEt₃ (730 μL, 5.2 mmol) was added dropwise at 0° C. and the resulting orange suspension was stirred at 0° C. for 4 h. H₂O (30 mL) was then added at 0° C. and the aqueous phase was extracted with EtOAc (3×40 mL). The combined organic extracts were dried over MgSO₄ and concentrated in vacuo to afford a brown-yellow oil. Purification by flash chromatography (0%, then 5%, then 10%, then 20% EtOAc in CH₂Cl₂) gave the title compound 48 (550 mg, 25%) as a yellow oil and an approximate 1:1 mixture of 48 and ethyl carbamate (806 mg). $R_f$ (5% EtOAc in CH₂Cl₂) 0.11, $R_f$ (20% EtOAc in CH₂Cl₂) 0.41; IR (ATR) $v_{max}$/cm⁻¹ 3370, 2976, 2933, 1716 (C=O), 1677 (C=O), 1508, 1391, 1364, 1250, 1151, 701; ¹H NMR (500 MHz, CDCl₃) δ inter alia 1.39-1.46 (18H, m), 3.24-3.32 (4H, m), 3.40-3.43 (2H, m), 3.69-3.73 (2H, m), 5.06-5.10 (1H, m), 6.85-6.89 (1H, m); ¹³C NMR (125 MHz, CDCl₃) δ inter alia 28.2, 28.4, 36.8, 37.3, 39.1, 39.4, 45.4, 45.9, 46.3, 47.8, 79.1, 79.3, 80.3, 80.5, 131.3, 131.5, 131.9, 132.0), 155.8, 155.9, 156.1, 165.0, 165.5, 168.1, 168.5; HRMS (ESI-TOF) m/z: [M+Na]⁺ Calcd for $C_{18}H_{28}^{79}BrN_3NaO_6^+$ 484.1054, found 484.1074.

d) tert-Butyl (2-(3a-bromo-4,7-dimethyl-1,3,8-trioxo-5,6-diphenyl-3a,4,7,7a-tetrahydro-1H-4,7-methanoisoindol-2(2H)-yl)ethyl)(2-((tert-butoxycarbonyl)amino)ethyl)carbamate (oCOm-22)

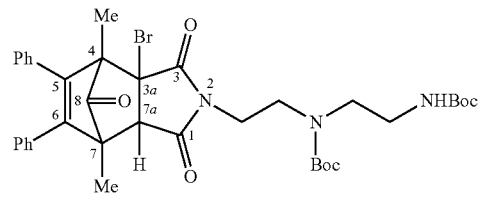

A suspension of bromo-maleimide 48 (275 mg, 0.60 mmol) and diene dimer 1 (163 mg, 0.31 mmol) in anhydrous toluene (5 mL) was placed under an argon atmosphere and then heated to reflux for 4 h. The reaction mixture was cooled to rt and the solvent removed in vacuo to afford a brown oil. Purification by flash chromatography (0%, then 5%, then 10% EtOAc in CH₂Cl₂) afforded the endo-isomer of the title compound oCOm-22 (261 mg, 60%) as a colourless foam and a 2:1 mixture of the endo:exo-isomers of oCOm-22 as a thick yellow oil (115 mg, 27%).

Data for endo-oCOm-22: Mp. 73-78° C. (slow decomp.); $R_f$ (5% EtOAc in CH₂Cl₂) 0.17, $R_f$ (10% EtOAc in CH₂Cl₂) 0.48; IR (ATR) $v_{max}$/cm⁻¹ 2976, 2922, 1791 (C=O), 1716 (C=O), 1685 (C=O), 1391, 1365, 1248, 1155, 760, 698; ¹H NMR (500 MHz, CDCl₃) δ inter alia 1.41-1.48 (18H, m), 1.60 (3H, s, CH₃), 1.61 (3H, s, CH₃), 3.25-3.32 (4H, m,), 3.45-3.51 (3H, m), 3.74-3.75 (2H, m), 4.94 (1H, br s), 6.83-6.86 (4H, m, Ph), 7.16-7.20 (6H, m, Ph); ¹³C NMR (125 MHz, CDCl₃) δ inter alia 11.5, 12.4, 28.4, 28.4), 37.9, 38.5, 39.4, 44.6, 45.0, 45.0, 46.7, 47.8, 56.2, 56.4, 58.7, 60.4, 61.0, 79.3, 80.6, 80.8, 128.1, 128.1, 128.2, 128.3, 129.3, 129.6, 132.4, 132.4, 132.5, 140.4, 144.6, 155.7, 155.9, 172.2, 172.6, 196.8, 197.0; HRMS (ESI-TOF) m/z: [M+Na]⁺ Calcd for $C_{37}H_{44}^{79}BrN_3NaO_7^+$ 744.2255, found 744.2231; RP-HPLC (10% to 100% B over 12.5 min, then 100% B for 2.5 min), $t_R$=15.61 min.

Exo-oCOm-22: $R_f$ (5% EtOAc in CH₂Cl₂) 0.07, $R_f$ (10% EtOAc in CH₂Cl₂) 0.37; RP-HPLC (10% to 100% B over 12.5 min, then 100% B for 2.5 min), $t_R$=15.61 min.

e) 2-(2-(2-Aminoethyl)aminoethyl)-3a-bromo-3a,4,7,7a-tetrahydro-4,7-dimethyl-5,6-diphenyl-4,7-methano-1H-isoindole-1,3,8(2H)-trione bis-trifluoroacetate salt (oCOm-23)

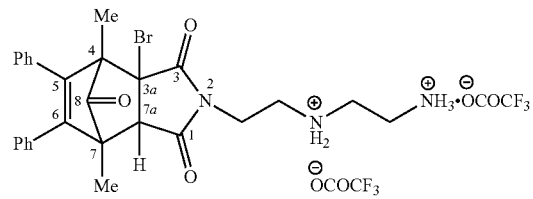

A solution of endo-Boc-protected oCOm-22 (261 mg, 0.36 mmol) in 1,4-dioxane (2 mL) was prepared under an ambient atmosphere. In a separate vessel, concentrated aqueous HCl (1.6 mL, 36%=11.65 M) was diluted with 1,4-dioxane (1.5 mL) to afford a solution of 6 M HCl in dioxane. The solution of Boc-protected oCOm-22 was placed in an ice bath prior to the addition of the 6 M HCl solution. The reaction mixture was allowed to warm to rt and monitored by RP-HPLC (10% to 100% B over 12.5 min, then 100% B for 2.5 min, 0.5 mL/min). Upon consumption of the starting material (4 h), the solvent was removed in vacuo to afford an off-white solid that was dissolved in distilled $H_2O$ (40 mL) and then lyophilised to obtain a crude fluffy powder. The crude product was dissolved in 10% $CH_3CN$ in $H_2O$ (2×5 mL) and loaded onto a pre-washed C-18 solid phase extraction cartridge (100% $CH_3CN$ [2×10 mL]), then 90%, then 50% $CH_3CN$ in $H_2O$ [1×10 mL each], 10% $CH_3CN$ in $H_2O$ [2×10 mL]). The product was eluted from the C-18 cartridge (20% to 40% $CH_3CN$ in $H_2O$ [10% increments, 2×10 mL each], then 50% to 100% $CH_3CN$ in $H_2O$ [10% increments, 10 mL each]). The fractions collected were analysed by RP-HPLC (10% to 100% B over 12.5 min, then 100% B for 2.5 min, $t_R$=7.96 min) and lyophilised to afford the endo-isomer of the title compound oCOm-23 (171 mg, 63%) as a white fluffy powder. Mp. 111-114° C. (slow decomp.); IR (ATR) $v_{max}$/cm$^{-1}$ 2965, 1786 (C=O), 1715 (C=O), 1670 (C=O), 1204, 1183, 1013, 825, 798, 722, 698; $^1$H NMR (400 MHz, DMSO-d6) δ 1.46 (3H, s, $CH_3$), 1.52 (3H, s, $CH_3$), 3.12-3.20 (6H, m), 3.79-3.90 (2H, m), 3.99 (1H, s, H-7a), 6.84-6.88 (4H, m, Ph), 7.21-7.24 (6H, m, Ph), 8.11 (3H, br s), 9.26-9.31 (2H, m); $^{13}$C NMR (125 MHz, DMSO-d6) δ 11.3, 11.8, 35.2, 35.7, 43.7, 44.1, 55.6, 58.6), 60.5, 128.1, 128.2, 128.3, 128.3, 129.2, 129.3, 132.2, 132.3, 139.5, 144.6, 171.9, 172.5, 196.5 (C=O, C-8); $^{19}$F NMR (376 MHz, DMSO-d6) δ −73.67, −73.66; HRMS (ESI-TOF) m/z: [M−[$^-O_2CCF_3$]$_2$−H]$^+$ Calcd for $C_{27}H_{29}^{79}BrN_3O_3^+$ 522.1387, found 522.1364; RP-HPLC (10% to 100% B over 12.5 min, then 100% B for 2.5 min), $t_R$=7.96 min.

f) tert-Butyl (3-((tert-butoxycarbonyl)amino)ethyl) (2-(4,7-dimethyl-1,3-dioxo-5,6-diphenylisoindolin-2-yl)ethyl)carbamate (BP-22)

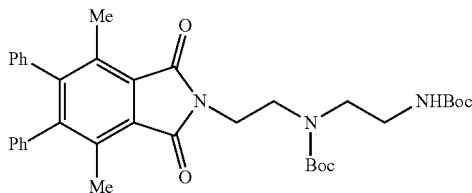

BP-22

To a solution of adduct oCOm-22 (220 mg, 0.31 mmol, endo:exo ~1:1) in anhydrous THF (4.9 mL) at 0° C. was added 1,8-diazabicyclo[5.4.0]undec-7-ene (90 µL, 0.60 mmol) dropwise. The brown reaction mixture was then allowed to warm to rt. Upon consumption of the starting material by TLC (approximately 30 min), a brown precipitate had formed and saturated $NH_4Cl$ (20 mL) was then added. The aqueous phase was extracted with EtOAc (3×10 mL). The combined organic extracts were dried over $MgSO_4$ and concentrated in vacuo to afford a brown crystalline solid. Purification by flash chromatography (0%, then 5%, then 10% EtOAc in $CH_2Cl_2$) furnished the title compound BP-22 (142 mg, 76%) as a white solid. Mp. 202-205° C.; $R_f$ (5% EtOAc in $CH_2Cl_2$) 0.17, $R_f$ (10% EtOAc in $CH_2Cl_2$) 0.54; IR (ATR) $v_{max}$/cm$^{-1}$ 3345, 2976, 2922, 1702 (C=O), 1677 (C=O), 1518, 1402, 1381, 1365, 1273, 1254, 1157, 760, 706; $^1$H NMR (500 MHz, CDCl$_3$) δ 1.32-1.35 (9H, m), 1.44 (9H, s), 2.39 (6H, s, $CH_3$), 3.31-3.41 (4H, m), 3.51-3.55 (2H, m), 3.83-3.86 (2H, m), 5.17-5.30 (1H, m), 6.86-6.88 (4H, m, Ph), 7.09-7.17 (6H, m, Ph); $^{13}$C NMR (125 MHz, CDCl$_3$) δ 15.6, 15.6, 28.0, 28.0, 28.1, 28.4), 35.8, 36.2, 39.4, 39.5, 45.8, 46.3, 46.6, 48.1, 79.1, 79.9, 80.1, 126.7, 126.8, 127.7, 128.1, 128.2, 129.4, 134.1, 134.4, 138.6, 138.8, 148.1, 148.5, 155.7, 156.0, 168.9, 169.2 (C=O, C-1 and C-3); HRMS (ESI-TOF) m/z: [M+Na]$^+$ Calcd for $C_{36}H_{43}N_3NaO_6^+$ 636.3044, found 636.3071; RP-HPLC (10% to 100% B over 12.5 min, then 100% B for 7.5 min), $t_R$=16.23 min.

g) 2-(2-(2-Aminoethyl)aminoethyl)-4,7-dimethyl-5,6-diphenyl-1H-isoindole-1,3,8(2H)-diione bis-trifluoroacetate salt (BP-23)

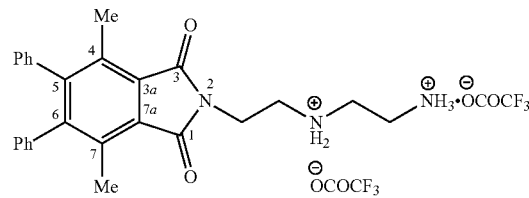

BP-23

A suspension of BP-22 (120 mg, 0.20 mmol) in 1,4-dioxane (2 mL) was prepared under an ambient atmosphere. In a separate vessel, concentrated HCl (1.2 mL) was diluted with 1,4-dioxane (0.5 mL) to afford a solution of 6 M HCl in dioxane which was then added dropwise to the solution of Boc-protected BP-22 at rt. Additional quantities of 1,4-dioxane (7 mL) and distilled $H_2O$ (5 mL) were added. The reaction mixture was stirred at rt and monitored by RP-HPLC (10% to 100% B over 12.5 min, then 100% B for 7.5 min, 0.5 mL/min). After stirring for 6 h, the reaction mixture was heated to 30° C. for 14.5 h and then 50° C. for 7 h. The solvent was removed in vacuo to afford a white precipitate that was dissolved in 10% 1,4-dioxane in $H_2O$ (22 mL) and lyophilised. The resulting white solid was then dissolved in 10% $CH_3CN$ in $H_2O$ (2×5 mL) and loaded onto a pre-washed C-18 solid phase extraction cartridge (100% $CH_3CN$ [2×10 mL]), then 90%, then 50% $CH_3CN$ in $H_2O$ [1×10 mL each], 10% $CH_3CN$ in $H_2O$ [2×10 mL]). The product was eluted from the C-18 cartridge (20% to 40% $CH_3CN$ in $H_2O$ [10% increments, 2×10 mL each], then 50% to 100% $CH_3CN$ in $H_2O$ [10% increments, 10 mL each]). The fractions collected were analysed by RP-HPLC (10% to 100% B over 12.5 min, then 100% B for 2.5 min, $t_R$=8.09 min) and lyophilised to afford the title compound BP-23 (102 mg, 82%) as a white powder. IR (ATR) $v_{max}$/cm$^{-1}$ 2976, 1765, 1700 (C=O), 1671 (C=O), 1429, 1404, 1202, 1187, 1140, 801, 754, 728, 699; $^1$H NMR (500 MHz, DMSO-d6) δ 2.32 (6H, s), 3.13 (2H, t, J=7.5 Hz), 3.24 (2H, t, J=7.5 Hz,), 3.33-3.34 (2H, m), 3.92 (2H, t, $^3J_{6',5'}$ 5.0), 6.94-6.96 (4H, m, Ph), 7.13-7.17 (2H, m, Ph), 7.20-7.24 (4H, m, Ph), 8.09 (3H, br s), 9.07 (2H, br s); $^{13}$C NMR (125 MHz, DMSO-d6) δ 15.2, 34.0, 35.1 ($CH_2$, C-3'), 44.1 ($CH_2$, C-2'), 45.4 ($CH_2$, C-5'), 117.1 (CF$_3$, q, $J_{C-F}$ 1191.7, $^-O_2C$ CF$_3$), 126.9, 127.8, 127.9, 129.2 (CH, Ph), 133.4, 138.2 (C$_{quat}$, Ph), 147.8, 158.2 (CF$_3$, q, J$_{C-F}$ 125.0, $^-$O$_2$CCF$_3$), 168.3 (C=O, C-1 and C-3); $^{19}$F NMR (376 MHz, DMSO-d6) δ −73.75; HRMS (ESI+): [M−[$^-$O$_2$CCF$_3$]$_2$—H]$^+$, found 414.2169, C$_{26}$H$_{28}$N$_3$O$_2^+$ requires 414.2176; RP-HPLC (10% to 100% B over 12.5 min, then 100% B for 2.5 min), t$_R$=8.09 min.

Synthesis of desbromo-oCOm-23 (DB-oCOm-23) as a Control Compound.

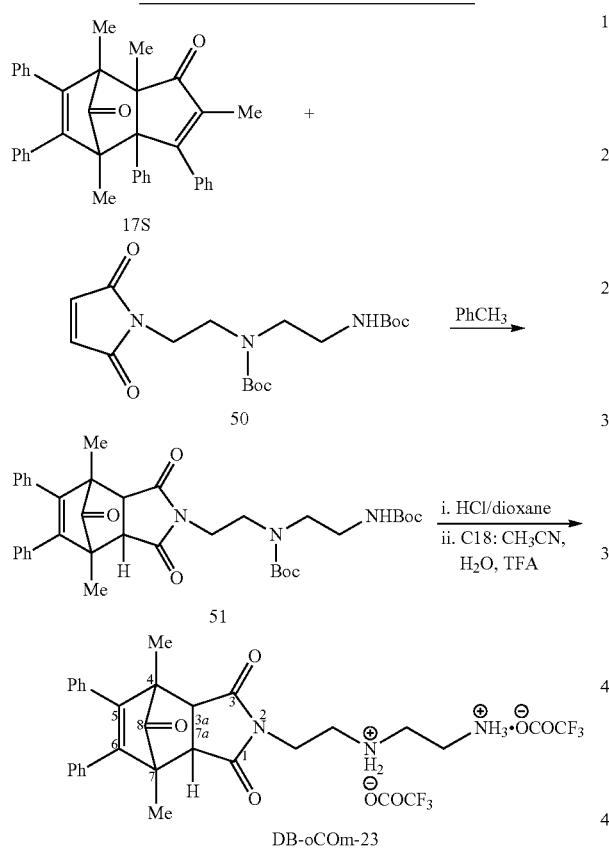

a) tert-Butyl (2-((tert-butoxycarbonyl)amino)ethyl) (2-(4,7-dimethyl-1,3,8-trioxo-5,6-diphenyl-3a,4,7, 7a-tetrahydro-1H-4,7-methanoisoindol-2(2H)-yl) ethyl)carbamate (51)

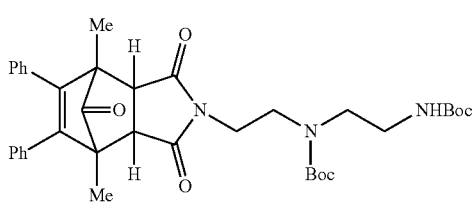

A suspension of maleimide 50 (109 mg, 0.28 mmol) and diene dimer 17 (111 mg, 0.29 mmol) in anhydrous toluene (1.7 mL) was placed under an argon atmosphere. The mixture was heated to reflux for 4 h and then allowed to cool to rt. The solvent was removed under reduced pressure to afford a brown oil. Purification by flash chromatography (0%, then 10%, then 20% EtOAc in CH$_2$Cl$_2$) furnished the title compound 51 (79.8 mg, 43%) as an inseparable mixture of endo- and exo-isomers (11:1) as a colourless foam. R$_f$ (20% EtOAc in CH$_2$Cl$_2$) 0.31; IR (ATR) ν$_{max}$/cm$^{-1}$ 2980 (C—H), 2936 (C—H), 1790 (C=O), 1702 (C=O), 1677 (C=O), 1392, 1248, 1164, 698; HRMS (ESI-TOF) m/z: [M+Na]$^+$ Calcd for C$_{37}$H$_{45}$N$_3$NaO$_7^+$ 666.3150, found 666.3169.

Endo-51 NMR data: $^1$H NMR (500 MHz, CDCl$_3$) δ inter alia 1.42-1.46 (18H, m), 1.56 (6H, s), 3.18-3.24 (4H, m), 3.27-3.31 (2H, m), 3.37-3.45 (2H, m), 3.64-3.68 (2H, m), 4.96-5.17 (1H, m), 6.87-6.89 (4H, m, Ph), 7.15-7.16 (6H, m, Ph); $^{13}$C NMR (125 MHz, CDCl$_3$) δ inter alia 12.2, 28.3, 28.4, 37.3, 37.9, 39.6, 44.8, 45.4, 48.1 (CH, C-3a and C-7a), 48.2, 56.4, 79.3, 79.4, 80.2, 127.6, 128.1, 129.6, 133.1, 141.7, 156.0, 156., 175.2, 175.9, 199.5, 200.0; RP-HPLC (10% to 100% B over 12.5 min, then 100% B for 7.5 min), t$_R$=14.97 min.

Exo-51 NMR data: $^1$H NMR (500 MHz, CDCl$_3$) δ inter alia 1.38, 7.01-7.05 (4H, m, Ph), 7.23-7.24 (6H, m, Ph); $^{13}$C NMR (125 MHz, CDCl$_3$) δ inter alia 9.1, 46.6, 128.3, 129.0); RP-HPLC (10% to 100% B over 12.5 min, then 100% B for 7.5 min), t$_R$=15.19 min.

b) 2-(2-(2-Aminoethyl)aminoethyl)-3a,4,7,7a-tetra-hydro-4,7-dimethyl-5,6-diphenyl-4,7-methano-1H-isoindole-1,3,8(2H)-trione bis-trifluoroacetate salt (DB-oCOm-23)

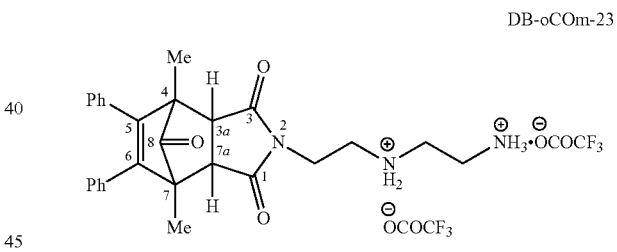

A suspension of 37 (80 mg, 0.12 mmol) in 1,4-dioxane (500 μL) was prepared under an ambient atmosphere. In a separate vessel, concentrated HCl (570 μL) was diluted with 1,4-dioxane (530 μL) to afford a solution of 6 M HCl in dioxane which was then added dropwise to the solution of 51 at rt. Additional 1,4-dioxane (1 mL) was added to allow for dissolution of the precipitate. The reaction mixture was stirred at rt and monitored by RP-HPLC (10% to 100% B over 12.5 min, then 100% B for 7.5 min, 0.5 mL/min). After stirring for 4 h the solvent was removed in vacuo. The resulting yellow precipitate was then dissolved in 10% CH$_3$CN in H$_2$O (2×5 mL) and loaded onto a pre-washed C-18 solid phase extraction cartridge (100% CH$_3$CN [2×10 mL]), then 90%, then 50% CH$_3$CN in H$_2$O [1×10 mL each], 10% CH$_3$CN in H$_2$O [2×10 mL]). The product was eluted from the C-18 cartridge (20% to 40% CH$_3$CN in H$_2$O [10% increments, 2×10 mL each], then 50% to 100% CH$_3$CN in H$_2$O [10% increments, 10 mL each]). The fractions collected were analysed by RP-HPLC (10% to 100% B over 12.5 min, then 100% B for 2.5 min, t$_R$=7.47 min). The initial fractions (20% CH$_3$CN in H$_2$O and the first 30% CH$_3$CN in H$_2$O collection) were found to contain unknown impurities that co-eluted with DB-oCOm-23 and were kept separate. Pending RP-HPLC analysis, the later fractions were pooled and lyophilised to afford the title compound DB-oCOm-23 (68 mg, 82%) as an approximately 15:1 mixture of endo- and exo-isomers in the form of a white powder). IR (ATR) $v_{max}$/cm$^{-1}$ 1773, 1707 (C=O), 1670 (C=O), 1396, 1199, 1132, 837, 799, 722, 698; HRMS (ESI-TOF) m/z: [M−[$^-$O$_2$CCF$_3$]$_2$—H]$^+$ Calcd for C$_{27}$H$_{30}$N$_3$O$_3$$^+$ 444.2282; Found 444.2291; RP-HPLC (10% to 100% B over 12.5 min, then 100% B for 2.5 min), $t_R$=7.47 min.

Endo-DB-oCOm-23 NMR data: $^1$H NMR (400 MHz, DMSO-d6) δ inter alia 1.43 (6H, s), 3.04-3.21 (6H, m), 3.52 (2H, s, H-3 and -7a), 3.71 (2H, t, J=5.9 Hz,), 6.85-6.88 (4H, m, Ph), 7.18-7.22 (6H, m, Ph), 7.93 (3H, br s), 8.88 (2H, br s); $^{13}$C NMR (125 MHz, DMSO-d6) δ inter alia 11.8, 34.9, 35.1, 43.8, 44.3, 47.7, 55.8, 127.6, 128.2, 129.3, 133.0, 141.3, 158.5 (CF$_3$, q, $^2J_{CF}$ 125.0, $^-$O$_2$CCF$_3$), 176.0, 198.9; $^{19}$F NMR (376 MHz, DMSO-d6) −73.69, −73.66 (6F, $^-$O$_2$CCF$_3$).

Exo-DB-oCOm-23 NMR data: $^1$H NMR (400 MHz, DMSO-d6) δ inter alia 1.20 (6H, s, 4-CH$_3$ and 7-CH$_3$), 3.44 (2H, s, 3a-H and 7a-H), 7.13-7.16 (4H, m, Ph), 7.27-7.32 (6H, m, Ph); $^{13}$C NMR (125 MHz, DMSO-d6) δ inter alia 9.0 (CH$_3$, 4-CH$_3$ and 7-CH$_3$).

Example 20 oCOm-24

N-(2-Hydroxy-1,1-bis(hydroxymethyl)ethyl)-3-(3a-bromo-4,7-dimethyl-1,3,8-trioxo-5,6-diphenyl-3a,4,7,7a-tetrahydro-1H-4,7-methanoisoindol-2(2H)-yl) propanamide: where R$_1$=R$_2$=Ph; R$_3$=R$_4$=Me; A$^3$=NR$^{14}$; R$^{14}$=CH$_2$CH$_2$CONHC(CH$_2$OH)$_3$; X=Br

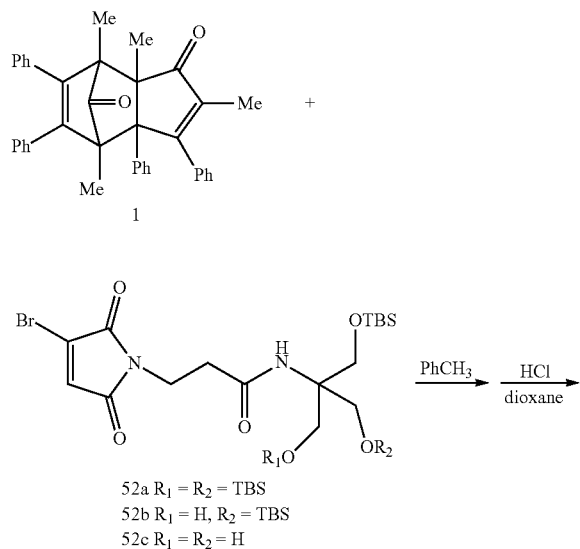

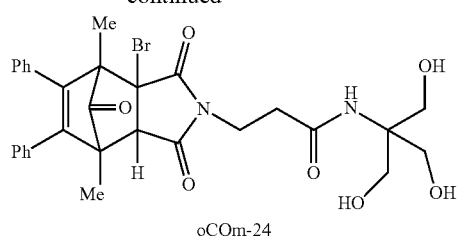

oCOm-24 a) Tri-tert-butyldimethylsilyloxy-protected maleimide 54

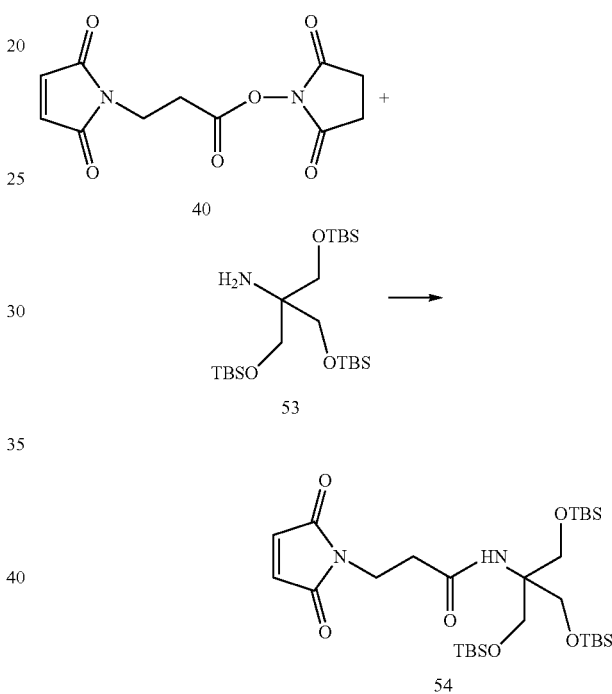

A solution of TBS-protected TRIS 53[29] (560 mg, 1.21 mmol) in CH$_2$Cl$_2$ (3 mL) was added to a suspension of succinimidyl ester 16 (242 mg, 0.91 mmol) in CH$_2$Cl$_2$ (2.5 mL) at rt. The reaction mixture was heated to 40° C. for 71.5 hours. After cooling to rt, saturated NH$_4$Cl (5 mL) was added and the aqueous phase extracted with EtOAc (3×15 mL). The combined organic extracts were washed with saturated NaCl (30 mL), dried over MgSO$_4$ and then concentrated in vacuo to obtain a red oil. Purification by flash chromatography (0%, then 10%, then 20%, then 100% EtOAc in petroleum ether) yielded the title compound549 (284 mg, 46%) as a pale yellow oil. R$_f$ (20% EtOAc in petroleum ether) 0.23; IR (ATR) $v_{max}$/cm$^{-1}$ 2955, 2928, 2884, 2856, 1708 (C=O), 1675 (C=O), 1473, 1404, 1256, 1090, 829, 775, 689; $^1$H NMR (400 MHz, CDCl$_3$) δ 0.03 (18H, s), 0.88 (27H, s), 2.45 (2H, t, J=8.0 Hz), 3.78-3.81 (8H, m,), 5.55 (1H, s), 6.68 (2H, s); $^{13}$C NMR (125 MHz, CDCl$_3$) δ −5.54, 18.2, 25.8, 35.2 (CH$_2$, C-3'), 60.6 (CH$_2$, 61.8, 134.1, 168.9, 170.3; HRMS (ESI-TOF) m/z: [M+H]$^+$ Calcd for C$_{29}$H$_{59}$N$_2$O$_6$Si$_3$$^+$ 615.3675, found 615.3665.

b) tert-butyldimethylsilyloxy-protected bromomaleimide 52a-c

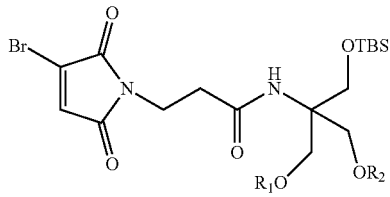

52a R₁ = R₂ = TBS
52b R₁ = H, R₂ = TBS
52c R₁ = R₂ = H

To a solution of TBS-protected maleimide 54 (108 mg, 0.18 mmol) in CCl$_4$ (1 mL) was added Br$_2$ (10 µL, 0.19 mmol) at rt. The reaction was stirred at rt for 1 h upon which NMR analysis showed consumption of the starting material. The solvent was removed in vacuo to obtain an orange oil that was then diluted in anhydrous THF (1 mL) and cooled to 0° C. NEt$_3$ (30 µL, 0.22 mmol) was added dropwise and the reaction mixture was stirred at 0° C. After 3 h, H$_2$O (1 mL) and then saturated NH$_4$Cl (2 mL) was added at 0° C. and the reaction mixture was allowed to warm to rt. The aqueous phase was extracted with EtOAc (3×7 mL) and the combined organic extracts were dried over MgSO$_4$ and concentrated in vacuo to afford a 1:2:2 mixture of the mono-di- and tri-TBS protected bromomaleimides as an orange oil. Purification by flash chromatography (0%, then 10%, then 20%, then 50% EtOAc in petroleum ether) afforded:

Tri-TBS-protected bromomaleimide 52a (19 mg, 15%) as a yellow amorphous solid. R$_f$ (10% EtOAc in petroleum ether) 0.21; IR (ATR) v$_{max}$/cm$^{-1}$ 3268 (br), 2958, 2927, 2855, 1702 (C=O), 1651 (C=O), 1538, 1405, 1046, 815, 763, 639; $^1$H NMR (400 MHz, CDCl$_3$) δ 0.03 (18H, s), 0.88 (27H, s), 2.46 (2H, t, J=8.0 Hz), 3.80 (6H, s), 3.83 (2H, t, J=8.0 Hz), 5.54 (1H, s), 6.85 (1H, s); $^{13}$C NMR (125 MHz, CDCl$_3$) δ −5.53, 18.2, 25.8, 35.0, 35.2, 60.7, 61.9, 131.4, 131.9, 165.0, 168.2, 168.6; HRMS (ESI-TOF) m/z: [M+Na]$^+$ Calcd for C$_{29}$H$_{57}$$^{79}$BrN$_2$NaO$_6$Si$_3$$^+$ 715.2600, found 715.2599.

Bis-TBS-protected bromomaleimide 52b (15 mg, 15%) as a yellow amorphous solid. R$_f$ (20% EtOAc in petroleum ether) 0.21; IR (ATR) v$_{max}$/cm$^{-1}$ 3272 (br), 2954, 2927, 2856, 2851, 1702 (C=O), 1625 (C=O), 1538, 1377, 1234, 1024, 832, 776, 669; $^1$H NMR (400 MHz, CDCl$_3$) δ 0.06, 0.07, 0.89, 2.51 (2H, t, J=7.2 Hz,), 3.43 (2H, d, J=9.5 Hz,), 3.68 (2H, s), 3.83-3.89 (4H, m, H), 6.06 (1H, s), 6.87 (1H, s); $^{13}$C NMR (125 MHz, CDCl$_3$) δ −5.58, 5.55, 18.2, 25.8, 35.1 35.2, 61.2, 62.2, 63.4, 131.5, 131.9, 165.0, 168.1), 170.2; HRMS (ESI-TOF) m/z: [M+H]$^+$ Calcd for C$_{23}$H$_{44}$$^{79}$BrN$_2$O$_6$Si$_2$$^+$ 579.1916, found 579.1904.

Mono-TBS-protected bromomaleimide 52c (7 mg, 8%) was isolated as a yellow amorphous solid. R$_f$ (20% EtOAc in petroleum ether) 0.16; IR (ATR) v$_{max}$/cm$^{-1}$ 3272 (br), 2953, 2927, 2883, 2855, 1702 (C=O), 1626 (C=O), 1471, 1462, 1249, 1024, 832, 773, 669; $^1$H NMR (400 MHz, CDCl$_3$) δ 0.09 (6H, s), 0.90 (9H, s), 2.57 (2H, t, J=7.0 Hz), 3.47 (2H, d, J=11.9 Hz), 3.67 (2H, s), 3.72 (2H, d J 11.9 Hz), 3.89 (2H, t, J=7.0 Hz,), 6.39 (1H, s), 6.88 (1H, s); $^{13}$C NMR (125 MHz, CDCl$_3$) δ −5.59, −3.59, 18.2, 25.6, 25.8, 35.0, 35.2, 61.4, 63.6, 131.5, 132.0, 165.1, 168.2, 170.9; HRMS (ESI-TOF) m/z: [M+H]$^+$ Calcd for C$_{17}$H$_{30}$$^{79}$BrN$_2$O$_6$Si$^+$ 465.1051, found 465.1024.

c) N-(2-Hydroxy-1,1-bis(hydroxymethyl)ethyl)-3-(3a-bromo-4,7-dimethyl-1,3,8-trioxo-5,6-diphenyl-3a,4,7,7a-tetrahydro-1H-4,7-methanoisoindol-2(2H)-yl)propanamide (oCOm-24)

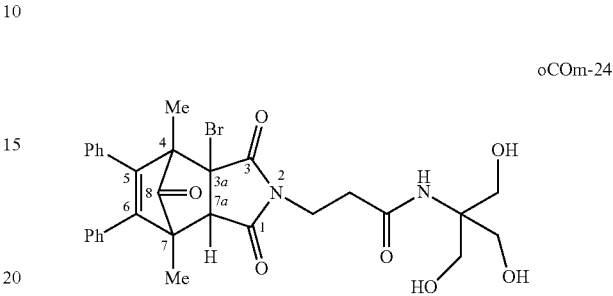

oCOm-24

To a solution containing a 1:2:3 ratio of TBS-protected bromomaleimides 52a:52b:52c (215 mg combined mass, 0.39 mmol) in anhydrous toluene (2.7 mL) was added diene dimer 17 (132 mg, 0.25 mmol). The reaction mixture was heated to reflux for 3 h and then cooled to rt. The solvent was removed in vacuo to obtain an orange oil. The crude mixture was semi-purified by flash chromatography (CH$_2$Cl$_2$ load, then 0%, then 10%, then 60% EtOAc in petroleum ether) to remove the excess diene dimer 17 and afford material containing a mixture of the tri-, bis- and mono TBS-protected cycloadducts (276 mg) which was used without further purification. A portion of the mixture of TBS-protected cycloadducts (148 mg) was dissolved in 1,4-dioxane (2.4 mL) under an ambient atmosphere. In a separate vessel, concentrated aqueous HCl (1 mL,) was diluted with 1,4-dioxane (960 µL) to afford a solution of 6 M HCl in dioxane. The solution of TBS-protected cycloadducts was placed in an ice bath prior to the addition of the 6 M HCl solution. The reaction mixture was allowed to warm to rt and monitored by RP-HPLC (10% to 100% B over 12.5 min, then 100% B for 2.5 min, 0.5 mL/min). Upon consumption of the starting material (3 h), the solvent was removed in vacuo. The residue obtained was dissolved in 20% CH$_3$CN in H$_2$O (10 mL) and then loaded onto a pre-washed C-18 solid phase extraction cartridge (100% CH$_3$CN [2×10 mL]), then 90%, then 50% CH$_3$CN in H$_2$O [1×10 mL each], 20% CH$_3$CN in H$_2$O [2×10 mL]). The compound was eluted from the C-18 cartridge (20% to 50% CH$_3$CN in H$_2$O [10% increments, 2×10 mL each], then 60% to 100% CH$_3$CN in H$_2$O [10% increments, 10 mL each]). The fractions collected were analysed by RP-HPLC (10% to 100% B over 12.5 min, then 100% B for 2.5 min, t$_R$=9.01 min [exo] and 9.20 min [endo]). The CH$_3$CN was removed from the appropriate fractions under reduced pressure and the remaining liquid was lyophilised to afford a yellow-white residue. This yellow-white residue was dissolved in 10% CH$_3$CN in H$_2$O (2×5 mL) and re-purified using a pre-washed C-18 solid phase extraction cartridge (same protocol as previously described). The compound was eluted from the C-18 cartridge (20% CH$_3$CN in H$_2$O [2×10 mL], 30% CH$_3$CN in H$_2$O [3×10 mL], 40% CH$_3$CN in H$_2$O [2×10 mL], then 50% to 100% CH$_3$CN in H$_2$O [10% increments, 10 mL each]). The fractions collected were analysed by RP-HPLC (10% to 100% B over 12.5 min, then 100% B for 2.5 min, t$_R$=9.01 min [exo] and 9.20 min [endo]) and the CH$_3$CN was removed from the appropriate fractions in vacuo. The remaining liquid was lyophilised to afford the title compound oCOm-24 as a colourless hygroscopic powder (8 mg, 3% over two steps, >99% purity, inseparable 8:1 mixture of endo:exo isomers) and a second fraction containing oCOm-24 as a colourless hygroscopic powder (11 mg, 4% over two steps, 86% purity, inseparable 3:1 mixture of endo:exo isomers). Mp. 92-96° C. (slow decomp.); IR (ATR) $v_{max}$/cm$^{-1}$ 3406 (O—H), 2935 (C—H), 2853 (C—H), 1747 (C=O), 1671 (C=O), 1601, 1122, 1065, 826, 799, 750, 722, 706; HRMS (ESI-TOF) m/z: [M+H]$^+$ Calcd for $C_{30}H_{32}{}^{79}BrN_2O_7{}^+$ 611.1387, found 611.1373.

Endo-oCOm-24 NMR data: $^1$H NMR (400 MHz, DMSO-d6) δ inter alia 1.46 (3H, s, CH$_3$), 1.49 (3H, s, CH$_3$), 2.69 (2H, t, J=7.4 Hz), 3.52-3.55 (4H, m), 3.75-3.88 (2H, m), 4.04 (1H, s, H-7a), 4.09-4.16, 5.42-5.45 (2H, m), 6.85-6.89 (4H, m, Ph), 7.22-7.24 (6H, m, Ph), 7.98 (2H, br s); $^{13}$C NMR (125 MHz, DMSO-d6) δ inter alia 11.2, 11.7, 31.0, 35.0, 55.8), 58.2, 58.8, 59.3, 59.4, 59.5, 60.0, 62.1, 128.3, 129.1, 129.4, 132.3, 132.3, 139.5, 144.6, 169.6, 171.8, 172.2, 196.6; RP-HPLC (10% to 100% B over 12.5 min, then 100% B for 2.5 min), $t_R$=9.20 min.

Exo-oCOm-24 NMR data: $^1$H NMR (400 MHz, DMSO-d6) δ inter alia 1.18 (3H, s, CH$_3$), 1.32 (3H, s, CH$_3$), 2.60 (2H, t, J=7.5 Hz), 3.94 (1H, s, H-7a), 7.17-7.29 (6H, m, Ph); $^{13}$C NMR (125 MHz, DMSO-d6) δ inter alia 30.7, 127.8, 128.1, 128.1); RP-HPLC (10% to 100% B over 12.5 min, then 100% B for 2.5 min), $t_R$=9.01 min.

d) N-(2-Hydroxy-1,1-bis(hydroxymethyl)ethyl)-4,7-dimethyl-1,3-dioxo-5,6-diphenylisoindol-2-yl)propanamide (BP-24)

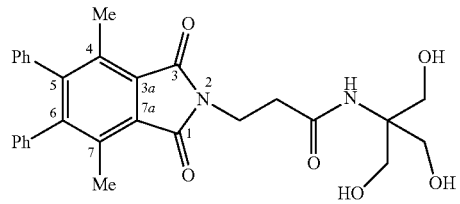

BP-24

To a solution of TBS-protected cycloadduct intermediates prepared above (127.6 mg, in anhydrous THF (2.5 mL) at rt was added an excess of 1,8-diazabicyclo[5.4.0]undec-7-ene (50 µL, 0.33 mmol) dropwise. After stirring at rt for 1 h, the solvent was removed in vacuo and the residue diluted in saturated NH$_4$Cl (5 mL). The aqueous phase was extracted with EtOAc (3×15 mL) and the combined organic extracts were dried over MgSO$_4$ and concentrated in vacuo to afford an oil that was used without further purification. This oil was diluted in 1,4-dioxane (1.5 mL) under an ambient atmosphere. In a separate vessel, concentrated aqueous HCl (770 µL) was diluted with 1,4-dioxane (770 µL) to afford a solution of 6 M HCl in dioxane which was then added dropwise to the reaction mixture at 0° C. and then allowed to warm to rt. The reaction mixture was monitored by RP-HPLC (10% to 100% B over 12.5 min, then 100% B for 4.5 min, 0.5 mL/min). Upon consumption of the starting material (1.5 h), the solvent was removed in vacuo to obtain a pale yellow residue. The crude residue was dissolved in approximately 18% CH$_3$CN in H$_2$O (5.5 mL, then 5 mL) and loaded onto a pre-washed C-18 solid phase extraction cartridge (100% CH$_3$CN [2×10 mL]), then 90%, then 50% CH$_3$CN in H$_2$O [1×10 mL each], 20% CH$_3$CN in H$_2$O [2×10 mL]). The product was eluted from the C-18 cartridge (20% CH$_3$CN in H$_2$O [2×10 mL], 30% CH$_3$CN in H$_2$O [3×10 mL], 40% CH$_3$CN in H$_2$O [2×10 mL], then 50% to 100% CH$_3$CN in H$_2$O [10% increments, 10 mL each]). The fractions collected were analysed by RP-HPLC (10% to 100% B over 12.5 min, then 100% B for 2.5 min, $t_R$=9.45 min) and lyophilised to afford the title compound BP-24 (34 mg, 17%) as a white hygroscopic powder. IR (ATR) $v_{max}$/cm$^{-1}$ 3424 (O—H), 2945, 2901, 1756 (C=O), 1697 (C=O), 1664 (C=O), 1395, 1374, 1168, 1133, 1074, 1055, 755, 698, 497; $^1$H NMR (400 MHz, DMSO-d6) δ 2.31 (6H, s, 2×CH$_3$), 2.77 (2H, t, J=7.3 Hz), 3.53 (4H, br s), 3.88 (2H, t, J=7.3 Hz), 4.14 (2H, s), 5.44 (2H, s), 6.96-6.99 (4H, m, Ph), 7.12-7.23 (6H, m, Ph), 7.99 (2H, br s); $^{13}$C NMR (125 MHz, DMSO-d6) δ 15.2, 32.2, 33.1, 59.4, 59.5, 62.0, 126.9, 127.6, 127.8, 129.3, 133.3, 138.2, 147.9, 168.1, 170.3; HRMS (ESI-TOF) m/z: [M+H]$^+$ Calcd for $C_{29}H_{31}N_2O_6{}^+$ 503.2177, found 503.2155; RP-HPLC (10% to 100% B over 12.5 min, then 100% B for 2.5 min), $t_R$=9.45 min.

Synthesis of Desbromo oCOm-24 (DB-oCOm-24) as a Control

Scheme 23b:
Synthesis of control compound DB-oCOm-24.

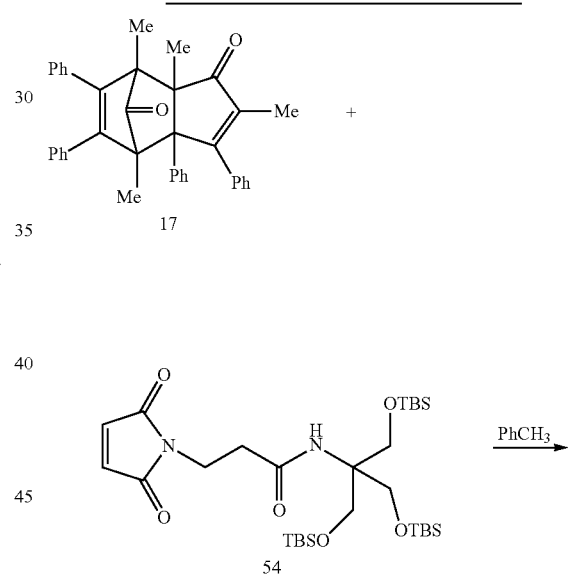

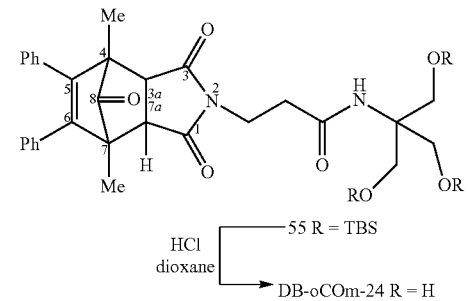

a) N-(2-tert-Butyldimethylsiloxy-1,1-bis(t-butyldimethylsiloxymethyl)ethyl)-3-(3a-bromo-4,7-dimethyl-1,3,8-trioxo-5,6-diphenyl-3a,4,7,7a-tetrahydro-1H-4,7-methanoisoindol-2(2H)-yl)propanamide (55)

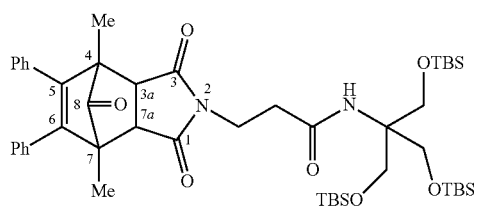

55

To a solution containing maleimide 54 (125 mg, 0.20 mmol) in anhydrous toluene (1.1 mL) was added diene dimer 1 (58 mg, 0.11 mmol). The reaction mixture was heated to reflux for 4 h and then cooled to rt. The solvent was removed in vacuo and the residue purified by flash chromatography (0%, then 5%, then 20% $Et_2O$ in petroleum ether) to afford the title compound 55 (89 mg, 50%) as an inseparable mixture of endo- and exo-isomers (9:1) which resembled a colourless foamy solid. $R_f$ endo-isomer (20% EtOAc in petroleum ether) 0.45, $R_f$ exo-isomer (20% EtOAc in petroleum ether) 0.34; IR (ATR) $v_{max}$/cm$^{-1}$ 2954 (C—H), 2927 (C—H), 2885 (C—H), 2855 (C—H), 1790 (C=O), 1771 (C=O), 1698 (C=O), 1505, 1250, 1080, 831, 774, 698; HRMS (ESI-TOF) m/z: [M+H]$^+$ Calcd for $C_{48}H_{75}N_2O_7Si_3^+$ 875.4877, found 875.4832.

Endo-55 NMR data: $^1$H NMR (500 MHz, CDCl$_3$) δ inter alia 0.03 (18H, s), 0.87 (27H, s), 1.56 (6H, s, 2×CH$_3$), 2.38-2.41 (2H, m), 3.20 (2H, s, H-3a and -7a), 3.76-3.83 (8H, m), 5.53 (1H, br s), 6.87-6.89 (4H, m, Ph), 7.14-7.16 (4H, m, Ph); $^{13}$C NMR (125 MHz, CDCl$_3$) δ inter alia—5.55, 12.2, 18.2, 25.8, 34.0, 35.5, 47.9, 56.5, 60.6, 61.9, 127.7, 128.1, 129.5, 133.0, 141.6, 168.6, 175.1, 199.5.

Exo-55 NMR data: $^1$H NMR (500 MHz, CDCl$_3$) δ inter alia 0.05 (18H, s), 0.89 (27H, s,), 1.38 (6H, s), 7.01-7.03 (4H, m, Ph), 7.22-7.24 (4H, m, Ph); $^{13}$C NMR (125 MHz, CDCl$_3$) δ inter alia 9.1, 173.2, 202.8.

b) Desbromo-CO Compound (DB-oCOm-24)

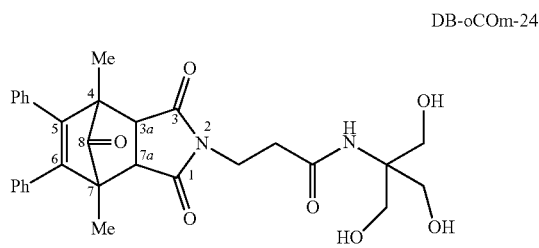 [SMILES: CC12C(=O)C(C)(C(c3ccccc3)=C1c1ccccc1)C1C(=O)N(CCC(=O)NC(CO)(CO)CO)C(=O)C12]

DB-oCOm-24

A solution of TBS-protected cycloadduct 55 (89 mg, 0.10 mmol, endo:exo, 9:1) in 1,4-dioxane (1 mL) was prepared under an ambient atmosphere. In a separate vessel, concentrated aqueous HCl (520 μL) was diluted with 1,4-dioxane (480 μL) to afford a solution of 6 M HCl in dioxane. The solution of TBS-protected cycloadduct 41 was placed in an ice bath prior to the addition of the 6 M HCl solution. The reaction mixture was allowed to warm to rt and monitored by RP-HPLC (10% to 100% B over 12.5 min, then 100% B for 2.5 min, 0.5 mL/min). Upon consumption of the starting material (1 h), the solvent was removed in vacuo to afford a yellow oil. The crude oil was dissolved in 10% CH$_3$CN in H$_2$O (2×5 mL) and loaded onto a pre-washed C-18 solid phase extraction cartridge (100% CH$_3$CN [2×10 mL]), then 90%, then 50% CH$_3$CN in H$_2$O [1×10 mL each], 10% CH$_3$CN in H$_2$O [2×10 mL]). The product was eluted from the C-18 cartridge (20% to 50% CH$_3$CN in H$_2$O [10% increments, 2×10 mL each], then 60% to 100% CH$_3$CN in H$_2$O [10% increments, 10 mL each]). The fractions collected were analysed by RP-HPLC (10% to 100% B over 12.5 min, then 100% B for 2.5 min, $t_R$=9.10 min) and lyophilised to afford the title compound DB-oCOm-24 (31 mg, 57%) as an inseparable mixture of endo- and exo-isomers (9:1) as a colourless hygroscopic powder. Mp. 39° C. (slow decomp.); IR (ATR) $v_{max}$/cm$^{-1}$ 2927, 1790 (C=O), 1704 (C=O), 1668 (C=O), 1441, 1393, 1177, 1128, 1074, 723, 698; HRMS (ESI-TOF) m/z: [M+H]$^+$ Calcd for $C_{30}H_{33}N_2O_7^+$ 533.2282, found 533.2283; RP-HPLC (10% to 100% B over 12.5 min, then 100% B for 2.5 min), $t_R$=9.10 min.

Endo-DB-oCOm-24 NMR data: $^1$H NMR (400 MHz, DMSO-d6) δ inter alia 1.41 (6H, s, 2×CH$_3$), 2.60 (2H, t, J=8.0 Hz), 3.49 (2H, s, H-3a and -7a), 3.50-3.55 (4H, m), 3.68 (2H, t, J=8.0 Hz), 4.12-4.16 (2H, m), 5.44 (2H, t, J=4.0 Hz), 6.86-6.89 (4H, m, Ph), 7.19-7.24 (6H, m, Ph), 7.98 (2H, br s); $^{13}$C NMR (125 MHz, DMSO-d6) δ inter alia 11.9, 31.3, 34.1, 47.4, 55.8, 59.4, 59.5, 62.1, 127.6, 128.1, 129.3, 133.1, 141.3, 169.8 (C=O, C-2'), 175.7, 199.1).

Exo-DB-oCOm-24 NMR data: $^1$H NMR (400 MHz, DMSO-d6) δ inter alia 1.18 (6H, s,2×CH$_3$), 3.44 (2H, s, H-3a and -7a), 7.14-7.16 (4H, m, Ph), 7.27-7.29 (4H, m, Ph); $^{13}$C NMR (125 MHz, DMSO-d6) δ inter alia 9.0, 129.0.

Example 21 oCOm-25 and -26 oCOm-26 5-(3a-Bromo-4,7-dimethyl-1,3,8-trioxo-5,6-diphenyl-2H-4,7-methanoisoindolin-2-yppentan-1-aminium 2,2,2-trifluoroacetate; Where R$^1$═R$^2$═Ph; R$^3$═R$^4$═Me; A$^3$═NR$^{14}$; R$^{14}$═(CH$_2$)$_5$NH$_2$.CF$_3$CO$_2$H; X═Br Scheme 24: Synthesis of oCOm-25 and -26

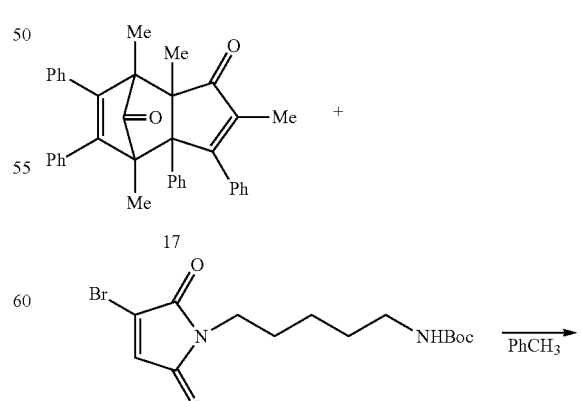

56

-continued

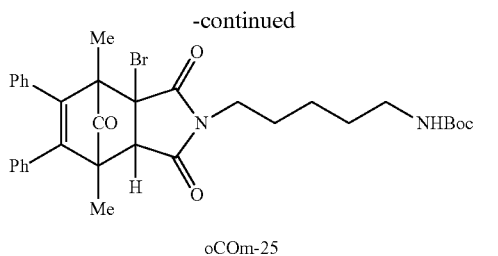

oCOm-25

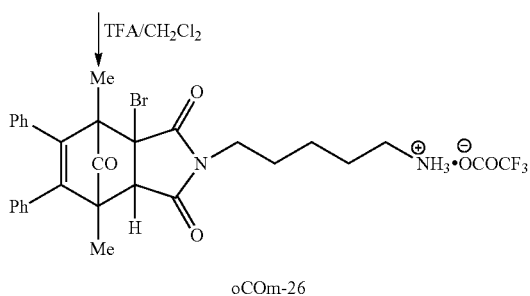

oCOm-26 a) 5'-(N-Maleimido)-1'-tert-butoxycarbonylamino-pentane (57)

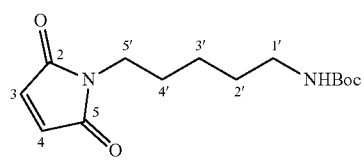

To a solution of 1,5-diaminopentane (0.86 g, 8.5 mmol) in water (100 mL) at 0° C. was added dropwise a solution of di-tert-butyl dicarbonate (0.46 g, 2.1 mmol) in 1,4-dioxane (150 mL), and the mixture stirred at room temperature for 16 h. The mixture was then concentrated by half in vacuo, filtered, and the filtrate extracted with ethyl acetate (3×). The combined organic layers were then dried over anhydrous magnesium sulfate, filtered and the solution concentrated in vacuo to afford a yellow oil, which was used without further purification. To a solution of the crude oil in saturated aqueous sodium bicarbonate (8 mL) at 0° C. was added 45 (248 mg, 1.0 mmol), and the mixture stirred at 0° C. for 30 minutes. A solution of acetonitrile/water (16 mL, 1:1 v/v) was then added and the mixture stirred at room temperature for 4 h. The mixture was then extracted with dichloromethane (3×), the combined organic layers dried over anhydrous magnesium sulfate, filtered and the solution concentrated in vacuo. Purification by column chromatography (EtOAc/hexanes, 1:2) afforded the title compound 57 (94 mg, 40%) as a colourless oil. $^1$H NMR (400 MHz, CDCl$_3$) δ 1.26-1.31 (2H, m, H-3'), 1.42 (9H, s, Boc), 1.45-1.52 (2H, m, H-2'), 1.55-1.63 (2H, m, H-4'), 3.06-3.09 (2H, m, H-1'), 3.50 (2H, t, J=7.2 Hz, H-5'), 4.50-4.55 (1H, m, NH), 6.67 (2H, s, H-3, H-4); $^{13}$C NMR (100 MHz, CDCl$_3$) δ 23.9 (CH$_2$, C-3'), 28.2 (CH$_2$, C-4'), 28.4 (3×CH$_3$, Boc), 29.5 (CH$_2$, C-2'), 37.6 (CH$_2$, C-5'), 40.3 (CH$_2$, C-1'), 79.0 (C, Boc), 134.1 (2×CH, C-3, C-4), 156.0 (C, Boc), 170.8 (2×C, C-2, C-5); ν$_{max}$ (cm$^{-1}$) 3365, 2939, 1698, 1675, 1529, 1412, 1272, 1165, 1117, 832, 695; HRMS-ESI [M+Na]$^+$ Calcd. for C$_{14}$H$_{22}$N$_2$O$_4$Na$^+$ 304.1472, found 305.1467.

5'-(3-Bromo-N-maleimido)-1'-tert-butoxycarbo-nylaminopentane (56)

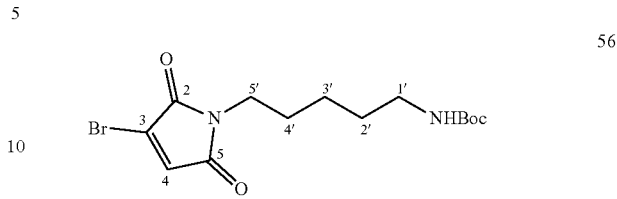

To a solution of 57 (13 mg, 0.05 mmol) and potassium carbonate (7 mg, 0.05 mmol) in chloroform (0.5 mL) was added bromine (3 μl, 0.05 mmol), and the mixture stirred at room temperature for 3 h. The mixture was then diluted with dichloromethane, washed with 5% aqueous sodium thiosulfate solution, dried over anhydrous magnesium sulfate, filtered and the solution concentrated in vacuo to afford a yellow oil, which was used without further purification. The crude oil was dissolved in tetrahydrofuran (0.5 mL) at 0° C., triethylamine (10 μl, 0.05 mmol) was added, and the mixture stirred at room temperature for 12 h. The mixture was then filtered and the solution concentrated in vacuo. Purification by column chromatography (EtOAc/hexanes, 1:3) afforded the title compound 56 (11 mg, 66%) as a yellow oil. $^1$H NMR (400 MHz, CDCl$_3$) δ 1.28-1.34 (2H, m, H-3'), 1.44 (9H, s, Boc), 1.45-1.54 (2H, m, H-2'), 1.58-1.65 (2H, m, H-4'), 3.07-3.12 (2H, m, H-1'), 3.56 (2H, t, J=7.2 Hz, H-5'), 4.52 (1H, br s, NH), 6.86 (1H, s, H-4); $^{13}$C NMR (100 MHz, CDCl$_3$) δ 23.8 (CH$_2$, C-3'), 28.2 (CH$_2$, C-4'), 28.4 (3×CH$_3$, Boc), 29.6 (CH$_2$, C-2'), 38.7 (CH$_2$, C-5'), 40.3 (CH$_2$, C-1'), 79.2 (C, Boc), 131.4 (C, C-3), 131.8 (CH, C-4), 156.0 (C, Boc), 165.4 (C, C-2 or C-5), 168.6 (C, C-2 or C-5); ν$_{max}$ (cm$^{-1}$) 3094, 2961, 1715, 1526, 1440, 1350, 1290, 1268, 1134, 976, 717; HRMS-ESI [M+Na]$^+$ Calcd. for C$_{14}$H$_{21}^{79}$BrN$_2$O$_4$Na$^+$ 383.0577, found 383.0564.

oCOm-25

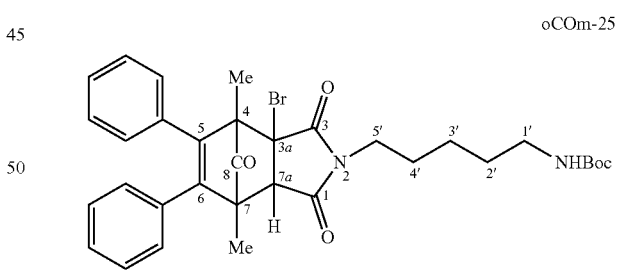

A solution of 56 (10 mg, 0.03 mmol) and diene dimer 17 (9 mg, 0.03 mmol) in toluene (0.5 mL) was heated at reflux for 4 h. The solution was then concentrated in vacuo and the residue purified by column chromatography (EtOAc/hexanes, 1:7) to afford the title compound oCOm-25 (14 mg, 82%) as a colourless residue in a 7:1 ratio of endo and exo isomers, respectively. ν$_{max}$ (cm$^{-1}$) 3416, 2932, 1787, 1709, 1365, 1173, 700; HRMS-ESI [M+Na]$^+$ Calcd. for C$_{33}$H$_{37}^{79}$BrN$_2$O$_5$Na$^+$ 643.1778, found 643.1799.

For the endo isomer; $^1$H NMR (400 MHz, CDCl$_3$) inter alia δ 1.28-1.34 (2H, m, H-3'), 1.43 (9H, s, Boc), 1.44-1.48 (2H, m, H-2'), 1.60 (3H, s, Me-7), 1.62 (3H, s, Me-4), 1.60-1.65 (2H, m, H-4'), 3.01-3.06 (2H, m, H-1'), 3.50 (1H, s, H-7a), 3.57 (2H, td, J=7.3, 2.3 Hz, H-5'), 4.46-4.51 (1H, m, NH), 6.84-6.90 (4H, m, Ph), 7.16-7.19 (6H, m, Ph); $^{13}$C NMR (100 MHz, CDCl$_3$) inter alia δ 11.6 (CH$_3$, Me-4), 12.4 (CH$_3$, Me-7), 23.8 (CH$_2$, C-3'), 27.2 (CH$_2$, C-4'), 28.4 (3×CH$_3$, Boc), 29.4 (CH$_2$, C-2'), 39.7 (CH$_2$, C-5'), 40.3 (CH$_2$, C-1'), 56.4 (C, C-7), 58.9 (C, C-3a), 60.3 (CH, C-7a), 60.7 (C, C-4), 79.1 (C, Boc), 128.1 (2×CH, Ph), 128.2 (2×CH, Ph), 128.3 (2×CH, Ph), 129.3 (2×CH, Ph), 129.7 (2×CH, Ph), 132.4 (C, Ph), 132.5 (C, Ph), 140.4 (C, C-5), 144.5 (C, C-6), 155.9 (C, Boc), 172.4 (C, C-1 or C-3), 172.6 (C, C-1 or C-3), 196.9 (C, C-8).

For the exo isomer; $^1$H NMR (400 MHz, CDCl$_3$) inter alia δ 3.10-3.14 (2H, m, H-1'), 3.36 (1H, s, H-7a); $^{13}$C NMR (100 MHz, CDCl$_3$) inter alia δ 128.0 (CH), 128.5 (CH), 130.5 (CH).

oCOm-26

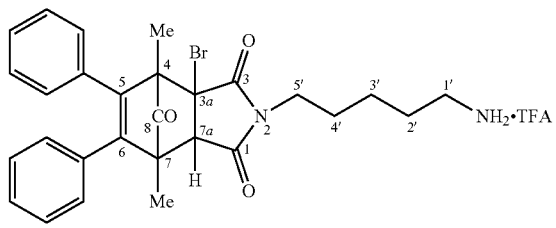

oCOm-26

A solution of oCOm-25 (7.2 mg, 0.01 mmol) and trifluoroacetic acid (0.1 mL) in dichloromethane (0.5 mL) was stirred at room temperature for 30 minutes. The solution was then concentrated in vacuo to afford the trifluoroacetate salt of the title compound 1=oCOM-26 (6.0 mg, 100%) as a pale yellow residue in a 9:1 ratio of endo and exo isomers, respectively. $v_{max}$ (cm$^{-1}$) 2934, 1782, 1709, 1677, 1443, 1392, 1200, 1179, 1136, 699; HRMS-ESI [M+Na]$^+$ Calcd. for $C_{28}H_{29}^{79}BrN_2O_3Na^+$ 543.1254, found 543.1256.

For the endo isomer; $^1$H NMR (400 MHz, CDCl$_3$) inter alia δ 1.28-1.33 (2H, m, H-3'), 1.59 (3H, s, Me-7), 1.61 (3H, s, Me-4), 1.58-1.66 (4H, m, H-2', H-4'), 2.83-2.90 (2H, m, H-1'), 3.52 (1H, s, H-7a), 3.54-3.60 (2H, m, H-5'), 4.89-5.26 (2H, m, NH$_2$), 6.82-6.67 (4H, m, Ph), 7.15-7.21 (6H, m, Ph); $^{13}$C NMR (100 MHz, CDCl$_3$) inter alia δ 11.6 (CH$_3$, Me-4), 12.4 (CH$_3$, Me-7), 23.1 (CH$_2$, C-3'), 26.6 (CH$_2$, C-2' or C-4'), 26.8 (CH$_2$, C-2' or C-4'), 39.2 (CH$_2$, C-5'), 39.8 (CH$_2$, C-1'), 56.4 (C, C-7), 58.8 (C, C-3a), 60.3 (CH, C-7a), 60.6 (C, C-4), 128.3 (4×CH, Ph), 128.4 (2×CH, Ph), 129.3 (2×CH, Ph), 129.6 (2×CH, Ph), 132.3 (C, Ph), 132.4 (C, Ph), 140.3 (C, C-5), 144.5 (C, C-6), 172.7 (C, C-1 or C-3), 172.9 (C, C-1 or C-3), 196.8 (C, C-8).

For the exo isomer; $^1$H NMR (400 MHz, CDCl$_3$) inter alia δ 3.38 (1H, s, H-7a); $^{13}$C NMR (100 MHz, CDCl$_3$) inter alia δ 128.0 (CH), 128.5 (CH), 130.5 (CH).

Example 22 oCOm-27 and -28 oCOm28 (2S)-2-Amino-6-(3a-bromo-4,7-dimethyl-1,3,8-trioxo-5,6-diphenyl-1,3,3a,4,7,7a-hexahydro-2H-4,7-methanoisoindol-2-yl)hexanoic acid trifluoroacetic acid salt; Where R$^1$=R$^2$=Ph; R$^3$=R$^4$=Me; A$^3$=NR$^{14}$; R$^{14}$=(CH$_2$)$_4$CH(NH$_2$.HOCOCF$_3$)CO$_2$H; X=Br Scheme 25:
Synthesis of oCOm-27 and -28

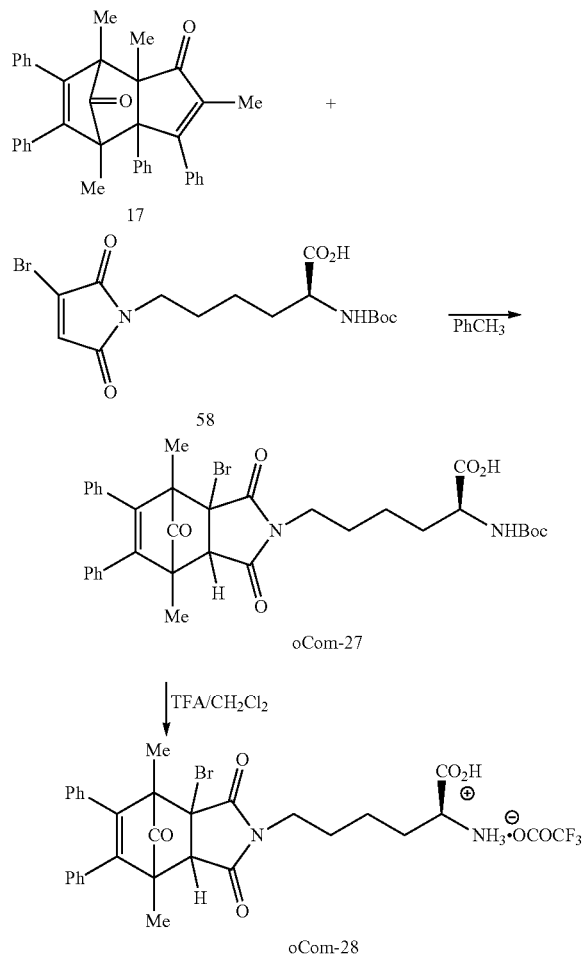

3-Bromo-N-ethoxycarbonylmaleimide (60)

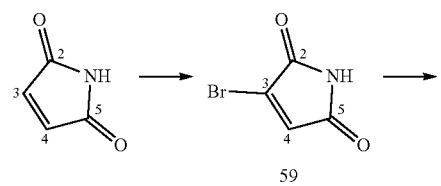

-continued

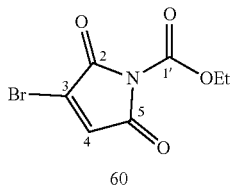

60

To a solution of maleimide (5.0 g, 51.5 mmol) in chloroform (60 mL) was added bromine (2.66 mL, 51.5 mmol), and the mixture stirred at reflux for 1 hour. The resulting solid was collected by filtration and washed with chloroform to afford a white solid, which was used without further purification. The crude solid was dissolved in tetrahydrofuran (60 mL) and saturated aqueous sodium bicarbonate (6 mL) and the mixture stirred at reflux for 18 h. The solution was then concentrated in vacuo and the resulting residue dissolved in ethyl acetate, washed with brine, dried over magnesium sulfate, filtered and the solution again concentrated in vacuo. Purification by column chromatography (EtOAc/hexanes, 1:2) afforded 3-bromomaleimide (59)[30] (4.63 g, 51%) as a pale yellow solid. m.p. 153-155° C. (Lit. 149-151° C.[30]). $^1$H NMR (400 MHz, CDCl$_3$) δ 6.89 (1H, s, H-4), 7.68 (1H, s, NH); $^{13}$C NMR (100 MHz, CDCl$_3$) δ 132.2 (C, C-3), 132.8 (CH, C-4), 164.8 (C, C-2 or C-5), 167.9 (C, C-2 or C-5); ν$_{max}$ (cm$^{-1}$) 3233, 3104, 2682, 1706, 1577, 1330, 1233, 1126, 997, 869 766. To a solution of 59 (523 mg, 3.0 mmol) and N-methylmorpholine (0.36 mL, 3.3 mmol) in ethyl acetate (30 mL) at 0° C. was added dropwise a solution of ethyl chloroformate (0.28 mL, 3.0 mmol) in ethyl acetate (10 mL), and the mixture stirred at 0° C. for 20 minutes, then room temperature for 1 hour. The mixture was then diluted with ethyl acetate, washed with brine, dried over anhydrous magnesium sulfate, filtered and the solution concentrated in vacuo. Purification by column chromatography (EtOAc/petroleum ether, 1:4) afforded the title compound 60 (581 mg, 79%) as a white solid. m.p. 73-76° C. $^1$H NMR (400 MHz, CDCl$_3$) δ 1.31 (3H, t, J=7.2 Hz, OCH$_2$CH$_3$), 4.33 (2H, q, J=7.2 Hz, OCH$_2$CH$_3$), 6.98 (1H, s, H-4); $^{13}$C NMR (100 MHz, CDCl$_3$) δ 14.0 (CH$_3$, OCH$_2$CH$_3$), 64.3 (CH$_2$, OCH$_2$CH$_3$), 132.8 (C, C-3), 133.1 (CH, C-4), 146.8 (C, C-1'), 160.9 (C, C-1 or C-3), 163.5 (C, C-1 or C-3); ν$_{max}$ (cm$^{-1}$) 3106, 2988, 1810, 1766, 1724, 1319, 1248, 1062, 749; HRMS-ESI [M+Na]$^+$ Calcd. for C$_7$H$_6$BrNO$_4$Na$^+$ 269.9372, found 269.9374.

(S)-6'-(3-Bromo-N-maleimido)-2'-tert-butoxycarbonylaminohexanoic acid (58)

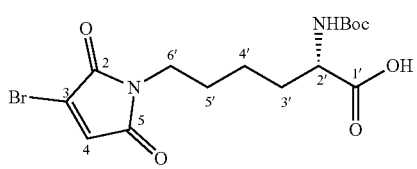

58

To a solution of Boc-L-lysine (421 mg, 1.7 mmol) in saturated aqueous sodium bicarbonate (10 mL) at 0° C. was added compound 60 (400 mg, 1.7 mL), and the mixture stirred at 0° C. for 90 minutes. The mixture was then acidified to pH 3 with sulphuric acid, extracted with dichloromethane (3×), the combined organic layers dried over anhydrous magnesium sulfate, filtered and the solution concentrated in vacuo. Purification by column chromatography (MeOH/DCM, 1:10) afforded the title compound 58 (257 mg, 37%) as a yellow oil. $^1$H NMR (400 MHz, CDCl$_3$) δ 1.39-1.45 (2H, m, H-4'), 1.45 (9H, s, Boc), 1.60-1.76 (3H, m, H$_b$-3', H-5'), 1.85-1.93 (1H, m, H$_a$-3'), 3.57 (2H, t, J=7.1 Hz, H-6'), 4.27-4.32 (1H, m, H-2'), 5.28 (1H, d, J=7.9 Hz, NH), 6.91 (1H, s, H-4), 10.20 (1H, br s, OH); $^{13}$C NMR (100 MHz, CDCl$_3$) δ 22.4 (CH$_2$, C-4), 27.9 (CH$_2$, C-5'), 28.3 (3×CH$_3$, Boc), 31.8 (CH$_2$, C-3'), 38.4 (CH$_2$, C-6'), 53.1 (CH, C-2'), 80.1 (C, Boc), 131.2 (C, C-3), 131.9 (CH, C-4), 155.6 (C, Boc), 165.3 (C, C-2), 168.6 (C, C-5), 176.5 (C, C-1'); ν$_{max}$ (cm$^{-1}$) 3353, 2934, 1699, 1368, 1164, 696; HRMS-ESI [M+K]$^+$ Calcd. for C$_{15}$H$_{21}$$^{79}$BrN$_2$O$_6$K$^+$ 443.0215, found 443.0215.

oCOm-27

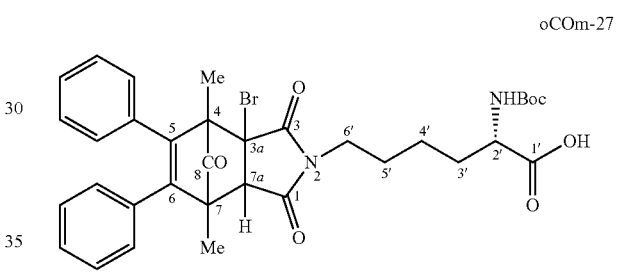

oCOm-27

A similar procedure to that previously described for the preparation of oCOm-25 was followed using 58 (100 mg, 0.25 mmol) and diene dimer 17 (58 mg, 0.22 mmol) in toluene (5 mL). Purification by column chromatography (MeOH/DCM, 1:10) afforded the title compound A2=oCOM-27 (135 mg, 91%) as an off-white solid in a 7:1 ratio of endo and exo isomers, respectively. m.p. 87-92° C. ν$_{max}$ (cm$^{-1}$) 2927, 2361, 2342, 1711, 1167, 760; HRMS-ESI [M+K]$^+$ Calcd. for C$_{34}$H$_{37}$$^{79}$BrN$_2$O$_7$K$^+$ 703.1416, found 703.1421.

For the endo isomer; $^1$H NMR (400 MHz, CDCl$_3$) inter alia δ 1.40-1.46 (2H, m, H-4'), 1.44 (9H, s, Boc), 1.60 (3H, s, Me-7), 1.61 (3H, s, Me-4), 1.63-1.73 (3H, m, H$_b$-3', H-5'), 1.84-1.89 (1H, m, H$_a$-3'), 3.50 (1H, s, H-7a), 3.55-3.60 (2H, m, H-6'), 4.20-4.25 (1H, m, H-2'), 5.06-5.09 (1H, m, NH), 6.83-6.89 (3.6H, m, Ph), 7.16-7.19 (5.4H, m, Ph); $^{13}$C NMR (100 MHz, CDCl$_3$) inter alia δ 11.5 (CH$_3$, Me-4), 12.4 (CH$_3$, Me-7), 22.4 (CH$_2$, C-4'), 27.1 (CH$_2$, C-3'), 28.3 (3×CH$_3$, Boc), 39.4 (CH$_2$, C-6'), 53.1 (CH, C-2'), 56.4 (C, C-7), 58.9 (C, C-3a), 60.3 (C, C-7a), 60.6 (C, C-4), 80.3 (C, Boc), 128.2 (4×CH, Ph), 128.3 (2×CH, Ph), 129.3 (2×CH, Ph), 129.6 (2×CH, Ph), 132.4 (C, Ph), 132.5 (C, Ph), 140.4 (C, C-5), 144.5 (C, C-6), 155.7 (C, Boc), 172.3 (C, C-1 or C-3), 172.6 (C, C-1 or C-3), 176.7 (C, C-1'), 197.0 (C C-8).

For the exo isomer; $^1$H NMR (400 MHz, CDCl$_3$) inter alia δ 3.37 (1H, s, H-7a); $^{13}$C NMR (100 MHz, CDCl$_3$) inter alia δ 8.1 (CH$_3$), 9.4 (CH$_3$), 128.0 (CH), 128.5 (CH), 130.5 (CH).

137

(2S)-2-Amino-6-(3a-bromo-4,7-dimethyl-1,3,8-trioxo-5,6-diphenyl-1,3,3a,4,7,7a-hexahydro-2H-4,7-methanoisoindol-2-yl)hexanoic acid trifluoroacetic acid salt (oCOm-28)

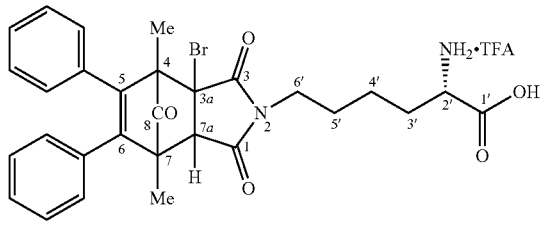

oCOm-28

A similar procedure to that previously described for the preparation of 1=oCOM-26 was followed using oCOm-27 (5.3 mg, 0.01 mmol) and trifluoroacetic acid (0.5 mL) in dichloromethane (0.5 mL) to afford the trifluoroacetate salt of the title compound 2=oCOM-28 (5.4 mg, 100%) as a pale brown residue in a 7:1 ratio of endo and exo isomers, respectively. $v_{max}$ (cm$^{-1}$) 3375, 1706, 1588, 1431, 1027, 951, 749; HRMS-ESI [M+Na]$^+$ Calcd. for $C_{29}H_{29}{}^{79}BrN_2O_5Na^+$ 587.1152, found 587.1156.

For the endo isomer; $^1$H NMR (500 MHz, CDCl$_3$) inter alia δ 1.35-1.46 (2H, m, H-4'), 1.57 (3H, s, Me-7), 1.59 (3H, s, Me-4), 1.54-1.62 (2H, m, H-3'), 1.68-1.87 (2H, m, H-5'), 3.84-3.53 (3H, m, H-6', H-7a), 3.79-3.81 (1H, m, H-2'), 6.80-6.86 (4H, m, Ph), 7.12-7.16 (6H, m, Ph); $^{13}$C NMR (75 MHz, CDCl$_3$) inter alia δ 11.5 (CH$_3$, Me-4), 12.3 (CH$_3$, Me-7), 56.3 (C, C-7), 58.8 (C, C-3a), 60.1 (CH, C-7a), 60.6 (C, C-4), 128.3 (6×CH, Ph), 129.2 (2×CH, Ph), 129.6 (2×CH, Ph), 132.3 (C, Ph), 132.4 (C, Ph), 140.4 (C, C-5), 144.6 (C, C-6), 172.7 (C, C-1 or C-3), 172.9 (C, C-1 or C-3), 175.1 (C, C-1'), 196.9 (C, C-8).

For the exo isomer; $^1$H NMR (500 MHz, CDCl$_3$) inter alia δ 3.37 (1H, s, H-7a).

Example 23 oCOm-29 and -30 oCOm-30: Methyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)hexanoate trifluoroacetic acid salt; Where R$^1$=R$^2$=Ph; R$^3$=R$^4$=Me; A$^3$=NR$^{14}$; R$^{14}$=(CH$_2$)$_4$CH(NH$_2$.HOCOCF$_3$)CO$_2$Me; X=Br Scheme 26:
Synthesis of oCOm-29 and -30

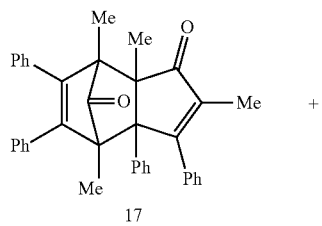

17

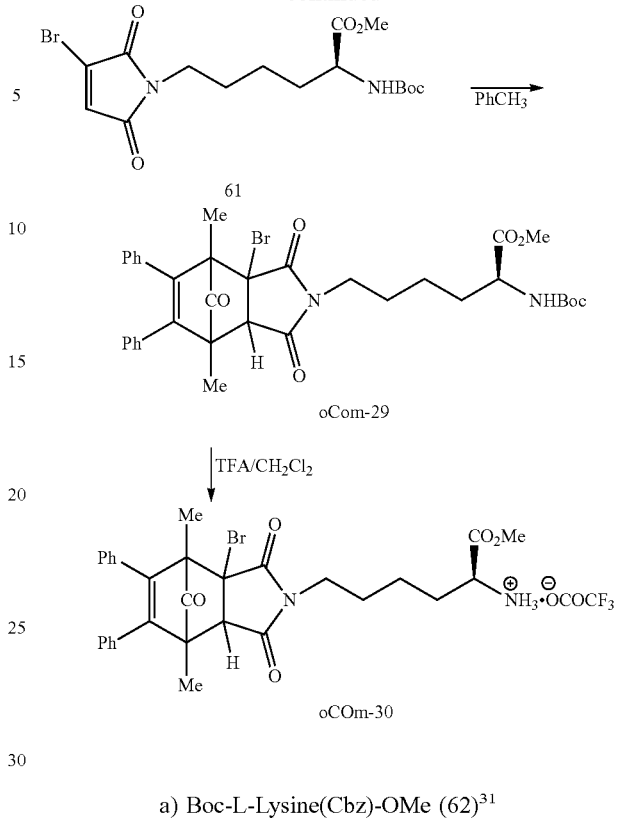

a) Boc-L-Lysine(Cbz)-OMe (62)$^{31}$

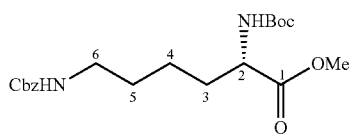

62

To a mixture of Boc-Lys(Cbz)-OH (5.0 g, 13.1 mmol) and potassium carbonate (3.6 g, 26.3 mmol) in dimethylformamide (10 mL) at 0° C. was added dropwise a solution of methyl iodide (1.23 mL, 19.7 mmol) in dimethylformamide (5 mL), and the mixture stirred at 0° C. for 10 min, then room temperature for 19 h. The mixture was then diluted with ethyl acetate, washed with water, then brine, dried over anhydrous magnesium sulfate, filtered and the solution concentrated in vacuo. Purification by column chromatography (EtOAc/hexanes, 1:2) afforded the title compound 62 (5.17 g, 99%) as a colourless oil. [α]$_D^{20.7}$ +7.0 (c 0.682 in CHCl$_3$) (lit$^{32}$+6.1 (c 2.90 in CHCl$_3$)); $^1$H NMR (400 MHz, CDCl$_3$) δ 1.36-1.40 (2H, m, H-4), 1.43 (9H, s, Boc), 1.43 (9H, s, Boc), 1.49-1.53 (2H, m, H-5), 1.59-1.66 (1H, m, H$_b$-3), 1.77-1.80 (1H, m, H$_a$-3), 3.15-3.20 (2H, m, H-6), 3.72 (3H, s, OMe), 4.25-4.30 (1H, m, H-2), 4.90-4.94 (1H, m, NH), 5.09 (2H, s, CH$_2$Ph), 5.10-5.15 (1H, m, NH), 7.30-7.35 (5H, m, 5×Ph); $^{13}$C NMR (100 MHz, CDCl$_3$) δ 22.4 (CH$_2$, C-4), 28.3 (3×CH$_3$, Boc), 29.4 (CH$_2$, C-3), 32.3 (CH$_2$, C-5), 40.6 (CH$_2$, C-6), 52.2 (CH$_3$, OMe), 53.2 (CH, C-2), 66.6 (CH$_2$, CH$_2$Ph), 79.9 (C, Boc), 128.06 (2×CH, Ph), 128.10 (CH, Ph), 128.5 (2×CH, Ph), 136.6 (C, Ph), 155.5 (C, Boc), 156.5 (C, Cbz), 173.3 (C, C-1); $v_{max}$(cm$^{-1}$) 3343, 2932, 1692, 1519, 1247, 1160, 1023, 750.

b) Methyl (S)-6'-(N-maleimido)-2'-tert-butoxycarbonylaminohexanoate (63)

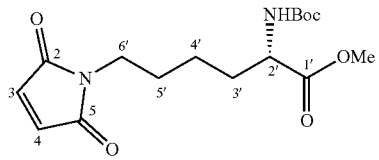

A solution of 62 (2.12 g, 5.4 mmol), acetic acid (1.5 mL) and palladium-on-carbon (0.2 g, 10% w/w) in methanol (30 mL) was stirred at room temperature under a hydrogen atmosphere for 90 minutes. The mixture was then filtered through Celite® and the solution concentrated in vacuo to afford a yellow oil, which was used without further purification. To the crude oil was added a mixture of 45 (1.36 g, 8.1 mmol) in saturated aqueous sodium bicarbonate (50 mL) at 0° C., and the mixture stirred at 0° C. for 10 minutes. Acetonitrile (25 mL) was then added and the mixture stirred at room temperature for 90 min. The mixture was then extracted with dichloromethane (3×), the combined organic layers dried over anhydrous magnesium sulfate, filtered and the solution concentrated in vacuo. Purification by column chromatography (EtOAc/hexanes, 1:2) afforded the title compound 63 (1.43 g, 78%) as a yellow oil. $[\alpha]_D^{23.7}$=+11.1 (c 1.00 in $CHCl_3$); $^1$H NMR (400 MHz, $CDCl_3$) δ 1.31-1.38 (2H, m, H-4'), 1.44 (9H, s, Boc), 1.59-1.67 (3H, m, H-5'), 1.79-1.83 (1H, m, $H_a$-3'), 3.51 (2H, t, J=7.2 Hz, H-6'), 3.74 (3H, s, OMe), 4.27 (1H, m, H-2'), 5.08 (1H, d, J=7.9 Hz, NH), 6.70 (2H, s, H-3, H-4); $^{13}$C NMR (100 MHz, $CDCl_3$) δ 22.4 ($CH_2$, C-4'), 28.0 ($CH_2$, C-5'), 28.3 (3×$CH_3$, Boc), 32.1 ($CH_2$, C-3'), 37.3 ($CH_2$, C-6'), 52.2 ($CH_3$, OMe), 53.2 (CH, C-2'), 79.8 (C, Boc), 134.1 (2×CH, C-3, C-4), 155.3 (C, Boc), 170.7 (2×C, C-2, C-5), 173.1 (C, C-1'); $v_{max}$ ($cm^{-1}$) 3374, 2952, 1698, 1365, 1160, 828, 694; HRMS-ESI $[M+Na]^+$ Calcd. for $C_{16}H_{24}N_2O_6Na^+$ 363.1527, found 363.1528.

c) Methyl (S)-6'-(3-bromo-N-maleimido)-2'-tert-butoxycarbonylaminohexanoate (61)

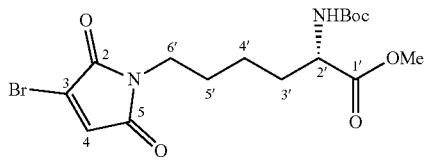 [SMILES: COC(=O)[C@H](CCCCN1C(=O)C=C(Br)C1=O)NC(=O)OC(C)(C)C]

A similar procedure to that previously described for the preparation of 56 was followed using 63 (524 mg, 1.5 mmol), potassium carbonate (233 mg, 1.7 mmol) and bromine (87 µL, 1.7 mmol) in chloroform (5 mL), then triethylamine (240 µL, 1.7 mmol) in tetrahydrofuran (10 mL). Purification by column chromatography (EtOAc/hexanes, 1:3) afforded the title compound 61 (413 mg, 64%) as a yellow oil. $[\alpha]_D^{21.7}$=+12.1 (c 0.560 in $CHCl_3$); $^1$H NMR (400 MHz, $CDCl_3$) δ 1.44 (9H, s, Boc), 1.28-1.86 (6H, m, H-3', H-4', H-5'), 3.55 (2H, t, J=7.2 Hz, H-6'), 3.74 (3H, s, OMe), 4.26-4.29 (1H, m, H-2'), 5.03 (1H, d, J=7.4 Hz, NH), 6.87 (1H, s, H-4); $^{13}$C NMR (100 MHz, $CDCl_3$) δ 22.4 ($CH_2$, C-4'), 28.0 ($CH_2$, C-5'), 28.3 (3×$CH_3$, Boc), 32.2 ($CH_2$, C-3'), 38.4 ($CH_2$, C-6'), 52.3 ($CH_3$, OMe), 53.1 (CH, C-2'), 79.9 (C, Boc), 131.3 (C, C-3), 131.8 (CH, C-4), 155.3 (C, Boc), 165.4 (C, C-2 or C-5), 168.6 (C, C-2 or C-5), 173.3 (C, C-1'); $v_{max}$($cm^{-1}$) 3482, 2952, 2358, 1713, 1507, 1366, 1164; HRMS-ESI $[M+Na]^+$ Calcd. for $C_{16}H_{23}^{79}BrN_2O_6Na^+$ 441.0632, found 441.0641.

d) oCOm-29

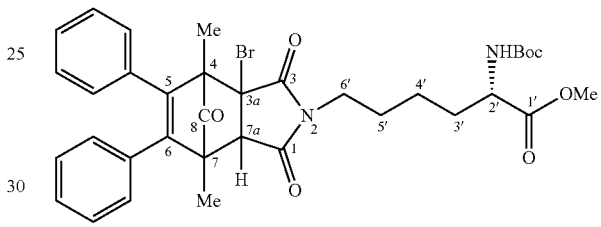

A similar procedure to that previously described for the preparation of oCOm-25 was followed using 61 (237 mg, 0.57 mmol) and 17 (162 mg, 0.62 mmol) in toluene (5 mL). Purification by column chromatography (EtOAc/hexanes, 1:3) afforded the title compound oCOm-29 (318 mg, 83%) as a pale yellow solid in a 5:1 ratio of endo and exo isomers, respectively. m.p. 69-72° C. $v_{max}$ ($cm^{-1}$) 3405, 2938, 1780, 1704, 1364, 1159, 699; HRMS-ESI $[M+Na]^+$ Calcd. for $C_{35}H_{39}^{79}BrN_2O_7Na^+$ 701.1833, found 701.1841.

For the endo isomer; $^1$H NMR (400 MHz, $CDCl_3$) inter alia δ 1.34-1.39 (2H, m, H-4'), 1.44 (9H, s, Boc), 1.60 (3H, s, Me-7), 1.62 (3H, s, Me-4), 1.63-1.68 (2H, m, H-5'), 1.75-1.83 (2H, m, H-3'), 3.50 (1H, s, H-7a), 3.53-3.58 (2H, m, H-6'), 3.72 (3H, s, OMe), 4.26-4.29 (1H, m, H-2'), 5.03 (1H, d, J=6.0 Hz, NH), 6.83-6.89 (4H, m, Ph), 7.15-7.20 (6H, m, Ph); $^{13}$C NMR (100 MHz, $CDCl_3$) inter alia δ 11.5 ($CH_3$, Me-4), 12.4 ($CH_3$, Me-7), 22.4 ($CH_2$, C-4'), 27.1 ($CH_2$, C-3'), 28.3 (3×$CH_3$, Boc), 32.0 ($CH_2$, C-5'), 39.3 ($CH_2$, C-6'), 52.3 ($CH_3$, OMe), 53.2 (CH, C-2'), 56.4 (C, C-7), 58.9 (C, C-3a), 60.3 (CH, C-7a), 60.6 (C, C-4), 79.9 (C, Boc), 128.1 (2×CH, Ph), 128.2 (2×CH, Ph), 128.3 (2×CH, Ph), 129.3 (2×CH, Ph), 129.6 (2×CH, Ph), 132.4 (C, Ph), 132.5 (C, Ph), 140.4 (C, C-5), 144.5 (C, C-6), 155.3 (C, Boc), 172.3 (C, C-1 or C-3), 172.5 (C, C-1 or C-3), 173.0 (C, C-1'), 196.9 (C, C-8).

For the exo isomer; $^1$H NMR (400 MHz, $CDCl_3$) inter alia δ 3.36 (1H, s, H-7a), 3.74 (3H, s, OMe); $^{13}$C NMR (100 MHz, $CDCl_3$) inter alia δ 8.1 ($CH_3$), 9.4 ($CH_3$), 31.9 ($CH_2$), 39.4 ($CH_2$), 128.0 (CH), 128.5 (CH), 130.5 (CH).

e) Methyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)hexanoate trifluoroacetic acid salt (oCOm-30)

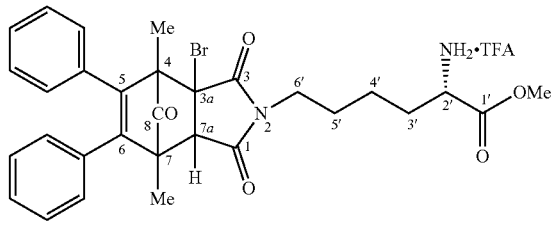

oCOm-30

A similar procedure to that previously described for the preparation of oCOm-26 was followed using oCOm-29 (27 mg, 0.04 mmol) and trifluoroacetic acid (0.25 mL) in dichloromethane (0.75 mL) to afford the trifluoroacetate salt of the title compound oCOm-30 (27 mg, 100%) as a pale yellow residue in a 5:1 ratio of endo and exo isomers, respectively. $v_{max}$ (cm$^{-1}$) 3475, 2934, 1787, 1749, 1709, 1674, 1200, 1181, 1136, 754; HRMS-ESI [M+Na]$^+$ Calcd. for $C_{30}H_{31}{}^{79}BrN_2O_5Na^+$ 601.1302, found 601.1309.

For the endo isomer; $^1$H NMR (400 MHz, CDCl$_3$) inter alia δ 1.29-1.45 (2H, m, H-4'), 1.59 (3H, s, Me-7), 1.61 (3H, s, Me-4), 1.63-1.67 (2H, m, H-3'), 1.96 (2H, m, H-5'), 3.52 (1H, s, H-7a), 3.54-3.59 (2H, m, H-6'), 3.79 (3H, s, OMe), 4.02 (1H, s, H-2'), 6.81-6.88 (4H, m, Ph), 7.13-7.20 (6H, m, Ph); $^{13}$C NMR (100 MHz, CDCl$_3$) inter alia δ 11.5 (CH$_3$, Me-4), 12.3 (CH$_3$, Me-7), 21.8 (CH$_2$, C-4'), 26.8 (CH$_2$, C-3'), 29.5 (CH$_2$, C-5'), 38.9 (CH$_2$, C-6'), 53.2 (CH, C-2'), 53.7 (CH$_3$, OMe), 56.4 (C, C-7), 58.7 (C, C-3a), 60.2 (CH, C-7a), 60.6 (C, C-4), 128.2 (2×CH, Ph), 128.3 (2×CH, Ph), 129.2 (2×CH, Ph), 129.6 (2×CH, Ph), 132.3 (C, Ph), 132.4 (C, Ph), 140.4 (C, C-5), 144.6 (C, C-6), 169.6 (C, C-1'), 172.7 (C, C-1 or C-3), 172.9 (C, C-1 or C-3), 196.8 (C, C-8).

For the exo isomer; $^1$H NMR (400 MHz, CDCl$_3$) inter alia δ 3.39 (1H, s, H-7a), 3.83 (3H, s, OMe); $^{13}$C NMR (100 MHz, CDCl$_3$) inter alia δ 128.0 (CH), 128.5 (CH), 130.5 (CH).

Example 24 oCOm-31 and -32 oCOM-32 Ethyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)hexanoate trifluoroacetic acid salt; Where R$^1$=R$^2$=Ph; R$^3$=R$^4$=Me; A$^3$=NR$^{14}$; R$^{14}$=(CH$_2$)$_4$CH(NH$_2$·HOCOCF$_3$)CO$_2$Et; X=Br Scheme 27:
Synthesis of oCOm-31 and -32

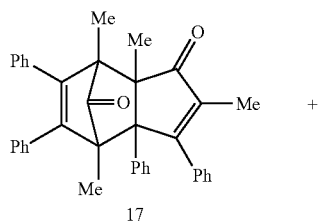

17

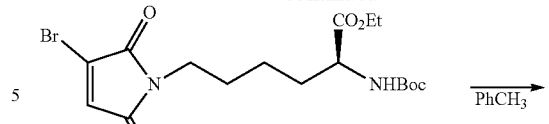

64

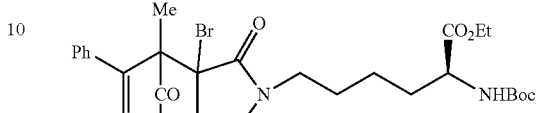

oCOm-31

↓ TFA/CH$_2$Cl$_2$

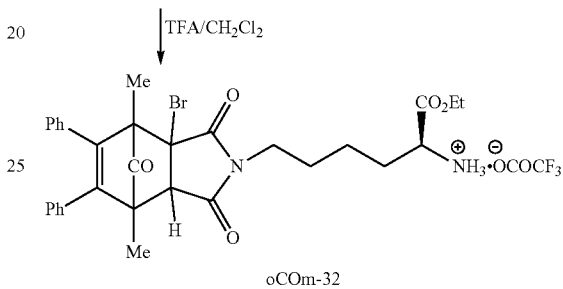

oCOm-32 a) Boc-L-Lysine(Cbz)-OEt (65)

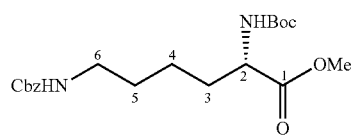

65

A similar procedure to that previously described for the preparation of 62 was followed using Boc-Lys(Cbz)-OH (2.0 g, 5.3 mmol), potassium carbonate (1.45 g, 10.5 mmol) and ethyl iodide (0.63 mL, 7.9 mmol) in dimethylformamide (6.5 mL). Purification by column chromatography (EtOAc/hexanes, 1:1) afforded the title compound 65 (2.15 g, 99%) as a colourless oil. [α]$_D^{22.5}$ +4.8 (c 1.00 in CHCl$_3$); $^1$H NMR (400 MHz, CDCl$_3$) δ 1.26 (3H, t, J=7.1 Hz, OCH$_2$CH$_3$), 1.33-1.39 (2H, m, H-4), 1.43 (9H, s, Boc), 1.48-1.54 (2H, m, H-5), 1.59-1.67 (1H, m, H$_b$-3), 1.75-1.82 (1H, m, H$_a$-3), 3.14-3.19 (2H, m, H-6), 4.17 (2H, q, J=7.1 Hz, OCH$_2$CH$_3$), 4.21-4.27 (1H, m, H-2), 5.02-5.06 (1H, m, NH), 5.08 (2H, s, CH$_2$Ph), 5.15-5.19 (1H, m, NH), 7.29-7.34 (5H, m, Ph); $^{13}$C NMR (100 MHz, CDCl$_3$) δ 14.2 (CH$_3$, OCH$_2$CH$_3$), 22.4 (CH$_2$, C-4), 28.3 (3×CH$_3$, Boc), 29.4 (CH$_2$, C-3), 32.3 (CH$_2$, C-5), 40.6 (CH$_2$, C-6), 53.3 (CH, C-2), 61.3 (CH$_2$, OCH$_2$CH$_3$), 66.5 (CH$_2$, CH$_2$Ph), 79.8 (C, Boc), 128.0 (2×CH, Ph), 128.1 (CH, Ph), 128.5 (2×CH, Ph), 136.7 (C, Ph), 155.5 (C, Boc), 156.5 (C, Cbz), 172.8 (C, C-1); $v_{max}$(cm$^{-1}$) 3337, 2935, 2359, 1694, 1518, 1246, 1162, 1025, 737; HRMS-ESI [M+Na]$^+$ Calcd. for $C_{21}H_{32}N_2O_6Na^+$ 431.2150, found 431.2150.

b) Ethyl (S)-6'-(N-maleimido)-2'-tert-butoxycarbonylaminohexanoate (66)

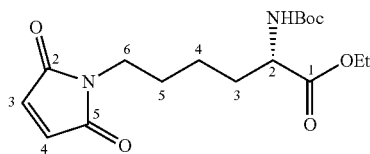

66

A similar procedure to that previously described for the preparation of 63 was followed using 65 (197 mg, 0.5 mmol), acetic acid (0.5 mL) and palladium-on-carbon (20 mg, 10% w/w) in methanol (6 mL), then 45 (143 mg, 0.6 mmol) in saturated aqueous sodium bicarbonate (10 mL) followed by acetonitrile/water (10 mL, 1:1 v/v). Purification by column chromatography (EtOAc/hexanes, 1:3) afforded the title compound 66 (99 mg, 58%) as a colourless oil. $[\alpha]_D^{20.6}$=+11.6 (c 0.90 in CHCl$_3$); $^1$H NMR (400 MHz, CDCl$_3$) δ 1.26 (3H, t, J=7.1 Hz, OCH$_2$CH$_3$), 1.29-1.37 (2H, m, H-4'), 1.43 (9H, s, Boc), 1.54-1.67 (3H, m, H$_b$-3', H-5'), 1.75-1.82 (1H, m, H$_a$-3'), 3.49 (2H, t, J=7.2 Hz, H-6'), 4.17 (2H, q, J=7.1 Hz, OCH$_2$CH$_3$), 4.20-4.26 (1H, m, H-2'), 5.01 (1H, d, J=7.8 Hz, NH), 6.67 (2H, s, H-3, H-4); $^{13}$C NMR (100 MHz, CDCl$_3$) δ 14.2 (CH$_3$, OCH$_2$CH$_3$), 22.5 (CH$_2$, C-4'), 28.1 (CH$_2$, C-5'), 28.3 (3×CH$_3$, Boc), 32.3 (CH$_2$, C-3'), 37.5 (CH$_2$, C-6'), 53.3 (CH, C-2'), 61.3 (CH$_2$, OCH$_2$CH$_3$), 79.8 (C, Boc), 134.1 (2×CH, C-3, C-4), 155.4 (C, Boc), 170.8 (2×C, C-2, C-5), 172.7 (C, C-1'); $v_{max}$(cm$^{-1}$) 3380, 2936, 2360, 1702, 1507, 1164, 829; HRMS-ESI [M+Na]$^+$ Calcd. for C$_{17}$H$_{26}$N$_2$O$_6$Na$^+$ 377.1673, found 377.1683.

c) Ethyl (S)-6'-(3-bromo-N-maleimido)-2'-tert-butoxycarbonylaminohexanoate (64)

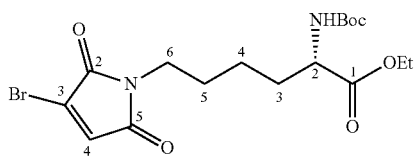

64

A similar procedure to that previously described for the preparation of 56 was followed using 66 (146 mg, 0.41 mmol), potassium carbonate (113 mg, 0.82 mmol) and bromine (23 μL, 0.45 mmol) in chloroform (2.5 mL), then triethylamine (63 μL, 0.45 mmol) in tetrahydrofuran (2.5 mL). Purification by column chromatography (EtOAc/hexanes, 1:3) afforded the title compound 64 (65 mg, 37%) as a yellow oil. $[\alpha]_D^{21.1}$=+5.85 (c 2.60 in CHCl$_3$); $^1$H NMR (400 MHz, CDCl$_3$) δ 1.25-1.29 (3H, m, OCH$_2$CH$_3$), 1.32-1.38 (2H, m, H-4'), 1.44 (9H, s, Boc), 1.57-1.67 (3H, m, H$_b$-3', H-5'), 1.77-1.84 (1H, m, H$_a$-3'), 3.53-3.57 (2H, m, H-6'), 4.17-4.24 (3H, m, H-2', OCH$_2$CH$_3$), 5.06 (1H, d, J=6.6 Hz, NH), 6.86 (1H, s, H-5); $^{13}$C NMR (100 MHz, CDCl$_3$) δ 14.2 (CH$_3$, OCH$_2$CH$_3$), 22.4 (CH$_2$, C-4'), 28.0 (CH$_2$, C-5'), 28.3 (3×CH$_3$, Boc), 32.2 (CH$_2$, C-3'), 38.4 (CH$_2$, C-6'), 53.2 (CH, C-2'), 61.3 (CH$_2$, OCH$_2$CH$_3$), 79.8 (C, Boc), 131.3 (C, C-4'), 131.8 (CH, C-5), 155.3 (C, Boc), 165.3 (C, C-1 or C-3), 168.5 (C, C-1 or C-3), 172.6 (C, C-1'); $v_{max}$(cm$^{-1}$) 2930, 1708, 1640, 1366, 1164, 695; HRMS-ESI [M+Na]$^+$ Calcd. for C$_{17}$H$_{25}$$^{79}$BrN$_2$O$_6$Na$^+$ 455.0788, found 455.0783.

d) oCOm-31

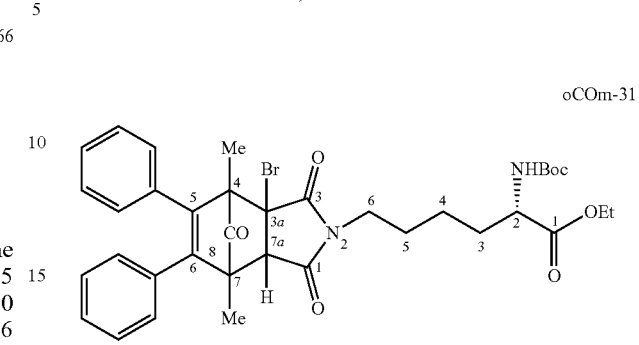

oCOm-31

A similar procedure to that previously described for the preparation of oCOm-25 was followed using 64 (62 mg, 0.14 mmol) and diene dimer 17 (41 mg, 0.16 mmol) in toluene (2.5 mL). Purification by column chromatography (EtOAc/hexanes, 1:1) afforded the title compound oCOm-31 (81 mg, 82%) as a pale yellow solid in a 6:1 ratio of endo and exo isomers, respectively. m.p. 50-52° C. $v_{max}$ (cm$^{-1}$) 3388, 2935, 2360, 1783, 1708, 1366, 1163, 752, 700; HRMS-ESI [M+Na]$^+$ Calcd. for C$_{36}$H$_{41}$$^{79}$BrN$_2$O$_7$Na$^+$ 715.1989, found 715.1977.

For the endo isomer; $^1$H NMR (400 MHz, CDCl$_3$) inter alia δ 1.27 (3H, t, J=7.0 Hz, OCH$_2$CH$_3$), 1.32-1.38 (2H, m, H-4'), 1.44 (9H, s, Boc), 1.60 (3H, s, Me-7), 1.62 (3H, s, Me-4), 1.57-1.67 (3H, m, H$_b$-3', H-5'), 1.76-1.83 (1H, m, H$_a$-3'), 3.50 (1H, s, H-7a), 3.54-3.58 (2H, m, H-6'), 4.15-4.26 (3H, m, H-2', OCH$_2$CH$_3$), 5.05 (1H, d, J=5.7 Hz, NH), 6.84-6.89 (4H, m, Ph), 7.16-7.22 (6H, m, Ph); $^{13}$C NMR (100 MHz, CDCl$_3$) inter alia δ 11.5 (CH$_3$, Me-4), 12.4 (CH$_3$, Me-7), 14.2 (CH$_3$, OCH$_2$CH$_3$), 22.4 (CH$_2$, C-4'), 27.1 (CH$_2$, C-5'), 28.3 (3×CH$_3$, Boc), 32.1 (CH$_2$, C-3'), 39.5 (CH$_2$, C-6'), 53.3 (CH, C-2'), 56.4 (C, C-7), 58.9 (C, C-3a), 60.3 (CH, C-7a), 60.6 (C, C-4), 61.4 (CH$_2$, OCH$_2$CH$_3$), 79.8 (C, Boc), 128.1 (2×CH, Ph), 128.2 (2×CH, Ph), 128.3 (2×CH, Ph), 129.3 (2×CH, Ph), 129.6 (2×CH, Ph), 132.4 (C, Ph), 132.5 (C, Ph), 140.4 (C, C-5), 144.5 (C, C-6), 155.4 (C, Boc), 172.3 (C, C-1 or C-3), 172.5 (C, C-1 or C-3, C-1'), 196.9 (C, C-8);

For the exo isomer; $^1$H NMR (400 MHz, CDCl$_3$) inter alia δ 3.36 (1H, s, H-7a); $^{13}$C NMR (100 MHz, CDCl$_3$) inter alia δ 8.1 (CH$_3$), 9.4 (CH$_3$), 31.9 (CH$_2$), 39.1 (CH$_2$), 57.1 (C), 59.0 (C), 128.0 (CH), 128.5 (CH), 130.5 (CH) 170.7 (C).

e) Ethyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)hexanoate trifluoroacetic acid salt (oCOm-32)

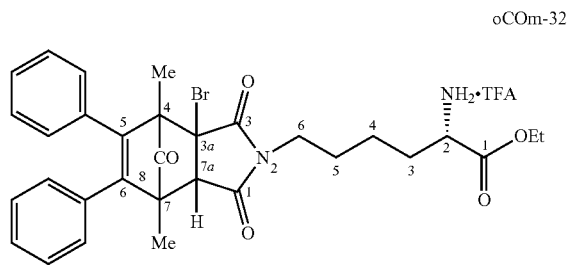

oCOm-32

A similar procedure to that previously described for the preparation of oCOm-26 was followed using OcOm-31 (80 mg, 0.12 mmol) and trifluoroacetic acid (0.5 mL) in dichloromethane (1.5 mL) to afford the trifluoroacetate salt of the title compound oCOm-32 (70 mg, 86%) as a pale brown residue in a 6:1 ratio of endo and exo isomers, respectively. $v_{max}$ (cm$^{-1}$) 3473, 2944, 1789, 1747, 1710, 1673, 1394, 1200, 1130, 755; HRMS-ESI [M+Na]$^+$ Calcd. for $C_{31}H_{33}{}^{79}BrN_2O_5Na^+$ 615.1465, found 615.1470.

For the endo isomer; $^1$H NMR (400 MHz, CDCl$_3$) inter alia δ 1.26 (3H, t, J=6.9 Hz, OCH$_2$CH$_3$), 1.59 (3H, s, Me-7), 1.61 (3H, s, Me-4), 1.34-1.64 (4H, m, H-5', H-4'), 1.92-1.95 (2H, m, H-3'), 3.51 (1H, s, H-7a), 3.53-3.58 (2H, m, H-6'), 3.95-3.99 (1H, m, H-2'), 4.23 (2H, m, OCH$_2$CH$_3$), 6.82-6.86 (4H, m, Ph), 7.13-7.18 (6H, m, Ph); $^{13}$C NMR (100 MHz, CDCl$_3$) inter alia δ 11.5 (CH$_3$, Me-4), 12.3 (CH$_3$, Me-7), 13.8 (CH$_3$, OCH$_2$CH$_3$), 21.9 (CH$_2$, C-4'), 26.8 (CH$_2$, C-3'), 29.7 (CH$_2$, C-5'), 39.1 (CH$_2$, C-6'), 53.1 (CH, C-2'), 56.4 (C, C-7), 58.8 (C, C-3a), 60.2 (CH, C-7a), 60.6 (C, C-4), 63.2 (CH$_2$, OCH$_2$CH$_3$), 128.21 (2×CH, Ph), 128.25 (2×CH, Ph), 128.3 (2×CH, Ph), 129.3 (2×CH, Ph), 129.6 (2×CH, Ph), 132.3 (C, Ph), 132.5 (C, Ph), 140.4 (C, C-5), 144.6 (C, C-6), 169.3 (C, C-1'), 172.5 (C, C-1 or C-3), 172.7 (C, C-1 or C-3), 196.8 (C, C-8).

For the exo isomer; $^1$H NMR (400 MHz, CDCl$_3$) inter alia δ 3.38 (1H, s, H-7a); $^{13}$C NMR (100 MHz, CDCl$_3$) inter alia δ 8.0 (CH$_3$), 9.2 (CH$_3$), 21.6 (CH$_2$), 38.8 (CH$_2$), 57.1 (C), 59.0 (C), 128.0 (CH), 128.5 (CH), 130.5 (CH), 132.6 (C), 132.8 (C), 144.9 (C), 170.8 (C), 170.9 (C).

Example 25 oCOm-33 and -34 oCOm-34 nPropyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)hexanoate trifluoroacetic acid salt; Where R$^1$=R$^2$=Ph; R$^3$=R$^4$=Me; A$^3$=NR$^{14}$; R$^{14}$=(CH$_2$)$_4$CH(NH$_2$·HOCOCF$_3$)CO$_2$nPr; X=Br Scheme 28: Synthesis of oCOm-33 and -34

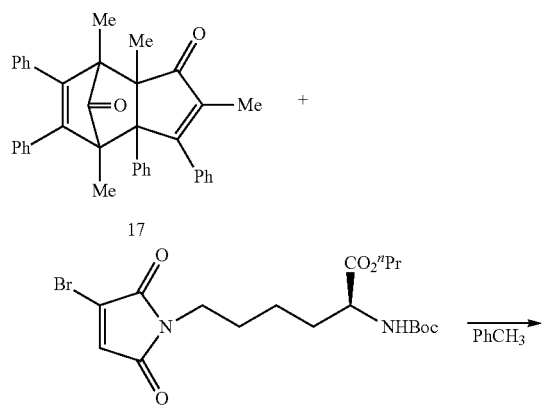

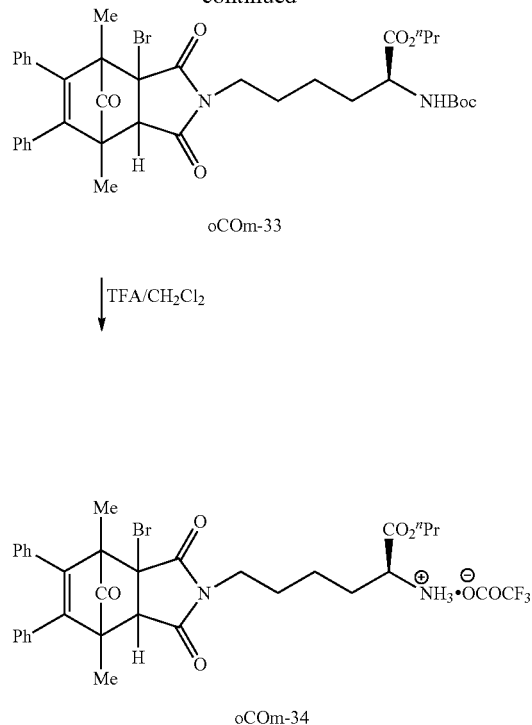

a) Boc-L-Lysine(Cbz)-O$^n$Pr (68)

A similar procedure to that previously described for the preparation of 62 was followed using Boc-Lys(Cbz)-OH (2.0 g, 5.3 mmol), potassium carbonate (1.45 g, 10.5 mmol) and n-propyl iodide (0.77 mL, 7.9 mmol) in dimethylformamide (6.5 mL). Purification by column chromatography (EtOAc/hexanes, 1:1) afforded the title compound 68 (2.23 g, 99%) as an off-white solid. m.p. 50-52° C. [α]$_D^{22.5}$+3.8 (c 1.00 in CHCl$_3$); $^1$H NMR (400 MHz, CDCl$_3$) δ 0.93 (3H, t, J=7.4 Hz, OCH$_2$CH$_2$CH$_3$), 1.35-1.40 (2H, m, H-4), 1.43 (9H, s, Boc), 1.50-1.55 (2H, m, H-5), 1.58-1.70 (3H, m, H$_b$-3, OCH$_2$CH$_2$CH$_3$), 1.76-1.82 (1H, m, H$_a$-3), 3.15-3.20 (2H, m, H-6), 4.03-4.13 (2H, m, OCH$_2$CH$_2$CH$_3$), 4.24-4.29 (1H, m, H-2), 4.94-4.98 (1H, m, NH), 5.08 (2H, s, CH$_2$Ph), 5.10-5.15 (1H, m, NH), 7.28-7.33 (5H, m, Ph); $^{13}$C NMR (100 MHz, CDCl$_3$) δ 10.3 (CH$_3$, OCH$_2$CH$_2$CH$_3$), 21.9 (CH$_2$, OCH$_2$CH$_2$CH$_3$), 22.4 (CH$_2$, C-4), 28.3 (3×CH$_3$, Boc), 29.4 (CH$_2$, C-3), 32.4 (CH$_2$, C-5), 40.6 (CH$_2$, C-6), 53.3 (CH, C-2), 66.6 (CH$_2$, CH$_2$Ph), 66.9 (CH$_2$, OCH$_2$CH$_2$CH$_3$), 79.8 (C, Boc), 128.0 (2×CH, Ph), 128.1 (CH, Ph), 128.5 (2×CH, Ph), 136.6 (C, Ph), 155.5 (C, Boc), 156.5 (C, Cbz), 172.8 (C, C-1); $v_{max}$(cm$^{-1}$) 3379, 3353, 2950, 2359, 172, 1684, 1517, 1246,1128, 1007, 740; HRMS-ESI [M+K]$^+$ Calcd. for $C_{22}H_{34}N_2O_6K^+$ 461.2048, found 461.2050.

b) n-Propyl (S)-6'-(N-maleimido)-2'-tert-butoxycarbonylaminohexanoate (69)

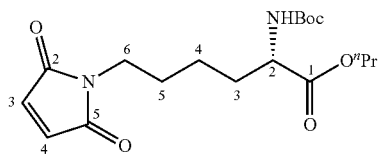

A similar procedure to that previously described for the preparation of 63 was followed using 69 (229 mg, 0.5 mmol), acetic acid (0.1 mL) and palladium-on-carbon (23 mg, 10% w/w) in methanol (7 mL), then 45 (161 mg, 0.7 mmol) in saturated aqueous sodium bicarbonate (10 mL) followed by acetonitrile/water (10 mL, 1:1 v/v). Purification by column chromatography (EtOAc/hexanes, 1:3) afforded the title compound 69 (153 mg, 77%) as a yellow oil. $[\alpha]_D^{20.9}$=+10.1 (c 0.36 in CHCl$_3$); $^1$H NMR (400 MHz, CDCl$_3$) δ 0.91-0.96 (3H, m, OCH$_2$CH$_2$CH$_3$), 1.27-1.38 (2H, m, H-4'), 1.43 (9H, s, Boc), 1.56-1.68 (5H, m, H-5', OCH$_2$CH$_2$CH$_3$), 1.77-1.83 (1H, m, H$_a$-3'), 3.47-3.51 (2H, m, H-6'), 4.06-4.08 (2H, m, OCH$_2$CH$_2$CH$_3$), 4.22-4.27 (1H, m, H-2'), 5.06 (1H, d, J=4.9 Hz, NH), 6.68 (2H, s, H-3, H-4); $^{13}$C NMR (100 MHz, CDCl$_3$) δ 10.3 (CH$_3$, OCH$_2$CH$_2$CH$_3$), 21.9 (CH$_2$, OCH$_2$CH$_2$CH$_3$), 22.5 (CH$_2$, C-4'), 28.0 (CH$_2$, C-5'), 28.3 (3×CH$_3$, Boc), 32.2 (CH$_2$, C-3'), 37.4 (CH$_2$, C-6'), 53.3 (CH, C-2'), 66.8 (CH$_2$, OCH$_2$CH$_2$CH$_3$), 79.7 (C, Boc), 134.0 (2×CH, C-3, C-4), 155.3 (C, Boc), 170.7 (2×C, C-2, C-5), 172.7 (C, C-1'); $v_{max}$(cm$^{-1}$) 3379, 2935, 2342, 1702, 1506, 1164, 829; HRMS-ESI [M+Na]$^+$ Calcd. for C$_{18}$H$_{28}$N$_2$O$_6$Na$^+$ 391.1840, found 391.1838.

c) n-Propyl (S)-6'-(3-bromo-N-maleimido)-2'-tert-butoxycarbonylaminohexanoate (67)

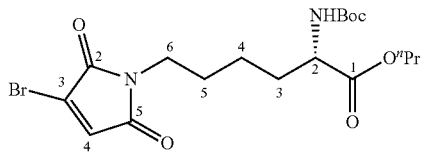

A similar procedure to that previously described for the preparation of 56 was followed using 69 (155 mg, 0.42 mmol), potassium carbonate (116 mg, 0.84 mmol) and bromine (24 μL, 0.46 mmol) in chloroform (2.5 mL), then triethylamine (64 μL, 0.46 mmol) in tetrahydrofuran (2.5 mL). Purification by column chromatography (EtOAc/hexanes, 1:3) afforded the title compound 67 (75 mg, 40%) as a yellow oil. $[\alpha]_D^{24.6}$=+8.2 (c 1.00 in CHCl$_3$); $^1$H NMR (400 MHz, CDCl$_3$) δ 0.92-0.96 (3H, m, OCH$_2$CH$_2$CH$_3$), 1.33-1.38 (2H, m, H-4'), 1.44 (9H, s, Boc), 1.60-1.69 (5H, m, H$_b$-3, H-5', OCH$_2$CH$_2$CH$_3$), 1.78-1.84 (1H, m, H$_a$-3'), 3.53-3.57 (2H, m, H-6'), 4.07-4.11 (2H, m, OCH$_2$CH$_2$CH$_3$), 4.24-4.28 (1H, m, H-2'), 5.07 (1H, d, J=7.8 Hz, NH), 6.87 (1H, s, H-4'); $^{13}$C NMR (100 MHz, CDCl$_3$) δ 10.3 (CH$_3$, OCH$_2$CH$_2$CH$_3$), 21.9 (CH$_2$, OCH$_2$CH$_2$CH$_3$), 22.4 (CH$_2$, C-4'), 28.0 (CH$_2$, C-5'), 28.3 (3×CH$_3$, Boc), 32.2 (CH$_2$, C-3'), 38.4 (CH$_2$, C-6'), 53.2 (CH, C-2'), 66.9 (CH$_2$, OCH$_2$CH$_2$CH$_3$), 79.8 (C, Boc), 131.3 (C, C-3), 131.8 (CH, C-4), 155.3 (C, Boc), 165.3 (C, C-2), 168.5 (C, C-5), 172.7 (C, C-1'); $v_{max}$(cm$^{-1}$) 3379, 2969, 1710, 1366, 1162, 761; HRMS-ESI [M+Na]$^+$ Calcd. for C$_{18}$H$_{27}$$^{79}$BrN$_2$O$_6$Na$^+$ 485.0684, found 485.0692.

d) oCOm-33

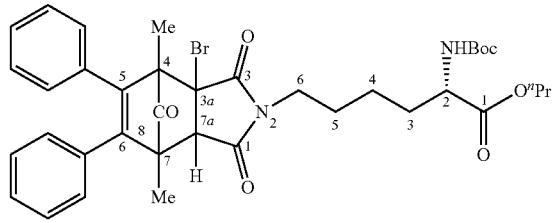

A similar procedure to that previously described for the preparation of oCOm-25 was followed using 67 (74 mg, 0.17 mmol) and diene dimer 17 (47 mg, 0.18 mmol) in toluene (2.5 mL). Purification by column chromatography (EtOAc/hexanes, 1:3) afforded the title compound oCOm-33 (95 mg, 81%) as a pale yellow solid in a 6:1 ratio of endo and exo isomers, respectively. m.p. 48-51° C. $v_{max}$ (cm$^{-1}$) 2936, 1788, 1709, 1365, 1165, 753, 699; HRMS-ESI [M+H]$^+$ Calcd. for C$_{37}$H$_{44}$$^{79}$BrN$_2$O$_7^+$ 707.2326, found 707.2324.

For the endo isomer; $^1$H NMR (400 MHz, CDCl$_3$) inter alia δ 0.94 (3H, t, J=7.4 Hz, OCH$_2$CH$_2$CH$_3$), 1.33-1.38 (2H, m, H-4'), 1.44 (9H, s, Boc), 1.60 (3H, s, Me-7), 1.62 (3H, s, Me-4), 1.60-1.69 (5H, m, H$_b$-3', H-5', OCH$_2$CH$_2$CH$_3$), 1.76-1.83 (1H, m, H$_a$-3'), 3.50 (1H, s, H-7a), 3.53-3.58 (2H, m, H-6'), 4.08 (2H, t, J=6.6 Hz, OCH$_2$CH$_2$CH$_3$), 4.22-4.28 (1H, m, H-2'), 5.05 (1H, d, J=7.0 Hz, NH), 6.84-6.88 (4H, m, Ph), 7.15-7.22 (6H, m, Ph); $^{13}$C NMR (100 MHz, CDCl$_3$) inter alia δ 10.3 (CH$_3$, OCH$_2$CH$_2$CH$_3$), 11.5 (CH$_3$, Me-4), 12.4 (CH$_3$, Me-7), 21.9 (CH$_2$, OCH$_2$CH$_2$CH$_3$), 22.4 (CH$_2$, C-4'), 27.1 (CH$_2$, C-5'), 28.3 (3×CH$_3$, Boc), 32.1 (CH$_2$, C-3'), 39.4 (CH$_2$, C-6'), 53.3 (CH, C-2'), 56.4 (C, C-7), 58.9 (C, C-3a), 60.3 (CH, C-7a), 60.6 (C, C-4), 66.9 (CH$_2$, OCH$_2$CH$_2$CH$_3$), 79.8 (C, Boc), 128.1 (2×CH, Ph), 128.2 (2×CH, Ph), 128.3 (2×CH, Ph), 129.3 (2×CH, Ph), 129.6 (2×CH, Ph), 132.4 (C, Ph), 132.5 (C, Ph), 140.4 (C, C-5), 144.5 (C, C-6), 155.4 (C, Boc), 172.3 (C, C-1 or C-3), 172.5 (C, C-1 or C-3), 172.6 (C, C-1'), 196.9 (C, C-8).

For the exo isomer; $^1$H NMR (400 MHz, CDCl$_3$) inter alia δ 3.36 (1H, s, H-7a), 5.18 (1H, d, J=7.0 Hz, NH); $^{13}$C NMR (100 MHz, CDCl$_3$) inter alia δ 8.1 (CH$_3$), 9.4 (CH$_3$), 32.0 (CH$_2$), 39.1 (CH$_2$), 53.4 (CH), 57.1 (C), 59.0 (C), 61.5 (C), 66.9 (CH$_2$), 128.0 (CH), 128.5 (CH), 130.5 (CH), 132.7 (C), 132.9 (C), 170.7 (C).

e) nPropyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)hexanoate trifluoroacetic acid salt (oCOm-34)

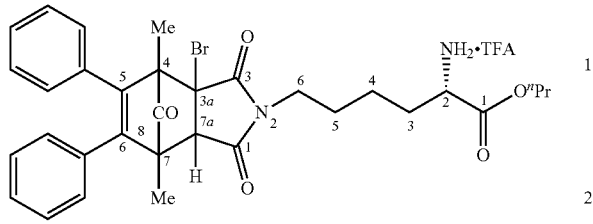

oCOm-34

A similar procedure to that previously described for the preparation of oCOm-26 was followed using oCOm-33 (85 mg, 0.12 mmol) and trifluoroacetic acid (0.5 mL) in dichloromethane (1.5 mL) to afford the trifluoroacetate salt of the title compound oCOm-34 (78 mg, 90%) as a pale brown residue in a 6:1 ratio of endo and exo isomers, respectively. $v_{max}$ (cm$^{-1}$) 2937, 1786, 1712, 1201, 1136, 700; HRMS-ESI [M+H]$^+$ Calcd. for $C_{32}H_{36}^{79}BrN_2O_5^+$ 607.1802, found 607.1798.

For the endo isomer; $^1$H NMR (400 MHz, CDCl$_3$) inter alia δ 0.92 (3H, t, J=7.5 Hz, OCH$_2$CH$_2$CH$_3$), 1.59 (3H, s, Me-7), 1.61 (3H, s, Me-4), 1.34-1.64 (6H, m, H-5', H-4', OCH$_2$CH$_2$CH$_3$), 1.94-1.98 (2H, m, H-3'), 3.51 (1H, s, H-7a), 3.54-3.60 (2H, m, H-6'), 3.98-4.02 (1H, m, H-2'), 4.13 (2H, t, J=6.3 Hz, OCH$_2$CH$_2$CH$_3$), 6.82-6.89 (4H, m, Ph), 7.15-7.19 (6H, m, Ph); $^{13}$C NMR (100 MHz, CDCl$_3$) inter alia δ 10.1 (CH$_3$, OCH$_2$CH$_2$CH$_3$), 11.5 (CH$_3$, Me-4), 12.3 (CH$_3$, Me-7), 21.6 (CH$_2$, OCH$_2$CH$_2$CH$_3$), 21.9 (CH$_2$, C-4'), 26.8 (CH$_2$, C-3'), 29.7 (CH$_2$, C-5'), 39.1 (CH$_2$, C-6'), 53.1 (CH, C-2'), 56.4 (C, C-7), 58.8 (C, C-3a), 60.2 (CH, C-7a), 60.6 (C, C-4), 68.6 (CH$_2$, OCH$_2$CH$_2$CH$_3$), 128.21 (2×CH, Ph), 128.24 (2×CH, Ph), 128.3 (2×CH, Ph), 129.3 (2×CH, Ph), 129.6 (2×CH, Ph), 132.3 (C, Ph), 132.4 (C, Ph), 140.4 (C, C-5), 144.6 (C, C-6), 169.4 (C, C-1'), 172.5 (C, C-1 or C-3), 172.7 (C, C-1 or C-3), 196.8 (C, C-8).

For the exo isomer; $^1$H NMR (400 MHz, CDCl$_3$) inter alia δ 3.37 (1H, s, H-7a); $^{13}$C NMR (100 MHz, CDCl$_3$) inter alia δ 8.0 (CH$_3$), 9.2 (CH$_3$), 26.7 (CH$_2$), 57.1 (CH), 59.0 (C), 128.0 (CH), 128.5 (CH), 130.5 (CH), 144.9 (CH), 170.8 (CH), 170.9 (CH), 198.3 (C).

Example 26 oCOm-35 and -36 oCOm-36 N,N-Dimethyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)-hexanamide trifluoroacetic acid salt; Where $R^1$=$R^2$=Ph; $R^3$=$R^4$=Me; $A^3$=NR$^{14}$; $R^{14}$=(CH$_2$)$_4$CH(NH$_2$.HOCOCF$_3$)CONMe$_2$; X=Br Scheme 29:
Synthesis of oCom-35 and -36

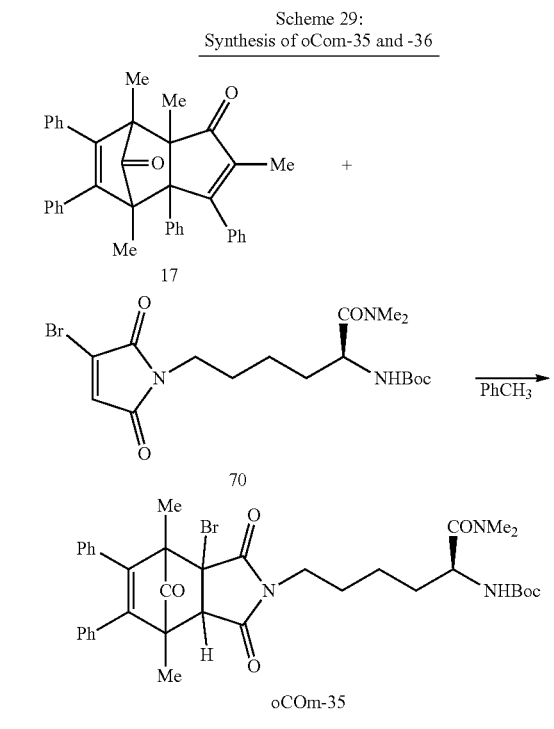

oCOm-35

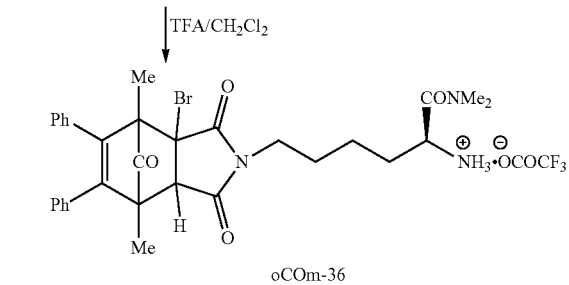

oCOm-36 a) N,N-Dimethyl (S)-6'-benzyloxycarbonylamino-2'-tert-butoxycarbonylaminohexanamide (71)

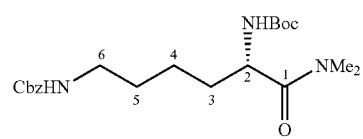

71

To a solution of 1-ethyl-3-(3-dimethylaminopropyl)carbodiimide hydrochloride (2.2 g, 11.6 mmol) and triethylamine (1.6 mL, 11.6 mmol) in dichloromethane (25 mL) at 0° C. was added Boc-Lys(Cbz)-OH (4.0 g, 10.5 mmol) and 4-dimethylaminopyridine (0.13 g, 1.05 mmol), and the mixture stirred at 0° C. for 10 min. A solution of dimethylamine hydrochloride (2.2 g, 11.6 mmol) and triethylamine (3.6 mL, 26.3 mmol) in dichloromethane (10 mL) was then added and the mixture stirred at room temperature for 16 h. The mixture was then washed with saturated aqueous sodium bicarbonate, then saturated aqueous ammonium chloride, dried over anhydrous magnesium sulfate, filtered and the solution concentrated in vacuo. Purification by column chromatography (MeOH:DCM, 1:20) afforded the title compound 71 (2.23 g, 52%) as a colourless oil. $[\alpha]_D^{18.4}$=+8.3 (c 1.47 in CHCl$_3$); $^1$H NMR (400 MHz, CDCl$_3$) δ 1.36-1.43 (2H, m, H-4), 1.40 (9H, s, Boc), 1.47-1.66 (4H, m, H-3, H-5), 2.93 (3H, s, NMe), 3.03 (3H, s, NMe), 3.13-3.20 (2H, m, H-6), 4.55-4.60 (1H, m, H-2), 4.94-4.98 (1H, m, NH), 5.07 (2H, s, CH$_2$Ph), 5.43 (1H, d, J=8.3 Hz, NH), 7.28-7.34 (5H, m, Ph); $^{13}$C NMR (100 MHz, CDCl$_3$) δ 22.3 (CH$_2$, C-4), 28.3 (3×CH$_3$, Boc), 29.3 (CH$_2$, C-3), 33.0 (CH$_2$, C-5), 35.7 (CH$_3$, NMe), 37.0 (CH$_3$, NMe), 40.8 (CH$_2$, C-6), 49.8 (CH, C-2), 66.5 (CH$_2$, CH$_2$Ph), 79.6 (C, Boc), 128.0 (2×CH, Ph), 128.1 (CH, Ph), 128.5 (2×CH, Ph), 136.7 (C, Ph), 155.7 (C, Boc), 156.5 (C, Cbz), 172.1 (C, C-1); ν$_{max}$(cm$^{-1}$) 3316, 2934, 2360, 2342, 1699, 1636, 1498, 1249, 1168, 754; HRMS-ESI [M+Na]$^+$ Calcd. for C$_{21}$H$_{33}$N$_3$O$_5$Na$^+$ 430.2312, found 430.2319.

b) N,N-Dimethyl (S)-6'-(N-maleimido)-2'-tert-butoxycarbonylaminohexanamide (72)

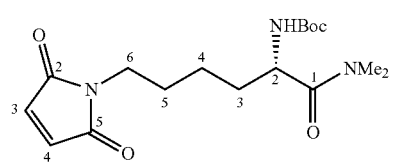

A similar procedure to that previously described for the preparation of 62 was followed using 71 (291 mg, 0.71 mmol), acetic acid (0.25 mL) and palladium-on-carbon (30 mg, 10% w/w) in methanol (5 mL), then 45 (213 mg, 0.86 mmol) in saturated aqueous sodium bicarbonate (14 mL) followed by acetonitrile (6 mL). Purification by column chromatography (EtOAc/hexanes, 3:1) afforded the title compound 72 (146 mg, 58%) as a yellow oil. $[\alpha]_D^{18.9}$=+16.1 (c 2.36 in CHCl$_3$); $^1$H NMR (400 MHz, CDCl$_3$) δ 1.32-1.38 (2H, m, H-4'), 1.42 (9H, s, Boc), 1.49-1.74 (4H, m, H-3', H-5'), 2.95 (3H, s, NMe), 3.07 (3H, s, NMe), 3.50 (2H, t, J=7.2 Hz, H-6'), 4.57 (1H, dt, J=8.4, 4.7 Hz, H-2'), 5.38 (1H, d, J=8.4 Hz, NH), 6.67 (2H, s, H-3, H-4); $^{13}$C NMR (100 MHz, CDCl$_3$) δ 22.2 (CH$_2$, C-4'), 28.2 (CH$_2$, C-5'), 28.4 (3×CH$_3$, Boc), 32.6 (CH$_2$, C-3'), 35.7 (CH$_3$, NMe), 37.1 (CH$_3$, NMe), 37.4 (CH$_2$, C-6'), 49.9 (CH, C-2'), 79.5 (C, Boc), 134.1 (2×CH, C-3, C-4), 155.5 (C, Boc), 170.8 (2×C, C-2, C-5), 172.1 (C, C-1'); ν$_{max}$(cm$^{-1}$) 2931, 1703, 1639, 1497, 1408, 1167, 695; HRMS-ESI [M+Na]$^+$ Calcd. for C$_{17}$H$_{27}$N$_3$O$_5$Na$^+$ 376.1843, found 376.1835.

c) N,N-Di methyl (S)-6'-(3-bromo-N-maleimido)-2'-tert-butoxycarbonylaminohexanamide (70)

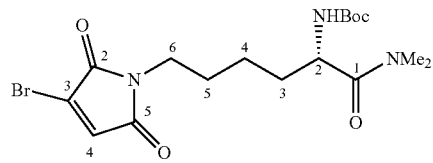

A similar procedure to that previously described for the preparation of 56 was followed using 72 (137 mg, 0.39 mmol), potassium carbonate (107 mg, 0.78 mmol) and bromine (22 μL, 0.43 mmol) in chloroform (2.5 mL), then triethylamine (59 μL, 0.43 mmol) in tetrahydrofuran (2.5 mL). Purification by column chromatography (EtOAc/hexanes, 1:2) afforded the title compound 70 (60 mg, 36%) as a yellow oil. $[\alpha]_D^{18.4}$=+9.73 (c 0.298 in CHCl$_3$); $^1$H NMR (400 MHz, CDCl$_3$) δ 1.33-1.39 (2H, m, H-4'), 1.39 (9H, s, Boc), 1.51-1.71 (4H, m, H-3', H-5'), 2.96 (3H, s, NMe), 3.08 (3H, s, NMe), 3.55 (2H, t, J=7.1 Hz, H-6'), 4.59 (1H, dt, J=8.3, 4.5 Hz, H-2'), 5.42 (1H, d, J=8.3 Hz, NH), 6.85 (1H, s, H-4); $^{13}$C NMR (100 MHz, CDCl$_3$) δ 22.2 (CH$_2$, C-4'), 28.1 (CH$_2$, C-5'), 28.4 (3×CH$_3$, Boc), 32.6 (CH$_2$, C-3'), 35.7 (CH$_3$, NMe), 37.1 (CH$_3$, NMe), 38.4 (CH$_2$, C-6'), 49.8 (CH, C-2'), 79.5 (C, Boc), 131.3 (C, C-3), 131.8 (CH, C-4), 155.6 (C, Boc), 165.3 (C, C-2 or C-5), 168.6 (C, C-2 or C-5), 172.0 (C, C-1'); ν$_{max}$(cm$^{-1}$) 2926, 2361, 2342, 1717, 1647, 1400, 1169; HRMS-ESI [M+Na]$^+$ Calcd. for C$_{17}$H$_{26}$$^{79}$BrN$_3$O$_5$Na$^+$ 454.0948, found 454.0943.

d) oCOm-35

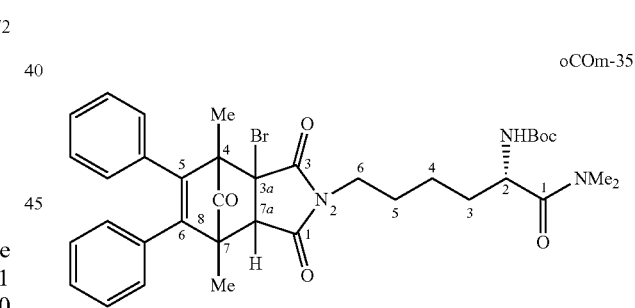

A similar procedure to that previously described for the preparation of oCOm-25 was followed using 70 (26 mg, 0.06 mmol) and diene dimer 17 (17 mg, 0.07 mmol) in toluene (2 mL). Purification by column chromatography (EtOAc/hexanes, 1:1) afforded the title compound oCOm-35 (32 mg, 77%) as a pale yellow solid in a 9:1 ratio of endo and exo isomers, respectively. m.p. 56-59° C. ν$_{max}$ (cm$^{-1}$) 3413, 2935, 1788, 1710, 1645, 1171, 756; HRMS-ESI [M+K]$^+$ Calcd. for C$_{36}$H$_{42}$$^{79}$BrN$_3$O$_6$K$^+$ 730.1889, found 730.1888.

For the endo isomer; $^1$H NMR (400 MHz, CDCl$_3$) inter alia δ 1.36-1.43 (2H, s, H-4'), 1.43 (9H, s, Boc), 1.60 (3H, s, Me-7), 1.61 (3H, s, Me-4), 1.51-1.69 (4H, m, H-3', H-5'), 2.95 (3H, s, NMe), 3.04 (3H, s, NMe), 3.50 (1H, s, H-7a), 3.53-3.58 (2H, m, H-6'), 4.56-4.64 (1H, m, H-2'), 5.39 (1H, d, J=8.3 Hz, NH), 6.83-6.88 (4H, m, Ph), 7.16-7.19 (6H, m, Ph); $^{13}$C NMR (100 MHz, CDCl$_3$) inter alia δ 11.5 (CH$_3$, Me-4), 12.4 (CH$_3$, Me-7), 22.2 (CH$_2$, C-4'), 27.2 (CH$_2$, C-5'), 28.4 (3×CH$_3$, Boc), 35.8 (CH$_3$, NMe), 32.5 (CH$_2$, C-3'), 37.1 (CH$_3$, NMe), 39.5 (CH$_2$, C-6'), 49.8 (CH, C-2'), 56.4 (C, C-7), 58.9 (C, C-3a), 60.3 (CH, C-7a), 60.6 (C, C-4), 79.6 (C, Boc), 128.1 (2×CH, Ph), 128.2 (2×CH, Ph), 128.3 (2×CH, Ph), 129.3 (2×CH, Ph), 129.6 (2×CH, Ph), 132.4 (C, Ph), 132.5 (C, Ph), 140.4 (C, C-5), 144.6 (C, C-6), 155.5 (C, Boc), 172.0 (C, C-1'), 172.3 (C, C-1 or C-3), 172.5 (C, C-1 or C-3), 196.9 (C, C-8).

For the exo isomer; $^1$H NMR (400 MHz, CDCl$_3$) inter alia δ 3.00 (3H, s, NMe), 3.10 (3H, s, NMe), 3.35 (1H, s, H-7a); $^{13}$C NMR (100 MHz, CDCl$_3$) inter alia δ 8.2 (CH$_3$), 9.4 (CH$_3$), 59.0 (C), 128.0 (CH), 128.5 (CH), 130.5 (CH).

e) oCOm-36 N,N-Dimethyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)-hexanamide trifluoroacetic acid salt (oCOm-36)

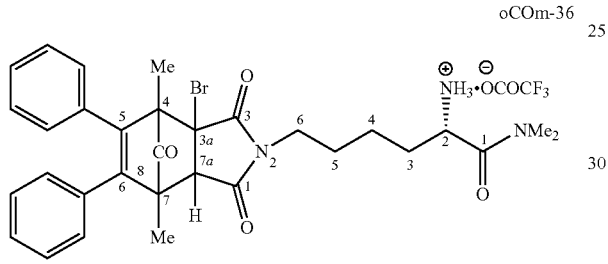

oCOm-36

A similar procedure to that previously described for the preparation of oCOm-261 was followed using oCOm-35 (27 mg, 0.04 mmol) and trifluoroacetic acid (0.2 mL) in dichloromethane (0.6 mL) to afford the trifluoroacetate salt of the title compound oCOm-36 (27 mg, 100%) as a pale yellow residue in a 9:1 ratio of endo and exo isomers, respectively. v$_{max}$ (cm$^{-1}$) 3465, 2945, 1780, 1710, 1651, 1158, 756; HRMS-ESI [M+H]$^+$ Calcd. for C$_{31}$H$_{35}$$^{79}$BrN$_3$O$_4$$^+$ 592.1805, found 592.1800.

For the endo isomer; $^1$H NMR (400 MHz, CDCl$_3$) inter alia δ 1.35-1.44 (2H, m, H-4'), 1.58 (3H, s, Me-7), 1.60 (3H, s, Me-4), 1.62-1.69 (2H, m, H-5'), 1.82-1.91 (2H, m, H-3'), 2.92 (3H, s, NMe), 2.97 (3H, s, NMe), 3.51 (1H, s, H-7a), 3.53-3.59 (2H, m, H-6'), 4.34-4.42 (1H, m, H-2'), 6.81-6.87 (4H, m, Ph), 7.13-7.18 (6H, m, Ph); $^{13}$C NMR (100 MHz, CDCl$_3$) δ 11.5 (CH$_3$, Me-4), 12.2 (CH$_3$, Me-7), 21.1 (CH$_2$, C-4'), 26.9 (CH$_2$, C-3'), 29.7 (CH$_2$, C-5'), 36.3 (CH$_3$, NMe), 37.0 (CH$_3$, NMe), 38.6 (CH$_2$, C-6'), 50.9 (CH, C-2'), 56.4 (C, C-7), 58.8 (C, C-3a), 60.2 (CH, C-7a), 60.6 (C, C-4), 128.2 (2×CH, Ph), 128.3 (4×CH, Ph), 129.3 (2×CH, Ph), 129.6 (2×CH, Ph), 132.3 (C, Ph), 132.4 (C, Ph), 140.3 (C, C-5), 144.6 (C, C-6), 172.7 (C, C-1 or C-3), 172.8 (C, C-1 or C-3, C-1'), 196.7 (C, C-8).

For the exo isomer; $^1$H NMR (400 MHz, CDCl$_3$) inter alia δ 3.04 (3H, m, NMe), 3.06 (3H, m, NMe), 3.36 (1H, s, H-7a); $^{13}$C NMR (100 MHz, CDCl$_3$) inter alia δ 128.0 (CH), 128.5 (CH), 129.4 (CH), 130.5 (CH).

Example 27 oCOm-37 and -38 oCOm-36 6-(3a-bromo-4,7-dimethyl-1,3,8-trioxo-5,6-diphenyl-1,3,3a,4,7,7a-hexahydro-2H-4,7-methanoisoindol-2-yl)-hexanoic acid; Where R$^1$=R$^2$=Ph; R$^3$=R$^4$=Me; A$^3$=NR$^{14}$; R$^{14}$=(CH$_2$)$_5$CO$_2$H; X=Br Scheme 30:
Synthesis of oCOm-37 and -38

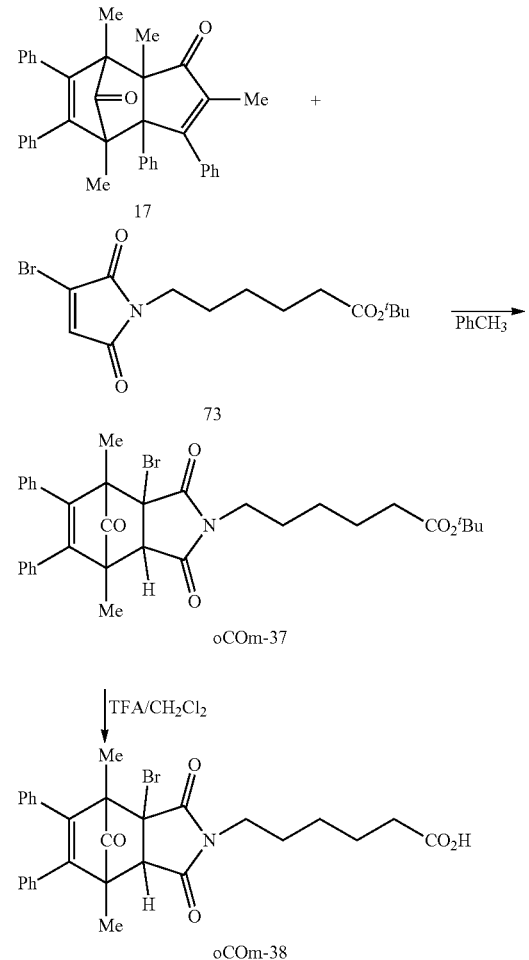

a) 6-Benzyloxycarbonylaminohexanoic acid (74)$^{33}$

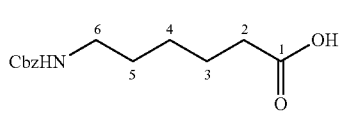

74

To a solution of 6-aminocaproic acid (1.0 g, 7.6 mmol) and sodium hydroxide (0.6 g, 15.2 mmol) in water (5 mL) at 0° C. was added dropwise a solution of benzyl chloroformate (1.6 g, 9.2 mmol) in tetrahydrofuran (4 mL), and the mixture stirred at 0° C. for 30 min, then room temperature for 5 h. The mixture was then concentrated by half in vacuo, acidified to pH 3 with aqueous citric acid (1 M), extracted with dichloromethane (3×), the combined organic layers dried over anhydrous magnesium sulfate and solution concentrated in vacuo to afford the title compound 74 (1.8 g, 89%) as a white solid, which was used without further purification. m.p. 47-50° C. (Lit 56° C.[34]). $^1$H NMR (400 MHz, CDCl$_3$) δ 1.33-1.40 (2H, m, H-4), 1.48-1.55 (2H, m, H-5), 1.61-1.68 (2H, m, H-3), 2.34 (2H, t, J=7.3 Hz, H-2), 3.17-3.22 (2H, m, H-6), 4.80-4.84 (1H, m, NH), 5.09 (2H, s, CH$_2$Ph), 7.26-7.38 (5H, m, Ph); $^{13}$C NMR (100 MHz, CDCl$_3$) δ 24.3 (CH$_2$, C-4), 26.1 (CH$_2$, C-3), 29.6 (CH$_2$, C-5), 33.8 (CH$_2$, C-2), 40.8 (CH$_2$, C-6), 66.7 (CH$_2$, CH$_2$Ph), 128.1 (3×CH, Ph), 128.5 (2×CH, Ph), 136.6 (C, Ph), 156.5 (C, Cbz), 178.8 (C, C-1); $v_{max}$ (cm$^{-1}$) 3331, 2944, 1687, 1527, 1252, 1140, 945.

b) tert-Butyl 6-benzyloxycarbonylaminohexanoate (75)[33]

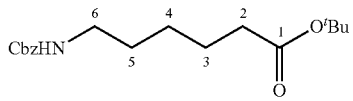

To a solution of 74 (0.63 g, 2.4 mmol) in toluene (20 mL) was added dropwise triethylamine (0.33 mL, 2.4 mmol) followed by 2,4,6-trichlorobenzoyl chloride (0.37 mL, 2.4 mmol), and the mixture stirred at room temperature for 1 h. A solution of tert-butanol (0.45 mL, 4.7 mmol) and 4-dimethylaminopyridine (0.58 g, 4.7 mmol) in toluene (5 mL) was added slowly and the mixture stirred at room temperature for a further 3 h. The mixture was then diluted with diethyl ether, washed with saturated aqueous sodium bicarbonate (2×), dried over anhydrous magnesium sulfate, filtered and the solution concentrated in vacuo. Purification by column chromatography (EtOAc/hexanes, 1:3) afforded the title compound 75 (0.56 g, 74%) as a colourless oil. $^1$H NMR (400 MHz, CDCl$_3$) δ 1.31-1.37 (2H, m, H-4), 1.43 (9H, s, OtBu), 1.47-1.53 (2H, m, H-5), 1.55-1.61 (2H, m, H-3), 2.20 (2H, t, J=7.4 Hz, H-2), 3.16-3.21 (2H, m, H-6), 4.78-4.82 (1H, m, NH), 5.09 (2H, s, CH$_2$Ph), 7.31-7.35 (5H, m, Ph); $^{13}$C NMR (100 MHz, CDCl$_3$) δ 24.6 (CH$_2$, C-3), 26.2 (CH$_2$, C-4), 28.1 (3×CH$_3$, OtBu), 29.6 (CH$_2$, C-5), 35.4 (CH$_2$, C-2), 40.9 (CH$_2$, C-6), 66.6 (CH$_2$, CH$_2$Ph), 80.1 (C, OtBu), 128.1 (3×CH, Ph), 128.5 (2×CH, Ph), 136.7 (C, Ph), 156.4 (C, Cbz), 173.0 (C, C-1); $v_{max}$ (cm$^{-1}$) 3325, 2934, 1693, 1527, 1251, 1132, 729;

c) tert-Butyl 6'-(N-maleimido)hexanoate (76)

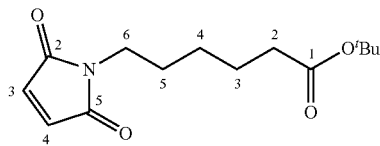

A similar procedure to that previously described for the preparation of 63 was followed using 75 (508 mg, 1.6 mmol) and palladium-on-carbon (50 mg, 10% w/w) in methanol (15 mL), then 45 (470 mg, 1.9 mmol) in saturated aqueous sodium bicarbonate (25 mL) followed by acetonitrile/water (40 mL, 1:1 v/v). Purification by column chromatography (EtOAc/hexanes, 1:3) afforded the title compound C7=76 (282 mg, 67%) as a yellow oil. $^1$H NMR (400 MHz, CDCl$_3$) δ 1.26-1.32 (2H, m, H-4'), 1.44 (9H, s, OtBu), 1.56-1.64 (4H, m, H-3', H-5'), 2.20 (2H, t, J=7.5 Hz, H-2'), 3.51 (2H, t, J=7.3 Hz, H-6'), 6.69 (2H, s, H-3, H-4); $^{13}$C NMR (100 MHz, CDCl$_3$) δ 24.6 (CH$_2$, C-3'), 26.2 (CH$_2$, C-4'), 28.1 (3×CH$_3$, OtBu), 28.2 (CH$_2$, C-5'), 35.3 (CH$_2$, C-2'), 37.7 (CH$_2$, C-6'), 80.1 (C, OtBu), 134.0 (2×CH, C-3, C-4), 170.8 (2×C, C-2, C-5), 172.9 (C, C-1'); $v_{max}$ (cm$^{-1}$) 2935, 1702, 1407, 1366, 1151, 827, 695; HRMS-ESI [M+Na]$^+$ Calcd. for C$_{14}$H$_{21}$NO$_4$Na$^+$ 290.1371, found 290.1363.

d) tert-Butyl 6'-(3-bromo-N-maleimido)hexanoate (73)

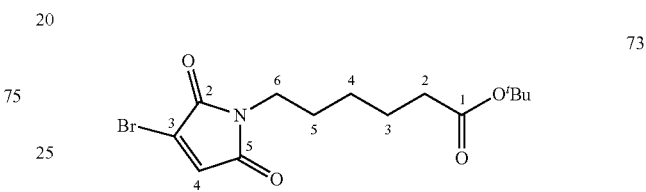

A similar procedure to that previously described for the preparation of 56 was followed using 76 (25 mg, 0.10 mmol), potassium carbonate (26 mg, 0.19 mmol) and bromine (5 µL, 0.11 mmol) in chloroform (1 mL), then triethylamine (15 µL, 0.11 mmol) in tetrahydrofuran (1 mL). Purification by column chromatography (EtOAc/hexanes, 1:3) afforded the title compound 73 (13 mg, 42%) as a yellow oil. $^1$H NMR (400 MHz, CDCl$_3$) δ 1.28-1.33 (2H, m, H-4'), 1.44 (9H, s, OtBu), 1.57-1.65 (4H, m, H-3', H-5'), 2.20 (2H, t, J=7.4 Hz, H-2'), 3.56 (2H, t, J=7.3 Hz, H-6'), 6.85 (1H, s, H-4); $^{13}$C NMR (100 MHz, CDCl$_3$) δ 24.5 (CH$_2$, C-3'), 26.1 (CH$_2$, C-4'), 28.1 (3×CH$_3$, OtBu), 28.2 (CH$_2$, C-5'), 35.3 (CH$_2$, C-2'), 38.7 (CH$_2$, C-6'), 80.1 (C, OtBu), 131.3 (C, C-3), 131.8 (CH, C-4), 165.3 (C, C-2 or C-5), 168.6 (C, C-2 or C-5), 172.9 (C, C-1'); $v_{max}$ (cm$^{-1}$) 2925, 1712, 1366, 1151, 848; HRMS-ESI [M+Na]$^+$ Calcd. for C$_{14}$H$_{20}$$^{79}$BrNO$_4$Na$^+$ 368.0468, found 368.0460.

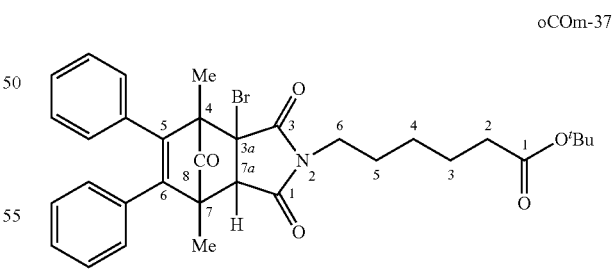

e) oCOm-37

A similar procedure to that previously described for the preparation of oCOm-25 was followed using 73 (13 mg, 0.04 mmol) and diene dimer 17 (12 mg, 0.05 mmol) in toluene (2 mL). Purification by column chromatography (EtOAc/hexanes, 1:1) afforded the title compound oCOM-37 (22 mg, 99%) as a pale yellow oil in a 6:1 ratio of endo and exo isomers, respectively. $v_{max}$ (cm$^{-1}$) 2934, 1786, 1709, 1365, 1151, 699; HRMS-ESI [M+Na]$^+$ Calcd. for $C_{33}H_{36}{}^{79}BrNO_5Na^+$ 628.1669, found 628.1690.

For the endo isomer; $^1H$ NMR (400 MHz, CDCl$_3$) inter alia δ 1.30-1.36 (2H, m, H-4'), 1.43 (9H, s, OtBu), 1.60 (3H, s, Me-7), 1.62 (3H, s, Me-4), 1.55-1.64 (4H, m, H-3', H-5'), 2.14 (2H, t, J=7.4 Hz, H-2'), 3.50 (1H, s, H-7a), 3.57 (2H, td, J=7.5, 3.0 Hz, H-6'), 6.85-6.90 (4H, m, Ph), 7.15-7.19 (6H, m, Ph); $^{13}C$ NMR (100 MHz, CDCl$_3$) inter alia δ 11.5 (CH$_3$, Me-4), 12.4 (CH$_3$, Me-7), 24.4 (CH$_2$, C-4'), 26.1 (CH$_2$, C-3'), 27.3 (CH$_2$, C-5'), 28.1 (3×CH$_3$, OtBu), 35.2 (CH$_2$, C-2'), 39.8 (CH$_2$, C-6'), 56.4 (C, C-7), 58.9 (C, C-3a), 60.3 (CH, C-7a), 60.7 (C, C-4), 80.1 (C, OtBu), 128.1 (2×CH, Ph), 128.2 (2×CH, Ph), 128.3 (2×CH, Ph), 129.3 (2×CH, Ph), 129.7 (2×CH, Ph), 132.4 (C, Ph), 132.5 (C, Ph), 140.4 (C, C-5), 144.5 (C, C-6), 172.3 (C, C-1'), 172.6 (C, C-1 or C-3), 172.8 (C, C-1 or C-3), 196.9 (C, C-8).

For the exo isomer; $^1H$ NMR (400 MHz, CDCl$_3$) inter alia δ 1.44 (9H, s, OtBu), 2.22 (2H, t, J=7.4 Hz, H-2'), 3.35 (1H, s, H-7a); $^{13}C$ NMR (100 MHz, CDCl$_3$) inter alia δ 8.1 (CH$_3$), 9.4 (CH$_3$), 59.1 (C), 128.0 (CH), 128.5 (CH), 130.5 (CH).

f) 6-(3a-bromo-4,7-dimethyl-1,3,8-trioxo-5,6-diphenyl-1,3,3a,4,7,7a-hexahydro-2H-4,7-methanoisoindol-2-yl)-hexanoic acid (oCOm-38)

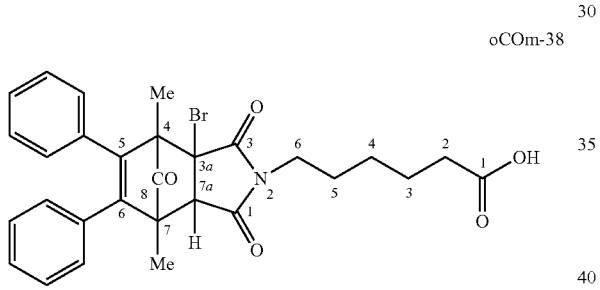

oCOm-38

A similar procedure to that previously described for the preparation of oCOm-26 was followed using oCOm-37 (21 mg, 0.04 mmol) and trifluoroacetic acid (0.1 mL) in dichloromethane (0.3 mL) to afford the title compound oCOm-38 (19 mg, 100%) as a pale brown residue in a 6:1 ratio of endo and exo isomers, respectively. $v_{max}$ (cm$^{-1}$) 2935, 1782, 1706, 1391, 1171, 910, 732; HRMS-ESI [M+Na]$^+$ Calcd. for $C_{29}H_{28}{}^{79}BrNO_5Na^+$ 572.1043, found 572.1041.

For the endo isomer; $^1H$ NMR (400 MHz, CDCl$_3$) inter alia δ 1.30-1.39 (2H, m, H-4'), 1.60 (3H, s, Me-7), 1.62 (3H, s, Me-4), 1.60-1.66 (4H, m, H-3', H-5'), 2.27 (2, t, J=7.4 Hz, H-2'), 3.51 (1H, s, H-7a), 3.59 (2H, td, J=11.0, 2.5 Hz, H-6'), 6.85-6.91 (4H, m, Ph), 7.17-7.20 (6H, m, Ph); $^{13}C$ NMR (100 MHz, CDCl$_3$) inter alia δ 11.5 (CH$_3$, Me-4), 12.4 (CH$_3$, Me-7), 24.0 (CH$_2$, C-4'), 26.0 (CH$_2$, C-3'), 27.2 (CH$_2$, C-5'), 33.5 (CH$_2$, C-2'), 39.7 (CH$_2$, C-6'), 56.4 (C, C-7), 58.9 (C, C-3a), 60.3 (CH, C-7a), 60.7 (C, C-4), 128.1 (2×CH, Ph), 128.2 (2×CH, Ph), 128.3 (2×CH, Ph), 129.3 (2×CH, Ph), 129.7 (2×CH, Ph), 132.4 (C, Ph), 132.5 (C, Ph), 140.4 (C, C-5), 144.5 (C, C-6), 172.4 (C, C-1 or C-3), 172.6 (C, C-1 or C-3), 178.6 (C, C-1'), 196.9 (C, C-8).

For the exo isomer; $^1H$ NMR (400 MHz, CDCl$_3$) inter alia δ 1.85-1.88 (4H, m, H-5'), 2.37 (2H, t, J=7.4 Hz, H-2'), 3.37 (1H, s, H-7a), 3.76-3.79 (2H, m, H-6'); $^{13}C$ NMR (100 MHz, CDCl$_3$) inter alia δ 128.0 (CH), 128.5 (CH), 130.5 (CH).

Example 28 oCOm-39 and -40

Methyl (2S) 2-amino-5-(3a-bromo-4,7-dimethyl-1,3,8-trioxo-5,6-diphenyl-1,3,3a,4,7,7a-hexahydro-2H-4,7-methanoisoindol-2-yl)-pentanoate trifluoroacetic acid salt; Where $R^1=R^2=Ph$; $R^3=R^4=Me$; $A^3=NR^{14}$; $R^{14}=(CH_2)_3CH(NH_2 \cdot HOCOCF_3)CO_2Me$; X=Br Scheme 31:
Synthesis of oCOm-39 and -40

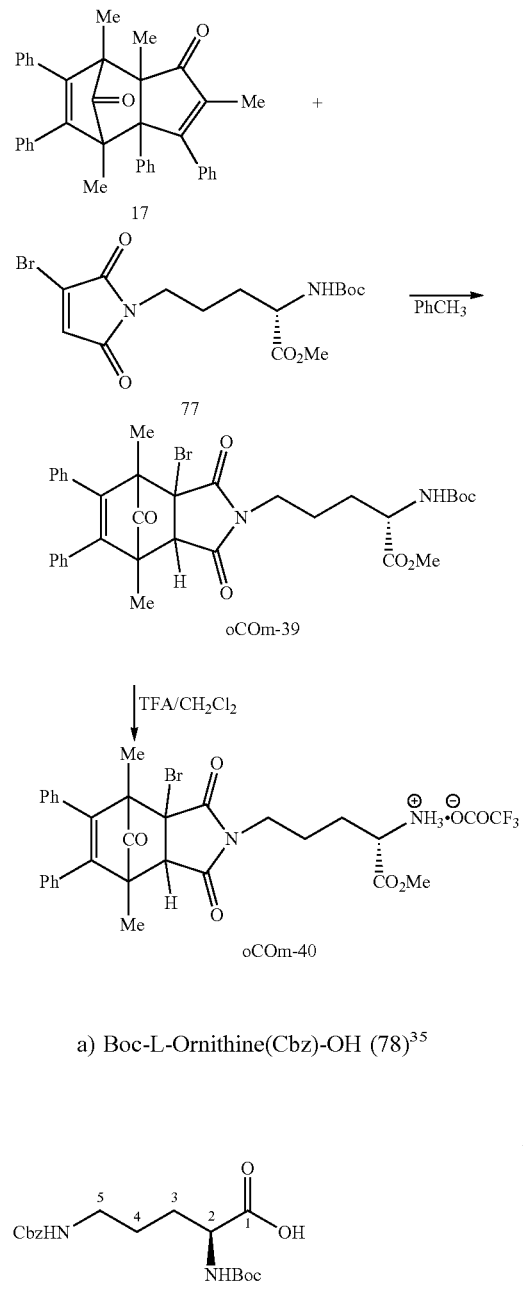

a) Boc-L-Ornithine(Cbz)-OH (78)$^{35}$

To a solution of L-ornithine hydrochloride (5.0 g, 29.7 mmol) in aqueous sodium hydroxide (50 mL, 0.5 M) was added a solution of copper sulfate (2.8 g, 17.8 mmol) in water (100 mL), and the mixture stirred at room temperature for 4 h. The mixture was then cooled to 0° C. before sodium bicarbonate (5.0 g, 59.4 mmol) and benzyl chloroformate (5.7 mL, 40.1 mmol) were added. The pH was then adjusted to pH 9 through the careful addition of aqueous sodium hydroxide (1.0 M), and the mixture stirred at room temperature for 4 h. The resulting solid was collected by filtration, washed with water, then diethyl ether, dissolved in aqueous EDTA (200 mL, 0.5 M) and stirred vigorously at room temperature for 14 h. The solid was again collected by filtration and washed with water to afford a crude solid, which was used without further purification. The crude solid was then dissolved in 1,4-dioxane/water (200 mL, 1:1 v/v) and the pH adjusted to pH 9 using aqueous sodium hydroxide (0.5 M). Di-tert-butyl dicarbonate (9.7 g, 44.6 mmol) was then added and the mixture stirred at room temperature for 24 h. The pH was maintained at pH 9 throughout the reaction using aqueous sodium hydroxide (0.5 M). The mixture was then acidified to pH 3 with aqueous citric acid (1.0 M), extracted with dichloromethane (3×), the combined organic layers dried over anhydrous magnesium sulfate, filtered and the solution concentrated in vacuo. Purification by column chromatography (MeOH:DCM 1:20) afforded the title compound 78 (7.7 g, 72%) as a colourless oil. $[\alpha]_D^{18.1}$ +9.5 (c 0.263 in CHCl$_3$); NMR (400 MHz, CDCl$_3$) δ 1.43 (9H, s, Boc), 1.58-1.71 (3H, m, H$_b$-3, H-4), 1.82-1.89 (1H, m, H$_a$-3), 3.17-3.21 (2H, m, H-5), 4.27-4.33 (1H, m, H-2), 5.08 (2H, s, CH$_2$Ph), 5.13 (1H, br s, NH), 5.29 (1H, br s, NH), 7.28-7.35 (5H, m, Ph), 8.86 (1H, br s, OH); $^{13}$C NMR (100 MHz, CDCl$_3$) δ 25.9 (CH$_2$, C-4), 28.3 (3×CH$_3$, Boc), 29.7 (CH$_2$, C-3), 40.5 (CH$_2$, C-5), 53.0 (CH, C-2), 66.8 (CH$_2$, CH$_2$Ph), 80.2 (C, Boc), 128.1 (3×CH, Ph), 128.5 (2×CH, Ph), 136.5 (C, Ph), 155.8 (C, Boc), 156.8 (C, Cbz), 176.0 (C, C-1); $v_{max}$(cm$^{-1}$) 3315, 2976, 1683, 1529, 1249, 1160, 1024, 696; HRMS-ESI [M+Na]$^+$ Calcd. for C$_{18}$H$_{26}$N$_2$O$_6$Na$^+$ 389.1683, found 389.1676.

b) Boc-L-Ornithine(Cbz)-OMe (79)

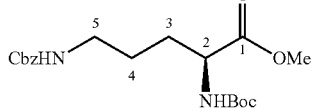

79

A similar procedure to that previously described for the preparation of 62 was followed using 78 (1.50 g, 4.1 mmol), potassium carbonate (0.87 g, 8.2 mmol) and methyl iodide (0.38 mL, 6.1 mmol) in dimethylformamide (5 mL). Purification by column chromatography (EtOAc/hexanes, 1:1) afforded the title compound 79 (1.53 g, 98%) as a white solid. m.p. 67-68° C. $[\alpha]_D^{17.6}$ +12.7 (c 1.41 in CHCl$_3$); $^1$H NMR (400 MHz, CDCl$_3$) δ 1.43 (9H, s, Boc), 1.52-1.83 (4H, m, H-3, H-4), 3.17-3.22 (2H, m, H-5), 3.72 (3H, s, OMe), 4.26-4.31 (1H, m, H-2), 4.96-4.99 (1H, m, NH), 5.09-5.14 (1H, m, NH), 7.31-7.35 (5H, m, Ph); $^{13}$C NMR (100 MHz, CDCl$_3$) δ 26.0 (CH$_2$, C-4), 28.3 (3×CH$_3$, Boc), 30.0 (CH$_2$, C-3), 40.5 (CH$_2$, C-5), 52.3 (CH$_3$, OMe), 53.1 (CH, C-2), 66.6 (CH$_2$, CH$_2$Ph), 80.0 (C, Boc), 128.1 (3×CH, Ph), 128.5 (2×CH, Ph), 136.6 (C, Ph), 155.4 (C, Boc), 156.4 (C, Cbz), 173.1 (C, C-1); $v_{max}$(cm$^{-1}$) 3332, 2953, 2361, 2342, 1697, 1521, 1251, 1162, 755; HRMS-ESI [M+Na]$^+$ Calcd. for C$_{19}$H$_{28}$N$_2$O$_6$Na$^+$ 403.1840, found 403.1844.

c) Methyl (S)-5'-(N-maleimido)-2'-tert-butoxycarbonylaminopentanoate (80)

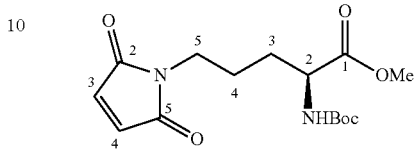

80

A similar procedure to that previously described for the preparation of 63 was followed using 79 (66 mg, 0.17 mmol), acetic acid (0.1 mL) and palladium-on-carbon (10 mg, 10% w/w) in methanol (1 mL), then 45 (126 mg, 0.51 mmol) in saturated aqueous sodium bicarbonate (2 mL) followed by acetonitrile/water (2 mL, 1:1 v/v). Purification by column chromatography (EtOAc/hexanes, 1:1) afforded the title compound 80 (46 mg, 83%) as a yellow solid. m.p. 65-68° C. $[\alpha]_D^{17.7}$ =+10.5 (c 0.62 in CHCl$_3$); $^1$H NMR (400 MHz, CDCl$_3$) δ 1.44 (9H, s, Boc), 1.56-1.83 (4H, m, H-3', H-4'), 3.54 (2H, t, J=6.7 Hz, H-5'), 3.74 (3H, s, OMe), 4.30-4.32 (1H, m, H-2'), 5.12 (1H, d, J=7.7 Hz, NH), 6.71 (2H, s, H-3, H-4); $^{13}$C NMR (100 MHz, CDCl$_3$) δ 24.6 (CH$_2$, C-4'), 28.3 (3×CH$_3$, Boc), 29.9 (CH$_2$, C-3'), 37.3 (CH$_2$, C-5'), 52.3 (CH$_3$, OMe), 53.0 (CH, C-2'), 79.9 (C, Boc), 134.1 (2×CH, C-3, C-4), 155.3 (C, Boc), 170.7 (2×C, C-2, C-5), 172.9 (C, C-1); $v_{max}$(cm$^{-1}$) 3361, 2956, 2361, 2342, 1699, 1366, 1206, 1162, 696; HRMS-ESI [M+H]$^+$ Calcd. for C$_{15}$H$_{23}$N$_2$O$_6$$^+$ 327.1551, found 327.1550.

d) Methyl (S)-5'-(3-bromo-N-maleimido)-2'-tert-butoxycarbonylaminopentanoate (77)

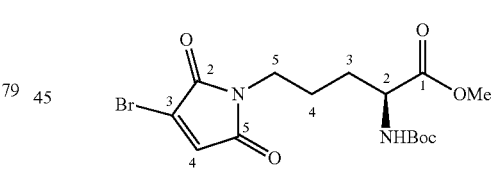

77

A similar procedure to that previously described for the preparation of 56 was followed using 80 (207 mg, 0.63 mmol), potassium carbonate (174 mg, 1.3 mmol) and bromine (40 μL, 0.70 mmol) in chloroform (3 mL), then triethylamine (100 μL, 0.70 mmol) in tetrahydrofuran (2 mL). Purification by column chromatography (EtOAc/hexanes, 1:3) afforded the title compound 77 (147 mg, 58%) as a yellow oil. $[\alpha]_D^{18.3}$ =+13.7 (c 0.57 in CHCl$_3$); $^1$H NMR (400 MHz, CDCl$_3$) δ 1.44 (9H, s, Boc), 1.56-1.85 (4H, m, H-3', H-4'), 3.58 (2H, t, J=7.0 Hz, H-5'), 3.74 (3H, s, OMe), 4.32 (1H, m, H-2'), 5.05 (1H, d, J=7.0 Hz, NH), 6.87 (1H, s, H-4); $^{13}$C NMR (100 MHz, CDCl$_3$) δ 24.5 (CH$_2$, C-4'), 28.3 (3×CH$_3$, Boc), 30.0 (CH$_2$, C-3'), 38.3 (CH$_2$, C-5'), 52.4 (CH$_3$, OMe), 52.9 (CH, C-2'), 80.0 (C, Boc), 131.4 (C, C-3), 131.8 (CH, C-4), 155.3 (C, Boc), 165.3 (C, C-2), 168.5 (C, C-5), 172.8 (C, C-1'); $v_{max}$(cm$^{-1}$) 3378, 2954, 2361, 2342, 1213, 1162; HRMS-ESI [M+H]$^+$ Calcd. for C$_{15}$H$_{22}$$^{79}$BrN$_2$O$_6$$^+$ 405.0656, found 405.0666.

e) oCOm-39

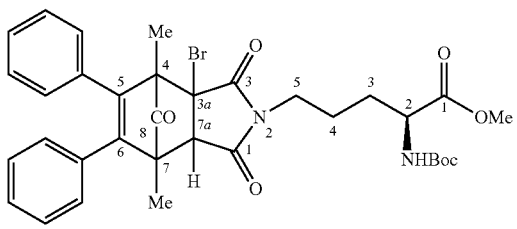

A similar procedure to that previously described for the preparation of oCOm-25 was followed using 77 (185 mg, 0.46 mmol) and diene dimer 17 (131 mg, 0.50 mmol) in toluene (7 mL). Purification by column chromatography (EtOAc/hexanes, 1:3) afforded the title compound oCOm-39 (265 mg, 87%) as a white solid in a 8:1 ratio of endo and exo isomers, respectively. m.p. 72-75° C. $v_{max}$ (cm$^{-1}$) 3386, 2978, 1783, 1708, 1365, 1160, 752, 699; HRMS-ESI [M+H]$^+$ Calcd. for $C_{34}H_{37}{}^{79}BrN_2O_7{}^+$ 687.1676, found 687.1667.

For the endo isomer; $^1$H NMR (400 MHz, CDCl$_3$) inter alia δ 1.43 (9H, s, Boc), 1.60 (3H, s, Me-7), 1.62 (3H, s, Me-4), 1.62-1.70 (3H, m, H$_b$-3', H-4'), 1.78-1.84 (1H, m, H$_a$-3'), 3.50 (1H, s, H-7a), 3.57-3.61 (2H, m, H-5'), 3.67 (3H, s, OMe), 4.29-4.33 (1H, m, H-2'), 4.96 (1H, d, J=7.9 Hz, NH), 6.83-6.88 (4H, m, Ph), 7.16-7.20 (6H, m, Ph); $^{13}$C NMR (100 MHz, CDCl$_3$) inter alia δ 11.5 (CH$_3$, Me-4), 12.4 (CH$_3$, Me-7), 23.7 (CH$_2$, C-4'), 28.3 (3×CH$_3$, Boc), 29.9 (CH$_2$, C-3'), 39.4 (CH$_2$, C-5'), 52.4 (CH$_3$, OMe), 52.9 (CH, C-2'), 56.4 (C, C-7), 58.9 (C, C-3a), 60.3 (C, C-7a), 60.7 (C, C-4), 80.1 (C, Boc), 128.2 (2×CH, Ph), 128.3 (4×CH, Ph), 129.3 (2×CH, Ph), 129.7 (2×CH, Ph), 132.4 (C, Ph), 132.5 (C, Ph), 140.4 (C, C-5), 144.5 (C, C-6), 155.3 (C, Boc), 172.3 (C, C-1 or C-3), 172.5 (C, C-1 or C-3), 172.7 (C, C-1'), 196.9 (C, C-8).

For the exo isomer; $^1$H NMR (400 MHz, CDCl$_3$) inter alia δ 1.45 (9H, s, Boc), 3.36 (1H, s, H-7a), 3.75 (3H, s, OMe); $^{13}$C NMR (100 MHz, CDCl$_3$) inter alia δ 8.1 (CH$_3$), 9.3 (CH$_3$), 128.0 (CH), 128.5 (CH), 130.5 (CH).

f) Methyl (2S) 2-amino-5-(3a-bromo-4,7-dimethyl-1,3,8-trioxo-5,6-diphenyl-1,3,3a,4,7,7a-hexahydro-2H-4,7-methanoisoindol-2-yl)-pentanoate trifluoroacetic acid salt (oCOm-40)

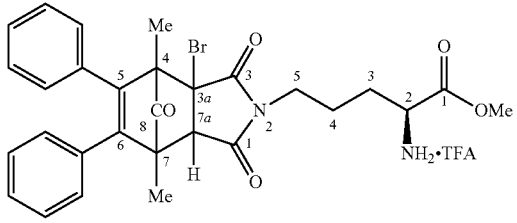

A similar procedure to that previously described for the preparation of oCOm-26 was followed using oCOm-39 (54 mg, 0.08 mmol) and trifluoroacetic acid (0.33 mL) in dichloromethane (1 mL) to afford the trifluoroacetate salt of the title compound oCOm-40 (54 mg, 100%) as a pale yellow residue in a 8:1 ratio of endo and exo isomers, respectively. $v_{max}$ (cm$^{-1}$) 2944, 1782, 1749, 1710, 1178, 757, 699; HRMS-ESI [M+H]$^+$ Calcd. for $C_{29}H_{30}{}^{79}BrN_2O_5{}^+$ 565.1333, found 565.1322.

For the endo isomer; $^1$H NMR (500 MHz, CDCl$_3$) inter alia δ 1.59 (3H, Me-7), 1.60 (3H, s, Me-4), 1.72-1.82 (2H, m, H-4'), 1.91-1.99 (2H, m, H-3'), 3.53 (1H, s, H-7a), 3.57-3.60 (2H, m, H-5'), 3.68 (3H, s, OMe), 4.00-4.03 (1H, m, H-2'), 6.80-6.85 (4H, m, Ph), 7.14-7.17 (6H, m, Ph); $^{13}$C NMR (125 MHz, CDCl$_3$) inter alia δ 11.5 (CH$_3$, Me-4), 12.3 (CH$_3$, Me-7), 23.0 (CH$_2$, C-4'), 27.3 (CH$_2$, C-3'), 38.6 (CH$_2$, C-5'), 52.5 (CH, C-2'), 53.4 (CH$_3$, OMe), 56.4 (C, C-7), 58.6 (C, C-3a), 60.2 (CH, C-7a), 60.7 (C, C-4), 128.2 (2×CH, Ph), 128.3 (2×CH, Ph), 128.4 (2×CH, Ph), 129.3 (2×CH, Ph), 129.6 (2×CH, Ph), 132.3 (C, Ph), 132.5 (C, Ph), 140.4 (C, C-5), 144.6 (C, C-6), 169.5 (C, C-1 or C-3), 172.5 (C, C-1 or C-3), 172.8 (C, C-1'), 196.8 (C, C-8).

For the exo isomer; $^1$H NMR (500 MHz, CDCl$_3$) inter alia δ 3.38 (1H, s, H-7a), 3.78 (3H, s, OMe); $^{13}$C NMR (125 MHz, CDCl$_3$) inter alia δ 128.0 (CH), 128.5 (CH), 130.5 (CH).

Example 29 oCOm-41

Methyl (2S)-2-acetamido-6-(3a-bromo-4,7-dimethyl-1,3,8-trioxo-5,6-diphenyl-1,3,3a,4,7,7a-hexahydro-2H-4,7-methanoisoindol-2-yl)hexanoate
Where R$^1$=R$^2$=Ph; R$^3$=R$^4$=Me; A$^3$=NR$^{14}$; R$^{14}$=(CH$_2$)$_4$CH(NHAc)CO$_2$Me; X=Br Scheme 32:
Synthesis of oCOm-41

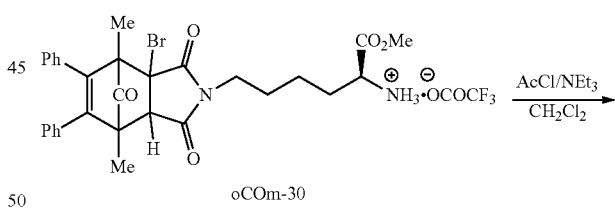

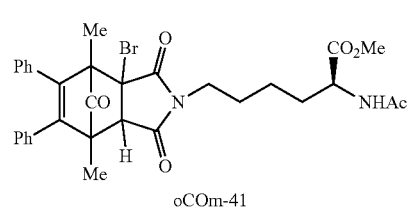

163
a) oCOm-41

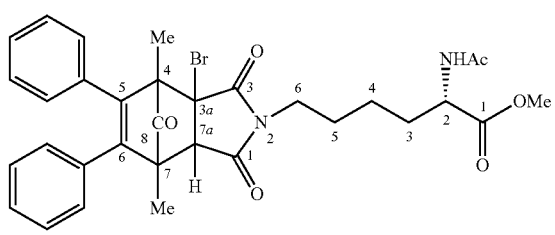

A solution of acetyl chloride (10 µl, 0.014 mmol) in dichloromethane (0.25 mL) was added to a solution of oCOm-30 (10 mg, 0.014 mmol) and triethylamine (16 µl, 0.012 mmol) in dichloromethane (0.75 mL) at 0° C., and then stirred at room temperature for 25 minutes. The solution was then washed with brine, dried over anhydrous magnesium sulfate and concentrated in vacuo. The crude product was purified by column chromatography (EtOAc/hexanes, 1:1) to afford the title compound oCOm-41 (7 mg, 79%) as a colourless oil in a 16:1 ratio of endo and exo isomers, respectively. $v_{max}$ (cm$^{-1}$) 3376, 2934, 1783, 1707, 1656, 1442, 1368, 1176, 699; HRMS-ESI [M+Na]$^+$ Calcd. for $C_{32}H_{33}{}^{79}BrN_2O_6Na^+$ 621.1595, found 621.1594.

For the endo isomer; $^1$H NMR (400 MHz, CDCl$_3$) (mixture of rotamers) inter alia δ 1.34-1.42 (2H, m, H-4'), 1.60 (3H, s, Me-7), 1.62 (3H, s, Me-4), 1.63-1.88 (4H, m, H-3', H-5'), 1.99 (3H, s, NHAc), 3.51 (1H, s, H-7a), 3.57 (2H, t, J=6.8 Hz, H-6'), 3.74 (3H, s, OMe), 4.53-4.60 (1H, m, H-2'), 6.02-6.06 (1H, m, NHAc), 6.83-6.89 (4H, m, Ph), 7.17-7.20 (6H, m, Ph); $^{13}$C NMR (100 MHz, CDCl$_3$) (mixture of rotamers) inter alia δ 11.5 (CH$_3$, Me-4), 12.4 (CH$_3$, Me-7), 22.2 (CH$_2$, C-4'), 23.2 (CH$_3$, —NHAc), 27.1 (CH$_2$, C-3'), 31.6 (CH$_2$, C-5'), 31.7 (CH$_2$, C-5'), 39.1 (CH$_2$, C-6'), 39.4 (CH$_2$, C-6'), 51.9 (CH, C-2'), 52.5 (CH$_3$, OMe), 56.4 (C, C-7), 58.9 (C, C-3a), 59.0 (C, C-3a), 60.3 (CH, C-7a), 60.6 (C, C-4), 128.2 (2×CH, Ph), 128.3 (4×CH, Ph), 129.3 (2×CH, Ph), 129.6 (2×CH, Ph), 132.4 (C, Ph), 132.5 (C, Ph), 140.4 (C, C-5), 144.5 (C, C-6), 144.6 (C, C-6), 169.9 (C, C-1'), 170.0 (C, C-1'), 172.4 (C, NHAc), 172.5 (C, NHAc), 172.6 (C, C-1 or C-3), 172.8 (C, C-1 or C-3), 196.8 (C, C-8).

For the exo isomer; $^1$H NMR (400 MHz, CDCl$_3$) inter alia δ 2.07 (3H, s, NHAc), 3.37 (1H, s, H-7a), 3.82 (3H, s, OMe).

164
Example 30 oCOm-42 and -43 oCOm-43 (1S)-1-amino-5-(3a-bromo-4,7-dimethyl-1,3,8-trioxo-5,6-diphenyl-1,3,3a,4,7,7a-hexahydro-2H-4,7-methanoisoindol-2-yl)-1-(3-methyl-1,2,4-oxadiazol-5-yl)pentane trifluoroacetic acid salt
Where R$^1$=R$^2$=Ph; R$^3$=R$^4$=Me; A$^3$=NR$^{14}$; R$^{14}$=(CH$_2$)$_4$CH(NH$_2$.HOCOCF$_3$)-5-(3-Me-(1,2,4-oxadiazol)yl): X=Br Scheme 33:
Synthesis of oCOm-42 and -43

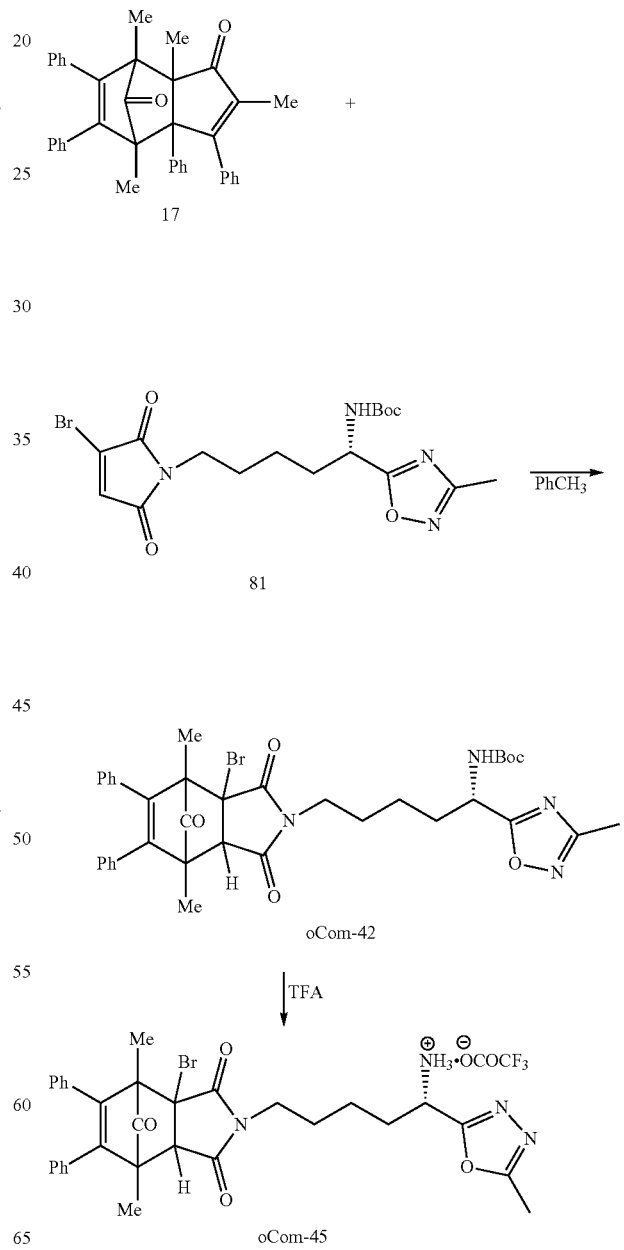

a) (S)-5'-Fluorenylmethyloxycarbonylamino-1'-(3"-methyl-1",2",4"-oxadiazol-5"-yl)-1'-tert-butoxycarbonylaminopentane (82)

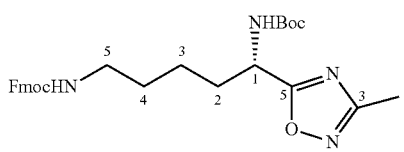

To a solution of Boc-Lys(Fmoc)-OH (1.11 g, 2.4 mmol) and N'-hydroxyacetimidamide[36] (0.21 g, 2.8 mmol) in dichloromethane (13.5 mL) and dimethylformamide (1.5 mL) at 0° C. was added N,N'-diisopropylcarbodiimide (0.36 g, 2.8 mmol) and 1-hydroxy-7-azabenzotriazole (0.39 g, 2.8 mmol), and the mixture stirred at 0° C. for 90 minutes, then room temperature for 3.5 h. The mixture was then diluted with ethyl acetate, washed with saturated aqueous sodium bicarbonate (2×), brine, then saturated aqueous ammonium chloride, dried over anhydrous magnesium sulfate, filtered and the solution concentrated in vacuo. The crude solid was then dissolved in ethanol (20 mL) and added to a solution of sodium acetate (0.21 g, 2.6 mmol) in water (3 mL), and the mixture heated at 90° C. for 6 h. The solution was then concentrated in vacuo, the residue dissolved in ethyl acetate, washed with brine, dried over anhydrous magnesium sulfate and the solution again concentrated in vacuo. Purification by column chromatography (EtOAc/hexanes, 1:1) afforded the title compound 82 (0.68 g, 57%) as a white solid. m.p. 121-123° C. $[\alpha]_D^{21.9}$=−21.2 (c 1.00 in CHCl$_3$); $^1$H NMR (400 MHz, CDCl$_3$) δ 1.40-1.45 (2H, m, H-3), 1.43 (9H, s, Boc), 1.51-1.59 (2H, m, H-4), 1.82-1.94 (2H, m, H-2), 2.37 (3H, s, 3'-Me), 3.16-3.21 (2H, m, H-5), 4.18-4.22 (1H, m, OCH$_2$CH), 4.39-4.42 (2H, m, OCH$_2$CH), 4.84-4.90 (1H, m, NH), 4.97-5.03 (1H, m, H-1), 5.18-5.22 (1H, m, NH), 7.31 (2H, t, J=7.4 Hz, Ph), 7.39 (2H, t, J=7.4 Hz, Ph), 7.58 (2H, d, J=7.4 Hz, Ph), 7.76 (2H, d, J=7.4 Hz, Ph); $^{13}$C NMR (100 MHz, CDCl$_3$) δ 11.6 (CH$_3$, 3'-Me), 22.3 (CH$_2$, C-3), 28.3 (3×CH$_3$, Boc), 29.4 (CH$_2$, C-4), 33.7 (CH$_2$, C-2), 40.5 (CH$_2$, C-5), 47.3 (CH, OCH$_2$CH), 48.1 (CH, C-1), 66.6 (CH$_2$, OCH$_2$CH), 80.6 (C, Boc), 120.0 (2×CH, Ph), 125.0 (2×CH, Ph), 127.1 (2×CH, Ph), 127.7 (2×CH, Ph), 141.4 (2×C, Ph), 144.0 (2×C, Ph), 155.1 (C, Boc), 156.5 (C, Fmoc), 167.1 (C, C-3'), 179.2 (C, C-5'); $v_{max}$ (cm$^{-1}$) 3325, 2932, 1681, 1516, 1261, 1158, 728; HRMS-ESI [M+Na]$^+$ Calcd. for C$_{28}$H$_{34}$N$_4$O$_5$Na$^+$ 529.2421, found 529.2421.

b) (S)-5'-(N-Maleimido)-1'-(3"-methyl-1",2",4"-oxadiazol-5"-yl)-1'-tert-butoxycarbonylaminopentane (83)

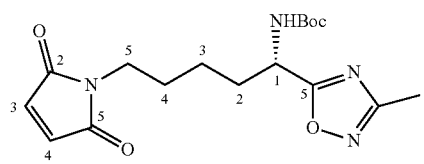

A solution of 82 (278 mg, 0.55 mmol) in Tesser's Base (20 mL, 1,4-dioxane/methanol/4M NaOH, 30:9:1 v/v/v) was stirred at room temperature for 10 minutes. The solution was then concentrated in vacuo to afford a yellow oil, which was used without further purification. To the crude oil was added a mixture of 45 (163 mg, 0.66 mmol) in saturated aqueous sodium bicarbonate (14 mL), and the mixture stirred at room temperature for 5 minutes. The mixture was then extracted with dichloromethane (3×), the combined organic layers dried over anhydrous magnesium sulfate, filtered and the solution concentrated in vacuo. Purification by column chromatography (EtOAc/hexanes, 1:2) afforded the title compound 83 (100 mg, 50%) as a yellow oil. $[\alpha]_D^{23.2}$=−1.0 (c 1.00 in CHCl$_3$); $^1$H NMR (400 MHz, CDCl$_3$) δ 1.33-1.41 (2H, m, H-3'), 1.44 (9H, s, Boc), 1.59-1.69 (2H, m, H-4'), 1.81-1.95 (2H, m, H-2'), 2.39 (3H, s, 3"-Me), 3.51 (2H, t, J=7.2 Hz, H-5'), 4.97-5.01 (1H, m, H-1'), 5.09 (1H, d, J=7.4 Hz, NH), 6.69 (2H, s, H-3, H-4); $^{13}$C NMR (100 MHz, CDCl$_3$) δ 11.5 (CH$_3$, 3"-Me), 22.4 (CH$_2$, C-3'), 27.9 (CH$_2$, C-4'), 28.3 (3×CH$_3$, Boc), 33.4 (CH$_2$, C-2'), 37.2 (CH$_2$, C-5'), 48.0 (CH, C-1'), 80.4 (C, Boc), 134.1 (2×CH, C-3, C-4), 155.0 (C, Boc), 167.1 (C, C-3"), 170.8 (2×C, C-2, C-5), 179.1 (C, C-5"); $v_{max}$ (cm$^{-1}$) 3336, 2925, 1702, 1514, 1367, 1164, 828; HRMS-ESI [M+Na]$^+$ Calcd. for C$_{17}$H$_{24}$N$_4$O$_5$Na$^+$ 387.1639, found 387.1652.

c) (S)-5'-(3-Bromo-N-maleimido)-1'-(3"-methyl-1",2",4"-oxadiazol-5"-yl)-1'-tert-butoxycarbonylaminopentane (81)

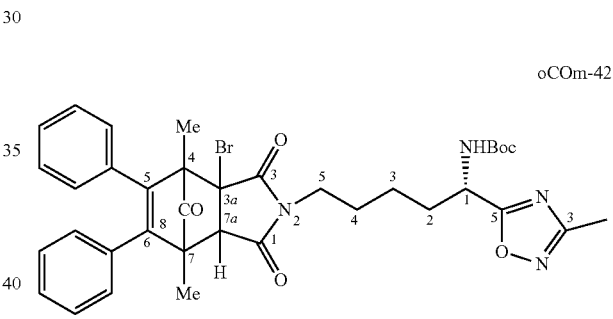

A similar procedure to that previously described for the preparation of 56 was followed using 83 (32 mg, 0.09 mmol), potassium carbonate (13 mg, 0.10 mmol) and bromine (10 μL, 0.10 mmol) in chloroform (1 mL), then triethylamine (14 μL, 0.10 mmol) in tetrahydrofuran (1 mL). Purification by column chromatography (EtOAc/hexanes, 1:3) afforded the title compound 81 (26 mg, 67%) as a yellow oil. $[\alpha]_D^{22.2}$=−1.2 (c 1.00 in CHCl$_3$); $^1$H NMR (400 MHz, CDCl$_3$) δ 1.34-1.41 (2H, m, H-3'), 1.45 (9H, s, Boc), 1.58-1.70 (2H, m, H-4'), 1.80-1.99 (2H, m, H-2'), 2.40 (3H, s, 3"-Me), 3.56 (2H, t, J=7.1 Hz, H-5'), 4.96-5.01 (1H, m, H-1'), 5.14-5.18 (1H, m, NH), 6.87 (1H, s, H-4); $^{13}$C NMR (100 MHz, CDCl$_3$) δ 11.7 (CH$_3$, 3"-Me), 22.4 (CH$_2$, C-3'), 27.9 (CH$_2$, C-4'), 28.4 (3×CH$_3$, Boc), 33.6 (CH$_2$, C-2'), 38.3 (CH$_2$, C-5'), 48.1 (CH, C-1'), 80.6 (C, Boc), 131.5 (C, C-3), 131.9 (CH, C-4), 155.1 (C, Boc), 165.4 (C, C-2 or C-5), 167.2 (C, C-3"), 168.7 (C, C-2 or C-5), 179.1 (C, C-5"); $v_{max}$ (cm$^{-1}$) 3336, 2932, 1710, 1512, 1395, 1366, 1162, 761; HRMS-ESI [M+Na]$^+$ Calcd. for C$_{17}$H$_{23}$$^{79}$BrN$_4$O$_5$Na$^+$ 465.0744, found 465.0738.

d) oCOm-42

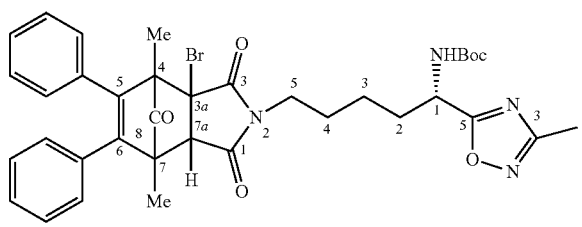

A similar procedure to that previously described for the preparation of oCOm-25 was followed using 81 (16 mg, 0.04 mmol) and diene dimer 17 (11 mg, 0.04 mmol) in toluene (1 mL). Purification by column chromatography (EtOAc/hexanes, 1:3) afforded the title compound oCOm-42 (20 mg, 80%) as a white residue in a 6:1 ratio of endo and exo isomers, respectively. $v_{max}$ (cm$^{-1}$) 3383, 2933, 1788, 1710, 1505, 1392, 1366, 1168, 700; HRMS-ESI [M+H]$^+$ Calcd. for $C_{36}H_{40}{}^{79}BrN_4O_6{}^+$ 703.2126, found 703.2127.

For the endo isomer; $^1$H NMR (400 MHz, CDCl$_3$) inter alia δ 1.40-1.46 (2H, m, H-3'), 1.44 (9H, s, Boc), 1.60 (3H, s, Me-7), 1.62 (3H, s, Me-4), 1.64-1.67 (2H, m, H-4'), 1.83-1.92 (2H, m, H-2'), 2.39 (3H, s, Me-3"), 3.50 (1H, s, H-7a), 3.54-3.58 (2H, m, H-5'), 4.93-4.99 (1H, m, H-1'), 5.09-5.13 (1H, m, NH), 6.83-6.88 (4H, m, Ph), 7.16-7.19 (6H, m, Ph); $^{13}$C NMR (100 MHz, CDCl$_3$) inter alia δ 11.52 (CH$_3$, Me-3"), 11.56 (CH$_3$, Me-4), 12.4 (CH$_3$, Me-7), 22.3 (CH$_2$, C-3'), 26.9 (CH$_2$, C-4'), 28.3 (3×CH$_3$, Boc), 33.3 (CH$_2$, C-2'), 39.1 (CH$_2$, C-5'), 48.1 (CH, C-1'), 56.4 (C, C-7), 58.9 (C, C-3a), 60.3 (CH, C-7a), 60.6 (C, C-4), 80.6 (C, Boc), 128.18 (2×CH, Ph), 128.25 (2×CH, Ph), 128.30 (2×CH, Ph), 129.3 (2×CH, Ph), 129.7 (2×CH, Ph), 132.4 (C, Ph), 132.5 (C, Ph), 140.4 (C, C-5), 144.6 (C, C-6), 155.0 (C, Boc), 167.1 (C, C-3"), 172.4 (C, C-1 or C-3), 172.6 (C, C-1 or C-3), 179.0 (C, C-5"), 196.9 (C, C-8).

For the exo isomer; $^1$H NMR (400 MHz, CDCl$_3$) inter alia δ 3.36 (1H, s, H-7a); $^{13}$C NMR (100 MHz, CDCl$_3$) inter alia δ 8.1 (CH$_3$), 9.4 (CH$_3$), 22.8 (CH$_2$), 29.4 (CH$_2$), 31.9 (CH$_2$), 59.0 (C), 128.0 (CH), 128.5 (CH), 130.5 (CH).

e) (1S)-1-amino-5-(3a-bromo-4,7-dimethyl-1,3,8-trioxo-5,6-diphenyl-1,3,3a,4,7,7a-hexahydro-2H-4,7-methanoisoindol-2-yl)-1-'-(3"-methyl-1",2",4"-oxadiazol-5"-yl)pentane trifluoroacetic acid salt (oCOm-43)

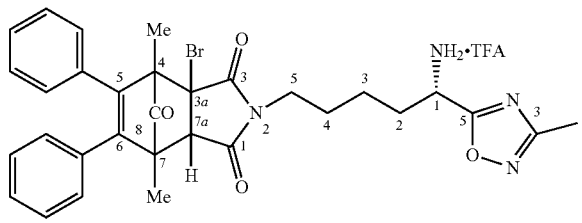

A similar procedure to that previously described for the preparation of oCOm-26 was followed using oCOm-42 (11.5 mg, 0.02 mmol) and trifluoroacetic acid (0.15 mL) in dichloromethane (0.5 mL) to afford the trifluoroacetate salt of the title compound oCOm-43 (12.0 mg, 100%) as a pale brown residue in a 6:1 ratio of endo and exo isomers, respectively. $v_{max}$ (cm$^{-1}$) 2928, 1782, 1711, 1674, 1442, 1200, 1180, 1137, 723; HRMS-ESI [M+H]$^+$ Calcd. for $C_{31}H_{32}{}^{79}BrN_4O_4{}^+$ 603.1601, found 603.1599.

For the endo isomer; $^1$H NMR (400 MHz, CDCl$_3$) inter alia δ 1.41-1.46 (2H, m, H-3'), 1.58 (3H, s, Me-7), 1.60 (3H, s, Me-4), 1.63-1.69 (2H, m, H-4'), 1.94-2.01 (2H, m, H-2'), 2.37 (3H, s, Me-3"), 3.51 (1H, s, H-7a), 3.53-3.58 (2H, m, H-5'), 4.29-4.35 (1H, m, H-1'), 6.81-6.85 (4H, m, Ph), 7.14-7.17 (6H, m, Ph); $^{13}$C NMR (100 MHz, CDCl$_3$) inter alia δ 11.2 (CH$_3$, Me-3"), 11.5 (CH$_3$, Me-4), 12.3 (CH$_3$, Me-7), 21.7 (CH$_2$, C-3'), 26.6 (CH$_2$, C-4'), 31.0 (CH$_2$, C-2'), 38.9 (CH$_2$, C-5'), 48.2 (CH, C-1'), 56.4 (C, C-7), 58.7 (C, C-3a), 60.2 (CH, C-7a), 60.6 (C, C-4), 128.1 (2×CH, Ph), 128.3 (2×CH, Ph), 128.4 (2×CH, Ph), 129.2 (2×CH, Ph), 129.6 (2×CH, Ph), 132.3 (C, Ph), 132.4 (C, Ph), 140.3 (C, C-5), 144.5 (C, C-6), 167.5 (C, C-3"), 172.7 (C, C-1 or C-3), 172.9 (C, C-1 or C-3), 174.2 (C, C-5"), 196.8 (C, C-8).

For the exo isomer; $^1$H NMR (400 MHz, CDCl$_3$) inter alia δ 3.36 (1H, s, H-7a); $^{13}$C NMR (100 MHz, CDCl$_3$) inter alia δ 128.0 (CH), 128.5 (CH), 130.5 (CH).

Example 31 oCOm-44 and -45 oCOm-45 (1S)-1-Amino-5-(3a-bromo-4,7-dimethyl-1,3,8-trioxo-5,6-diphenyl-1,3,3a,4,7,7a-hexahydro-2H-4,7-methanoisoindol-2-yl)-1-(5-methyl-1,3,-oxadiazol-2-yl)pentane trifluoroacetic acid salt
Where R$^1$=R$^2$=Ph; R$^3$=R$^4$=Me; A$^3$=NR$^{14}$; R$^{14}$=(CH$_2$)$_4$CH(NH$_2$·HOCOCF$_3$)-2-(5-Me-(1,3,4-oxadiazol)yl); X=Br Scheme 34:
Synthesis of oCOm-44 and -45

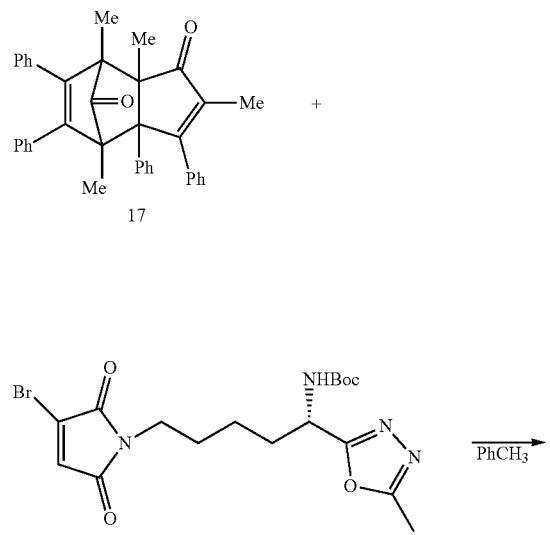

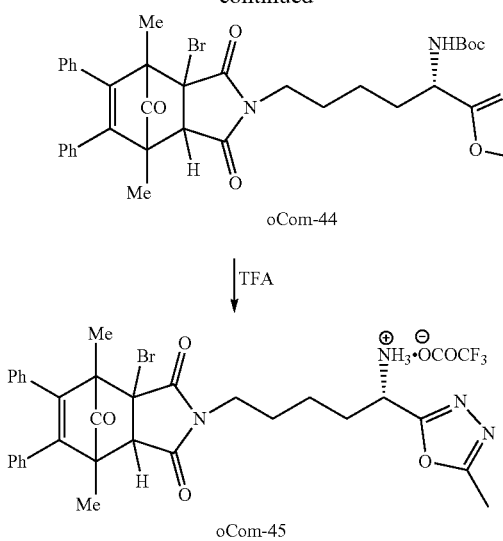

oCom-44

↓ TFA

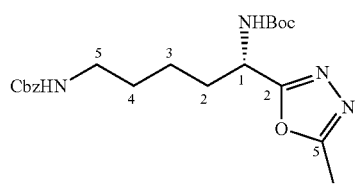

oCom-45 a) (S)-5'-Benzyloxycarbonylamino-1'-(5"-methyl-1", 3",4"-oxadiazol-2"-yl)-1'-tert-butoxycarbonylaminopentane (85)

85

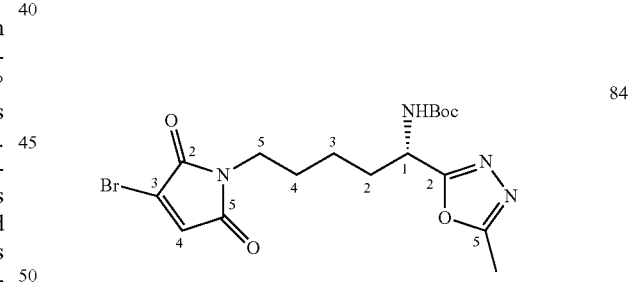

To a solution of Boc-Lys(Cbz)-OH (1.50 g, 3.9 mmol) in dichloromethane (30 mL) at 0° C. was added carbonyldiimidazole (0.70 g, 4.3 mmol), and the mixture stirred at 0° C. for 30 min. Acetohydrazide[37] (0.29 g, 7.9 mmol) was added and the mixture stirred at 0° C. for a further 2 h. Triphenylphosphine (2.07 g, 7.9 mmol) and carbon tetrabromide (3.61 g, 7.9 mmol) were added and the mixture was stirred at 0° C. for a further 4 h. The mixture was then diluted with dichloromethane, washed with saturated aqueous sodium bicarbonate, then water, dried over anhydrous magnesium sulfate, filtered and the solution concentrated in vacuo. Purification by column chromatography (EtOAc/hexanes, 1:1) afforded the title compound 85 (0.98 g, 60%) as a yellow oil. $v_{max}$ (cm$^{-1}$) 3343, 2933, 1689, 1256, 1163, 727; $^1$H NMR (400 MHz, CDCl$_3$) inter alia δ 1.40-1.46 (2H, m, H-3), 1.43 (9H, s, Boc), 1.51-1.59 (2H, m, H-4), 1.79-1.99 (2H, m, H-2), 2.51 (3H, s, 5'-Me), 3.17-3.21 (2H, m, H-5), 4.91-4.97 (2H, m, NH, H-1), 5.09 (2H, s, CH$_2$Ph), 5.23-5.27 (1H, m, NH), 7.29-7.35 (5H, m, Ph); $^{13}$C NMR (100 MHz, CDCl$_3$) inter alia δ 11.0 (CH$_3$, 5'-Me), 22.4 (CH$_2$, C-3), 28.3 (3×CH$_3$, Boc), 29.4 (CH$_2$, C-4), 33.3 (CH$_2$, C-2), 40.5 (CH$_2$, C-5), 47.0 (CH, C-1), 66.7 (CH$_2$, CH$_2$Ph), 80.4 (C, Boc), 128.1 (3×CH, Ph), 128.5 (2×CH, Ph), 136.6 (C, Ph), 155.2 (C, Boc), 156.6 (C, Cbz), 164.0 (C, C-5'), 166.9 (C, C-2'); HRMS-ESI [M+Na]$^+$ Calcd. for C$_{21}$H$_{30}$N$_4$O$_5$Na$^+$ 441.2108, found 441.2118.

b) (S)-5'-(N-Maleimido)-1'-(5"-methyl-1",3",4"-oxadiazol-2"-yl)-1'-tert-butoxycarbonylaminopentane (86)

86

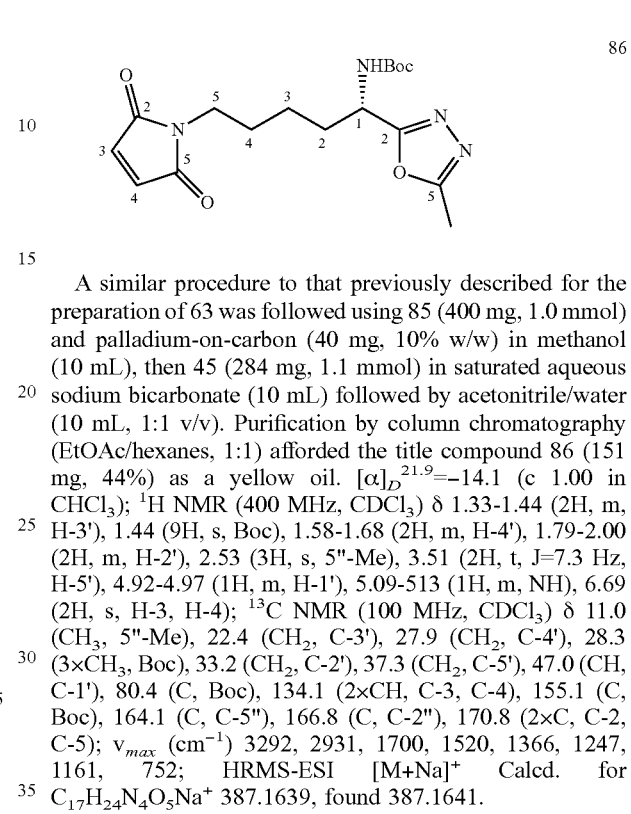

A similar procedure to that previously described for the preparation of 63 was followed using 85 (400 mg, 1.0 mmol) and palladium-on-carbon (40 mg, 10% w/w) in methanol (10 mL), then 45 (284 mg, 1.1 mmol) in saturated aqueous sodium bicarbonate (10 mL) followed by acetonitrile/water (10 mL, 1:1 v/v). Purification by column chromatography (EtOAc/hexanes, 1:1) afforded the title compound 86 (151 mg, 44%) as a yellow oil. $[\alpha]_D^{21.9}$=−14.1 (c 1.00 in CHCl$_3$); $^1$H NMR (400 MHz, CDCl$_3$) δ 1.33-1.44 (2H, m, H-3'), 1.44 (9H, s, Boc), 1.58-1.68 (2H, m, H-4'), 1.79-2.00 (2H, m, H-2'), 2.53 (3H, s, 5"-Me), 3.51 (2H, t, J=7.3 Hz, H-5'), 4.92-4.97 (1H, m, H-1'), 5.09-513 (1H, m, NH), 6.69 (2H, s, H-3, H-4); $^{13}$C NMR (100 MHz, CDCl$_3$) δ 11.0 (CH$_3$, 5"-Me), 22.4 (CH$_2$, C-3'), 27.9 (CH$_2$, C-4'), 28.3 (3×CH$_3$, Boc), 33.2 (CH$_2$, C-2'), 37.3 (CH$_2$, C-5'), 47.0 (CH, C-1'), 80.4 (C, Boc), 134.1 (2×CH, C-3, C-4), 155.1 (C, Boc), 164.1 (C, C-5"), 166.8 (C, C-2"), 170.8 (2×C, C-2, C-5); $v_{max}$ (cm$^{-1}$) 3292, 2931, 1700, 1520, 1366, 1247, 1161, 752; HRMS-ESI [M+Na]$^+$ Calcd. for C$_{17}$H$_{24}$N$_4$O$_5$Na$^+$ 387.1639, found 387.1641.

c) (S)-5'-(3-Bromo-N-maleimido)-1'-(5"-methyl-1",3",4"-oxadiazol-2"-yl)-1'-tert-butoxycarbonylaminopentane (84)

84

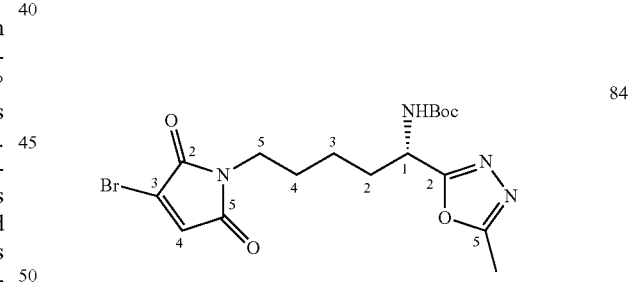

A similar procedure to that previously described for the preparation of 56 was followed using 86 (110 mg, 0.30 mmol), potassium carbonate (46 mg, 0.33 mmol) and bromine (20 µL, 0.33 mmol) in chloroform (3 mL), then triethylamine (50 µL, 0.33 mmol) in tetrahydrofuran (3 mL). Purification by column chromatography (EtOAc/hexanes, 1:1) afforded the title compound 84 (85 mg, 63%) as a yellow oil. $[\alpha]_D^{23.3}$=−12.2 (c 1.00 in CHCl$_3$); $^1$H NMR (400 MHz, CDCl$_3$) δ 1.35-1.42 (2H, m, H-3'), 1.45 (9H, s, Boc), 1.61-1.69 (2H, m, H-4'), 1.79-2.01 (2H, m, H-2'), 2.53 (3H, s, 5"-Me), 3.56 (2H, t, J=7.1 Hz, H-5'), 4.93-4.98 (1H, m, H-1'), 5.08-5.12 (1H, m, NH), 6.86 (1H, s, H-4); $^{13}$C NMR (100 MHz, CDCl$_3$) δ 11.0 (CH$_3$, 5"-Me), 22.3 (CH$_2$, C-3'), 27.9 (CH$_2$, C-4'), 28.3 (3×CH$_3$, Boc), 33.1 (CH$_2$, C-2'), 38.3 (CH$_2$, C-5'), 46.9 (CH, C-1'), 80.5 (C, Boc), 131.4 (C, C-3), 131.8 (CH, C-4), 155.1 (C, Boc), 164.1 (C, C-5"), 165.3 (C, C-2 or C-5), 166.7 (C, C-2"), 168.6 (C, C-2 or C-5); $v_{max}$ (cm$^{-1}$) 3332, 2926, 1713, 1366, 1164, 732; HRMS-ESI [M+Na]$^+$ Calcd. for $C_{17}H_{23}{}^{79}BrN_4O_5Na^+$ 465.0744, found 465.0741.

d) oCOm-44

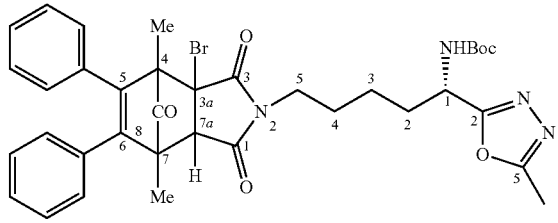 [SMILES: Cc1nnc([C@H](CCCCN2C(=O)C3C4(C)C(=O)C(C)(C(c5ccccc5)=C4c4ccccc4)C3(Br)C2=O)NC(=O)OC(C)(C)C)o1]

A similar procedure to that previously described for the preparation of oCOm-25 was followed using 84 (59 mg, 0.13 mmol) and diene dimer 17 (41 mg, 0.16 mmol) in toluene (2 mL). Purification by column chromatography (EtOAc/hexanes, 1:2) afforded the title compound oCOm-44 (95 mg, 99%) as an off-white residue in a 6:1 ratio of endo and exo isomers, respectively. $v_{max}$ (cm$^{-1}$) 3341, 2928, 1788, 1711, 1366, 1170, 701; HRMS-ESI [M+K]$^+$ Calcd. for $C_{36}H_{39}{}^{79}BrN_4O_6K^+$ 741.1685, found 741.1686.

For the endo isomer; $^1$H NMR (400 MHz, CDCl$_3$) inter alia δ 1.40-1.46 (2H, m, H-3'), 1.44 (9H, s, Boc), 1.60 (3H, s, Me-7), 1.62 (3H, s, Me-4), 1.64-1.67 (2H, m, H-4'), 1.81-1.96 (2H, m, H-2'), 2.52 (3H, s, Me-5"), 3.50 (1H, s, H-7a), 3.54-3.60 (2H, m, H-5'), 4.93-4.97 (1H, m, H-1'), 5.09-5.12 (1H, m, NH), 6.83-6.88 (4H, m, Ph), 7.17-7.19 (6H, m, Ph); $^{13}$C NMR (100 MHz, CDCl$_3$) inter alia δ 11.0 (CH$_3$, Me-5"), 11.5 (CH$_3$, Me-4), 12.4 (CH$_3$, Me-7), 22.2 (CH$_2$, C-3'), 26.9 (CH$_2$, C-4'), 28.3 (3×CH$_3$, Boc), 32.9 (CH$_2$, C-2'), 39.1 (CH$_2$, C-5'), 47.0 (CH, C-1'), 56.4 (C, C-7), 58.9 (C, C-3a), 60.3 (CH, C-7a), 60.6 (C, C-4), 80.4 (C, Boc), 128.20 (2×CH, Ph), 128.27 (2×CH, Ph), 128.32 (2×CH, Ph), 129.3 (2×CH, Ph), 129.7 (2×CH, Ph), 132.4 (C, Ph), 132.5 (C, Ph), 140.4 (C, C-5), 144.6 (C, C-6), 155.1 (C, Boc), 164.1 (C, C-5"), 166.7 (C, C-2"), 172.4 (C, C-1 or C-3), 172.6 (C, C-1 or C-3), 196.9 (C, C-8).

For the exo isomer; $^1$H NMR (400 MHz, CDCl$_3$) inter alia δ 3.36 (1H, s, H-7a); $^{13}$C NMR (100 MHz, CDCl$_3$) inter alia δ 128.0 (CH), 128.3 (CH), 130.5 (CH).

e) (1S)-1-Amino-5-(3a-bromo-4,7-dimethyl-1,3,8-trioxo-5,6-diphenyl-1,3,3a,4,7,7a-hexahydro-2H-4,7-methanoisoindol-2-yl)-1-'-(5-methyl-1,3,'-oxadiazol-2-yl)pentane trifluoroacetic acid salt (oCOm-45)

A similar procedure to that previously described for the preparation of oCOm-26 was followed using oCOm-44 (11.5 mg, 0.02 mmol) and trifluoroacetic acid (0.15 mL) in dichloromethane (0.5 mL) to afford the trifluoroacetate salt of the title compound oCOm-45 (11.4 mg, 100%) as a pale brown residue in a 8:1 ratio of endo and exo isomers, respectively. $v_{max}$ (cm$^{-1}$) 2932, 1782, 1710, 1675, 1443, 1200, 1178, 1137, 723; HRMS-ESI [M+Na]$^+$ Calcd. for $C_{31}H_{31}{}^{79}BrN_4O_4Na^+$ 625.1415, found 625.1421.

For the endo isomer; $^1$H NMR (400 MHz, CDCl$_3$) inter alia δ 1.40-1.45 (2H, m, H-3'), 1.58 (3H, s, Me-7), 1.60 (3H, s, Me-4), 1.62-1.68 (2H, m, H-4'), 2.09-2.15 (2H, m, H-2'), 2.48 (3H, s, Me-5"), 3.50 (1H, s, H-7a), 3.51-3.55 (2H, m, H-5'), 4.65-4.70 (1H, m, H-1'), 6.81-6.85 (4H, m, Ph), 7.15-7.17 (6H, m, Ph); $^{13}$C NMR (100 MHz, CDCl$_3$) inter alia δ 10.8 (CH$_3$, Me-5"), 11.5 (CH$_3$, Me-4), 12.3 (CH$_3$, Me-7), 21.9 (CH$_2$, C-3'), 26.7 (CH$_2$, C-4'), 30.9 (CH$_2$, C-2'), 39.0 (CH$_2$, C-5'), 47.2 (CH, C-1'), 56.4 (C, C-7), 58.9 (C, C-3a), 60.2 (CH, C-7a), 60.6 (C, C-4), 128.2 (2×CH, Ph), 128.3 (4×CH, Ph), 129.3 (2×CH, Ph), 129.6 (2×CH, Ph), 132.4 (C, Ph), 132.5 (C, Ph), 140.4 (C, C-5), 144.6 (C, C-6), 163.2 (C, C-5"), 170.9 (C, C-2"), 172.4 (C, C-1 or C-3), 172.6 (C, C-1 or C-3), 196.9 (C, C-8).

For the exo isomer; $^1$H NMR (400 MHz, CDCl$_3$) inter alia δ 3.35 (1H, s, H-7a), 3.76-3.80 (2H, m, H-5'); $^{13}$C NMR (100 MHz, CDCl$_3$) inter alia δ 128.0 (CH), 128.5 (CH), 130.5 (CH).

Example 32 oCOM-46

3a,4,7,7a-Tetrahydro-7a-bromo-4,7-dimethyl-5,6-diphenyl-4,7-methanoisobenzofuran-1,3,8-trione: Where $R^1$=$R^2$=Ph; $R^3$=$R^4$=Me; $A^3$=O; X=Br Scheme 35:
Synthesis of oCOm-46 and base promoted release of carbon monoxide forming BP-46

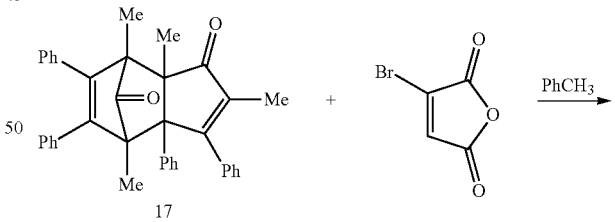

oCOm-45

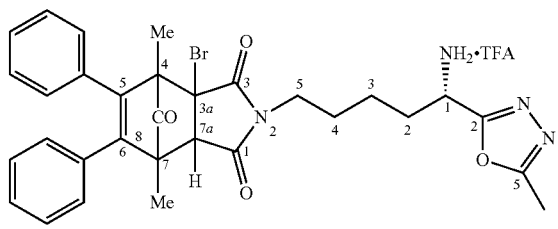

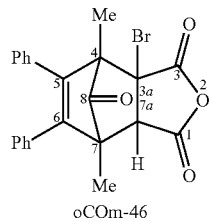

oCOm-46

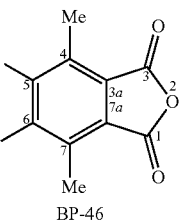

BP-46 a) 3a,4,7,7a-Tetrahydro-7a-bromo-4,7-dimethyl-5,6-diphenyl-1H-4,7-methanoisobenzofuran-1,3,8(2H)-trione (oCOm-46)

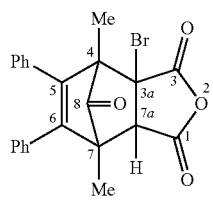

The dimer of 2,5-dimethyl-3,4-diphenylcyclopentadien-1-one (17) (253 mg, 0.970 mmol) and bromomaleic anhydride (343 mg, 1.94 mmol) were refluxed in benzene (15 mL) for 5 h. The orange solution was concentrated in vacuo. The product was triturated in ether to afford the title compound oCOm-46 (323 mg, 76%) as a white solid. m.p. 150° C. $^1$H NMR (500 MHz, CDCl$_3$) δ 1.62 (3H, s, CH$_3$-7), 1.65 (3H, s, CH$_3$-4), 3.74 (3H, s, H-7a), 6.93-6.98 (4H, m, 4×Ph-H), 7.17-7.24 (6H, m, 6×Ph-H) $^{13}$C NMR (125 MHz, CDCl$_3$) δ 11.16, 12.06, 56.60, 57.41, 60.07, 128.45, 128.51, 128.62, 128.64, 129.42, 129.77, 131.74, 131.83, 141.09, 145.58, 166.78, 166.93, 195.28; $v_{max}$ (cm$^{-1}$) 1776 (C=O), 1214 (C—O—C); HRMS-ESI [M+Na]$^+$ Calcd. for C$_{23}$H$_{17}$$^{79}$BrO$_4$Na$^+$ 459.0202, found 458.9982. Anal. Calcd. for C$_{23}$H$_{17}$BrO$_4$: C, 63.17; H, 3.92; Br, 18.27. Found: C, 63.00; H, 3.84; Br, 18.02.

b) 4,7-Dimethyl-5,6-diphenyl-1,3-isobenzofurandione (BP-46)

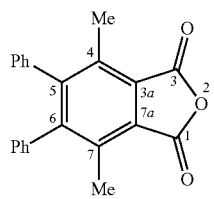

Triethylamine (0.2 mL, 1.44 mmol) was added to oCOm-46 (105 mg, 0.239 mmol) in dry THF (10 mL). The mixture was stirred for 3 h. The solution was washed with 1M HCl, dried over anhydrous magnesium sulfate and concentrated in vacuo to afford the title compound BP-46 (76.8 mg, 98%) as a white solid. $v_{max}$ (cm$^{-1}$) 3240 (O—H), 1767 (C=O), 1646 (C=O), 1210 (C—O—C). $^1$H NMR (400 MHz, CDCl$_3$) δ 2.43 (6H, s, 2×Me), 6.86-6.93 (4H, m, 4×Ph-H), 7.17-7.23 (6H, m, 6×Ph-H); $^{13}$C NMR (100 MHz, CDCl$_3$) δ 16.07, 127.39, 127.8, 128.12, 129.34, 136.84, 138.01, 150.68, 163.56; HRMS-ESI [M+Na]$^+$ Calcd. for C$_{22}$H$_{16}$O$_3$Na$^+$ 351.0992, found 351.1008.

Example 33 oCOm-47

3a-Bromo-3a,4,7,7a-tetrahydro-4,7-dimethyl-2-(2-propyn-1-yl)-5,6-diphenyl-4,7-methano-1H-isoindole-1,3,8(2H)-trione: Where R$^1$=R$^2$=Ph; R$^3$=R$^4$=Me; A$^3$=NR$^{14}$; R$^{14}$=CH$_2$CCH; X=Br

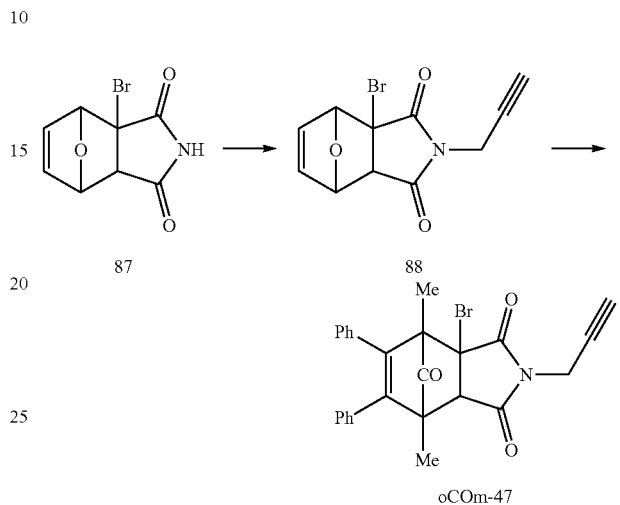

a) 3a-Bromo-2-(2-propyn-1-yl)-3a,4,7,7a-tetrahydro-4,7-epoxy-5,6-diphenyl-4,7-methano-1H-isoindole-1,3,8(2H)-dione (88)

To a mixture of furan adduct 87 (3.50 g, 14.0 mmol), propargyl alcohol (0.93 mL, 15.5 mmol) and triphenylphosphine (4.10 g, 16 mmol) in THF (20 mL) at 0° C. was added DIAD (3.4 mL, 15.8 mmol) dropwise. The mixture was warmed to room temperature and stirred for 18 h. The solvent was removed and the residue columned (DCM/PE 3:2 to DCM gradient elution) to give the title compound 88 (3.39 g, 94%) as a white solid. $^1$H NMR (500 MHz, CDCl$_3$) δ 2.67 (1H, t, J=2.5 Hz), 3.33 (1H, s), 4.72 (2H, d, J=2.6 Hz), 5.73 (2H, ddd, J=3.6, 1.5, 0.9 Hz), 7.07-7.11 (2H, m, J=1.3, 0.5 Hz); $^{13}$C NMR (126 MHz, CDCl$_3$) δ 28.89, 55.10, 56.07, 72.30, 72.32, 75.71, 82.71, 82.74, 83.35, 83.38, 136.71, 172.00, 172.02; HRMS-ESI [M+Na]$^+$ Calcd. for C$_{11}$H$_8$$^{79}$BrNO$_3$Na 303.9580, found 303.9569.

b) 3a-Bromo-3a,4,7,7a-tetrahydro-4,7-dimethyl-2-(2-propyn-1-yl)-5,6-diphenyl-4,7-methano-1H-isoindole-1,3,8(2H)-trione (oCOm-47)

A solution of furan adduct 88 (317 mg, 1.12 mmol) in toluene (25 mL) in an open flask was heated at 110 C (caution) for 13 h. After this time the mixture was cooled and diene dimer 17 (730 mg, 1.40 mmol) was added. A reflux condenser was attached to the flask and the mixture heated at 100° C. for 2 h. The solvent was removed and the residue columned (PE to 9:1 PE/EtOAc) to give the title compound oCOm-47 (484 mg, 91%, endo:exo=14:1) as a white foam.

For the endo isomer: $^1$H NMR (500 MHz, CDCl$_3$) δ inter alia 1.61 (3H, s), 1.63 (s, 3H), 2.03 (1H, t, J=2.5 Hz,), 3.53 (1H, s), 4.35 (2H, t, J 2.5 Hz), 6.83-7.37 (10H, m); $^{13}$C NMR (126 MHz, CDCl$_3$) δ 11.64, 12.49, 29.08, 56.38, 58.88, 60.63, 60.66, 60.77, 72.82, 72.83, 75.78, 128.18, 128.23, 129.64, 130.02, 132.43, 132.52, 140.55, 144.76, 171.08, 171.46, 196.71.

For the exo isomer $^1$H NMR (500 MHz, CDCl$_3$) δ inter alia δ 1.38 (3H, s), 1.50 (3H, s), 2.26 (1H, t, J=2.5 Hz), 3.40 (1H, s).

HRMS-ESI [M+Na]$^+$ Calcd. for C$_{26}$H$_{20}$$^{79}$BrNO$_3$Na$^+$ 496.0519, found 496.0490.

Example 34 oCOm-48 3a-Bromo-3a,4,7,7a-tetrahydro-4,7-dimethyl-2-(2-propyn-1-yl)-5,6-diphenyl-4,7-methano-1H-isoindole-1,3,8(2H)-trione: Where R$^1$=R$^2$=Ph; R$^3$=R$^4$=Me; A$^3$=NR$^{14}$; R$^{14}$=(CH$_2$)$_4$CH(NH$_2$.HOCOCF$_3$)-2-(5-Me-(1,3,4-oxadiazol)yl); X=Br

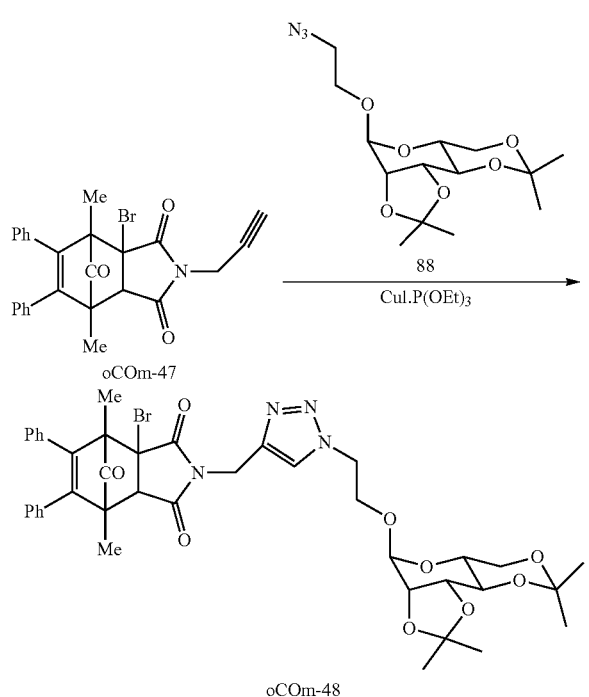

A mixture of oCOm-47 (0.200g, 0.71 mmol), azide 88 (0.280 g, 0.85 mmol), and iodo(triethyl phosphite)copper(I) (0.013 g, 0.035 mmol) in THF (5 mL) was heated at 50° C. for 7 h. The solvent was removed and the residue columned (CH$_2$Cl$_2$/EA 4:1 as eluent) to give a 1:1 mixture of diastereoisomers of oCOm-48 (0.274 g, 48%) as a white foam. $^1$H NMR (500 MHz, CD$_3$COCD$_3$) δ 1.29 (3H, 2×s), 1.32, CH$_3$), 1.45 (3H, s, CH$_3$), 1.46 (3H, s, CH$_3$), 1.54 (3H, 2×s, CH$_3$), 1.56 and 1.57 (3H, 2×s, CH$_3$), 3.21-3.29 (1H, m), 3.64, –3.76 (1H, m), 3.78-3.84 (2H, m), 3.97-4.07 (2H, m), 4.09-4.12 (1H, m), 4.45-4.55 (2H, m) 4.90 (2H, s), 4.99 (1H, d, J=1 Hz), 6.80-6.88 (4H, m), 7.16-7.24 (6H, m), 7.95 (1H, 2×s), $^{13}$C NMR (126 MHz, CD$_3$COCD$_3$) δ 11.91, 12.45, 12.47, 19.14, 26.56, 26.57, 28.39, 35.78, 35.79, 50.47, 57.00, 60.19, 60.21, 60.50, 60.53, 60.55, 61.32, 61.34, 62.44, 62.47, 66.29, 66.33, 73.38, 75.73, 76.68, 98.43, 98.48, 100.00, 109.72, 125.60, 125.63, 128.79, 128.80, 128.82, 128.89, 128.91, 128.94, 130.37, 130.39, 130.71, 133.54, 133.63, 133.66, 141.06, 141.72, 145.80, 145.81, 172.41, 172.50, 172.58, 172.68, 197.18. HRMS-ESI [M+Na]$^+$ Calcd. for C$_{40}$H$_{43}$$^{79}$BrN$_4$O$_9$Na$^+$ 825.2016, found 825.2014.

Example 35 oCOm-49

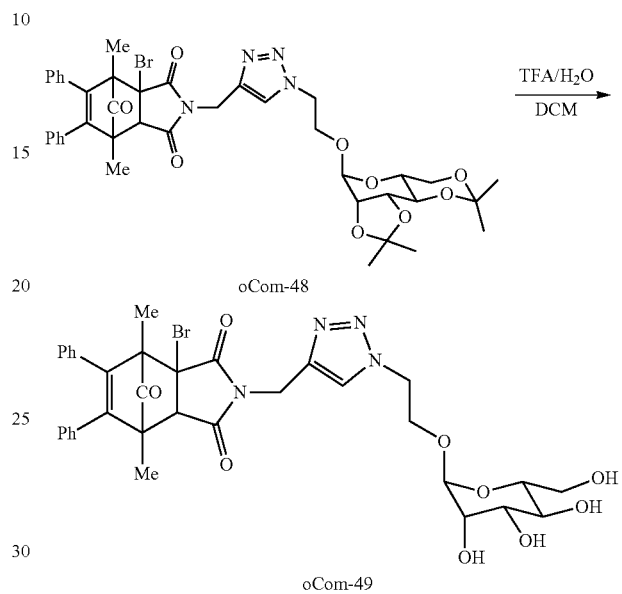

Water (0.2 mL, 11.1 mmol) and TFA (0.15 mL, 1.95 mmol) was added to a solution of oCOm-48 (0.127 g, 0.158 mmol) in DCM (15 mL). The suspension was stirred at rt for 3 h. The solvent was removed in vacuo and the residue obtained was dissolved in approximately 20% CH$_3$CN in H$_2$O (2×5 mL) and then loaded onto a pre-washed C-18 solid phase extraction cartridge (100% CH$_3$CN [2×10 mL]), then 90%, then 50% CH$_3$CN in H$_2$O [1×10 mL each], 20% CH$_3$CN in H$_2$O [2×10 mL]). The compound was eluted from the C-18 cartridge (10% to 80% CH$_3$CN in 0.1% aqueous TFA [10% increments, 2×10 mL each]. The fractions collected were analysed by RP-HPLC (10% to 100% B over 12.5 min, then 100% B for 2.5 min). The fractions were analysed by HPLC and the solvent from the pooled fractions (t$_R$=10.2 min) was partially removed by rotary evaporation. The remaining solution was freeze-dried to give the title compound oCOm-49 (0.104 g, 94% yield) as a fluffy white solid. $^1$H NMR (500 MHz, DMSO-d6) δ 1.44 (3 H, s), 1.48 (3H, s), 3.11-3.17 (1H, m), 3.34-3.45 (3H, m), 3.53 (2H, dd, J=1.7 and 2.9 Hz)), 3.62 (1H, dt, J=11.6 and 2.1 Hz), 3.64-3.70 (1H,m), 3.82-3.88 (1H, m), 4.08 (1H, s), 4.39 (1H, dt, J=15.5 and 5.2 Hz), 4.59 (1H, t, J=1.8 Hz), 4.79 (2H, s), 6.71-6.77 (4H, m), 7.15-7.22 (6H, m), 8.00 (1H, s); $^{13}$C NMR (126 MHz, DMSO-d6) δ 11.28, 11.69, 34.58, 49.21, 55.67, 58.22, 59.01, 59.94, 61.15, 64.70, 66.77, 70.05, 70.82, 74.14, 99.75, 99.79, 124.72, 127.92, 127.96, 128.07, 128.09, 129.10, 129.41, 132.11, 132.12, 132.23, 132.25, 139.42, 139.44, 140.11, 144.47, 171.43, 171.47, 171.84, 171.89, 196.65. HRMS-ESI [M+Na]$^+$ Calcd. for C$_{34}$H$_{35}$$^{79}$BrN$_4$O$_9$Na$^+$ 745.1480, found 745.1487. HPLC t$_R$=10.2 min (100%).

C. Preparation of Norbornenone Compounds of Formula 1b

The following compounds exemplify compounds according to Formula 1b as described herein:

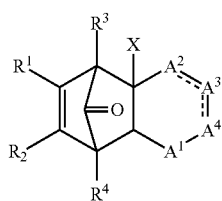

Formula 1b

Example 36 oCOm-51

4a,7-Dibromo-1,4-dimethyl-2,3-diphenyl-1,4,4a,8a-tetrahydro-1,4-methanonaphthalene-5,8,9-trione:
Where $R^1=R^2=Ph$, $R^3=R^4=Me$; $X=Br$;
$A^1=A^2=CO$; $A^3=CH$; $A^4=CBr$

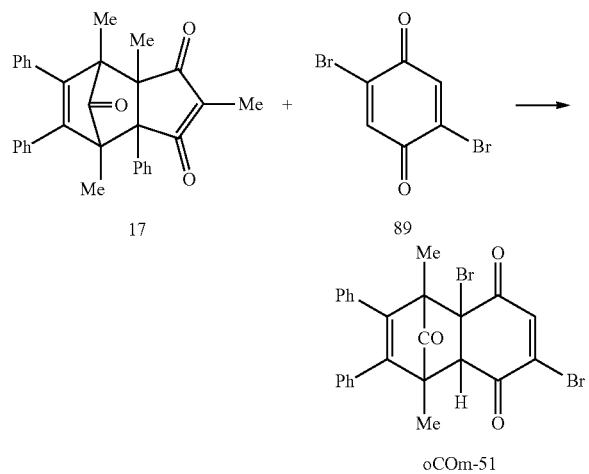

4a,7-Dibromo-1,4-dimethyl-2,3-diphenyl-1,4,4a,8a-tetrahydro-1,4-methanonaphthalene-5,8,9-trione (oCOm-51)

A mixture of diene dimer 17 (400 mg, 0.81 mmol) and 2,5-dibromo-1,4-benzoquinone (89)[38] (490 mg, 1.84 mmol) was suspended in benzene (10.7 mL) and then heated to reflux The reaction mixture was cooled to room temperature and concentrated in vacuo to yield a yellow-orange solid. Recrystallisation of the crude solid (twice) from a 5:1 mixture of hot $CHCl_3$:petroleum ether (12 mL) gave a mixture of bright yellow crystals embedded with smaller amounts of darker yellow-orange crystals. The two crystals types were physically separated by spatula to afford the title compound oCOm-51 (543 mg, 66%) as a 28:1 mixture of endo and exo-isomers in the form of yellow crystals. Mp. 157-160° C., IR (ATR) $v_{max}/cm^{-1}$ 1786 (C=O), 1770 (C=O), 1691 (C=O), 1670 (C=O), 1239, 993, 750, 696; HRMS (ESI-TOF) m/z: $[M+Na]^+$ Calcd for $C_{25}H_{18}{}^{79}Br^{81}BrNaO_3{}^+$ 548.9496, found 548.9539.

Endo-oCOm-51 NMR data: $^1H$ NMR (500 MHz, $CDCl_3$) δ inter alia 1.57 (3H, s, $CH_3$) 1.68 (3H, s, $CH_3$), 3.99 (1H, s, H-8a), 6.72-6.75 (2H, m, Ph), 6.77-6.81 (2H, m, Ph), 7.14-7.22 (6H, m, Ph), 7.55 (1H, s); $^{13}C$ NMR (125 MHz, $CDCl_3$) δ inter alia 11.1, 11.8, 58.8, 62.8, 63.5, 65.0, 128.2, 128.3, 128.4, 128.4 129.2, 129.6, 132.1, 132.4 ($C_{quat}$, Ph), 140.2, 144.0, 145.3, 145.5, 185.9, 186.8, 196.5.

Exo-oCOm48 NMR data: $^1H$ NMR (500 MHz, $CDCl_3$) δ inter alia 0.97 (3H, s, $CH_3$), 1.34 (3H, s, $CH_3$).

B. Biological Examples: Characterising Carbon Monoxide Release from Norbornenone Compounds

Example 37

Materials and Methods

Chemicals used in the following protocols were obtained from BDH (Palmerston North, NZ) or Sigma-Aldrich (Castle Hill, NSW, Australia), unless otherwise specified. University of Wisconsin (UW) organ storage (Belzer UW® Cold Storage Solution) and perfusion (Belzer UW® Machine Perfusion Solution) solutions were kindly donated by Bridge to Life Ltd (SC, USA). CO gas was obtained from BOC (Dunedin, New Zealand). Tri-carbonyldichlororuthenium (II) dimer (CORM-2) was obtained from Sigma-Aldrich and dissolved in 0.1% DMSO. The CO donor compounds oCOm-1 to oCOm-26 were synthesised as described. oCOm-19 was initially dissolved in 0.1% DMSO while oCOm-21, oCOm-23, oCOm-24 were dissolved directly in deionised, distilled water. All procedures in this study were approved and conducted in accordance with the guidelines of the Animal Ethics Committee at the University of Otago and complied with the University of Otago "Code of Ethical Conduct for the Manipulation of Animals" and the "Use of Laboratory Animals (NIH Publication No. 85-23, 1996)".

Example 38

Detection of Carbon Monoxide Release

The time-course of CO release from oCOm-19, oCOm-21, oCOm-23 and oCOm-24 was confirmed by HPLC analysis of the breakdown of CO donor compounds to their CO depleted form, as described above. In addition, the rate of CO release was measured in different physiological solutions at pH 7.4, 37° C.: phosphate buffered saline (PBS), Tris-sucrose buffer and UW solution using an amperiometric CO selective electrode (ISO-COP-2, World Precision Instruments (WPI), Inc, Sarasota, USA). The amount of CO released was recorded as the magnitude of electrode current generated on CO diffusion through a selective gas permeable membrane and oxidised to $CO_2$ on the electrode. Current changes were recorded using a WPI TRB4100 4-channel free radical analyser with the poise potential set to 950 mV. Solutions of oCOm-19, oCOm-21 and oCOm-23 were freshly prepared in ultrapure water (nominally pH 6.9) and 10 μL immediately injected into a water jacketed chamber containing 500 μL of PBS or Tris-HCl or UW solutions at a physiological pH to give a final CO donor concentration of 5 to 100 μM. The effect of pH upon the release of CO was assessed by adjusting the pH of Tris sucrose buffer to pH 6.6 using HCl and to pH 8.5 using NaOH. The electrode was calibrated against a range of concentrations of (14.3-71.4 μM) of CO gas saturated deionised $H_2O$ at both 37 and 8° C. (pH 6.9) rapidly injected into the chamber using a gas tight syringe. The concentration of CO gas present was calculated using a concentration of 1000 μM of CO at 1 atmosphere for a CO saturated solution in water with a Henry's constant of $9.9 \times 10^{-4}$ (Techman SM). All values are the mean±SD for three replicate runs. As these CO donors are intended for use in a range of nomothermic, ambient and hypothermic protocols we also investigated the effect of temperature on the rate of CO release using a circulating water bath set at 37, 30 and 20° C. (Techne, Bibby Scientific, Staffordhsire UK) and 8° C. (Colora Taüchkuhler, Watson-Victor, Australia.)

Example 39

Measurement of CO Binding to Myoglobin

CO released from oCOm-19 and oCOm-21 was measured using an established carboxymyoglobin spectrophotometric assay,[39] adapted to a 96 well plate format to enable the simultaneous correction at all absorbance wavelengths arising from any potential interference from the donor compounds.[40] Freshly prepared horse heart myoglobin (66 µM) in a PBS solution (pH 7.4) was reduced with 10% w/v sodium dithionite and added to a 96 well plate. The CO donors, oCOm-19 and oCOm-21, as well as the commercially available CO donor, CORM-2 were added to each well in triplicate to produce a final concentration range of 100-800 µM and 50 µL paraffin oil added to each well to prevent the diffusion of gases. Absorption spectra ($\lambda$ 500-600 nm) were run at ten minute intervals using a Spectramax 96-well spectrophotometer (Molecular Devices, Crawley, UK) at 37° C. CO gas saturated PBS (714 µM), was employed as a positive control.

Example 40

Selective Imaging of Carbon Monoxide in Living Cells

A palladium CO-responsive small-molecule fluorescent probe (COP-1) was synthesised and carbonylation of the probe by CO confirmed as previously described.[41] A final concentration of 2 nM of COP-1 was added to each well of a 96-well plate containing 200 µL of $Mg^{2+}$ and $Ca^{2+}$ free phosphate solution (DPS, 37° C.). CORM-2, oCOm-19 and oCOm-21 (1-100 µM) were added to wells in triplicate, and zeroed against an equivalent volume of vehicle control added to COP-1. Emission spectra ($\lambda$ 400-600 nm) were recorded at regular time intervals for one hour using a Spectromax Gemini fluorescent plate reader (Molecular Devices, Crawley, UK) at 37° C., ($\lambda_{ex}$ 475 nm, and the $\lambda_{em}$ 500 nm measured).

The ability of the CO donors to increase intracellular levels of CO was tested in Madin Darby Canine Kidney (MDCK) cells. 96 well black-walled tissue culture plates were seeded with MDCK cells at $1 \times 10^6$ cells/mL in advanced Glutamax® DMEM containing 1% glutamine, and supplemented with 5% foetal bovine serum and 1% antibiotic (Gibco Life Technologies, Auckland NZ) and incubated at 37° C., 65% relative humidity for 48 hours. The media was replaced with fresh media and oCOm-21, oCOm-23, debromo-oCOM-21 (a structural analogue of oCOm-21 which does not release CO) and spent oCOm-23 (left in solution (pH 7.4) for over 48 hours to release all CO) dissolved in sterile DPS were added in triplicate at 5 to 50 µM final concentration. Cells were incubated for 1 hour at either 8 or 37° C. then 1 µM COP-1 in DPS added per well and cells incubated for a further 15 minutes. Cells were imaged on a fluorescent inverted microscope (Nikon Eclipse Ti-E).

Example 41

Cell Toxicity

The loss of cell adhesion for anchorage-dependent cell lines, such as MDCK, represents a surrogate marker of imminent cellular demise which can be measured by the crystal violet cell adhesion (CVCA) assay.[42] MDCK cells were grown in DMEM supplemented with 4% donor calf serum and 1% antibiotic (Gibco Life Technologies, Auckland NZ) and plated at $1 \times 10^6$ cells/mL in 24 well plates. CO donor compounds, CO expired compounds (left in solution for over 48 hours) or non CO releasing, debromo derivatives were dissolved in either ultrapure water or for non-water soluble compounds, in DMSO and diluted to 20-100 µM (to a final concentration of 1% DMSO where appropriate). Cells were exposed to CO donor compounds or the respective vehicle control solution for 1 hour at 37° C. prior to washing and incubating for a further 23 hours in fresh media. Cells were fixed in 96% ethanol and stained in 0.05% crystal violet solution in 20% ethanol, prior to washing and solubilising (24 hours) in 2 mL 0.1% acetic acid in 50% ethanol. Sample solutes (100 µL) from each well were transferred into a 96 well plate and absorbance measured at 585 nm. Cell survival was reported as a percentage of the value obtained for cells exposed to vehicle only and used to plot a concentration-response curve for each compound from which an $EC_{50}$ value was obtained.

Example 42

Oral Bioavailability

Male Sprague Dawley rats (300-320 g) were orally dosed with either oCOm-19 (133.33 µmol/kg) or oCOm-21 (33.33 µmol/kg) in ultra-pure water by oral gavage. Animals were observed every 15 minutes for any changes in behaviour or signs of distress. Tail vein blood samples were collected in heparinised capillary tubes immediately prior to and at 1-3 hours post CO-donor administration. Blood gas analysis on each sample was performed using a Radiometer ABL800 Flex analyser.

Example 43

Static Storage of Biological Specimens

The following protocol was used to assess the ex vivo protective effects of the oCOm compounds in solid, non-perfused biological tissues. Male Sprague Dawley (SD) rats (280-310 g) were decapitated and the hearts rapidly excised. Hearts were cut into 1 mm thick sections and placed in 3 ml of DMEM in sterile 24 well tissue culture plates. Two tissues sections from each heart were immediately stained without storing, with 1% 2,3,5-Triphenyltetrazolium chloride (TTC) in glucose supplemented DMEM for 15 minutes at 37° C. with continuous shaking. Theses tissues represent the baseline tissue viability prior to storage. This staining technique requires active dehydrogenase enzymes to be present in order to convert TCC to a brick red formazan pigment. Tissues were then fixed for 20 minutes in 5% neutral buffered formalin. Control samples were stored in DMEM alone, while test samples from the same hearts were stored in DMEM plus either oCOm-21 or BP-21 (3 µM) for either 24 or 48 hours on ice. Tissues were then stained with TTC and fixed as above. One control tissue section was left unstained for comparison. All samples were sectioned transversely, photographed and staining intensity assessed qualitatively.

Example 44

Isolated Rat Aortic Ring Preparations

Transverse ring sections of aorta were isolated from male Lewis rats (350±450 g, n=5-6 per group) under halothane anaesthesia and suspended under 2 g tension in an organ bath containing 10 mL of oxygenated (95% $O_2$/5% $CO_2$) Krebs Henseleit (KH) buffer containing 118 mM NaCl, 4.7 mM KCl, 1.2 mM $KH_2PO_4$, 1.2 mM $MgSO_4.7H_2O$, 22 mM $NaHCO_3$, 11 mM glucose, 0.03 mM $K^+$EDTA, and 2.5 mM $CaCl_2$ as previously described.[43] Indomethacin (10 μM) was present in the buffer to exclude endogenous prostaglandins as potential modulators of vascular tone. Relaxation responses to oCOm-19 or oCOm-21 (0.01-300 μM) were assessed using individual dosing in tissues pre-contracted with phenylephrine (0.1 μM). All results were subsequently expressed as a percentage of the maximal phenylephrine-induced contraction. Following repeat wash steps with Krebs Henseleit buffer, smooth muscle function and viability was confirmed by repeating the contractile response to phenylephrine. Aortic responses to individual $EC_{50}$ concentrations of either CO donor in phenylephrine vasoconstricted rings were repeated separately, in the presence of the CO-chelator, myoglobin (5 μM) and the selective, irreversible inhibitor of sGC 1H-(1,2,4)oxadiazolo[4,3-a]quinoxalin-1-one, (ODQ, 10 μM), as previously described.[44]

Example 45

Isolated Rat Kidney Perfusion Protocol

Male Lewis rats (280-310 g) were anaesthetised and maintained under gaseous anaesthesia using halothane (1-2%), $O_2$ (500 mL/min) and $N_2O$ (800 mL/min) prior to surgery. Core temperature was maintained at 37° C. using a thermostatically controlled heating blanket. Once the core reflex was abolished, heparin (monoparin sodium CP Pharmaceuticals, Irl., 5000 IU/kg body weight) and mannitol (1 g/kg body weight) were administered through the right femoral vein in order to prevent thrombotic occlusion and promote osmotic diuresis. A laparotomy was performed to expose the superior mesenteric artery as well as the right kidney, renal artery and ureter. The ureter was cannulated proximal to the bladder and the superior mesenteric artery ligated at the distal end with a 4-0 silk suture to allow insertion of a 20 g cannula and guide wire through the mesenteric artery to the renal artery. The renal perfusion cannula was secured using 4-0 silk suture and the kidney excised and positioned on the hypothermic pulsatile perfusion rig. A fixed 5 min ischaemic period was allowed between the insertion of the cannula and commencement of perfusion to mimic the clinical "no touch" time for transplant organ retrieval. Excess extra-renal tissue was removed and the kidney equilibrated (30 min) to the hypothermic pulsatile perfusion protocol conducted at 8° C. with UW Machine Perfusion solution. Renal perfusion pressure was increased to 130 mmHg and perfusion maintained for 55 min. oCOm-21 (3 μM, 30 μM or vehicle only; n=5 separate animals/group) was then added directly to the UW Machine Perfusion solution and circulated through the kidney for 80 min. At the end of the treatment period the kidney was flushed with fresh UW Cold Storage Solution and stored in fresh storage solution for 16 hours at 4° C. To simulate organ re-implantation at the end of the storage period the kidney underwent warm perfusion (37° C.) in a cell free blood substitute (6.7% BSA in KH buffer (pH 7.4) supplemented with additional glucose (50 nM) and amino acids (lysine 0.73 mM, tyrosine 0.12 mM, cysteine 0.65 mM, aspartate 0.2 mM, glutamate 0.5 mM, asparagine 0.2 mM, glutamine 2 mM, serine 0.6 mM and glycine 1.18 mM) for a 45 minute equilibration period. Perfusion pressure was clamped at 130 mmHg and the initial renal perfusion parameters of flow rate (mL/min) and renal vascular resistance (mmHg/ml/min) of each kidney on reperfusion were recorded. The change in renal vascular resistance (ΔR, mmHg/mL/min) was recorded in response to infusion of increasing concentrations of angiotensin II (1 pM-10 μM). After negating the bolus administration component of response, a concentration-response curve was generated comparing renal responsiveness in kidneys pre-treated with UW Machine Perfusion solution in the presence and absence of oCOm-21 at 3 and 30 μM. The perfusion and storage protocol is summarised in FIG. 1.

In separate experiments, kidneys isolated after UW Machine perfusion in the presence and absence of oCOm-21 were stored and reperfused as above and fixed in 10% neutral buffered formalin (24 hours). The kidneys were paraffin-embedded and 5 μm thick tissue sections prepared for staining. Kidney sections were deparaffinised in xylene and rehydrated with sequentially decreasing concentrations of ethanol. DNA strand breaks were assessed enzymatically using an ApopTag® Peroxidase kit (Millpore, Germany) to detect the presence of free DNA 3'-OH termini.[45] Sections were incubated with proteinase K (1:2500) for 20 minutes followed by hydrogen peroxide (3%) for 5 minutes. ApopTag immunohistochemistry was performed as per the manufacturer's instructions. Horse-radish peroxidase (HRP)-labelled anti-digoxigenin conjugate (65 μL/5 $cm^2$) was applied to each section prior to visualisation using a 3,3-diaminobenzidine kit (DAB; Vector Laboratories, USA) with Gill's haematoxylin used as a counterstain.

Example 46

Isolated Rat Heart Perfusion Protocol

Male Sprague-Dawley rats (280-310 g, n=5 animals/group) were anesthetised with halothane and systemically heparinised (5000 IU, iv). The hearts were rapidly excised and placed into an ice cold (4° C.) modified KH buffer [118 mM NaCl, 4.7 mM KCl, 1.2 mM $MgSO_4$, 1.2 mM $KH_2PO_4$, 24 mM $NaHCO_3$, 11.1 mM glucose, 1.2 mM $CaCl_2$ (pH 7.4)]. The hearts were cannulated and perfused at 37° C. with oxygenated (95% $O_2$/5% $CO_2$) KH buffer in the Langendorff mode at a constant pressure of 100 cm $H_2O$ as described previously.[46] The base of the pulmonary artery was cut to assist drainage. After 20 min of equilibration, pre-ischaemic left ventricular (LV) mechanical indices, measured using an intraventricular balloon-pressure transducer, and coronary effluent flow were recorded at a set left ventricular end-diastolic pressure of 10 mm Hg. LV function was characterised by left ventricular developed pressure (LVDP) derived from the difference between peak systolic pressure and end diastolic pressure. The peak rates of rise and fall in the first derivative of LV pressure (dP/dtmax and dP/dtmin, respectively) and heart rate (HR) were measured using Chart v6 (AD Instruments, Castle Hill, Australia). Following 10 min normoxic perfusion, oCOm-21 (3 μM) was administered for 20 min prior to ischaemia. oCOm-21

(stock solution of 5 mM) was infused using a 1 mL syringe driver (Beehive Hamilton) to achieve a concentration of 3 µM to the heart adjusted for flow rate every 5 min. The heart was then subjected to 30 min warm (37° C.) global zero flow ischaemia. The heart was normoxically reperfused for 60 min with haemodynamic and coronary flow parameters reassessed at 0, 15, 30, 45 and 60 min post-ischaemia.

Example 47

Statistical Analysis

Statistical analysis was performed using Prism™ v.6 (GraphPad, San Diego, USA). Statistical differences between carboxyhaemoglobin levels in pre- and post-treatment groups were determined using the Student t-test. For cell toxicity, statistical significance was determined using 2-way ANOVA with the Bonferroni post hoc test. For aortic ring studies, and renal perfusion parameters data were analysed using a One-way ANOVA with Bonferroni post-hoc. Cardiac haemodynamics data were analysed using a Two-way repeated measure ANOVA with Bonferroni post-hoc. Statistical significance was determined as P<0.05. Data are presented as mean±SEM.

Example 48

Detection of Carbon Monoxide Release and Carbonmonoxymyoglobin Binding

Figure 2:
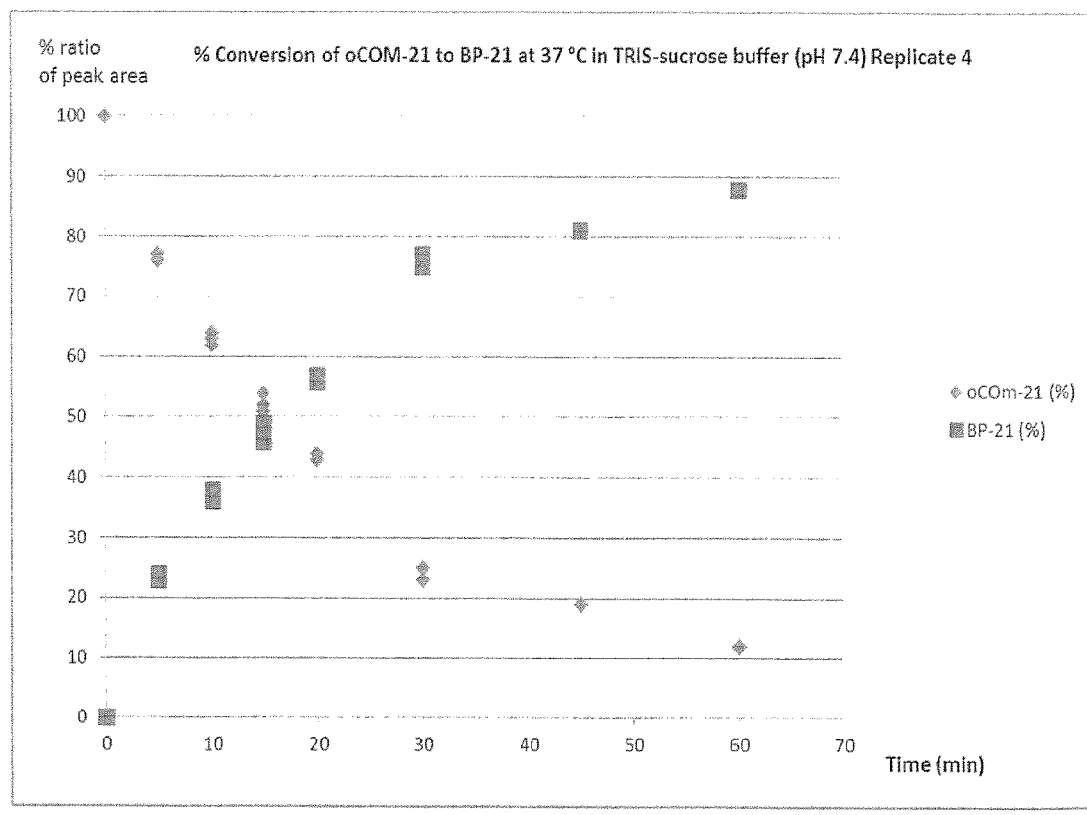
FIG. 2 shows a CO-release study demonstrated using HPLC analysis of oCOm-21 in TRIS-sucrose buffer (pH 7.4) at 37° C. Disappearance of the retention peak corresponded to the donor molecule breakdown and release of CO and the appearance of a retention peak corresponded to the formation of the breakdown product over a two hour period.

The release of CO from the CO donor compounds was demonstrated using HPLC analysis which showed the disappearance of a retention peak corresponding to the donor molecule and the appearance of a retention peak corresponding to its breakdown product over a two hour period (FIG. 2). The CO donor variants released CO at different rates. 50% of the donor CO maximum release capacity was depleted by 40 (oCOm-19), 19 (oCOm-21) and 75 (oCOm-23) minutes respectively.

Figure 3:
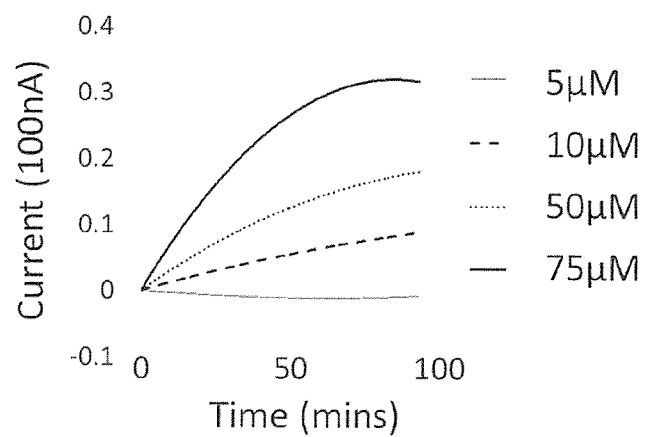
FIG. 3 shows a concentration-dependent increase in the CO specific current, as measured by an amperiometric CO selective electrode, in response to increased concentrations of the CO donor oCOm-19 in a physiological buffer (Tris sucrose pH 7.4, 37° C.) over an 80 minute period.
Figure 4:
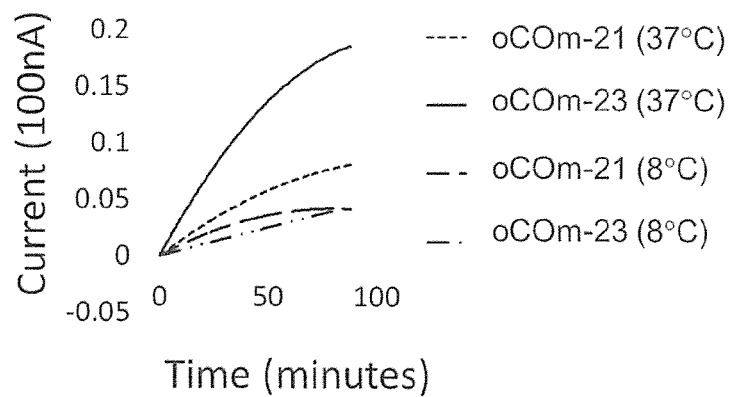
FIG. 4 shows the effect of temperature (normothermic (37° C.) versus hypothermic conditions (8° C.)) on CO release from oCOm-21 (75 μM) and oCOm-23 (75 μM) in Tris sucrose buffer (pH 7.4) and measured using an amperiometric CO selective electrode.
Figure 5:
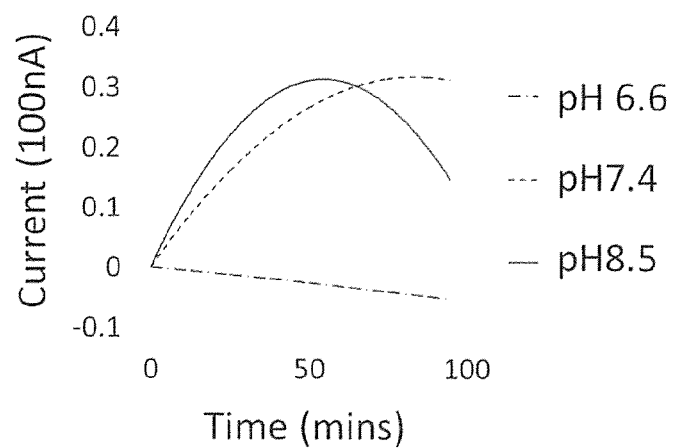
FIG. 5 shows the effect of changes in pH (pH 6.6, 7.4, and 8.5) on CO release from oCOm-19 (75 μM in Tris sucrose buffer) measured using an amperiometric CO selective electrode.
Figure 6:
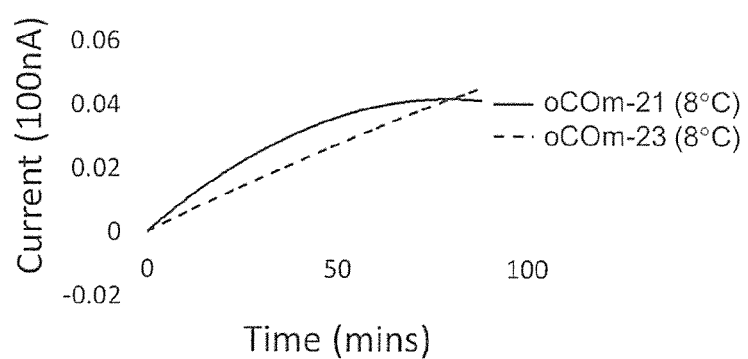
FIG. 6 shows a comparison of the rate of CO release from oCOm-21 (75 μM) and oCOm-23 (75 μM) at 8° C. in UW storage solution (pH7.4) measured using an amperiometric CO selective electrode.

The peak and slope of recorded amperiometric CO electrode current was seen to increase with increasing concentrations of CO donor (FIG. 3). CO release from CO donors oCOm-19, oCOm-21 and oCOm-23 into either UW Machine Perfusion solution or Tris sucrose buffer was sustained for over 80 minutes in this study (FIGS. 3-6). oCOm-23 released more CO and more rapidly than oCOm-21 when dissolved in Tris sucrose buffer (FIG. 4). The rate of CO release was seen to increase in basic buffer and was halted in acidic conditions (FIG. 5). CO release occurred at a reduced rate at 8° C. in UW storage solution (FIG. 6).

The rate of release of CO recorded from both oCOm-21 and oCOm-23 was similar in UW solution compared to Tris buffer. Furthermore, the rate of donor molecule CO release was also reduced in either media under hypothermic (8° C.) compared to normothermic (37° C.) conditions. Due to the changing solubility of CO with temperature, the effect of temperature on the electrode and the consumption of CO by the electrode in generating the current, the actual amounts of CO released at different temperatures were more accurately quantified by HPLC analysis.

Figure 7:
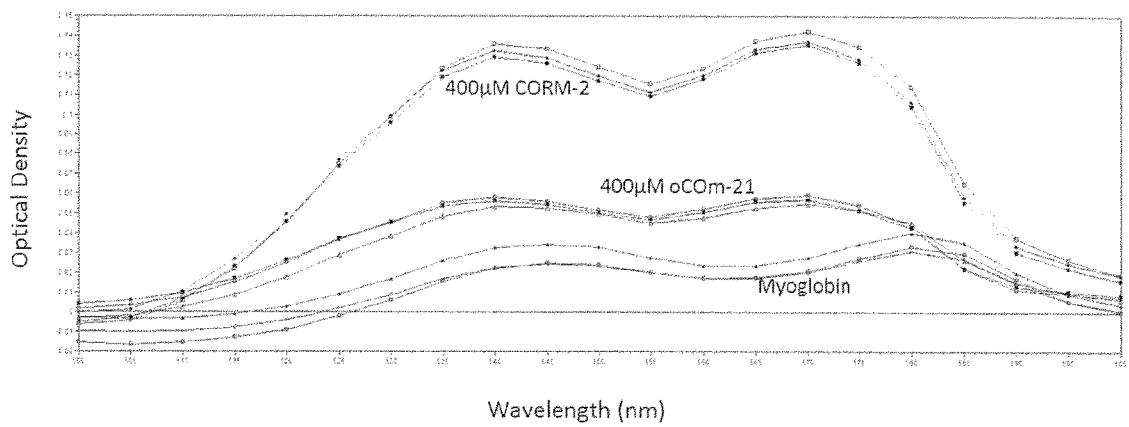
FIG. 7 shows a characteristic shift in the absorbance maxima of myoglobin from 545 and 580 nm for reduced myoglobin to 540 nm and 570 nm respectively for carbonmonoxymyoglobin in the presence of CO donors oCOm-21 (400 μM) or CORM2 (400 μM) after 80 minutes incubation at room temperature.

The generation of physiologically active CO by the CO donor compounds was demonstrated by myoglobin binding studies, measured as a shift in the absorbance spectra peaks to 540 nm (FIG. 7). CORM2 was included as a positive control. Assays repeated over 5 to 90 minutes to increasing concentrations of oCOm-19 and oCOm-21 (25 to 400 µM) showed both a time- and concentration-dependent increase in carbonmonoxymyoglobin formation (data not shown).

Example 49

Selective Imaging of Carbon Monoxide in Living Cells

Figure 8:
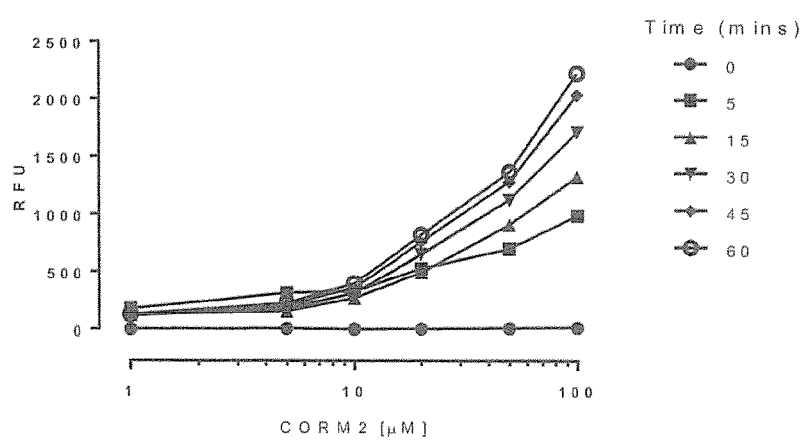
FIG. 8 shows the concentration and time dependent response of a palladium CO-responsive small-molecule fluorescent probe (COP-1) to CO gas in a physiological buffer.

The ability of COP-1 to produce a fluorescent signal response directly proportional to concentration of CO was confirmed by recording responses to COP-1 incubation (5-60) min with increasing concentrations of CORM2 (1-50 µM) (FIG. 8.)

Figure 9:
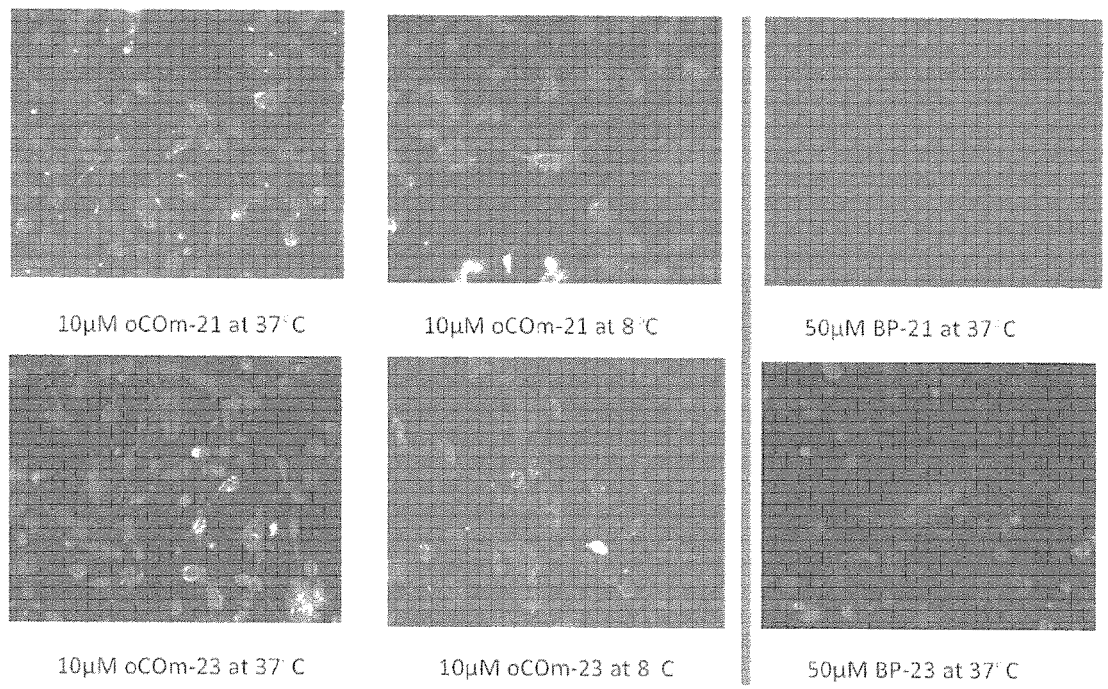
FIG. 9 shows confirmation of increased intracellular CO levels following exposure of MDCK cells to oCOm-21 (10 μM) or oCOm-23 (10 μM) compared to their respective inactive compounds at both 37° C. and 8° C. as indicated by COP-1 fluorescence.

CO penetration into the cytoplasm of cultured MDCK cells exposed to oCOm-21 and oCOm-23 was confirmed by fluorescence imaging. Increased BODIPY fluorescence intensity was observed in MDCK cells incubated with 10-50 µM oCOm-21 and oCOm-23 at both 37° C. and 8° C. Only background levels of fluorescence were observed when cells were exposed to the CO depleted donor molecules (FIG. 9).

Example 50

Cell Toxicity

Figure 10:
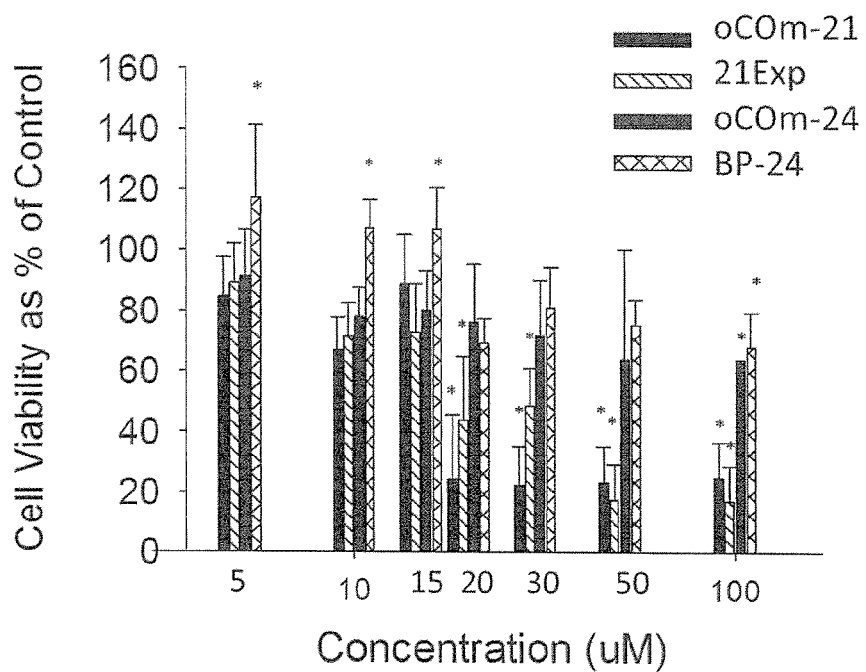
FIG. 10 shows MDCK cell viability following exposure to oCOm-21 and oCOm-24 individually, their inactive debromo (BP-21) analogues, or the CO expired (oCOm-21 exp) compound at 37° C.

Changes in the R groups incorporated into the core structure of the CO donor compounds had a significant effect on cellular toxicity (Table 1). oCOm-1 demonstrated the greatest toxicity and whilst oCOm-17 and oCOm-12 were the least toxic, their lack of solubility in water hindered their use in physiological buffers. Replacement of the R group with an amine to produce oCOm-21 provided solubility in physiological buffers and no significant toxicity at concentrations up to 20 µM. The toxicity observed to oCOm-21 was further reduced at 8° C. (Table 1). Substitution of the R group in oCOm-23 with a diamine resulted in increased solubility but also increased toxicity (Table 1). Substitution of the R group in oCOm-24 with a Tris group linked via a propanamide resulted in decreased solubility and toxicity (Table 1 and FIG. 10).

TABLE 1

Solubility and Toxicity characteristics for CO donor compounds

| Active Compound | EC$_{50}$ (µM) | Solubility in water at 21° C. (mg/ml) | Inactive Compound | EC$_{50}$(µM) |
|---|---|---|---|---|
| oCOm-1 * | 4.6 | NS | BP-1 | >200 |
| oCOm-17* | 216 | NS | BP-17 | 159 |
| oCOm-12* | 224 | NS | BP-12 | 196 |
| oCOm-15* | 183 | NS | BP-15 | >200 |
| oCOm-13* | 52.2 | NS | BP-13 | 25.3 |
| oCOm-8* | 23.1 | NS | BP-8 | NA |
| oCOm-19 | 86 | 3.2 | BP-19 | >100 |
| oCOm -21 | 11.2 | 10.8 | BP-21 | 21 |
| oCOm -21 at 8° C. | 250 | <3.9 | BP-21 at 8° C. | NA |
| oCOm-23 | 10.1 | 18.2 | BP-23 | >100 |
| oCOm-23 at 8° C. | >200 | 17.6 | BP-23 at 8° C. | NA |
| oCOm-24 | >100** | 5 | Exp-oCOm-24 | >100 |
| oCOM-28 | >100** | NS | | |
| oCOM-30 | >100 | NS | | |
| oCOM-40 | >100 | NS | | |
| oCOM-32 | >100 | NS | | |
| oCOM-34 | >100 | NS | | |
| oCOM-41 | >100 | NS | | |
| oCOM-36 | >100 | NS | | |
| oCOM-38 | >100 | NS | | |
| oCOM-45 | >100 | NS | | |

TABLE 1-continued

Solubility and Toxicity characteristics for CO donor compounds

| Active Compound | $EC_{50}$ (μM) | Solubility in water at 21° C. (mg/ml) | Inactive Compound | $EC_{50}$(μM) |
|---|---|---|---|---|
| oCOM-43 | >100 | NS | | |
| oCOM-49 | >200 | 0.9 | | |

Comparison of MDCK or *MDA-MB-231 cell viability assessed using the crystal violet assay after 23 hrs following an initial 1 hr exposure to the CO donors at 37° C., or their inactive debromo, or CO depleted analogues. Toxicity was reported as $EC_{50}$ values calculated from percentage cell survival using Origin Pro8 software (OriginLab, MA, USA). NA=not assessed. NS=not soluble in water. ** compounds showed a significant increase in cell number at concentrations above 20 uM. Substituting the ethyl amimium group ($R^{14}$) of oCOm-21 with a mannopyranoside linked via a triazole resuled in oCOm-49 with much reduced toxicity albeit with decreased water solubility.

Example 51

Oral Bioavailability

Oral bioavailability of CO from oCOm-19 and oCOm-21 was demonstrated by an increase in circulating carboxyhaemoglobin in rats exposed to CO the donors by oral gavage. Low but significantly increased levels of carboxyhaemoglobin were maintained for 2 hours following exposure to 33.3 μmol/kg of oCOm-21 and for 3 hours following exposure to 133.3 μmol/kg of oCOm-19. Administration of the same concentrations of the non CO releasing analogue of oCOm-19 (DB-13) failed to elevate carboxyhaemoglobin (Table 2).

TABLE 2

% Plasma carboxyhaemoglobin recorded at 1-3 hours following CO donor administration.

| | % Carboxyhaemoglobin in blood | | | |
|---|---|---|---|---|
| | Pre-dosing | 1 hour post | 2 hours post | 3 hours post |
| oCOm -19 133.3 μmol/kg | 0.7 ± 0.28 | 0.9 ± 0 | 1.2 ± 0 | 1.3 ± 0.14* |
| oCOm -21 33.3 μmol/kg | 0.54 ± 0.36 | 1.52 ± 0.44* | 1.74 ± 0.45* | 1.25 ± 0.42 |
| DB-13 133.3 μmol/kg | 0.57 ± 0.25 | 0.63 ± 0.54 | 0.04 ± 0.65 | 0.63 ± 0.47 |

Effects on circulating carboxyhaemoglobin levels of oCOm-19 and oCOm-21 administered by oral gavage in Sprague Dawley rats (n = 3).
Data expressed as expressed as mean ± SEM.
*indicates P < 0.05 compared to the pre-dosing level as determined by Student t test.

One animal exposed to oCOm-19 showed body pressing behaviour indicative of abdominal discomfort, no other signs of distress or discomfort were noted in any other animals. Comparative earlier studies (unpublished work) have shown that, rats exposed to 20 ppm CO gas over a 2 or 7 day duration resulted in equivalent carboxyhaemoglobin levels of 1.1±0.25% and 2±0.75% respectively. The majority of published in vivo studies demonstrating the protective effects of CO gas have utilised between 20-1000 ppm.[47, 48, 49, 50, 51, 52, 53, 54, 55]

Example 52

Preservation of Tissue Viability

Figure 11:
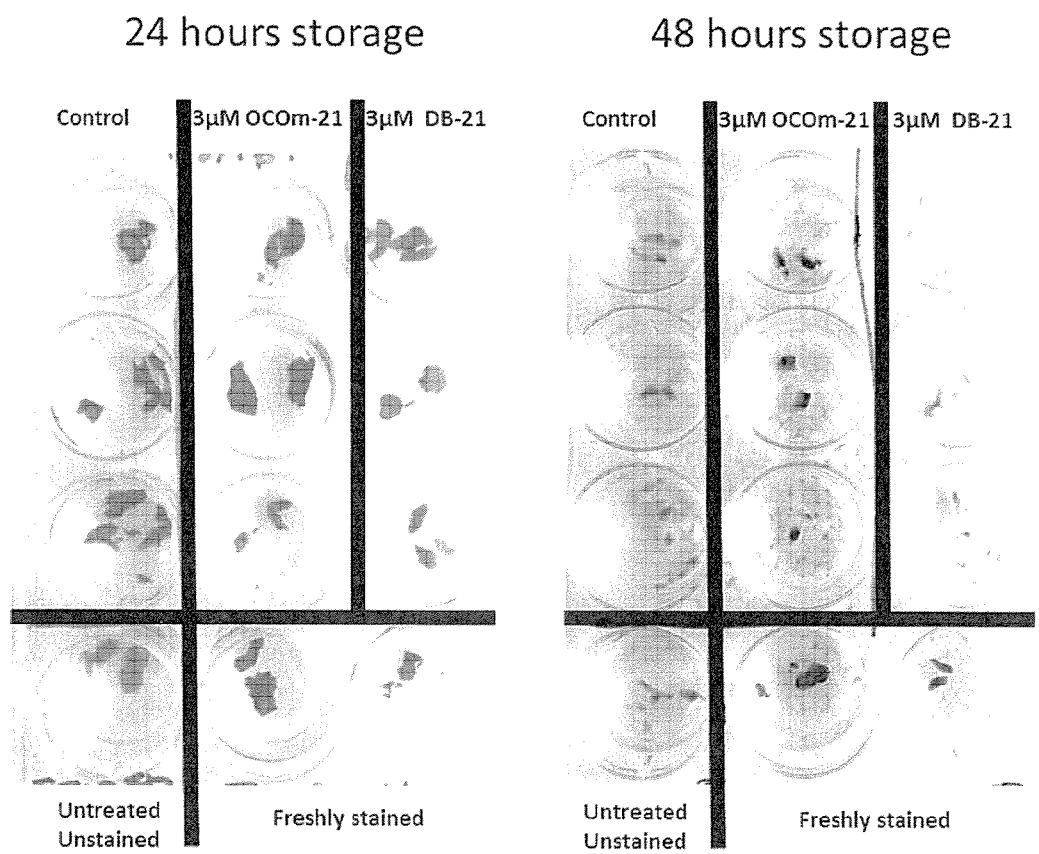
FIG. 11 shows improved tissue viability (indicated using the tissue viability stain TTC) when cardiac tissue is stored in media containing 3 μM oCOm-21, compared to media alone or media containing 3 μM DB-21 the non CO releasing analogue of oCOm-21.

The addition of 3 μM oCOm-21 to the solid myocardium stored in DMEM media improved tissue viability following both 24 and 48 hours cool static storage, as demonstrated by TTC staining. Formazan staining, consistent with active dehydrogenase activity was clearly visible in all tissues after 24 hours storage, except in the unstained control. However, staining was more intense at the core of those tissues stored in the presence of 3 μM oCOm-21. TTC staining was still clearly visible after 48 hours in those tissues stored in the presence of 3 μM oCOm-21 and in tissues stained immediately at time zero post-harvest. However, little staining was visible in tissues stored in DMEM alone, DMEM+3 μM DB-21 or in unstained tissue by 48 hours (FIG. 11).

Example 53

Vasodilation in Isolated Rat Aortic Rings

Figure 12:
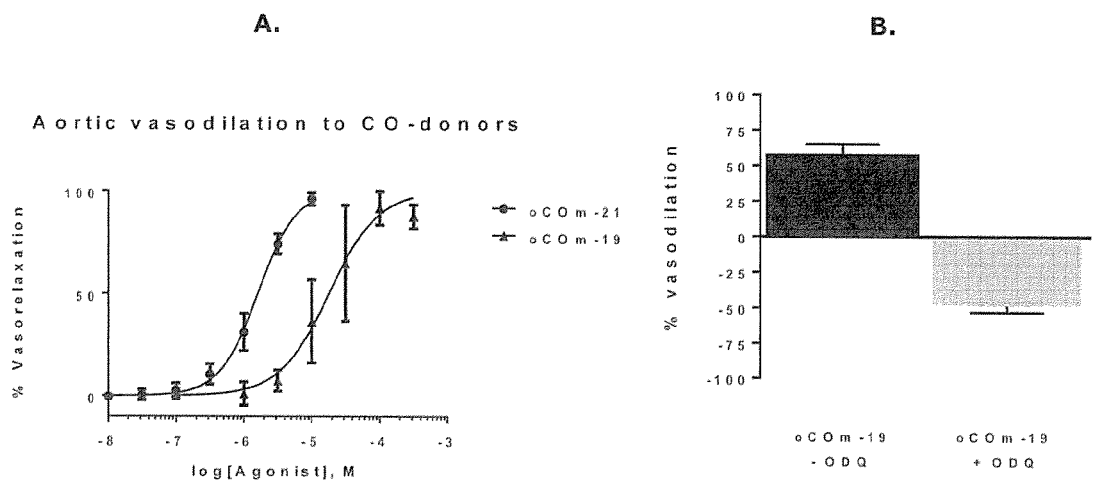
FIG. 12 shows the vasorelaxant effects of the CO-donors oCOm-19 and oCOm-21 and the inhibition of this effect by the guanylate cyclase inhibitor ODQ in isolated rat aortic rings at 37° C.

Both oCOm-19 and oCOm-21 produced reversible, concentration-dependent vasorelaxant responses at 37° C. (FIG. 12) which were attenuated by both guanylate cyclase inhibition (ODQ) and by myoglobin CO chelation. The non CO releasing analogue BP-19 was shown to have no vasorelaxant effect.

Example 54

Isolated Rat Kidney Perfusion

Figure 13:
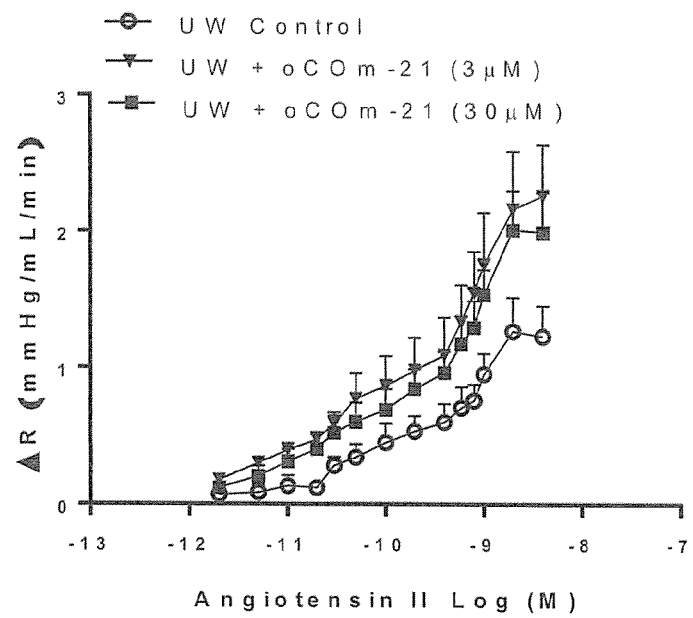
FIG. 13 shows improved renovascular resistance to angiotensin II after normothermic reperfusion of kidneys following hypothermic perfusion in the presence of oCOm-21 and cold storage protocols illustrated in FIG. 1.
Figure 14:
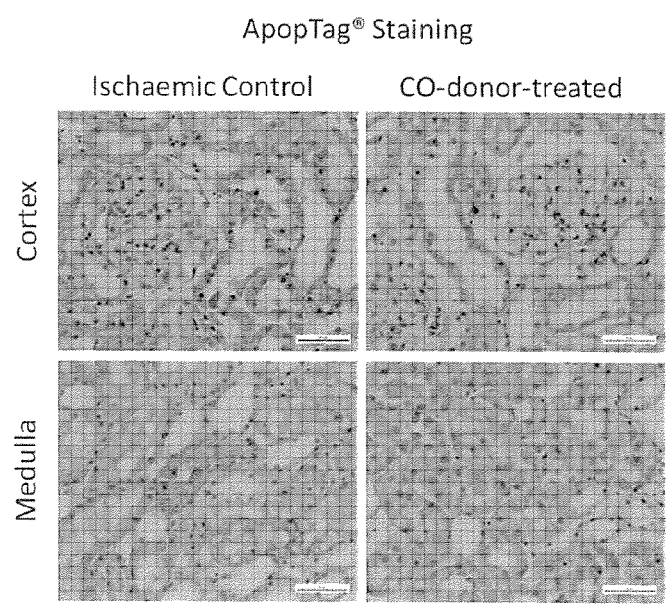
FIG. 14 shows reduced tissue apoptosis (indicated using ApopTag® DAB brown staining) in ischaemic reperfused kidneys hypothermically (8° C.) perfused with UW Machine Perfusion solution containing oCOm-21 (3 μM) compared to UW perfusion alone.

The addition of 3 μM of CO donor compound oCOm-21 to UW Machine Perfusion solution (8° C.) reduced renal vascular resistance on normothermic reperfusion (Table 3) and improved smooth muscle responsiveness to angiotensin II by shifting the concentration response curve to the left (FIG. 13). Addition of a ten-fold higher concentration of (oCOm-21 30 μM) failed to increase the vasoconstrictor response to the same angiotensin II concentrations. Histological examination of the cortical and inner medullary stripe regions from kidneys subjected to UW Machine Perfusion solutions showed that the supplementation of the UW perfusion solution with oCOm-21 (3 μM) reduced the degree of apoptosis in hypothermically perfused and stored tissues compared to control tissues (FIG. 14).

TABLE 3

Initial renal perfusion parameters on reperfusion.

| Groups | UW Control | UW + oCOM-21 (3 μM) |
|---|---|---|
| Flow Rate (mL/min) | 31.0 ± 1.7 | 33.8 ± 1.2 |
| Resistance (mmHg/mL/min) | 4.5 ± 0.2* | 3.9 ± 0.2* |

Perfusate flow rate and renal vascular resistance on normothermic reperfusion in isolated rat kidneys following 80 minutes perfusion with 3 μM oCOm-21 and 16 hours cold storage. Data was analysed using a One-way ANOVA with Bonferroni post-hoc test and expressed as mean ± SEM.
*P < 0.05 = 3 μM oCOm-21 group vs control.

Example 55

Isolated Perfused Hearts

Figure 15:
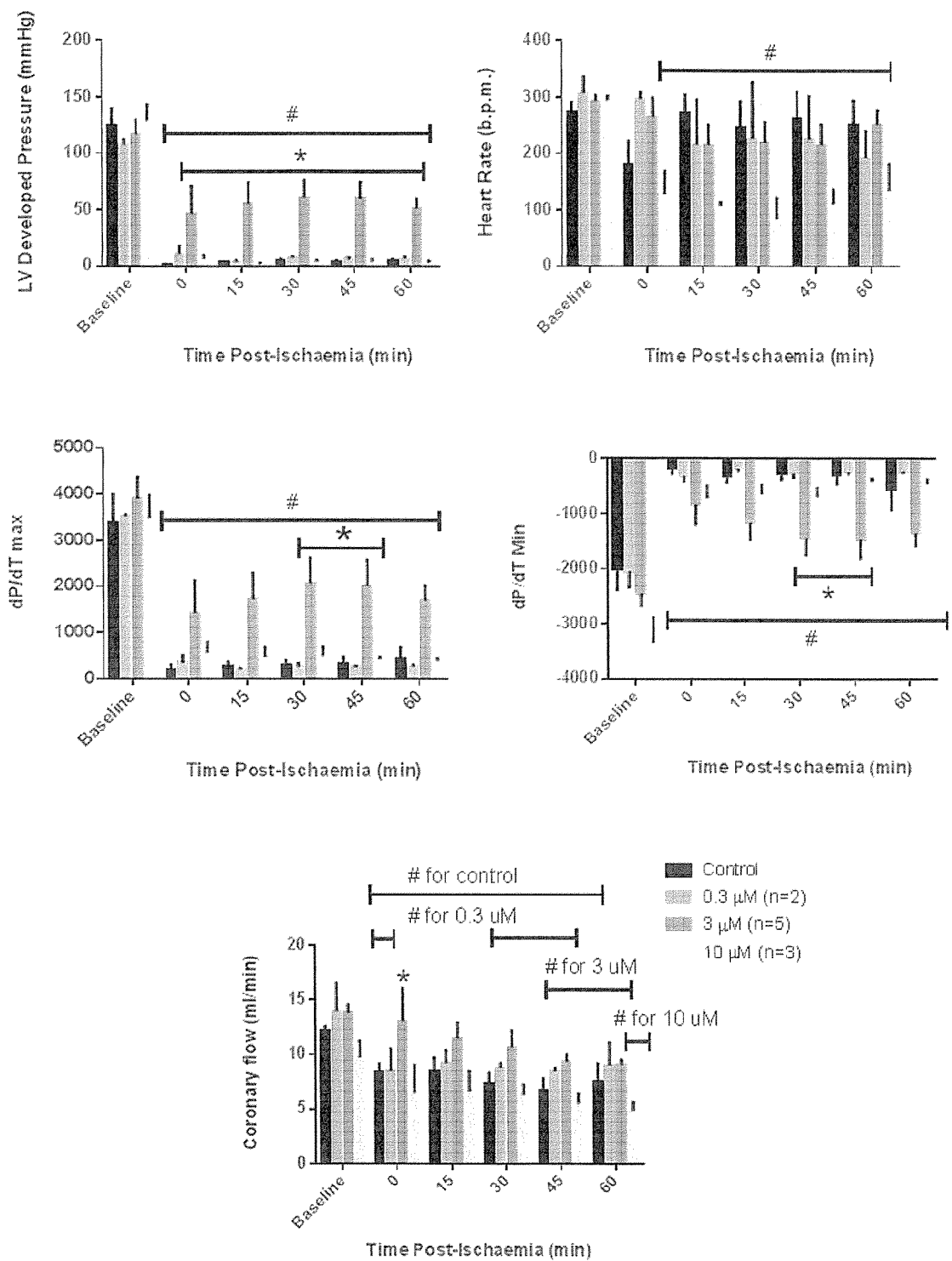
FIG. 15 shows that normothermic (37° C.) preconditioning of isolated rat hearts with oCOm-21 (3 μM) prior to 30 min of normothermic ischaema protects post-reperfusion cardiac haemodynamic indices.

Administration of 3 μM oCOm-21 to isolated normothermically perfused rat hearts for 20 minutes immediately prior to a warm (37° C.) global ischaemic period (30 min) attenuated the extent of ischaemic reduction in LVDP, dP/dt max and dP/dt min coronary flow rate compared to controls (FIG. 15). There was no significant effect on heart rate.

Example 56

Summary /Conclusions

The rate of release of CO from the CO donor molecules varied with changes in the R groups enabling the tailoring of CO release rates to different applications. oCOm-21 released 50% of its CO within 20 minutes when dissolved in UW solution as determined by HPLC analysis. Amphoteric CO electrode measurements confirmed that the release of low levels of CO from oCOm-21 was sustained over 90 minutes which is ideal for organ perfusion protocols. The release of CO from the donor molecules was also demonstrated by its binding to myoglobin under physiological pH conditions. The rate of CO release increased in basic (pH≥7.4) buffer and was halted in acidic buffer as predicted from their chemistry. This stability in acidic conditions would enable the preparation of the donor in a mildly acidic solution prior to delivery in a physiological pH perfusion buffer enhancing its usability in a clinical setting. This stability would also aid the application of these compounds as oral therapeutics as CO release is inhibited in the acidic conditions present in the stomach and upper part of the small intestine. Absorption of the CO donor in the rat model resulting in pH activation of the drug in the plasma and release of low levels of CO was confirmed by the formation of carboxyhaemoglobin.

No significant toxicity was seen at 37° C. at the concentration (3 μM oCOm-21) used for renal perfusion studies. The toxicity of oCOm-21 was even lower at 8° C. (LD50>200 μM at 8° C. versus 11.2 μM at 37° C., with no toxicity up to 100 μM) in MDCK cell culture further expanding the effective range at lower temperatures. Further reductions in toxicity obtained with oCOm 24 and oCOm49 show that changes to the structure of this family of CO donor molecules can be made to reduce toxicity if required for other applications.

The ability of these compounds to increase cytoplasmic concentrations of CO was demonstrated by activation of the fluorescent CO specific probe COP-1. Incubation with either oCOm-21 or oCOm-23 (10 μM) in culture media increased intracellular CO at both 37° C. and 8° C. in MDCK cells.

Oral exposure of rats to oCOm-19 (133.3 μmol/kg) and oCOm-21 (33.3 μmol/kg) resulted in increases in blood carboxyhaemoglobin levels comparable to a 1 day exposure to 20 ppm CO gas, a dose previously shown to be protective in a variety of animal models of ischaemia reperfusion injury.[47, 48, 49, 50, 51, 52, 53, 54, 55] The finding that these organic CO donor molecules can effectively release CO systemically in vivo after oral delivery is an important step toward developing protective therapeutic strategies for the wide range of diseases where low dose CO has been shown to be beneficial (Ghosh 2010; Ryter 2004; Lavitrano 2004; Goebel 2008; Fujita 2001; Lancel 2009; Nakao 2006; Pannen 1998; Zhou 2005; Nikolic 2015).[50, 52, 54, 56, 57, 58, 59, 60, 61]

The addition of OCOm-21 to tissue storage media visibly improved the viability of 24 and 48 hour statically stored solid cardiac tissue. This demonstrates the potential of these compounds to prolong the preservation of fresh biological tissues for a variety of applications, including (e.g.) tumour tissue being transported for xenotransplantation, hair follicles for htero or homotopic transplantation, ovarian tissue for preservation prior to chemotherapy, sperm preservation for clinical and agricultural applications, and clinical samples for histological evaluation.

In aortic ring preparations oCOm-19 and oCOm-21 demonstrated reversible, concentration-dependent vasorelaxation at 37° C. This vasorelaxation was attenuated by guanylate cyclase inhibition indicating that the compound was acting via known CO signalling pathways and inhibited by myoglobin CO chelation (data not shown here) demonstrating the effect was due to CO release.

The addition of 3 μM of CO donor compound oCOm-21 to hypothermic UW Machine Perfusion solution improved renal haemodynamic indices and vasoresponsiveness on reperfusion in isolated, perfused rat kidneys. By incorporating a 5 minute warm ischaemic period at the start of our study protocol for organ retrieval and perfusion, our model mimics the minimal no-touch ischaemic time observed clinically in non-heart beating donation after pronunciation of cardio-respiratory death. Histological examination of the renal tissue showed reduced apoptosis and improved renal structure compared to kidneys perfused with UW alone.

Equally valuably haemodynamic parameters were improved upon reperfusion in isolated rat hearts exposed to 30 minutes warm (normothermic) ischaemia when 3 μM of CO donor compound oCOm-21 was added to the KrebsHenseleit perfusion buffer. This indicates that oCOm-21 may be of value as a therapeutic adjunct to clinical procedures associated with warm IR injury.

In summary Applicant's data shows that oCOm-21, a non-metal based pH activated CO donor offers organ protection in both hypothermic and normothermic transplant perfusion and storage protocols.

REFERENCES

1. Ghosh, S.; Gal, J.; Marczin, N., Carbon monoxide: endogenous mediator, potential diagnostic and therapeutic target. *Annals of Medicine* (London, United Kingdom) 2010, 42 (1), 1-12.
2. Freiberger, J. J. CO as a Stimulant for Mitochondrial Biogenesis in Human. https://clinicaltrials.gov/ct2/show/NCT01727167.
3. Beth Israel Deaconess Medical Centre, Boston. https://www.clinicaltrials.gov/ct2/show/NCT00531856
4. Caumartin, Y.; Stephen, J.; Deng, J. P.; Lian, D.; Lan, Z.; Liu, W.; Garcia, B.; Jevnikar, A. M.; Wang, H.; Cepinskas, G.; Luke, P. P. W., Carbon monoxide-releasing molecules protect against ischemia-reperfusion injury during kidney transplantation. *Kidney International* 2011, 79 (10), 1080-1089.

5. Gautam, P.; Bhanage, B. M., Recent advances in the transition metal catalyzed carbonylation of alkynes, arenes and aryl halides using CO surrogates. *Catalysis Science & Technology* 2015, 5 (10), 4663-4702.

6. Goodman, M., Peptide homologs, isosteres, and isomers: a general approach to structure-activity relationships. *Biopolymers* 1985, 24 (1), 137-55.

7. Parker, S. P., *McGraw-Hill Dictionary of Chemical Terms*. McGraw-Hill Book company: New York, 1984.

8. Wilen, E. E. S., *Stereochemistry of Organic Compounds*. John Wiley & Sons, Inc: New York.

9. Theodora W. Greene, P. G. M. W., *Protective Groups in Organic Synthesis*. 3rd ed.; 1999.

10. Remington, J. P.; Gennaro, A. R., *Remington: The Science and Practice of Pharmacy*, 19th ed., Easton, Pa.: Mack Publishing, (1995)

11. Motterlini, R.; Clark, J. E.; Foresti, R.; Sarathchandra, P.; Mann, B. E.; Green, C. J., Carbon monoxide-releasing molecules: characterization of biochemical and vascular activities. *Circ. Res* 2002, 90 (2), E17-E24.

12. Kibbe, A. H., *Handbook of Pharmaceutical Excipients, Edition*, 3. sup. rd, American Pharmaceutical Association, Washington, Washingon, D.C. (2000)

13. Bon, D.; Chatauret, N.; Giraud, S.; Thuillier, R.; Favreau, F.; Hauet, T., New strategies to optimize kidney recovery and preservation in transplantation. *Nature Reviews Nephrology* 2012, 8 (6), 339-347.

14. Yang, J.-S.; Huang, H.-H.; Lin, S.-H., Facile Multistep Synthesis of Isotruxene and Isotruxenone. *Journal of Organic Chemistry* 2009, 74 (10), 3974-3977.

15. Banwell, M. G.; Jones, M. T.; Loong, D. T. J.; Lupton, D. W.; Pinkerton, D. M.; Ray, J. K.; Willis, A. C., A Pd(0)-catalyzed Ullmann cross-coupling/reductive cyclization approach to C-3 mono-alkylated oxindoles and related compounds. *Tetrahedron* 2010, 66 (47), 9252-9262.

16. Sahoo, M. K.; Mhaske, S. B.; Argade, N. P., Facile routes to alkoxymaleimides/maleic anhydrides. *Synthesis* 2003, (3), 346-349.

17. Pyriadi, T. M.; Kaleefa, H., Synthesis and attempted polymerization of N-arylmaleimides substituted with allylamino or cyclopropylamino groups at 2-position. *Journal of Polymer Science, Polymer Chemistry Edition* 1984, 22 (1), 129-34.

18. Benitez, A.; Herrera, F. R.; Romero, M.; Talamas, F. X.; Muchowski, J. M., Site Selectivity of the Diels-Alder Reactions of 3-[1-(tert-Butyldimethylsilyloxy)vin-1-yl]furan and 3-(Propen-2-yl)furan. Synthesis of 4-Substituted Benzofurans. *Journal of Organic Chemistry* 1996, 61 (4), 1487-92.

19. Marculescu, C.; Kossen, H.; Morgan, R. E.; Mayer, P.; Fletcher, S. A.; Tolner, B.; Chester, K. A.; Jones, L. H.; Baker, J. R., Aryloxymaleimides for cysteine modification, disulfide bridging and the dual functionalization of disulfide bonds. *Chemical Communications* (Cambridge, United Kingdom) 2014, 50 (54), 7139-7142.

20. Tedaldi, L. M.; Smith, M. E. B.; Nathani, R. I.; Baker, J. R., Bromomaleimides: new reagents for the selective and reversible modification of cysteine. *Chemical Communications* (Cambridge, United Kingdom) 2009, (43), 6583-6585.

21. Su, Y.-C.; Lo, Y.-L.; Hwang, C.-C.; Wang, L.-F.; Wu, M. H.; Wang, E.-C.; Wang, Y.-M.; Wang, T.-P., Azide-alkyne cycloaddition for universal post-synthetic modifications of nucleic acids and effective synthesis of bioactive nucleic acid conjugates. *Organic & Biomolecular Chemistry* 2014, 12 (34), 6624-6633.

22. El-Mandy, A. F. M.; Shibata, T.; Kabashima, T.; Kai, M., Dendrimer-like polymeric DNAs as chemiluminescence probes for amplified detection of telomere DNA on a solid-phase membrane. *Chemical Communications* (Cambridge, United Kingdom) 2014, 50 (7), 859-861.

23. Foley, T. L.; Yasgar, A.; Garcia, C. J.; Jadhav, A.; Simeonov, A.; Burkart, M. D., Preparation of FRET reporters to support chemical probe development. *Organic & Biomolecular Chemistry* 2010, 8 (20), 4601-4606.

24. Eckstein, P.; Ritter, H., Microwave-assisted synthesis, transesterification and polymerization of N-(2-acetoxyethyl-)maleimide. *Designed Monomers and Polymers* 2005, 8 (6), 601-607.

25. Gaidamaviciute, E.; Tauraite, D.; Gagilas, J.; Lagunavicius, A., Site-directed chemical modification of archaeal *Thermococcus litoralis* Sh1B DNA polymerase: Acquired ability to read through template-strand uracils. *Biochimica et Biophysica Acta, Proteins and Proteomics* 2010, 1804 (6), 1385-1393.

26. Mitrovic, A.; Todorovic, N.; Zekic, A.; Stankovic, D.; Milic, D.; Maslak, V., Synthesis, Electrochemistry, and Hierarchical Self-Organization of Fulleropyrrolidine-Phthalimide Dyads. *European Journal of Organic Chemistry* 2013, 2013 (11), 2188-2193.

27. Keller, O.; Rudinger, J., Preparation and some properties of maleimido acids and maleoyl derivatives of peptides. *Helvetica Chimica Acta* 1975, 58 (2), 531-41.

28. Andruszkiewicz, R.; Gronek, E.; Haluszczak, J., Facile Synthetic Route to Selectively Protected Spermidine Homologues. *Synthetic Communications* 2008, 38 (6), 905-913.

29. Otis, F.; Voyer, N.; Polidori, A.; Pucci, B., End group engineering of artificial ion channels. *New Journal of Chemistry* 2006, 30 (2), 185-190.

30. Marculescu, C.; Kossen, H.; Morgan, R. E.; Mayer, P.; Fletcher, S. A.; Tolner, B.; Chester, K. A.; Jones, L. H.; Baker, J. R., Aryloxymaleimides for cysteine modification, disulfide bridging and the dual functionalization of disulfide bonds. *Chem. Commun.* 2014, 50 (54), 7139-7142.

31. Wan, W.; Huang, Y.; Wang, Z.; Russell, W. K.; Pai, P.-J.; Russell, D. H.; Liu, W. R., A facile system for genetic incorporation of two different noncanonical amino acids into one protein in *Escherichia coli*. *Angewandte Chemie, International Edition* 2010, 49 (18), 3211-3214, S3211/1-S3211/27.

32. Wan, W.; Huang, Y.; Wang, Z.; Russell, W. K.; Pai, P.-J.; Russell, D. H.; Liu, W. R., A Facile System for Genetic Incorporation of Two Different Noncanonical Amino Acids into One Protein in *Escherichia coli*. *Angew. Chem. Int. Ed.* 2010, 49 (18), 3211-3214.

33. Schmuck, C.; Rehm, T.; Geiger, L.; Schaefer, M., Synthesis and Self-Association Properties of Flexible Guanidiniocarbonylpyrrole-Carboxylate Zwitterions in DMSO: Intra-versus Intermolecular Ion Pairing. *Journal of Organic Chemistry* 2007, 72 (16), 6162-6170.

34. Schmuck, C.; Rehm, T.; Geiger, L.; Schäfer, M., Synthesis and Self-Association Properties of Flexible Guanidiniocarbonylpyrrole-Carboxylate Zwitterions in DMSO: Intra-versus Intermolecular Ion Pairing. *The Journal of Organic Chemistry* 2007, 72 (16), 6162-6170.

35. Ramakrishna, N. V. S.; More, T. S.; Khandelwal, Y.; Naik, R. G.; Lal, B.; Gupte, R. D.; Vadlamudi, R. V. S. V., Synthesis of RGD peptidomimetic analogs of 2,5-diketopiperazine. *Indian Journal of Chemistry, Section B: Organic Chemistry Including Medicinal Chemistry* 1999, 38B (12), 1331-1337.

36. Eloy, F.; Lenaers, R., Chemistry of amidoximes and related compounds. *Chem. Rev.* 1962, 62, 155-83.

37. Hurd, C. D.; Mori, R. I., Acylhydrazones and 1,2,3-thiadiazoles. *Journal of the American Chemical Society* 1955, 77, 5359-64.
38. Lopez-Alvarado, P.; Avendano, C.; Menendez, J. C., Efficient, multigram-scale synthesis of three 2,5-dihalobenzoquinones. *Synthetic Communications* 2002, 32 (20), 3233-3239.
39. Motterlini, R.; Clark, J. E.; Foresti, R.; Sarathchandra, P.; Mann, B. E.; Green, C. J., Carbon monoxide-releasing molecules. Characterization of biochemical and vascular activities. *Circulation Research* 2002, 90 (2), e17-e24.
40. Atkin, A. J.; Lynam, J. M.; Moulton, B. E.; Sawle, P.; Motterlini, R.; Boyle, N. M.; Pryce, M. T.; Fairlamb, I. J. S., Modification of the deoxy-myoglobin/carbonmonoxy-myoglobin UV-vis assay for reliable determination of CO-release rates from organometallic carbonyl complexes. *Dalton Transactions* 2011, 40 (21), 5755-5761.
41. Michel, B. W.; Lippert, A. R.; Chang, C. J., A Reaction-Based Fluorescent Probe for Selective Imaging of Carbon Monoxide in Living Cells Using a Palladium-Mediated Carbonylation. *Journal of the American Chemical Society* 2012, 134 (38), 15668-15671.
42. Mickuviene, I.; Kirveliene, V.; Juodka, B., Experimental survey of non-clonogenic viability assays for adherent cells in vitro. *Toxicology in Vitro* 2004, 18 (5), 639-648.
43. Sammut, I. A.; Foresti, R.; Clark, J. E.; Exon, D. J.; Vesely, M. J. J.; Sarathchandra, P.; Green, C. J.; Motterlini, R., Carbon monoxide is a major contributor to the regulation of vascular tone in aortas expressing high levels of heme oxygenase-1. *British Journal of Pharmacology* 1998, 125 (7), 1437-1444.
44. Kumari, S.; Sammut, I. A.; Giles, G. I., The design of nitric oxide donor drugs: s-nitrosothiol tDodSNO is a superior photoactivated donor in comparison to GSNO and SNAP. *Eur. J Pharmacol* 2014, 737, 168-176.
45. Darzynkiewicz, Z.; Galkowski, D.; Zhao, H., Analysis of apoptosis by cytometry using TUNEL assay. *Methods* 2008, 44 (3), 250-254.
46. Adlam, V. J.; Harrison, J. C.; Porteous, C. M.; James, A. M.; Smith, R. A.; Murphy, M. P.; Sammut, I. A., Targeting an antioxidant to mitochondria decreases cardiac ischemia-reperfusion injury. *FASEB J* 2005, 19 (9), 1088-1095.
47. Nakao, A.; Faleo, G.; Nalesnik, M. A.; Seda-Neto, J.; Kohmoto, J.; Murase, N., Low-dose carbon monoxide inhibits progressive chronic allograft nephropathy and restores renal allograft function. *Am J Physiol Renal Physiol* 2009, 297 (1), F19-F26.
48. Nakao, A.; Neto, J. S.; Kanno, S.; Stolz, D. B.; Kimizuka, K.; Liu, F.; Bach, F. H.; Billiar, T. R.; Choi, A. M.; Otterbein, L. E.; Murase, N., Protection against ischemia/reperfusion injury in cardiac and renal transplantation with carbon monoxide, biliverdin and both. *Am. J. Transplant* 2005, 5 (2), 282-291.
49. Neto, J. S.; Nakao, A.; Toyokawa, H.; Nalesnik, M. A.; Romanosky, A. J.; Kimizuka, K.; Kaizu, T.; Hashimoto, N.; Azhipa, O.; Stolz, D. B.; Choi, A. M.; Murase, N., Low-dose carbon monoxide inhalation prevents development of chronic allograft nephropathy. *Am. J. Physiol Renal Physiol* 2006, 290 (2), F324-F334.
50. Lavitrano, M.; Smolenski, R. T.; Musumeci, A.; Maccherini, M.; Slominska, E.; Di, F. E.; Bracco, A.; Mancini, A.; Stassi, G.; Patti, M.; Giovannoni, R.; Froio, A.; Simeone, F.; Forni, M.; Bacci, M. L.; D'Alise, G.; Cozzi, E.; Otterbein, L. E.; Yacoub, M. H.; Bach, F. H.; Calise, F., Carbon monoxide improves cardiac energetics and safeguards the heart during reperfusion after cardiopulmonary bypass in pigs. *FASEB J* 2004, 18 (10), 1093-1095.

51. Bak, I.; Varadi, J.; Nagy, N.; Vecsernyes, M.; Tosaki, A., The role of exogenous carbon monoxide in the recovery of post-ischemic cardiac function in buffer perfused isolated rat hearts. *Cell Mol. Biol.* (Noisy. -le-grand) 2005, 51 (5), 453-459.
52. Goebel, U.; Siepe, M.; Mecklenburg, A.; Stein, P.; Roesslein, M.; Schwer, C. I.; Schmidt, R.; Doenst, T.; Geiger, K. K.; Pahl, H. L.; Schlensak, C.; Loop, T., Carbon monoxide inhalation reduces pulmonary inflammatory response during cardiopulmonary bypass in pigs. *Anesthesiology* 2008, 108 (6), 1025-1036.
53. Gunther, L.; Berberat, P. O.; Haga, M.; Brouard, S.; Smith, R. N.; Soares, M. P.; Bach, F. H.; Tobiasch, E., Carbon monoxide protects pancreatic beta-cells from apoptosis and improves islet function/survival after transplantation. *Diabetes* 2002, 51 (4), 994-999.
54. Nakao, A.; Toyokawa, H.; Abe, M.; Kiyomoto, T.; Nakahira, K.; Choi Augustine, M. K.; Nalesnik Michael, A.; Thomson Angus, W.; Murase, N., Heart allograft protection with low-dose carbon monoxide inhalation: effects on inflammatory mediators and alloreactive T-cell responses. *Transplantation* 2006, 81 (2), 220-30.
55. Nakao, A.; Kimizuka, K.; Stolz Donna, B.; Seda Neto, J.; Kaizu, T.; Choi Augustine, M. K.; Uchiyama, T.; Zuckerbraun Brian, S.; Bauer Anthony, J.; Nalesnik Michael, A.; Otterbein Leo, E.; Geller David, A.; Murase, N., Protective effect of carbon monoxide inhalation for cold-preserved small intestinal grafts. *Surgery* 2003, 134 (2), 285-92.
56. Ghosh, S.; Gal, J.; Marczin, N., Carbon monoxide: endogenous mediator, potential diagnostic and therapeutic target. *Ann. Med* 2010, 42 (1), 1-12.
57. Ryter, S. W.; Otterbein, L. E., Carbon monoxide in biology and medicine. *Bioessays* 2004, 26 (3), 270-280.
58. Fujita, T.; Toda, K.; Karimova, A.; Yan, S.-F.; Naka, Y.; Yet, S.-F.; Pinsky, D. J., Paradoxical rescue from ischemic lung injury by inhaled carbon monoxide driven by derepression of fibrinolysis. *Nature Medicine* (New York, N.Y., United States) 2001, 7 (5), 598-604.
59. Lancel, S.; Hassoun, S. M.; Favory, R.; Decoster, B.; Motterlini, R.; Neviere, R., Carbon monoxide rescues mice from lethal sepsis by supporting mitochondrial energetic metabolism and activating mitochondrial biogenesis. *Journal of Pharmacology and Experimental Therapeutics* 2009, 329 (2), 641-648.
60. Pannen, B.; Kohler, N.; Hole, B.; Bauer, M.; Clemens, M. G.; Geiger, K. K., Protective role of endogenous carbon monoxide in hepatic microcirculatory dysfunction after hemorrhagic shock in rats. *Journal of Clinical Investigation* 1998, 102 (6), 1220-1228.
61. Zhou, Z.; Song, R.; Fattman Cheryl, L.; Greenhill, S.; Alber, S.; Oury Tim, D.; Choi Augustine, M. K.; Morse, D., Carbon monoxide suppresses bleomycin-induced lung fibrosis. *The American journal of pathology* 2005, 166 (1), 27-37.

The invention claimed is:

1. A norbornenone compound of Formula 1, or a biologically or pharmaceutically acceptable salt thereof:

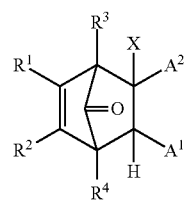

Formula 1 wherein

R$^1$, R$^2$, R$^3$ and R$^4$, are each independently selected from hydrogen, halo, CN, NO$_2$, OC(O)R$^5$, C(O)R$^5$, C(O)OR$^5$, OR$^5$, OS(O)$_2$R$^5$, NR$^5$R$^6$, SR$^5$, C$_{1-20}$alkyl, C$_{2-20}$alkenyl, C$_{2-20}$alkynyl, monocyclic or polycyclic carbocyclyl or heterocyclyl, polyethylene glycol, amino acid, and saccharide;

wherein the C$_{1-20}$alkyl, C$_{2-20}$alkenyl, C$_{2-20}$alkynyl, are each optionally interrupted with one or more heteroatoms selected from O, N and S; and wherein the C$_{1-20}$alkyl, C$_{2-20}$alkenyl, C$_{2-20}$alkynyl, carbocycle, and heterocycle, are each optionally substituted with 1-3 substituents independently selected from halo, CN, NO$_2$, OC(O)R$^5$, C(O)R$^5$, C(O)OR$^5$, OR$^5$, OS(O)$_2$R$^5$, NR$^5$R$^6$, SR$^5$, polyethylene glycol, amino acid, and saccharide; and R$^5$ and R$^6$ are each independently selected from hydrogen, C$_{1-10}$alkyl, and C$_{1-10}$haloalkyl; and wherein two or more of R$^1$, R$^2$, R$^3$ and R$^4$, may together form an optionally substituted monocyclic or polycyclic carbocyclyl or heterocyclyl;

X is selected from halo, OS(O)$_2$R$^7$, OS(O)$_2$OR$^7$, and R$^7$ is selected from hydrogen, C$_{1-10}$alkyl, C$_{1-10}$haloalkyl, aryl, arylalkyl and arylhaloalkyl;

A$^1$ and A$^2$ are each independently selected from hydrogen, halo, CN, NO$_2$, S(O)R$^9$, S(O)$_2$R$^9$, S(O)$_2$OR$^9$, SR$^9$, NR$^9$R$^{10}$, C(=O)R$^9$, C(=S)R$^9$, C(=CR$^{10}$R$^{11}$)R$^9$, or A$^1$ and A$^2$ together form an optionally substituted monocyclic or polycyclic carbocyclyl or heterocyclyl; R$^9$ is selected from hydrogen, hydroxyl, C$_{1-20}$alkyl, C$_{1-20}$haloalkyl, aryl, arylalkyl and arylhaloalkyl; and R$^{10}$ and R$^{11}$ are each independently selected from hydrogen, C$_{1-10}$alkyl, and C$_{1-10}$haloalkyl;

with the proviso that a compound of Formula 1 does not include any of the following compounds:

3,3a,5,6-tetrachloro-3a,4,7,7a-tetrahydro-4,7-methano-1H-indene-1,8-dione;

(1α,4 α,4aβ,4b α,5β,8β,8a αβ, 12bβ) 8a,12b-dibromo-1,2,3,4,5,6,7,8-octachloro-1,4,4a,4b,5,8,8a,12b-octahydro-1,4:5,8-dimethanotriphenylene-13,14-dione;

4,7,7a-tribromo-3a,4,7,7a-tetrahydro-2,3,5,6-tetraphenyl-4,7-methano-1H-indene-1,8-dione;

7,7a-dibromo-2,3,4,5-tetrachloro-3a,4,7,7a-tetrahydro-4,7-methano-1H-indene-1,8-dione; and 4,7a-dibromo-2,3,6,7-tetrachloro-3a,4,7,7a-tetrahydro-4,7-methano-1H-indene-1,8-dione.

2. The norbornenone compound or salt of claim 1, wherein X is selected from iodo, bromo, chloro, OS(O)$_2$R$^7$, and OS(O)$_2$OR$^7$; and R$^7$ is independently selected from hydrogen, C$_{1-4}$alkyl, C$_{1-4}$haloalkyl, phenyl, phenylalkyl and phenylhaloalkyl.

3. The norbornenone compound or salt of claim 1, wherein R$^1$, R$^2$, R$^3$ and R$^4$, are each independently selected from hydrogen, halo, C$_{1-10}$alkyl, C$_{2-10}$alkenyl, C$_{2-10}$alkynyl, monocyclic or bicyclic C$_{3-12}$carbocyclyl, and monocyclic or bicyclic C$_{3-12}$heterocyclyl, polyethylene glycol, and a saccharide; wherein the alkyl, alkenyl, alkynyl, carbocyclyl, and heterocyclyl group, are each optionally substituted with 1-3 substituents independently selected from halo, CN, NO$_2$, OC(O)R$^5$, C(O)R$^5$, C(O)OR$^5$, OR$^5$, OS(O)$_2$R$^5$, NR$^5$R$^6$, SR$^5$, polyethylene glycol, and mono- or poly-saccharide; and R$^5$ and R$^6$ are each independently selected from hydrogen, C$_{1-4}$alkyl, and C$_{1-4}$haloalkyl.

4. The norbornenone compound or salt of claim 1, wherein R$^1$, R$^2$, R$^3$ and R$^4$, are each independently selected from C$_{1-10}$alkyl, C$_{2-10}$alkenyl, C$_{2-10}$alkynyl, monocyclic or bicyclic C$_{3-12}$carbocyclyl, and monocyclic or bicyclic C$_{3-12}$heterocyclyl, polyethylene glycol, and a saccharide; wherein the alkyl, alkenyl, alkynyl, carbocyclyl, and heterocyclyl group, are each optionally substituted with 1-3 substituents independently selected from halo, CN, NO$_2$, OC(O)R$^5$, C(O)R$^5$, C(O)OR$^5$, OR$^5$, OS(O)$_2$R$^5$, NR$^5$R$^6$, SR$^5$, polyethylene glycol, and mono- or poly-saccharide; and R$^5$ and R$^6$ are each independently selected from hydrogen, C$_{1-4}$alkyl, and C$_{1-4}$haloalkyl.

5. The norbornenone compound or salt of claim 1, wherein R$^1$, R$^2$, R$^3$ and R$^4$, are each independently selected from C$_{1-6}$alkyl and monocyclic aryl or hetaryl; wherein the alkyl, aryl and hetaryl group, are each optionally substituted with 1-3 substituents independently selected from halo, CN, NO$_2$, OC(O)R$^5$, C(O)R$^5$, C(O)OR$^5$, OR$^5$, OS(O)$_2$R$^5$, NR$^5$R$^6$, SR$^5$, polyethylene glycol, and mono-, di-, or trisaccharide; and R$^5$ and R$^6$ are each independently selected from hydrogen, C$_{1-4}$alkyl, and C$_{1-4}$haloalkyl.

6. The norbornenone compound or salt of claim 1, wherein A$^1$ and A$^2$ are each independently selected from halo, CN, NO$_2$, S(O)R$^9$, S(O)$_2$R$^9$, S(O)$_2$OR$^9$, SR$^9$, NR$^9$R$^{10}$, C(=O)R$^9$, C(=S)R$^9$, C(=CR$^{10}$R$^{11}$)R$^9$, or A$^1$ and A$^2$ together form an optionally substituted monocyclic or polycyclic carbocyclyl or heterocyclyl; R$^9$ is selected from hydrogen, C$_{1-6}$alkyl, C$_{1-6}$haloalkyl, phenyl, phenylalkyl and phenylhaloalkyl; and R$^{10}$ and R$^{11}$ are each independently selected from hydrogen, C$_{1-4}$alkyl, and C$_{1-4}$haloalkyl.

7. The norbornenone compound or salt of claim 1, wherein A$^1$ and A$^2$ are each independently selected from halo, C(=O)R$^9$, C(=S)R$^9$, C(=CR$^{10}$R$^{11}$)R$^9$, or A$^1$ and A$^2$ together form an optionally substituted monocyclic carbocyclyl or heterocyclyl; and R$^9$, R$^{10}$ and R$^{11}$, are as defined in claim 4.

8. The norbornenone compound or salt of claim 1, wherein the compound of Formula 1 is selected from a compound of Formula 1a or Formula 1b, or a pharmaceutically acceptable salt thereof:

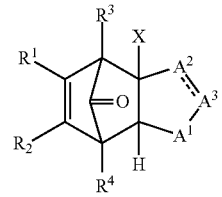

Formula 1a

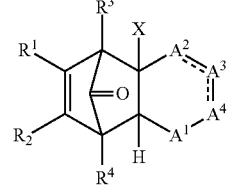

Formula 1b wherein each A$^1$ is independently selected from C=O, C=S, C=CR$^{12}$R$^{13}$, S=O, S(=O)$_2$, S, NR$^{14}$;

each A$^2$, A$^3$ and A$^4$, are independently selected from CR$^{14}$R$^{15}$, CR$^{14}$, C=O, C=S, C=CR$^{12}$R$^{13}$, S=O, S(=O)$_2$, O, S, SN, NR$^{14}$; and the dotted lines denote optional double bonds;

R$^{12}$ and R$^{13}$ are each independently selected from hydrogen, C$_{1-10}$alkyl, and C$_{1-10}$haloalkyl;

R$^{14}$ and R$^{15}$ are each independently selected from hydrogen, halo, CN, NO$_2$, OC(O)R$^5$, C(O)R$^5$, C(O)OR$^5$, OR$^5$, OS(O)$_2$R$^5$, NR$^5$R$^6$, SR$^5$, C$_{1-20}$alkyl, C$_{2-20}$alkenyl, C$_{2-20}$alkynyl, monocyclic and polycyclic carbocyclyl or heterocyclyl, polyethylene glycol, amino acid, and mono- or poly-saccharide; wherein the C$_{1-20}$alkyl, C$_{2-20}$alkenyl, C$_{2-20}$alkynyl, are each optionally interrupted with one or more heteroatoms selected from O, N and S; and wherein the C$_{1-20}$alkyl, C$_{2-20}$alkenyl, C$_{2-20}$alkynyl, carbocycle, and heterocycle, are each optionally substituted with one or more substituents independently selected from halo, CN, NO$_2$, OC(O)R$^5$, C=O, C(O)R$^5$, C(O)OR$^5$, OR$^5$, OS(O)$_2$R$^5$, NR$^5$R$^6$, SR$^5$, monocyclic and polycyclic heterocyclyl, polyethylene glycol, amino acid, and mono- or poly-saccharide; and R$^5$ and R$^6$ are each independently selected from hydrogen, C$_{1-10}$alkyl, and C$_{1-10}$haloalkyl.

9. The norbornenone compound or salt of Formula 1a or Formula 1b of claim 8, wherein A$^1$ is C=O.

10. The norbornenone compound or salt of Formula 1a or Formula 1b of claim 8, wherein:
each A$^1$ and A$^2$ are independently selected from C=O, C=S, C=CR$^{12}$R$^{13}$, S=O, S(=O)$_2$, S, NR$^{14}$; and
each A$^3$ and A$^4$ are independently selected from CR$^{14}$R$^{15}$, CR$^{14}$, C=O, C=S, C=CR$^{12}$R$^{13}$, S=O, S(=O)$_2$, O, S, NR$^{14}$; and R$^{12}$, R$^{13}$, R$^{14}$, and R$^{15}$, are as defined in claim 6.

11. The norbornenone compound or salt of Formula 1a or Formula 1b of claim 10, wherein each A$^1$ and A$^2$ is C=O.

12. The norbornenone compound or salt of claim 1, wherein the compound of Formula 1 or Formula 1a is selected from a compound of Formula 1a(i), or a pharmaceutically acceptable salt thereof:

Formula 1a(i)

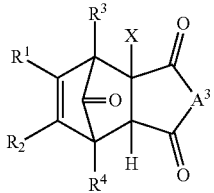

wherein
A$^3$ is selected from O, S, CR$^{14}$R$^{15}$ and NR$^{14}$;
R$^{14}$ and R$^{15}$ are each independently selected from hydrogen, halo, CN, NO$_2$, OC(O)R$^5$, C(O)R$^5$, C(O)OR$^5$, OR$^5$, OS(O)$_2$R$^5$, NR$^5$R$^6$, SR$^5$, C$_{1-20}$alkyl, C$_{2-20}$alkenyl, C$_{2-20}$alkynyl, monocyclic and polycyclic carbocyclyl or heterocyclyl, polyethylene glycol, amino acid, and mono- or poly-saccharide; wherein the C$_{1-20}$alkyl, C$_{2-20}$alkenyl, C$_{2-20}$alkynyl, are each optionally interrupted with one or more heteroatoms selected from O, N and S; and wherein the C$_{1-20}$alkyl, C$_{2-20}$alkenyl, C$_{2-20}$alkynyl, carbocycle, and heterocycle, are each optionally substituted with one or more substituents independently selected from halo, CN, NO$_2$, OC(O)R$^5$, C=O, C(O)R$^5$, C(O)OR$^5$, OR$^5$, OS(O)$_2$R$^5$, NR$^5$R$^6$, SR$^5$, monocyclic and polycyclic heterocyclyl, polyethylene glycol, amino acid, and mono- or poly-saccharide; and R$^5$ and R$^6$ are each independently selected from hydrogen, C$_{1-10}$alkyl, and C$_{1-10}$haloalkyl.

13. The norbornenone compound or salt of claim 8, wherein R$^{14}$ and R$^{15}$ are each independently selected from C$_{1-20}$alkyl, C$_{2-20}$alkenyl, C$_{2-20}$alkynyl, monocyclic and polycyclic carbocyclyl or heterocyclyl, polyethylene glycol, amino acid, and mono- or poly-saccharide; wherein the C$_{1-20}$alkyl, C$_{2-20}$alkenyl, C$_{2-20}$alkynyl, are each optionally interrupted with one or more heteroatoms selected from O, N and S; and wherein the C$_{1-20}$alkyl, C$_{2-20}$alkenyl, C$_{2-20}$alkynyl, carbocycle, and heterocycle, are each optionally substituted with one or more substituents independently selected from halo, CN, NO$_2$, OC(O)R$^5$, C=O, C(O)R$^5$, C(O)OR$^5$, OR$^5$, OS(O)$_2$R$^5$, NR$^5$R$^6$, SR$^5$, monocyclic and polycyclic heterocyclyl, polyethylene glycol, amino acid, and mono-, di- or tri-saccharide; and R$^5$ and R$^6$ are each independently selected from hydrogen, C$_{1-10}$alkyl, and C$_{1-10}$haloalkyl.

14. The norbornenone compound or salt of claim 8, wherein R$^{14}$ and R$^{15}$ are each independently selected from C$_{1-20}$alkyl, C$_{2-20}$alkenyl, C$_{2-20}$alkynyl, and phenyl; wherein the C$_{1-20}$alkyl, C$_{2-20}$alkenyl, C$_{2-20}$alkynyl, are each optionally interrupted with one or more heteroatoms selected from O, N and S; and wherein the C$_{1-20}$alkyl, C$_{2-20}$alkenyl, C$_{2-20}$alkynyl, phenyl, are each optionally substituted with one to four substituents independently selected from halo, CN, NO$_2$, OC(O)R$^5$, C=O, C(O)R$^5$, C(O)OR$^5$, OR$^5$, OS(O)$_2$ R$^5$, NR$^5$R$^6$, SR$^5$, monocyclic and polycyclic heterocyclyl, polyethylene glycol, amino acid, and mono-, di- or tri-saccharide; and R$^5$ and R$^6$ are each independently selected from hydrogen, C$_{1-10}$alkyl, and C$_{1-10}$haloalkyl.

15. The norbornenone compound or salt of claim 8, wherein A$^3$ is NR$^{14}$, and R$^{14}$ is selected from C$_{1-20}$alkyl, C$_{2-20}$alkenyl, C$_{2-20}$alkynyl, and phenyl; wherein the C$_{1-20}$alkyl, C$_{2-20}$alkenyl, C$_{2-20}$alkynyl, are each optionally interrupted with one to four heteroatoms selected from O, N and S, and optionally interrupted with one to four groups, in either orientation, selected from —NR$^5$—, —NR$^5$—C(O)—, —C(O)—O—, and —NR$^5$—C(O)—O—; and wherein the C$_{1-20}$alkyl, C$_{2-20}$alkenyl, C$_{2-20}$alkynyl, phenyl, are each optionally substituted or terminated with one to four substituents independently selected from halo, CN, NO$_2$, OC(O)R$^5$, C=O, C(O)R$^5$, C(O)OR$^5$, OR$^5$, OS(O)$_2$R$^5$, NR$^5$R$^6$, SR$^5$, monocyclic and polycyclic heterocyclyl, polyethylene glycol, amino acid, and mono-, di- or tri-saccharide; and R$^5$ and R$^6$ are each independently selected from hydrogen, C$_{1-10}$alkyl, and C$_{1-10}$haloalkyl.

16. A norbornenone compound selected form any one of the following compounds, or a pharmaceutically acceptable salt thereof:

| Compound Structure | Compound Name |
| --- | --- |
| 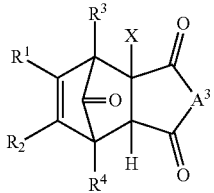<br>oCOm-1 | 3a-Bromo-3a,4,7,7a-tetrahydro-4,7-dimethyl-2,5,6-triphenyl-4,7-methano-1H-isoindole-1,3,8(2H)-trione; |

| Compound Structure | Compound Name |
|---|---|
| 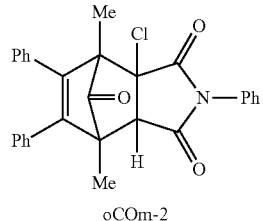 [SMILES: CC12C(=O)C(C)(C(c3ccccc3)=C1c1ccccc1)C1(Cl)C(=O)N(c3ccccc3)C(=O)C21]
oCOm-2 | 3a-Chloro-3a,4,7,7a-tetrahydro-4,7-dimethyl-2,5,6-triphenyl-4,7-methano-1H-isoindole-1,3,8(2H)-trione |
| 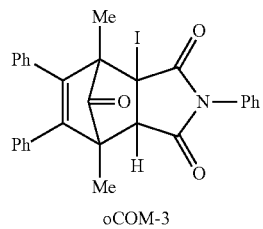 [SMILES: CC12C(=O)C(C)(C(c3ccccc3)=C1c1ccccc1)C1(I)C(=O)N(c3ccccc3)C(=O)C21]
oCOM-3 | 3a-Iodo-3a,4,7,7a-tetrahydro-4,7-dimethyl-2,5,6-triphenyl-4,7-methano-1H-isoindole-1,3,8(2H)-trione |
| 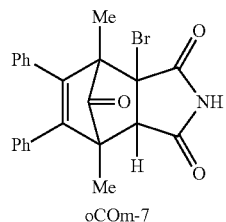 [SMILES: CC12C(=O)C(C)(C(c3ccccc3)=C1c1ccccc1)C1(Br)C(=O)NC(=O)C21]
oCOm-7 | 3a-Bromo-4,7-dimethyl-5,6-diphenyl-3a,4,7,7a-tetrahydro-1H-4,7-methanoisoindole-1,3,8(2H)-trione |
| 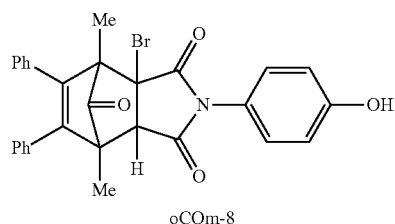 [SMILES: CC12C(=O)C(C)(C(c3ccccc3)=C1c1ccccc1)C1(Br)C(=O)N(c3ccc(O)cc3)C(=O)C21]
oCOm-8 | 3a-Bromo-3a,4,7,7a-tetrahydro-4,7-dimethyl-2-(4-hydroxyphenyl)-5,6-diphenyl-4,7-methano-1H-isoindole-1,3,8(2H)-trione |
| 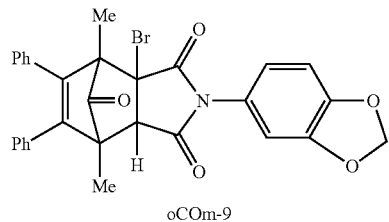 [SMILES: CC12C(=O)C(C)(C(c3ccccc3)=C1c1ccccc1)C1(Br)C(=O)N(c3ccc4c(c3)OCO4)C(=O)C21]
oCOm-9 | 3a-Bromo-3a,4,7,7a-tetrahydro-4,7-dimethyl-5,6-diphenyl-2-tri-(3,4-methylenedioxyphenyl)-4,7-methano-1H-isoindole-1,3,8(2H)-trione |
| 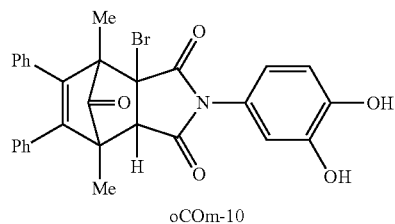 [SMILES: CC12C(=O)C(C)(C(c3ccccc3)=C1c1ccccc1)C1(Br)C(=O)N(c3ccc(O)c(O)c3)C(=O)C21]
oCOm-10 | 3a-Bromo-3a,4,7,7a-tetrahydro-4,7-dimethyl-2-(3,4-dihydroxyphenyl)-5,6-diphenyl-4,7-methano-1H-isoindole-1,3,8(2H)-trione |

| Compound Structure | Compound Name |
| --- | --- |
| 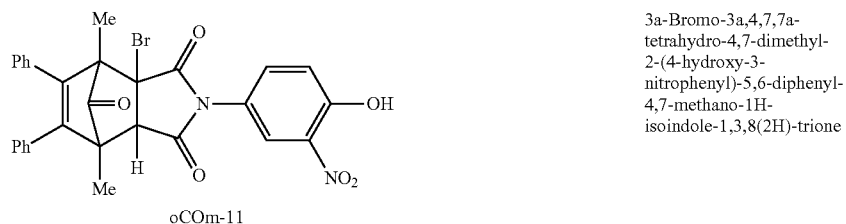<br>oCOm-11 | 3a-Bromo-3a,4,7,7a-tetrahydro-4,7-dimethyl-2-(4-hydroxy-3-nitrophenyl)-5,6-diphenyl-4,7-methano-1H-isoindole-1,3,8(2H)-trione |
| 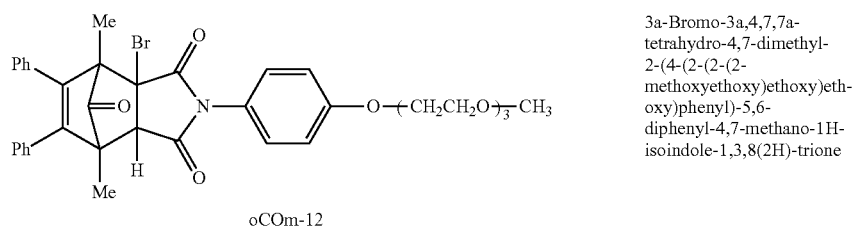<br>oCOm-12 | 3a-Bromo-3a,4,7,7a-tetrahydro-4,7-dimethyl-2-(4-(2-(2-(2-methoxyethoxy)ethoxy)ethoxy)phenyl)-5,6-diphenyl-4,7-methano-1H-isoindole-1,3,8(2H)-trione |
| <br>oCOm-13<br>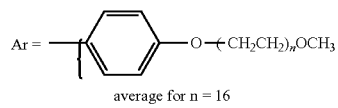<br>average for n = 16 | 3a-Bromo-3a,4,7,7a-tetrahydro-4,7-dimethyl-2-(4-(2-methoxy(2-polyethoxy)phenyl)-5,6-diphenyl-4,7-methano-1H-isoindole-1,3,8(2H)-trione |
| 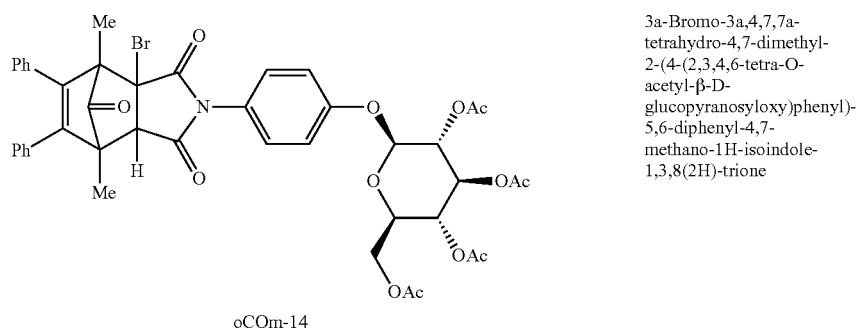<br>oCOm-14 | 3a-Bromo-3a,4,7,7a-tetrahydro-4,7-dimethyl-2-(4-(2,3,4,6-tetra-O-acetyl-β-D-glucopyranosyloxy)phenyl)-5,6-diphenyl-4,7-methano-1H-isoindole-1,3,8(2H)-trione |
| <br>oCOm-15<br>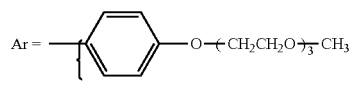 | 3a-Bromo-3a,4,7,7a-tetrahydro-4,7-dimethyl-2,5,6-tri-(4-(2-(2-(2-methoxyethoxy)ethoxy)ethoxy)phenyl)-4,7-methano-1H-isoindole-1,3,8(2H)-trione |

-continued

| Compound Structure | Compound Name |
|---|---|
| 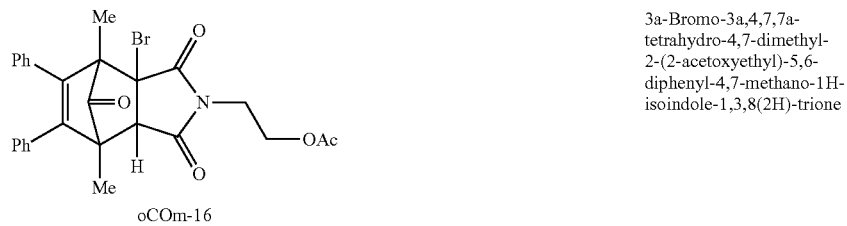<br>oCOm-16 | 3a-Bromo-3a,4,7,7a-tetrahydro-4,7-dimethyl-2-(2-acetoxyethyl)-5,6-diphenyl-4,7-methano-1H-isoindole-1,3,8(2H)-trione |
| 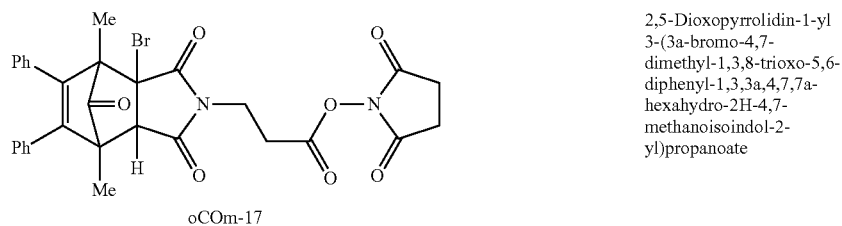<br>oCOm-17 | 2,5-Dioxopyrrolidin-1-yl 3-(3a-bromo-4,7-dimethyl-1,3,8-trioxo-5,6-diphenyl-1,3,3a,4,7,7a-hexahydro-2H-4,7-methanoisoindol-2-yl)propanoate |
| 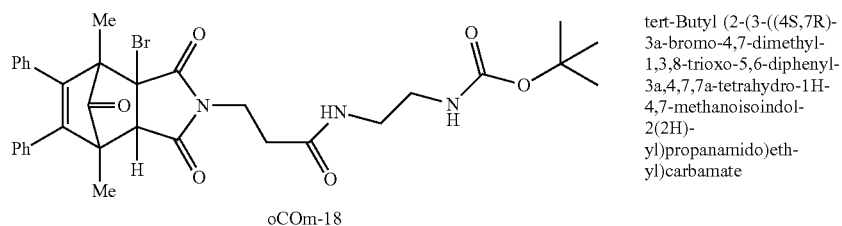<br>oCOm-18 | tert-Butyl (2-(3-((4S,7R)-3a-bromo-4,7-dimethyl-1,3,8-trioxo-5,6-diphenyl-3a,4,7,7a-tetrahydro-1H-4,7-methanoisoindol-2(2H)-yl)propanamido)ethyl)carbamate |
| 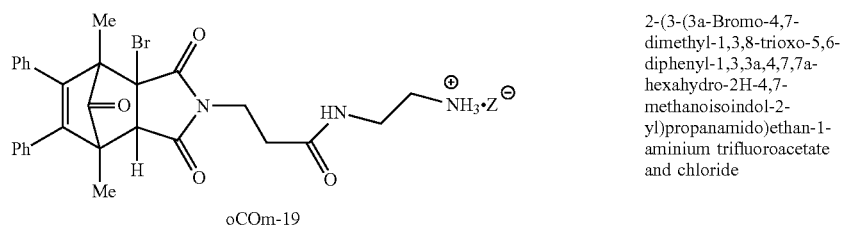<br>oCOm-19 | 2-(3-(3a-Bromo-4,7-dimethyl-1,3,8-trioxo-5,6-diphenyl-1,3,3a,4,7,7a-hexahydro-2H-4,7-methanoisoindol-2-yl)propanamido)ethan-1-aminium trifluoroacetate and chloride |
| 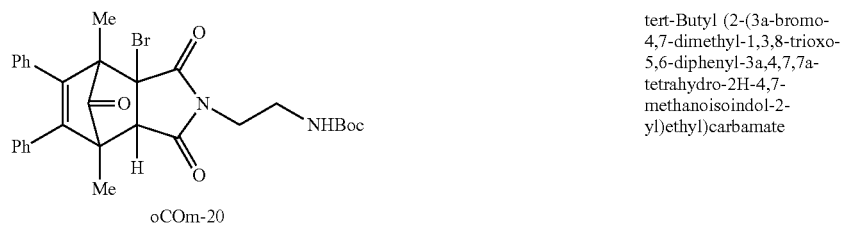<br>oCOm-20 | tert-Butyl (2-(3a-bromo-4,7-dimethyl-1,3,8-trioxo-5,6-diphenyl-3a,4,7,7a-tetrahydro-2H-4,7-methanoisoindol-2-yl)ethyl)carbamate |
| 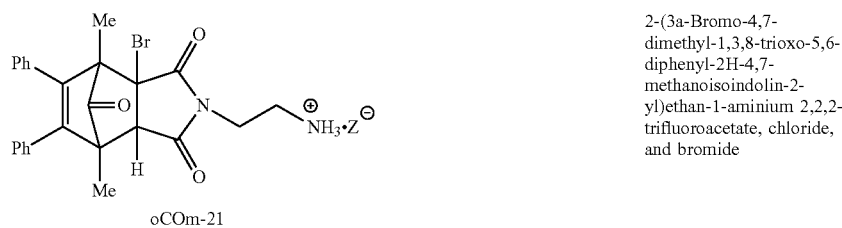<br>oCOm-21 | 2-(3a-Bromo-4,7-dimethyl-1,3,8-trioxo-5,6-diphenyl-2H-4,7-methanoisoindolin-2-yl)ethan-1-aminium 2,2,2-trifluoroacetate, chloride, and bromide |

| Compound Structure | Compound Name |
|---|---|
| 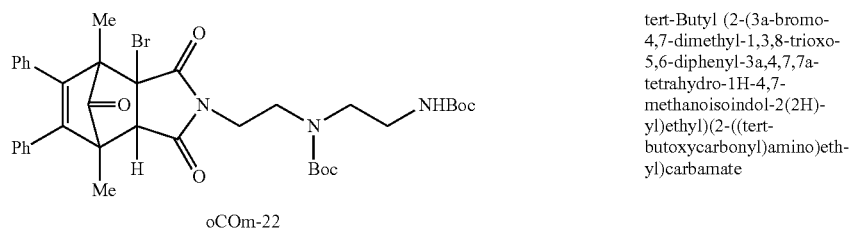<br>oCOm-22 | tert-Butyl (2-(3a-bromo-4,7-dimethyl-1,3,8-trioxo-5,6-diphenyl-3a,4,7,7a-tetrahydro-1H-4,7-methanoisoindol-2(2H)-yl)ethyl)(2-((tert-butoxycarbonyl)amino)ethyl)carbamate |
| 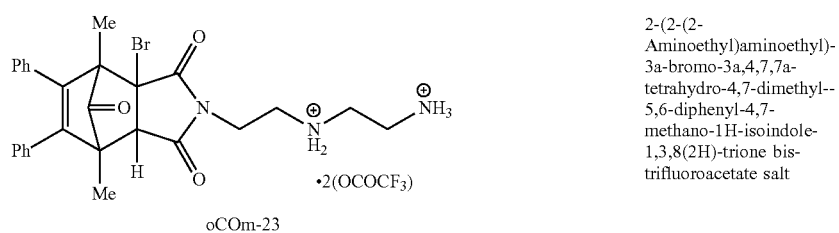<br>oCOm-23 | 2-(2-(2-Aminoethyl)aminoethyl)-3a-bromo-3a,4,7,7a-tetrahydro-4,7-dimethyl--5,6-diphenyl-4,7-methano-1H-isoindole-1,3,8(2H)-trione bis-trifluoroacetate salt |
| 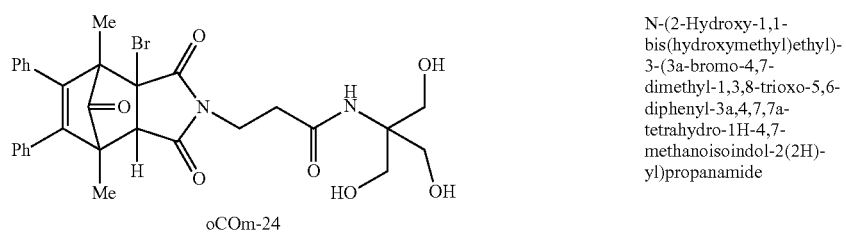<br>oCOm-24 | N-(2-Hydroxy-1,1-bis(hydroxymethyl)ethyl)-3-(3a-bromo-4,7-dimethyl-1,3,8-trioxo-5,6-diphenyl-3a,4,7,7a-tetrahydro-1H-4,7-methanoisoindol-2(2H)-yl)propanamide |
| 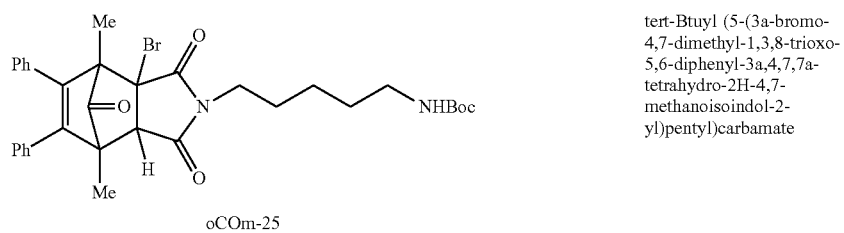<br>oCOm-25 | tert-Btuyl (5-(3a-bromo-4,7-dimethyl-1,3,8-trioxo-5,6-diphenyl-3a,4,7,7a-tetrahydro-2H-4,7-methanoisoindol-2-yl)pentyl)carbamate |
| 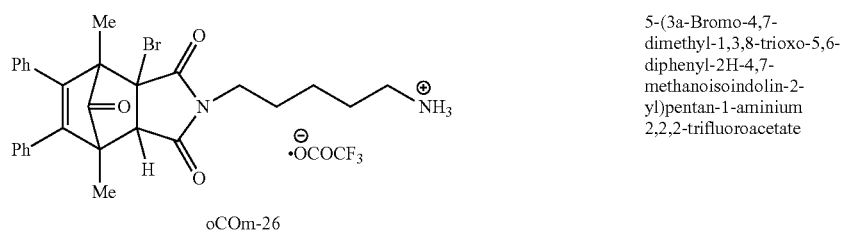<br>oCOm-26 | 5-(3a-Bromo-4,7-dimethyl-1,3,8-trioxo-5,6-diphenyl-2H-4,7-methanoisoindolin-2-yl)pentan-1-aminium 2,2,2-trifluoroacetate |
| 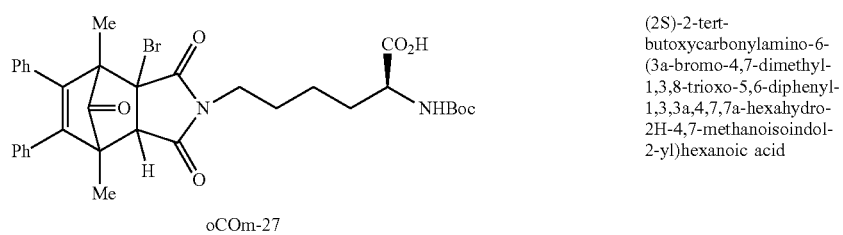<br>oCOm-27 | (2S)-2-tert-butoxycarbonylamino-6-(3a-bromo-4,7-dimethyl-1,3,8-trioxo-5,6-diphenyl-1,3,3a,4,7,7a-hexahydro-2H-4,7-methanoisoindol-2-yl)hexanoic acid |

-continued

| Compound Structure | Compound Name |
|---|---|
| 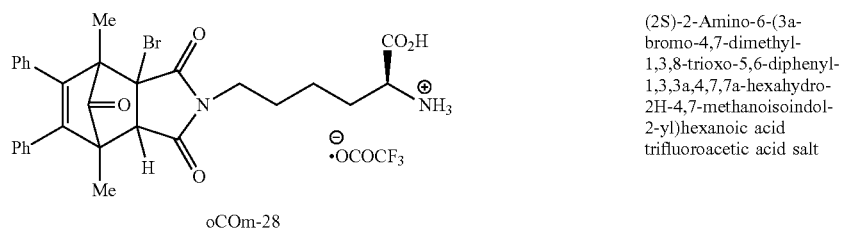<br>oCOm-28 | (2S)-2-Amino-6-(3a-bromo-4,7-dimethyl-1,3,8-trioxo-5,6-diphenyl-1,3,3a,4,7,7a-hexahydro-2H-4,7-methanoisoindol-2-yl)hexanoic acid trifluoroacetic acid salt |
| 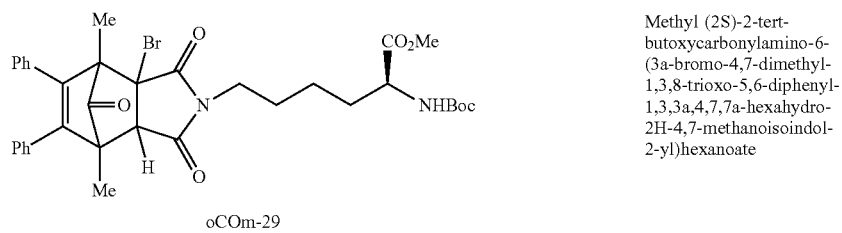<br>oCOm-29 | Methyl (2S)-2-tert-butoxycarbonylamino-6-(3a-bromo-4,7-dimethyl-1,3,8-trioxo-5,6-diphenyl-1,3,3a,4,7,7a-hexahydro-2H-4,7-methanoisoindol-2-yl)hexanoate |
| 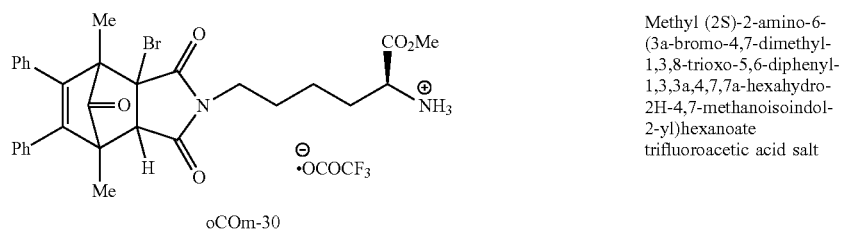<br>oCOm-30 | Methyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)hexanoate trifluoroacetic acid salt |
| 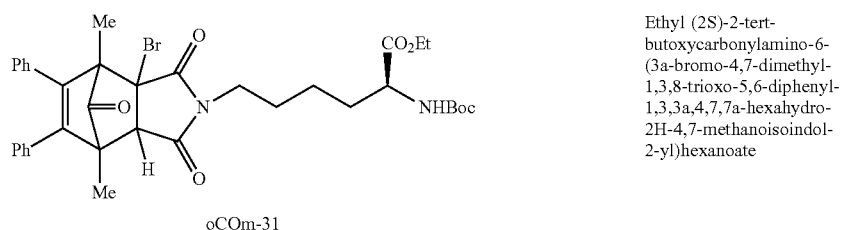<br>oCOm-31 | Ethyl (2S)-2-tert-butoxycarbonylamino-6-(3a-bromo-4,7-dimethyl-1,3,8-trioxo-5,6-diphenyl-1,3,3a,4,7,7a-hexahydro-2H-4,7-methanoisoindol-2-yl)hexanoate |
| 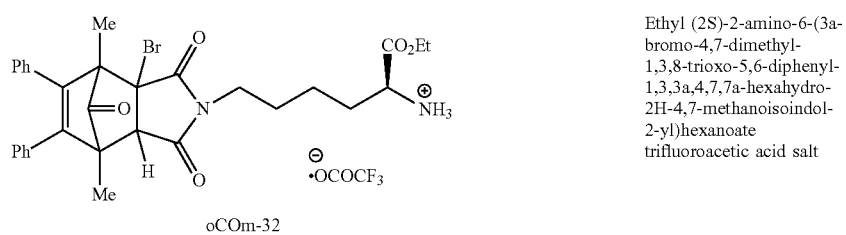<br>oCOm-32 | Ethyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)hexanoate trifluoroacetic acid salt |
| 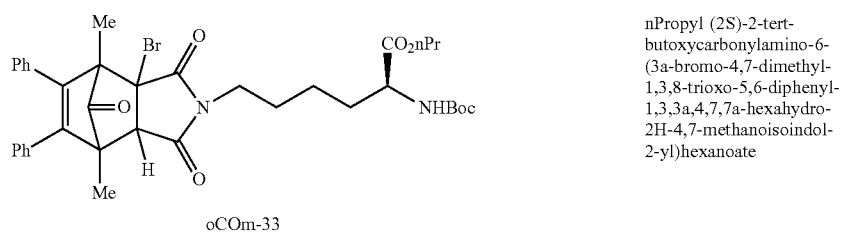<br>oCOm-33 | nPropyl (2S)-2-tert-butoxycarbonylamino-6-(3a-bromo-4,7-dimethyl-1,3,8-trioxo-5,6-diphenyl-1,3,3a,4,7,7a-hexahydro-2H-4,7-methanoisoindol-2-yl)hexanoate |

-continued

| Compound Structure | Compound Name |
| --- | --- |
| oCOm-34 | nPropyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)hexanoate trifluoroacetic acid salt |
| oCOm-35 | N,N-Dimethyl (2S)-2-tert-butoxycarbonylamino-6-(3a-bromo-4,7-dimethyl-1,3,8-trioxo-5,6-diphenyl-1,3,3a,4,7,7a-hexahydro-2H-4,7-methanoisoindol-2-yl)hexanamide |
| oCOm-36 | N,N-Dimethyl (2S)-2-amino-6-(3a-bromo-4,7-dimethyl-1,3,8-trioxo-5,6-diphenyl-1,3,3a,4,7,7a-hexahydro-2H-4,7-methanoisoindol-2-yl)hexanamide trifluoroacetic acid salt |
| oCOm-37 | tert-Butyl 6-(3a-bromo-4,7-dimethyl-1,3,8-trioxo-5,6-diphenyl-1,3,3a,4,7,7a-hexahydro-2H-4,7-methanoisoindol-2-yl)hexanoate |
| oCOm-38 | 6-(3a-bromo-4,7-dimethyl-1,3,8-trioxo-5,6-diphenyl-1,3,3a,4,7,7a-hexahydro-2H-4,7-methanoisoindol-2-yl)hexanoic acid |
| oCOm-39 | Methyl (2S)-2-tert-butoxycarbonylamino-5-(3a-bromo-4,7-dimethyl-1,3,8-trioxo-5,6-diphenyl-1,3,3a,4,7,7a-hexahydro-2H-4,7-methanoisoindol-2-yl)pentanoate |

-continued

| Compound Structure | Compound Name |
|---|---|
| oCOm-40 | Methyl (2S)-2-amino-5-(3a-bromo-4,7-dimethyl-1,3,8-trioxo-5,6-diphenyl-1,3,3a,4,7,7a-hexahydro-2H-4,7-methanoisoindol-2-yl)pentanoate trifluoroacetic acid salt |
| oCOm-41 | Methyl (2S)-2-acetamido-6-(3a-bromo-4,7-dimethyl-1,3,8-trioxo-5,6-diphenyl-1,3,3a,4,7,7a-hexahydro-2H-4,7-methanoisoindol-2-yl)hexanoate |
| oCOm-42 | (1S)-1-tert-butoxycarbonylamino-5-(3a-bromo-4,7-dimethyl-1,3,8-trioxo-5,6-diphenyl-1,3,3a,4,7,7a-hexahydro-2H-4,7-methanoisoindol-2-yl)-1-(3-methyl-1,2,4-oxadiazol-5'-yl)pentane |
| oCOm-43 | (1S)-1-amino-5-(3a-bromo-4,7-dimethyl-1,3,8-trioxo-5,6-diphenyl-1,3,3a,4,7,7a-hexahydro-2H-4,7-methanoisoindol-2-yl)-1-(3-methyl-1,2,4-oxadiazol-5-yl)pentane trifluoroacetic acid salt |
| oCOm-44 | (1S)-1-tert-butoxycarbonylamino-5-(3a-bromo-4,7-dimethyl-1,3,8-trioxo-5,6-diphenyl-1,3,3a,4,7,7a-hexahydro-2H-4,7-methanoisoindol-2-yl)-1-(5-methyl-1,3,4-oxadiazol-2-yl)pentane |
| oCOm-45 | (1S)-1-Amino-5-(3a-bromo-4,7-dimethyl-1,3,8-trioxo-5,6-diphenyl-1,3,3a,4,7,7a-hexahydro-2H-4,7-methanoisoindol-2-yl)-1-(5-methyl-1,3,4-oxadiazol-2-yl)pentane trifluoroacetic acid salt |

| Compound Structure | Compound Name |
| --- | --- |
| oCOm-46 | 3a,4,7,7a-Tetrahydro-7a-bromo-4,7-dimethyl-5,6-diphenyl-1H-4,7-methanoisobenzofuran-1,3,8(2H)-trione |
| oCOm-47 | 3a-Bromo-3a,4,7,7a-tetrahydro-4,7-dimethyl-2-(2-propyn-1-yl)-5,6-diphenyl-4,7-methano-1H-isoindole-1,3,8(2H)-trione |
| oCOm-48 | 3a-Bromo-3a,4,7,7a-tetrahydro-4,7-dimethyl-2-[[1-(2-(2:3,4:6-bis-O-(1-methylethylidene)-α-D-mannopyranosyloxy)ethyl]-1H-1,2,3-triazol-4yl]methyl-5,6-diphenyl-4,7-methano-1H-isoindole-1,3,8(2H)-trione |
| oCOm-49 | 3a-Bromo-3a,4,7,7a-tetrahydro-4,7-dimethyl-2-[[1-(2-α-D-mannopyranosyloxy)ethyl]-1H-1,2,3-triazol-4yl]methyl-5,6-diphenyl-4,7-methano-1H-isoindole-1,3,8(2H)-trione |
| oCOm-50 | 2-Bromo-1,4-dimethyl-7-oxo-5,6-diphenyl-bicyclo[2.2.1]hept-5-ene-2,3-dicarboxylic acid |

| Compound Structure | Compound Name |
|---|---|
| 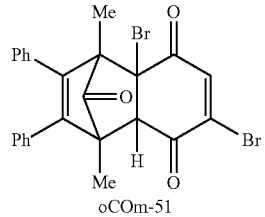 oCOm-51 | 4a,7-Dibromo-1,4-dimethyl-2,3-diphenyl-1,4,4s,8a-tetrahydro-1,4-methanonaphthalene-5,8,9-trione. |
* * * * *